US007288369B2

(12) United States Patent
Lemon et al.

(10) Patent No.: US 7,288,369 B2
(45) **Date of Patent: *Oct. 30, 2007**

(54) REPLICATION COMPETENT HEPATITIS C VIRUS AND METHODS OF USE

(75) Inventors: Stanley M. Lemon, Galveston, TX (US); MinKyung Yin, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 119 days.

This patent is subject to a terminal disclaimer.

(21) Appl. No.: 11/006,313

(22) Filed: Dec. 6, 2004

(65) Prior Publication Data

US 2005/0153281 A1 Jul. 14, 2005

Related U.S. Application Data

(63) Continuation of application No. 10/259,275, filed on Sep. 27, 2002, now Pat. No. 6,921,634, which is a continuation-in-part of application No. 09/747,419, filed on Dec. 23, 2000, now abandoned.

(60) Provisional application No. 60/338,123, filed on Nov. 13, 2001, provisional application No. 60/325,236, filed on Sep. 27, 2001, provisional application No. 60/171,909, filed on Dec. 23, 1999.

(51) Int. Cl.
*C12Q 1/70* (2006.01)
*C12N 15/63* (2006.01)

(52) U.S. Cl. .............................................. 435/5; 435/6

(58) Field of Classification Search ............... 435/69.1, 435/320.1, 91.4; 424/228.1
See application file for complete search history.

(56) References Cited

U.S. PATENT DOCUMENTS

| | | | | |
|---|---|---|---|---|
| 5,766,906 | A | 6/1998 | Lemon et al. | |
| 5,846,767 | A | 12/1998 | Halpin et al. | |
| 5,874,565 | A | 2/1999 | Rice et al. | |
| 5,912,167 | A | 6/1999 | Palmenberg et al. | |
| 6,127,116 | A | 10/2000 | Rice et al. | |
| 6,392,028 | B1 | 5/2002 | Rice, III et al. | |
| 6,689,559 | B2 | 2/2004 | Wimmer et al. | |
| 6,930,095 | B2 * | 8/2005 | Bichko | 514/44 |
| 6,943,246 | B2 | 9/2005 | Rice et al. | |
| 7,049,428 | B1 | 5/2006 | Rice, III et al. | |
| 2002/0155582 | A1 | 10/2002 | Lemon et al. | |
| 2003/0125541 | A1 | 7/2003 | Lemon et al. | |

FOREIGN PATENT DOCUMENTS

| | | |
|---|---|---|
| WO | WO 00/14263 | 3/2000 |
| WO | WO 02/059321 | 8/2002 |

OTHER PUBLICATIONS

Zhong et al. PNAS, 2005, vol. 102, No. 26, pp. 9294-9299.*
Graham et al. Antiviral Research 2006, vol. 69, pp. 24-30.*
Kanda et al. J. Virol. 2006, vol. 80, No. 9, p. 4633-4639.*
Heller et al. PNAS, 2005, vol. 102, No. 7, pp. 2579-2583.*
Cai et al. J. Virol. 2005, vol. 79, No. 22, pp. 13963-13973.*
Murry et al. J. Virol. 2003, vol. 77, No. 5, pp. 2928-2935.*
Bartenschlager et al. Journal of General Virology 2000, vol. 81, pp. 1631-1648.*
Bukh et al., "Mutations that permit efficient replication of hepatitis C virus RNA in Huh-7 cells prevent productive replication in chimpanzees," *PNAS*, Oct. 29, 2002;99(22):14416-14421.
Ausubel et al., eds., *Current Protocols in Molecular Biology*, vol. 1-4, John Wiley & Sons, U.S.; title page, publication page and table of contents only, 12 pgs. (1994).
Bartenschlager et al., "Replication of hepatitis C virus," *Journal of General Virology*, 2000,81: 1631-48.
Beard et al., "An Infectious Molecular Clone of a Japanese Genotype Ib Hepatitis C Virus," *Hepatology*, Jul. 1999;30(1):316-24.
Berger et al., "Secreted Placental Alkaline Phosphatase: A Powerful New Quantitative Indicator of Gene Expression in Eukaryotic Cells," *Gene*. Jun. 15, 1988;66(1):1-10.
Bieniasz et al., "Highly Divergent Lentiviral Tat Proteins Activate Viral Gene Expression by a Common Mechanism," *Mol Cell Biol*. Jul. 1999;19(7):4592-9.
"BLAST," National Institutes of Health, Bethesda, MD [online]. Retrieved from Internet on Apr. 17, 2001. <URL:http://www.ncbi.nlm.nih.gov/gorf/b12.html>, 2 pgs.
Blight et al., "Efficient Initiation of HCV RNA Replication in Cell Culture," *Science*, Dec. 8, 2000;290(5498):1972-5.
Bukh et al., "Sequence analysis of the 5' noncoding region of hepatitis C virus," *Proc. Nat. Acad. Sci. USA*, 1992;89: 4942-46.
Cullen,"*Trans*-activation of Human Immunodeficiency Virus Occurs via a Bimodal Mechanism," *Cell*. Sep. 26, 1986;46(7):973-82.
Cullen, Bryan R., "HIV-1 Auxiliary Proteins: Making Connections in a Dying Cell," *Cell*, 1998;93: 685-92.
Forns et al., "Hepatitis C Virus Lacking the Hypervariable Region 1 of the Second Envelope Protein Is Infectious and Causes Acute Resolving or Persistent Infection in Chimpanzees," *Proc Natl Acad Sci U S A*. Nov. 21, 2000;97(24):13318-23.
Frese et al., "Interferon-α inhibits hepatitis C virus subgenomic RNA replication by an MxA-independent pathway," *J. Gen. Virol.*, Apr. 2001;82 (pt.4): 723-33.
Fujisawa et al., "The Indirect Association of Human T-cell Leukemia Virus *tax* Protein with DNA Results in Transcriptional Activation," *J Virol*. Aug. 1991;65(8):4525-8.

(Continued)

*Primary Examiner*—Bruce R. Campell
*Assistant Examiner*—Bao Qun Li
(74) *Attorney, Agent, or Firm*—Mueting, Raasch & Gebhardt, P.A.

(57) ABSTRACT

The present invention provides a replication competent hepatitis C virus that includes a heterologous polynucleotide. The invention also includes methods for modifying a hepatitis C virus polynucleotide, selecting a replication competent hepatitis C virus polynucleotide, detecting a replication competent hepatitis C virus polynucleotide, and identifying a compound that inhibits replication of a hepatitis C virus polynucleotide.

11 Claims, 62 Drawing Sheets

OTHER PUBLICATIONS

Guo et al., "Identification of a Novel RNA Species in Cell Lines Expressing HCV Subgenomic Replicons," Abstract P045, 7th International Meeting on Hepatitis C Virus and Related Viruses (Molecular Virology and Pathogenesis), The Marriott Resort Hotel, Gold Coast, Queensland, Australia, Dec. 3-7, 2000.
Guo et al., "Effect of Alpha Interferon on the Hepatitis C Virus Replicon," *J. Virol.*, 2001; 75: 8516-23.
Hadzopoulou-Cladaras et al., "The *rev* (*trs/art*) Protein of Human Immunodeficieny Virus Type 1 Affects Viral mRNA and Protein Expression via a *cis*-acting Sequence in the *env* Region," *J Virol.* Mar. 1989;63(3):1265-74.
Harlow et al., *Antibodies: A Laboratory Manual*, Cold Spring Harbor Laboratory Press, Cold Spring Harbor, NY; title page, publisher's page, and table of contents, 9 pages (1988).
Hayashi et al., "Molecular cloning and heterogeneity of the human hepatitis C virus (HCV) genome," *J. Hepatol.*, 1993;17: S94-S107.
Honda et al., "Stability of a stem-loop involving the initiator AUG controls the efficiency of internal initiation of translation of hepatitis C virus RNA," *RNA*, 1996;2: 955-68.
Ikeda et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells," *J. Virol.*, Mar. 2002;76(6): 2997-3006.
Kim et al., "Domains I and II in the 5' Nontranslated Region of the HCV Genome Are Required for RNA Replication," *Biochem Biophys Res Comm.*, 2002;290: 105-112.
Kolykhalov et al., "Identification of a Highly Conserved Sequenced Element at the 3' Terminus of Hepatitis C Virus Genome RNA," *J Virol.* Jun. 1996;70(6):3363-71.
Kolykhalov et al., "Hepatitis C Virus-encoded Enzymatic Activities and Conserved RNA Elements in the 3' Nontranslated Region Are Essential for Virus Replication In Vivo," *J Virol.* Feb. 2000;74(4):2046-51.
Krieger et al., "Enhancement of Hepatitis C Virus RNA Replication by Cell Culture-Adaptive Mutations," *J. Virol.*, 2001;75: 4614-24.
Lai et al., "Generation and Characterization of a Hepatitis C Virus NS3 Protease-dependent Bovine Viral Diarrhea Virus," *J Virol.* Jul. 2000;74(14):6339-47.
Lanford et al., "Lack of Detection of Negative-strand Hepatitis C Virus RNA in Peripheral Blood Mononuclear Cells and Other Extrahepatic Tissues by the Highly Strand-specific rTth Reverse Transcriptase PCR," *J Virol.* Dec. 1995;69(12):8079-83.
Lemon, "Selection of Cell Culture-adapted Hepatitis C RNA," Grant Abstract for Grant No. 2U19AI40035-050001 [online]. National Institute of Allergy and Infectious Diseases, National Institutes of Health; project dates Aug. 1, 1996 to Jul. 31, 2005. Retrieved from the Internet on Apr. 17, 2001; URL: <http://commons.cit.nih.gov/crisp/crisp_lib.getdoc?textkey=6340699&p_query=&ticket=1907498&p_audit_session_id=4197699&p_keywords=>, 2 pages.
Lemon, "The Southeastern Cooperative Hepatitis C Research Group," Grant Abstract for Grant No. 2U19AI40035-05 [online]. National Institute of Allergy and Infectious Diseases, National Institutes of Health; project dates Aug. 1, 1996 to Jul. 31, 2005. Retrieved from the Internet on Apr. 17, 2001; URL: <http://commons.cit.nih.gov/crisp/crisp_lib.getdoc?textkey=6199426&p_query=&ticket=1907498&p_audit_session_id=4197699&p_keywords=>, 2 pages.
Li et al., "Cellular response to conditional expression of Hepatitis C virus core protein in Huh7 cultured human hepatoma cells," *Hepatology*, May 2002;35(5):1237-1246.
Lohmann et al. "Replication of Subgenomic Hepatitis C Virus RNAs in a Hepatoma Cell Line," *Science*. Jul. 2, 1999;285(5424):110-3.
Lohmann et al., "Adaptation of Selectable HCV Replicon to a Human Hepatoma Cell Line," Abstract P038, 7th International Meeting on Hepatitis C Virus and Related Viruses (Molecular Virology and Pathogenesis), The Marriott Resort Hotel, Gold Coast, Queensland, Australia, Dec. 3-7, 2000.
Lohmann et al. "Mutations in Hepatitis C Virus RNAs Conferring Cell Culture Adaptation," *J Virol.* Feb. 2001;75(3):1437-49.
Naryshikin et al., "RNA Recognition and Regulation of HIV-1 Gene Expression by Viral Factor Tat," *Biochemistry*, 1998;63: 489-503.
National Center for Biotechnology Information, National Library of Medicine, National Institutes of Health, Bethesda, MD, GenBank Locus No. AB030907, Accession No. AB030907, "Hepatitis C virus type 2b gene for polyprotein, complete cds, isolate:JPUT971017," [online]. Retrieved from the Internet on Apr. 17, 2001:<URL:http://www.ncbi.nlm.nih.gov/entrez/query.fcgi?cmd=Retrieve&db=Nucleotide&list_uids=9757541&dopt=GenBank>, 8 pages.
National Center for Biotechnology Information, National Library of Medicine, National Institutes of Health, Bethesda, MD, GenBank Locus No. AF011751, Accession No. AF011751, "Hepatitis C virus strain H77 pCV-H77C polyprotein gene, complete cds." [online]. Retrieved from the Internet on Apr. 26, 2001:<URL:http://www.ncbi.nlm.nih.gov/entrez/query.fcgi?cmd=Retrieve&db=Nucleotide&list_uids=2327070&dopt=GenBank>, 7 pages.
National Center for Biotechnology Information, National Library of Medicine, National Institutes of Health, Bethesda, MD, GenBank Locus No. AF033819, Accession No. AF033819, "HIV-1, complete genome," [online]. Retrieved from the Internet on Apr. 17, 2001:<URL:http://www.ncbi.nlm.nih.gov/entrez/query.fcgi?cmd=Retrieve&db=Nucleotide&list_uids=4558520&dopt=GenBank>, 9 pages.
National Center for Biotechnology Information, National Library of Medicine, National Institutes of Health, Bethesda, MD, GenBank Locus No. AF139594, Accession No. AF139594, "Hepatitis C virus strain HCV-N, complete genome," [online]. Retrieved from the Internet on Apr. 17, 2001:<URL:http://www.ncbi.nlm.nih.gov/entrez/query.fcgi?cmd=Retrieve&db=Nucleotide&list_uids=5532421&dopt=GenBank>, 7 pages.
National Center for Biotechnology Information, National Library of Medicine, National Institutes of Health, Bethesda, MD, GenBank Locus No. AF238481, Accession No. AF238481, "Hepatitis C virus 2a polyprotein gene, complete cds," [online]. Retrieved from the Internet on Apr. 17, 2001:<URL:http://www.ncbi.nlm.nih.gov/entrez/query.fcgi?cmd=Retrieve&db=Nucleotide&list_uids=7329200&dopt=GenBank>, 6 pages.
National Center for Biotechnology Information, National Library of Medicine, National Institutes of Health, Bethesda, MD, GenBank Locus No. SSE242652, Accession No. AJ242652, "Hepatitis C virus replicon I377/NS3-3'UTR," [online]. Retrieved from the Internet on Feb. 18, 2003:<URL:http://www.ncbi.nlm.nih.gov/entrez/query.fcgi?cmd=Retrieve&db=Nucleotide&list_uids=5441834&dopt=GenBank>, 7 pages.
National Center for Biotechnology Information, National Library of Medicine, National Institutes of Health, Bethesda, MD, GenBank Locus No. HCJ238799, Accession No. AJ238799, "Hepatitis C virus type 1b complete genome, isolate Con1," [online]. Retrieved from the Internet on Apr. 17, 2001:<URL:http://www.ncbi.nlm.nih.gov/entrez/query.fcgi?cmd=Retrieve&db=Nucleotide&list_uids=5420376&dopt=GenBank>, 8 pages.
Pelletier, et al., "Internal Initiation of Translation of Eukaryotic mRNA Directed by a Sequence Derived from Poliovirus RNA," *Nature*. Jul. 28, 1988;334(6180):320-5.
Pietschmann et al., "Characterization of Cell Lines Carrying Self-Replicating Hepatitis C Virus RNAs," *J. Virol.* 2001;75: 1252-64.
Rethwilm et al., "The Transcriptional Transactivator of Human Foamy Virus Maps to the *bel* J Genomic Region," *Proc Natl Acad Sci U S A*. Feb. 1, 1991;88(3):941-5.
Reynolds et al., "Unique features of internal initiation of hepatitis C virus RNA translation," *EMBO J.*, 1995;14: 6010-20.
Reynolds et al., "Internal initiation of translation of hepatitis C virus RNA: The ribosome entry site is at the authentic initiation codon," *RNA*, 1996; 2: 867-78.
Rijinbran et al., "The influence of downstream protein-coding sequence on internal ribosome entry on hepatitis C virus and other flavivirus RNAs," *RNA*, 2001;7: 585-97.
Ryan et al., "Foot-and-Mouth Disease Virus 2A Oligopeptide Mediated Cleavage of an Artificial Polyprotein," *EMBO J.* Feb. 15, 1994;13(4):928-33.
Simmonds, "Variability of Hepatitis C Virus," *Hepatology*, Feb. 1995;21(2):570-83.

Takeuchi et al., "Real-time Detection System for Quantification of Hepatitis C Virus Genome," *Gastroenterology*. Mar. 1999;116(3):636-42.
Tatusova, et al. "BLAST 2 Sequences, a New Tool for Comparing Protein and Nucleotide Sequences," *FEMS Microbiol Lett*. May 15, 1999;174(2):247-50.
Tauz et al., "Processing of Poly-ubiquitin in the Polyprotein of an RNA Virus," *Virology*, Nov. 1993;197(1):74-85.
Whetter et al., "Analysis of Hepatitis a Virus Translation in a T7 Polymerase-expressing Cell Line," *Arch Virol Suppl*. 1994;9: 291-8.
Whetter et al., "Low Efficiency of the 5' Nontranslated Region of Hepatitis A Virus RNA in Directing Cap-Independent Translation in Permissive Monkey Kidney Cells," *J. Virol*., 1994;68: 5253-63.
Xu et al., "Synthesis of a novel hepatitis C virus protein by ribosomal frameshift," *EMBO J*., 2001;20:3840-48.
Yamada et al., "Genetic Organization and Diversity of the 3' Noncoding Region of the Hepatitis C Virus Genome," *Virology*. Sep. 1, 1996;223(1):255-61.
Yanagi et al., "Transcripts from a Single Full-length cDNA Clone of Hepatitis C Virus Are Infectious When Directly Transfected into the Liver of a Chimpanzee," *Proc Natl Acad Sci U S A*. Aug. 5, 1997;94(16):8738-43.
Yanagi et al., "In vivo Analysis of the 3' Untranslated Region of the Hepatitis C Virus after in vitro Mutagenesis of an Infectious cDNA Clone," *Proc Natl Acad Sci U S A*. Mar. 2, 1999;96(5):2291-5.
Yi et al., "Infectious Discistronic Hepatitis C Virus (HCV) RNA That Facilitates the Rescue of Virus from Synthetic RNA and the Monitoring of Viral Replication in Cultured Cells," presented at 7th International Meeting on Hepatitis C Virus and Related Viruses (Molecular Virology and Pathogenesis), The Marriott Resort Hotel, Gold Coast, Queensland, Australia, Dec. 3-7, 2000; abstract and poster (30 pages).
Yoo et al., "Transfection of a Differentiated Human Hepatoma Cell Line (Huh7) with In Vitro-transcribed Hepatitis C Virus (HCV) RNA and Establishment of a Long-term Culture Persistently Infected with HCV," *J Virol*. Jan. 1995;69(1):32-8.
Ikeda et al., "Human hepatocyte clonal cell lines that support persistent replication of hepatits C virus," *Virus Research*, 1998; 56:157-167.
Iacovacci et al. "Molecular Characterization and Dynamics of Hepatitis C Virus Replication in Human Fetal Hepatocytes Infected In Vitro" *Hepatology* 1997;26(5):1328-1337.
Kato et al., "Susceptibility of Human T-Lymphotropic Virus Type I Infected Cell Line MT-2 to Hepatitis C Virus Infection," *Biochemical and Biophysical Research Communications*, Jan. 26, 1995; 206(3):863-869.
Kato et al., "Replication of Hepatitis C Virus in Cultured Non-neoplastic Human Hepatocytes," *Jpn. J. Cancer Res*., Aug. 1996;87:787-792.
Lanford et al. "Demonstration of in Vitro Infection Chimpanzee Hepatocytes with Hepatitis C Virus Using Strand-Specific RT/PCR" *Virology* 1994;202(2):606-614.
Nakajima et al., "Characterization of Long-Term Cultures of Hepatitis C Virus," *Journal of Virology*, May 1996;70(5):3325-3329.
Shimizu et al., "Evidence for in vitro replication of hepatitis C virus genome in a human T-cell line," *Proc. Natl. Acad. Sci. USA*, Jun. 1992;89:5477-5481.
Shimizu et al., "Correlation between the infectivity of hepatitis C virus in vivo and its infectivity in vitro," *Proc. Natl. Acad. Sci. USA*, Jul. 1993;90:6037-6041.
Shimizu et al., "Infection of a chimpanzee with hepatitis C virus grown in cell culture" *J. Of General Virology* 1998;79:1383-1386.
Blight et al., "Efficient Replication of Hepatitis C Virus Genotype 1a RNAs in Cell Culture," *Journal of Virology*, 2003; 77(5):3181-3190.
Grobler et al., "Identification of a Key Determinant of Hepatitis C Virus Cell Culture Adaptation in Domain II of NS3 Helicase," *Journal of Biological Chemistry*, 2003; 278(19):16741-16746.
Gu et al., "Replication Studies Using Genotype 1a Subgenomic Hepatitis C Virus Replicons," *Journal of Virology*, 2003; 77(9):5352-5359.
Landford et al., "Antiviral Effect and Virus-Host Interactions in Response to Alpha Interferon, Gamma Interferon, Poly(I)-Poly(C), Tumor Necrosis Factor Alpha, and Ribavirin in Hepatitis C Virus Subgenomic Replicons," *Journal of Virology*, 2003; 77(2):1092-1104.
Yi et al., "Subgenomic Hepatitis C Virus Replicons Inducing Expression of a Secreted Enzymatic Reporter Protein," *Virology*, 2002; 304(2):197-210.
Yi et al., "Adaptive Mutations Producing Efficient Replication of Genotype 1a Hepatitis C Virus RNA in Normal Huh7 Cells," *Journal of Virology*, 2004; 78(15):7904-7915.

* cited by examiner

*Fig. 9a₁*

```
                        |  10      |  20      |  30      |  40      |  50      |  60      |  70      |  80
SEQ ID NO:17    1 GCCAGCCCCC TGATGGGGGC GACACTCCAC CATGAATCAC TCCCCTGTGA GGAACTACTG TCTTCACGCA GAAAGCGTCT 80
               81 AGCCATGGCG TTAGTATGAG TGTCGTGCAG CCTCCAGGAC CCCCCCTCCC GGGAGAGCCA TAGTGGTCTG CGGAACCGGT 160
              161 GAGTACACCG GAATTGCCAG GACGACCGGG TCCTTTCTTG GATAAACCCG CTCAATGCCT GGAGATTTGG GCGTGCCCCC 240
              241 GCAAGACTGC TAGCCGAGTA GTGTTGGGTC GCGAAAGGCC TTGTGGTACT GCCTGATAGG GTGCTTGCGA GTGCCCCGGG 320
              321 AGGTCTCGTA GACCGTGCAC CATGAGCACG AATCCTAAAC CTCAAAGAAA AACCAAACGT AACACCAACC GTCGCCCACA 400
              401 GGACGTCAAG TTCCCGGGTG GCGGTCAGAT CGTTGGTGGA GTTTACTTGT TGCCGCGCAG GGGCCCTAGA TTGGGTGTGC 480
              481 GCGCGACGAG GAAGACTTCC GAGCGGTCGC AACCTCGAGG TAGACGTCAG CCTATCCCCA AGGCACGTCG GCCCGAGGGC 560
              561 AGGACCTGGG CTCAGCCCGG GTACCCTTGG CCCCTCTATG GCAATGAGGG TTGCGGGTGG GCGGGATGGC TCCTGTCTCC 640
              641 CCGTGGCTCT CGGCCTAGCT GGGGCCCCAC AGACCCCCGG CGTAGGTCGC GCAATTTGGG TAAGGTCATC GATACCCTTA 720
              721 CGTGCGGCTT CGCCGACCTC ATGGGGTACA TACCGCTCGT CGGCGCCCCT CTTGGAGGCG CTGCCAGGGC CCTGGCGCAT 800
              801 GGCGTCCGGG TTCTGGAAGA CGGCGTGAAC TATGCAACAG GGAACCTTCC TGGTTGCTCT TTCTCTATCT TCCTTCTGGC 880
              881 CCTGCTCTCT TGCCTGACTG TGCCCGCTTC AGCCTACCAA GTGCGCAATT CCTCGGGGCT TTACCATGTC ACCAATGATT 960
              961 GCCCTAACTC GAGTATTGTG TACGAGGCGG CCGATGCCAT CCTGCACACT CCGGGGTGTG TCCCTTGCGT TCGCGAGGGT 1040
             1041 AACGCCTCGA GGTGTTGGGT GGCGGTGACC CCCACGGTGG CCACCAGGGA CGGCAAACTC CCCACAACGC AGCTTCGACG 1120
             1121 TCATATCGAT CTGCTTGTCG GGAGCGCCAC CCTCTGCTCG GCCCTCTACG TGGGGGACCT GTGCGGGTCT GTCTTTCTTG 1200
             1201 TTGGTCAACT GTTTACCTTC TCTCCCAGGC GCCACTGGAC GACGCAAGAC TGCAATTGTT CTATCTATCC CGGCCATATA 1280
             1281 ACGGGTCATC GCATGGCATG GGATATGATG ATGAACTGGT CCCCTACGGC AGCGTTGGTG GTAGCTCAGC TGCTCCGGAT 1360
             1361 CCCACAAGCC ATCATGGACA TGATCGCTGG TGCTCACTGG GGAGTCCTGG CGGGCATAGC GTATTTCTCC ATGGTGGGGA 1440
             1441 ACTGGGCGAA GGTCCTGGTA GTGCTGCTGC TATTTGCCGG CGTCGACGCG GAAACCCACG TCACCGGGGG AAATGCCGGC 1520
             1521 CGCACCACGG CTGGGCTTGT TGGTCTCCTT ACACCAGGCG CCAAGCAGAA CATCCAACTG ATCAACACCA ACGGCAGTTG 1600
             1601 GCACATCAAT AGCACGGCCT TGAATTGCAA TGAAAGCCTT AACACCGGCT GGTTAGCAGG GCTCTTCTAT CAACACAAAT 1680
             1681 TCAACTCTTC AGGCTGTCCT GAGAGGTTGG CCAGCTGCCG ACGCCTTACC GATTTTGCCC AGGGCTGGGG TCCTATCAGT 1760
             1761 TATGCCAACG GAAGCGGCCT CGACGAACGC CCCTACTGCT GGCACTACCC TCCAAGACCT TGTGGCATTG TGCCCGCAAA 1840
             1841 GAGCGTGTGT GGCCCGGTAT ATTGCTTCAC TCCCAGCCCC GTGGTGGTGG GAACGACCGA CAGGTCGGGC GCGCCTACCT 1920
             1921 ACAGCTGGGG TGCAAATGAT ACGGATGTCT TCGTCCTTAA CAACACCAGG CCACCGCTGG GCAATTGGTT CGGTTGTACC 2000
             2001 TGGATGAACT CAACTGGATT CACCAAAGTG TGCGGAGCGC CCCCTTGTGT CATCGGAGGG GTGGGCAACA ACACCTTGCT 2080
             2081 CTGCCCCACT GATTGCTTCC GCAAACATCC GGAAGCCACA TACTCTCGGT GCGGCTCCGG TCCCTGGATT ACACCCAGGT 2160
             2161 GCATGGTCGA CTACCCGTAT AGGCTTTGGC ACTATCCTTG TACCATCAAT TACACCATAT TCAAAGTCAG GATGTACGTG 2240
             2241 GGAGGGGTCG AGCACAGGCT GGAAGCGGCC TGCAACTGGA CGCGGGGCGA ACGCTGTGAT CTGGAAGACA GGGACAGGTC 2320
             2321 CGAGCTCAGC CCGTTGCTGC TGTCCACCAC ACAGTGGCAG GTCCTTCCGT GTTCTTTCAC GACCCTGCCA GCCTTGTCCA 2400
             2401 CCGGCCTCAT CCACCTCCAC CAGAACATTG TGGACGTGCA GTACTTGTAC GGGGTAGGGT CAAGCATCGC GTCCTGGGCC 2480
             2481 ATTAAGTGGG AGTACGTCGT TCTCCTGTTC CTTCTGCTTG CAGACGCGCG CGTCTGCTCC TGCTTGTGGA TGATGTTACT 2560
```

```
2561 CATATCCCAA GCGGAGGCGG CTTTGGAGAA CCTCGTAATA CTCAATGCAG CATCCCTGGC CGGGACGCAC GGTCTTGTGT 2640
2641 CCTTCCTCGT GTTCTTCTGC TTTGCGTGGT ATCTGAAGGG TAGGTGGGTG CCCGGAGCGG TCTACGCCCT CTACGGGATG 2720
2721 TGGCCTCTCC TCCTGCTCCT GCTGGCGTTG CCTCAGCGGG CATACGCACT GGACACGGAG GTGGCCGCGT CGTGTGGCGG 2800
2801 CGTTGTTCTT GTCGGGTTAA TGGCGCTGAC TCTGTCGCCA TATTACAAGC GCTATATCAG CTGGTGCATG TGGTGGCTTC 2880
2881 AGTATTTTCT GACCAGAGTA GAAGCGCAAC TGCACGTGTG GGTTCCCCCC CTCAACGTCC GGGGGGGGCG CGATGCCGTC 2960
2961 ATCTTACTCA TGTGTGTAGT ACACCCGACC CTGGTATTTG ACATCACCAA ACTACTCCTG GCCATCTTCG GACCCCTTTG 3040
3041 GATTCTTCAA GCCAGTTTGC TTAAAGTCCC CTACTTCGTG CGCGTTCAAG GCCTTCTCCG GATCTGCGCG CTAGCGCGGA 3120
3121 AGATAGCCGG AGGTCATTAC GTGCAAATGG CCATCATCAA GTTAGGGGCG CTTACTGGCA CCTATGTGTA TAACCATCTC 3200
3201 ACCCCTCTTC GAGACTGGGC GCACAACGGC CTGCGAGATC TGGCCGTGGC TGTGGAACCA GTCGTCTTCT CCCGAATGGA 3280
3281 GACCAAGCTC ATCACGTGGG GGGCAGATAC CGCCGCGTGC GGTGACATCA TCAACGGCTT GCCCGTCTCT GCCCGTAGGG 3360
3361 CCCAGGAGAT ACTGCTTGGG CCAGCCGACG GAATGGTCTC CAAGGGGTGG AGGTTGCTGG CGCCCATCAC GGCGTACGCC 3440
3441 CAGCAGACGA GAGGCCTCCT AGGGTGTATA ATCACCAGCC TGACTGGCCG GGACAAAAAC CAAGTGGAGG GTGAGGTCCA 3520
3521 GATCGTGTCA ACTGCTACCC AAACCTTCCT GGCAACGTGC ATCAATGGGG TATGCTGGAC TGTCTACCAC GGGGCCGGAA 3600
3601 CGAGGACCAT CGCATCACCC AAGGGTCCTG TCATCCAGAT GTATACCAAT GTGGACCAAG ACCTTGTGGG CTGGCCCGCT 3680
3681 CCTCAAGGTT CCCGCTCATT GACACCCTGT ACCTGCGGCT CCTCGGACCT TTACCTGGTC ACGAGGCACG CCGATGTCAT 3760
3761 TCCCGTGCGC CGGCGAGGTG ATAGCAGGGG TAGCCTGCTT TCGCCCCGGC CCATTTCCTA CTTGAAAGGC TCCTCGGGGG 3840
3841 CTCCGCTGTT GTGCCCCGCG GGACACGCCG TGGGCCTATT CAGGGCCGCG GTGTGCACCC GTGGAGTGGC TAAAGCGGTG 3920
3921 GACTTTATCC CTGTGGAGAA CCTAGGGACA ACCATGAGAT CCCCGGTGTT CACGGACAAC TCCTCTCCAC CAGCAGTGCC 4000
4001 CCAGAGCTTC CAGGTGGCCC ACCTGCATGC TCCCACCGGC AGCGGTAAGA GCACCAAGGT CCCGGCTGCG TACGCAGCCC 4080
4081 AGGGCTACAA GGTGTTGGTG CTCAACCCCT CTGTTGCTGC AACGCTGGGC TTTGGTGCTT ACATGTCCAA GGCCCATGGG 4160
4161 GTTGATCCTA ATATCAGGAC CGGGGTGAGA ACAATTACCA CTGGCAGCCC CATCACGTAC TCCACCTACG GCAAGTTCCT 4240
4241 TGCCGACGGC GGGTGCTCAG GAGGTGCTTA TGACATAATA ATTTGTGACG AGTGCCACTC CACGGATGCC ACATCCATCT 4320
4321 TGGGCATCGG CACTGTCCTT GACCAAGCAG AGACTGCGGG GGCGAGACTG GTTGTGCTCG CCACTGCTAC CCCTCCGGGC 4400
4401 TCCGTCACTG TGTCCCATCC TAACATCGAG GAGGTTGCTC TGTCCACCAC CGGAGAGATC CCCTTTTACG GCAAGGCTAT 4480
4481 CCCCCTCGAG GTGATCAAGG GGGGAAGACA TCTCATCTTC TGCCACTCAA AGAAGAAGTG CGACGAGCTC GCCGCGAAGC 4560
4561 TGGTCGCATT GGGCATCAAT GCCGTGGCCT ACTACCGCGG TCTTGACGTG TCTGTCATCC CGACCAGCGG CGATGTTGTC 4640
4641 GTCGTGTCGA CCGATGCTCT CATGACTGGC TTTACCGGCG ACTTCGACTC TGTGATAGAC TGCAACACGT GTGTCACTCA 4720
4721 GACAGTCGAT TTCAGCCTTG ACCCTACCTT TACCATTGAG ACAACCACGC TCCCCCAGGA TGCTGTCTCC AGGACTCAAC 4809
4801 GCCGGGGCAG GACTGGCAGG GGGAAGCCAG GCATCTATAG ATTTGTGGCA CCGGGGGAGC GCCCCTCCGG CATGTTCGAC 4880
4881 TCGTCCGTCC TCTGTGAGTG CTATGACGCG GGCTGTGCTT GGTATGAGCT CACGCCCGCC GAGACTACAG TTAGGCTACG 4960
4961 AGCGTACATG AACACCCCGG GGCTTCCCGT GTGCCAGGAC CATCTTGAAT TTTGGGAGGG CGTCTTTACG GGCCTCACTC 5040
5041 ATATAGATGC CCACTTTTTA TCCCAGACAA AGCAGAGTGG GGAGAACTTT CCTTACCTGG TAGCGTACCA AGCCACCGTG 5120
```

```
5121 TGCGCTAGGG CTCAAGCCCC TCCCCCATCG TGGGACCAGA TGTGGAAGTG TTTGATCCGC CTTAAACCCA CCCTCCATGG 5200
5201 GCCAACACCC CTGCTATACA GACTGGGCGC TGTTCAGAAT GAAGTCACCC TGACGCACCC AATCACCAAA TACATCATGA 5280
5281 CATGCATGTC GGCCGACCTG GAGGTCGTCA CGAGCACCTG GGTGCTCGTT GGCGGCGTCC TGGCTGCTCT GGCCGCGTAT 5360
5361 TGCCTGTCAA CAGGCTGCGT GGTCATAGTG GGCAGGATCG TCTTGTCCGG GAAGCCGGCA ATTATACCTG ACAGGGAGGT 5440
5441 TCTCTACCAG GAGTTCGATG AGATGGAAGA GTGCTCTCAG CACTTACCGT ACATCGAGCA AGGGATGATG CTCGCTGAGC 5520
5521 AGTTCAAGCA GAAGGCCCTC GGCCTCCTGC AGACCGCGTC CCGCCATGCA GAGGTTATCA CCCCTGCTGT CCAGACCAAC 5600
5601 TGGCAGAAAC TCGAGGTCTT TTGGGCGAAG CACATGTGGA ATTTCATCAG TGGGATACAA TACTTGGCGG GCCTGTCAAC 5680
5681 GCTGCCTGGT AACCCCGCCA TTGCTTCATT GATGGCTTTT ACAGCTGCCG TCACCAGCCC ACTAACCACT GGCCAAACCC 5760
5761 TCCTCTTCAA CATATTGGGG GGGTGGGTGG CTGCCCAGCT CGCCGCCCCC GGTGCCGCTA CTGCCTTTGT GGGTGCTGGC 5840
5841 CTAGCTGGCG CCGCCATCGG CAGCGTTGGA CTGGGGAAGG TCCTCGTGGA CATTCTTGCA GGGTATGGCG CGGGCGTGGC 5920
5921 GGGAGCTCTT GTAGCATTCA AGATCATGAG CGGTGAGGTC CCCTCCACGG AGGACCTGGT CAATCTGCTG CCCGCCATCC 6000
6001 TCTCGCCTGG AGCCCTTGTA GTCGGTGTGG TCTGCGCAGC AATACTGCGC CGGCACGTTG GCCCGGGCGA GGGGGCAGTG 6080
6081 CAATGGATGA ACCGGCTAAT AGCCTTCGCC TCCCGGGGGA ACCATGTTTC CCCCACGCAC TACGTGCCGG AGAGCGATGC 6160
6161 AGCCGCCCGC GTCACTGCCA TACTCAGCAG CCTCACTGTA ACCCAGCTCC TGAGGCGACT GCATCAGTGG ATAAGCTCGG 6240
6241 AGTGTACCAC TCCATGCTCC GGTTCCTGGC TAAGGGACAT CTGGGACTGG ATATGCGAGG TGCTGAGCGA CTTTAAGACC 6320
6321 TGGCTGAAAG CCAAGCTCAT GCCACAACTG CCTGGGATTC CCTTTGTGTC CTGCCAGCGC GGGTATAGGG GGGTCTGGCG 6400
6401 AGGAGACGGC ATTATGCACA CTCGCTGCCA CTGTGGAGCT GAGATCACTG GACATGTCAA AAACGGGACG ATGAGGATCG 6480
6481 TCGGTCCTAG GACCTGCAGG AACATGTGGA GTGGGACGTT CCCCATTAAC GCCTACACCA CGGGCCCCTG TACTCCCCTT 6560
6561 CCTGCGCCGA ACTATAAGTT CGCGCTGTGG AGGGTGTCTG CAGAGGAATA CGTGGAGATA AGGCGGGTGG GGGACTTCCA 6640
6641 CTACGTATCG GGTATGACTA CTGACAATCT TAAATGCCCG TGCCAGATCC CATCGCCCGA ATTTTTCACA GAATTGGACG 6720
6721 GGGTGCGCCT ACACAGGTTT GCGCCCCCTT GCAAGCCCTT GCTGCGGGAG GAGGTATCAT TCAGAGTAGG ACTCCACGAG 6800
6801 TACCCGGTGG GGTCGCAATT ACCTTGCGAG CCCGAACCGG ACGTAGCCGT GTTGACGTCC ATGCTCACTG ATCCCTCCCA 6880
6881 TATAACAGCA GAGGCGGCCG GGAGAAGGTT GGCGAGAGGG TCACCCCCTT CTATGGCCAG CTCCTCGGCT AGCCAGCTGT 6960
6961 CCGCTCCATC TCTCAAGGCA ACTTGCACCG CCAACCATGA CTCCCCTGAC GCCGAGCTCA TAGAGGCTAA CCTCCTGTGG 7040
7041 AGGCAGGAGA TGGGCGGCAA CATCACCAGG GTTGAGTCAG AGAACAAAGT GGTGATTCTG GACTCCTTCG ATCCGCTTGT 7120
7121 GGCAGAGGAG GATGAGCGGG AGGTCTCCGT ACCTGCAGAA ATTCTGCGGA AGTCTCGGAG ATTCGCCCGG GCCCTGCCCG 7200
7201 TCTGGGCGCG GCCGGACTAC AACCCCCCGC TAGTAGAGAC GTGGAAAAAG CCTGACTACG AACCACCTGT GGTCCATGGC 7280
7281 TGCCCGCTAC CACCTCCACG GTCCCCTCCT GTGCCTCCGC CTCGGAAAAA GCGTACGGTG GTCCTCACCG AATCAACCCT 7360
7361 ATCTACTGCC TTGGCCGAGC TTGCCACCAA AAGTTTTGGC AGCTCCTCAA CTTCCGGCAT TACGGGCGAC AATACGACAA 7440
7441 CATCCTCTGA GCCCGCCCCT TCTGGCTGCC CCCCCGACTC CGACGTTGAG TCCTATTCTT CCATGCCCCC CCTGGAGGGG 7520
7521 GAGCCTGGGG ATCCGGATCT CAGCGACGGG TCATGGTCGA CGGTCAGTAG TGGGGCCGAC ACGGAAGATG TCGTGTGCTG 7600
7601 CTCAATGTCT TATTCCTGGA CAGGCGCACT CGTCACCCCG TGCGCTGCGG AAGAACAAAA ACTGCCCATC AACGCACTGA 7680
7681 GCAACTCGTT GCTACGCCAT CACAATCTGG TGTATTCCAC CACTTCACGC AGTGCTTGCC AAAGGCAGAA GAAAGTCACA 7760
7761 TTTGACAGAC TGCAAGTTCT GGACAGCCAT TACCAGGACG TGCTCAAGGA GGTCAAAGCA GCGGCGTCAA AAGTGAAGGC 7840
7841 TAACTTGCTA TCCGTAGAGG AAGCTTGCAG CCTGACGCCC CCACATTCAG CCAAATCCAA GTTTGGCTAT GGGGCAAAAG 7920
7921 ACGTCCGTTG CCATGCCAGA AAGGCCGTAG CCCACATCAA CTCCGTGTGG AAAGACCTTC TGGAAGACAG TGTAACACCA 8000
```

```
8001  ATAGACACTA CCATCATGGC CAAGAACGAG GTTTTCTGCG TTCAGCCTGA GAAGGGGGGT CGTAAGCCAG CTCGTCTCAT 8080
8081  CGTGTTCCCC GACCTGGGCG TGCGCGTGTG CGAGAAGATG GCCCTGTACG ACGTGGTTAG CAAGCTCCCC CTGGCCGTGA 8160
8161  TGGGAAGCTC CTACGGATTC CAATACTCAC CAGGACAGCG GGTTGAATTC CTCGTGCAAG CGTGGAAGTC CAAGAAGACC 8240
8241  CCGATGGGGT TCTCGTATGA TACCCGCTGT TTTGACTCCA CAGTCACTGA GAGCGACATC CGTACGGAGG AGGCAATTTA 8320
8321  CCAATGTTGT GACCTGGACC CCCAAGCCCG CGTGGCCATC AAGTCCCTCA CTGAGAGGCT TTATGTTGGG GGCCCTCTTA 8400
8401  CCAATTCAAG GGGGGAAAAC TGCGGCTACC GCAGGTGCCG CGCGAGCGGC GTACTGACAA CTAGCTGTGG TAACACCCTC 8480
8481  ACTTGCTACA TCAAGGCCCG GGCAGCCTGT CGAGCCGCAG GGCTCCAGGA CTGCACCATG CTCGTGTGTG GCGACGACTT 8560
8561  AGTCGTTATC TGTGAAAGTG CGGGGGTCCA GGAGGACGCG GCGAGCCTGA GAGCCTTCAC GGAGGCTATG ACCAGGTACT 8640
8641  CCGCCCCCCC CGGGGACCCC CCACAACCAG AATACGACTT GGAGCTTATA ACATCATGCT CCTCCAACGT GTCAGTCGCC 8720
8721  CACGACGGCG CTGGAAAGAG GGTCTACTAC CTTACCCGTG ACCCTACAAC CCCCCTCGCG AGAGCCGCGT GGGAGACAGC 8800
8801  AAGACACACT CCAGTCAATT CCTGGCTAGG CAACATAATC ATGTTTGCCC CCACACTGTG GGCGAGGATG ATACTGATGA 8880
8881  CCCATTTCTT TAGCGTCCTC ATAGCCAGGG ATCAGCTTGA ACAGGCTCTT AACTGTGAGA TCTACGGAGC CTGCTACTCC 8960
8961  ATAGAACCAC TGGATCTACC TCCAATCATT CAAAGACTCC ATGGCCTCAG CGCATTTTCA CTCCACAGTT ACTCTCCAGG 9040
9041  TGAAATCAAT AGGGTGGCCG CATGCCTCAG AAAACTTGGG GTCCCGCCCT TGCGAGCTTG GAGACACCGG GCCCGGAGCG 9120
9121  TCCGCGCTAG GCTTCTGTCC AGAGGAGGCA GGGCTGCCAT ATGTGGCAAG TACCTCTTCA ACTGGGCAGT AAGAACAAAG 9200
9201  CTCAAACTCA CTCCAATAGC GGCCGCTGGC CGGCTGGACT TGTCCGGTTG GTTCACGGCT GGCTACAGCG GGGGAGACAT 9280
9281  TTATCACAGC GTGTCTCATG CCCGGCCCCG CTGGTTCTGG TTTTGCCTAC TCCTGCTCGC TGCAGGGGTA GGCATCTACC 9360
9361  TCCTCCCCAA CCGATGAAGG TTGGGGTAAA CACTCCGGCC TcttaagGTT ATTTTCCACC ATATTGCCGT CTTTTGGCAA 9440
9441  TGTGAGGGCC CGGAAACCTG GCCCTGTCTT CTTGACGAGC ATTCCTAGGG GTCTTTCCCC TCTCGCCAAA GGAATGCAAG 9520
9521  GTCTGTTGAA TGTCGTGAAG GAAGCAGTTC CTCTGGAAGC TTCTTGAAGA CAAACAACGT CTGTAGCGAC CCTTTGCAGG 9600
9601  CAGCGGAACC CCCCACCTGG CGACAGGTGC CTCTGCGGCC AAAAGCCACG TGTATAAGAT ACACCTGCAA AGGCGGCACA 9680
9681  ACCCCAGTGC CACGTTGTGA GTTGGATAGT TGTGGAAAGA GTCAAATGGC TCTCCTCAAG CGTATTCAAC AAGGGGCTGA 9760
9761  AGGATGCCCA GAAGGTACCC CATTGTATGG GATCTGATCT GGGGCCTCGG TGCACATGCT TTACGTGTGT TTAGTCGAGG 9840
9841  TTAAAAAACG TCTAGGCCCC CCGAACCACG GGGACGTGGT TTTCCTTTGA AAAACACGAT GATAATATGA GGCCTATGGA 9920
9921  GCCAGTAGAT CCTAGACTAG AGCCCTGGAA GCATCCAGGA AGTCAGCCTA AAACTGCTTG TACCAATTGC TATTGTAAAA 10000
10001 AGTGTTGCTT TCATTGCCAA GTTTGTTTCA TAACAAAAGC CTTAGGCATC TCCTATGGCA GGAAGAAGCG GAGACAGCGA 10080
10081 CGAAGACCTC CTCAAGGCAG TCAGACTCAT CAAGTTTCTC TATCAAAGCA ACCCACCTCC CAATCCCGAG GGGACCCGAC 10160
10161 AGGCCCGAAG GAAGAATTCG ACCTTCTTAA GCTTGCGGGA GACGTCGAGT CCAACCCTGG GCCCGGATCC ATGGCCAAGT 10240
10241 TGACCAGTGC CGTTCCGGTG CTCACCGCGC GCGACGTCGC CGGAGCGGTC GAGTTCTGGA CCGACCGGCT CGGGTTCTCC 10320
10321 CGGGACTTCG TGGAGGACGA CTTCGCCGGT GTGGTCCGGG ACGACGTGAC CCTGTTCATC AGCGCGGTCC AGGACCAGGT 10400
10401 GGTGCCGGAC AACACCCTGG CCTGGGTGTG GGTGCGCGGC CTGGACGAGC TGTACGCCGA GTGGTCGGAG GTCGTGTCCA 10480
10481 CGAACTTCCG GGACGCCTCC GGGCCGGCCA TGACCGAGAT CGGCGAGCAG CCGTGGGGGC GGGAGTTCGC CCTGCGCGAC 10560
10561 CCGGCCGGCA ACTGCGTGCA CTTCGTGGCC GAGGAGCAGG ACTGActtaa gCCATTTCCT GTTTTTTTTT TTTTTTTTTT 10640
10641 TTTTTTTTTC TTTTTTTTTT TCTTTCCTTT CCTTCTTTTT TTCCTTTCTT TTTCCCTTCT TTAATGGTGG CTCCATCTTA 10720
10721 GCCCTAGTCA CGGCTAGCTG TGAAAGGTCC GTGAGCCGCA TGACTGCAGA GAGTGCTGAT ACTGGCCTCT CTGCAGATCA 10800
      TGT
```

```
                 342/1
                 atg agc acg aat cct aaa cct caa aga aaa acc aaa cgt aac acc aac cgt cgc cca cag
SEQ ID NO:20     Met Ser Thr Asn Pro Lys Pro Gln Arg Lys Thr Lys Arg Asn Thr Asn Arg Arg Pro Gln

                 402/21
                 gac gtc aag ttc ccg ggt ggc ggt cag atc gtt ggt gga gtt tac ttg ttg ccg cgc agg
                 Asp Val Lys Phe Pro Gly Gly Gly Gln Ile Val Gly Gly Val Tyr Leu Leu Pro Arg Arg

                 462/41
                 ggc cct aga ttg ggt gtg cgc gcg acg agg aag act tcc gag cgg tcg caa cct cga ggt
                 Gly Pro Arg Leu Gly Val Arg Ala Thr Arg Lys Thr Ser Glu Arg Ser Gln Pro Arg Gly

                 522/61
                 aga cgt cag cct atc ccc aag gca cgt cgg ccc gag ggc agg acc tgg gct cag ccc ggg
                 Arg Arg Gln Pro Ile Pro Lys Ala Arg Arg Pro Glu Gly Arg Thr Trp Ala Gln Pro Gly

                 582/81
                 tac cct tgg ccc ctc tat ggc aat gag ggt tgc ggg tgg gcg gga tgg ctc ctg tct ccc
                 Tyr Pro Trp Pro Leu Tyr Gly Asn Glu Gly Cys Gly Trp Ala Gly Trp Leu Leu Ser Pro

                 642/101
                 cgt ggc tct cgg cct agc tgg ggc ccc aca gac ccc cgg cgt agg tcg cgc aat ttg ggt
                 Arg Gly Ser Arg Pro Ser Trp Gly Pro Thr Asp Pro Arg Arg Arg Ser Arg Asn Leu Gly

                 702/121
                 aag gtc atc gat acc ctt acg tgc ggc ttc gcc gac ctc atg ggg tac ata ccg ctc gtc
                 Lys Val Ile Asp Thr Leu Thr Cys Gly Phe Ala Asp Leu Met Gly Tyr Ile Pro Leu Val

                 762/141
                 ggc gcc cct ctt gga ggc gct gcc agg gcc ctg gcg cat ggc gtc cgg gtt ctg gaa gac
                 Gly Ala Pro Leu Gly Gly Ala Ala Arg Ala Leu Ala His Gly Val Arg Val Leu Glu Asp

                 822/161
                 ggc gtg aac tat gca aca ggg aac ctt cct ggt tgc tct ttc tct atc ttc ctt ctg gcc
                 Gly Val Asn Tyr Ala Thr Gly Asn Leu Pro Gly Cys Ser Phe Ser Ile Phe Leu Leu Ala

                 882/181                                 CORE <-|-> E1
                 ctg ctc tct tgc ctg act gtg ccc gct tca gcc|tac caa gtg cgc aat tcc tcg ggg ctt
                 Leu Leu Ser Cys Leu Thr Val Pro Ala Ser Ala Tyr Gln Val Arg Asn Ser Ser Gly Leu

                 942/201
                 tac cat gtc acc aat gat tgc cct aac tcg agt att gtg tac gag gcg gcc gat gcc atc
                 Tyr His Val Thr Asn Asp Cys Pro Asn Ser Ser Ile Val Tyr Glu Ala Ala Asp Ala Ile
```

```
1002/221
ctg cac act ccg ggg tgt gtc cct tgc gtt cgc gag ggt aac gcc tcg agg tgt tgg gtg
Leu His Thr Pro Gly Cys Val Pro Cys Val Arg Glu Gly Asn Ala Ser Arg Cys Trp Val

1062/241
gcg gtg acc ccc acg gtg gcc acc agg gac ggc aaa ctc ccc aca acg cag ctt cga cgt
Ala Val Thr Pro Thr Val Ala Thr Arg Asp Gly Lys Leu Pro Thr Thr Gln Leu Arg Arg

1122/261
cat atc gat ctg ctt gtc ggg agc gcc acc ctc tgc tcg gcc ctc tac gtg ggg gac ctg
His Ile Asp Leu Leu Val Gly Ser Ala Thr Leu Cys Ser Ala Leu Tyr Val Gly Asp Leu

1182/281
tgc ggg tct gtc ttt ctt gtt ggt caa ctg ttt acc ttc tct ccc agg cgc cac tgg acg
Cys Gly Ser Val Phe Leu Val Gly Gln Leu Phe Thr Phe Ser Pro Arg Arg His Trp Thr

1242/301
acg caa gac tgc aat tgt tct atc tat ccc ggc cat ata acg ggt cat cgc atg gca tgg
Thr Gln Asp Cys Asn Cys Ser Ile Tyr Pro Gly His Ile Thr Gly His Arg Met Ala Trp

1302/321
gat atg atg atg aac tgg tcc cct acg gca gcg ttg gtg gta gct cag ctg ctc cgg atc
Asp Met Met Met Asn Trp Ser Pro Thr Ala Ala Leu Val Val Ala Gln Leu Leu Arg Ile

1362/341
cca caa gcc atc atg gac atg atc gct ggt gct cac tgg gga gtc ctg gcg ggc ata gcg
Pro Gln Ala Ile Met Asp Met Ile Ala Gly Ala His Trp Gly Val Leu Ala Gly Ile Ala

1422/361
tat ttc tcc atg gtg ggg aac tgg gcg aag gtc ctg gta gtg ctg ctg cta ttt gcc ggc
Tyr Phe Ser Met Val Gly Asn Trp Ala Lys Val Leu Val Val Leu Leu Leu Phe Ala Gly
            E1<-|->E2
1482/381
gtc gac gcg|gaa acc cac gtc acc ggg gga aat gcc ggc cgc acc acg gct ggg ctt gtt
Val Asp Ala Glu Thr His Val Thr Gly Gly Asn Ala Gly Arg Thr Thr Ala Gly Leu Val

1542/401
ggt ctc ctt aca cca ggc gcc aag cag aac atc caa ctg atc aac acc aac ggc agt tgg
Gly Leu Leu Thr Pro Gly Ala Lys Gln Asn Ile Gln Leu Ile Asn Thr Asn Gly Ser Trp
```

```
1602/421
cac atc aat agc acg gcc ttg aat tgc aat gaa agc ctt aac acc ggc tgg tta gca ggg
His Ile Asn Ser Thr Ala Leu Asn Cys Asn Glu Ser Leu Asn Thr Gly Trp Leu Ala Gly

1662/441
ctc ttc tat caa cac aaa ttc aac tct tca ggc tgt cct gag agg ttg gcc agc tgc cga
Leu Phe Tyr Gln His Lys Phe Asn Ser Ser Gly Cys Pro Glu Arg Leu Ala Ser Cys Arg

1722/461
cgc ctt acc gat ttt gcc cag ggc tgg ggt cct atc agt tat gcc aac gga agc ggc ctc
Arg Leu Thr Asp Phe Ala Gln Gly Trp Gly Pro Ile Ser Tyr Ala Asn Gly Ser Gly Leu

1782/481
gac gaa cgc ccc tac tgc tgg cac tac cct cca aga cct tgt ggc att gtg ccc gca aag
Asp Glu Arg Pro Tyr Cys Trp His Tyr Pro Pro Arg Pro Cys Gly Ile Val Pro Ala Lys

1842/501
agc gtg tgt ggc ccg gta tat tgc ttc act ccc agc ccc gtg gtg gtg gga acg acc gac
Ser Val Cys Gly Pro Val Tyr Cys Phe Thr Pro Ser Pro Val Val Val Gly Thr Thr Asp

1902/521
agg tcg ggc gcg cct acc tac agc tgg ggt gca aat gat acg gat gtc ttc gtc ctt aac
Arg Ser Gly Ala Pro Thr Tyr Ser Trp Gly Ala Asn Asp Thr Asp Val Phe Val Leu Asn

1962/541
aac acc agg cca ccg ctg ggc aat tgg ttc ggt tgt acc tgg atg aac tca act gga ttc
Asn Thr Arg Pro Pro Leu Gly Asn Trp Phe Gly Cys Thr Trp Met Asn Ser Thr Gly Phe

2022/561
acc aaa gtg tgc gga gcg ccc cct tgt gtc atc gga ggg gtg ggc aac aac acc ttg ctc
Thr Lys Val Cys Gly Ala Pro Pro Cys Val Ile Gly Gly Val Gly Asn Asn Thr Leu Leu

2082/581
tgc ccc act gat tgc ttc cgc aaa cat ccg gaa gcc aca tac tct cgg tgc ggc tcc ggt
Cys Pro Thr Asp Cys Phe Arg Lys His Pro Glu Ala Thr Tyr Ser Arg Cys Gly Ser Gly

2142/601
ccc tgg att aca ccc agg tgc atg gtc gac tac ccg tat agg ctt tgg cac tat cct tgt
Pro Trp Ile Thr Pro Arg Cys Met Val Asp Tyr Pro Tyr Arg Leu Trp His Tyr Pro Cys

2202/621
acc atc aat tac acc ata ttc aaa gtc agg atg tac gtg gga ggg gtc gag cac agg ctg
Thr Ile Asn Tyr Thr Ile Phe Lys Val Arg Met Tyr Val Gly Gly Val Glu His Arg Leu
```

```
2262/641
gaa gcg gcc tgc aac tgg acg cgg ggc gaa cgc tgt gat ctg gaa gac agg gac agg tcc
Glu Ala Ala Cys Asn Trp Thr Arg Gly Glu Arg Cys Asp Leu Glu Asp Arg Asp Arg Ser

2322/661
gag ctc agc ccg ttg ctg ctg tcc acc aca cag tgg cag gtc ctt ccg tgt tct ttc acg
Glu Leu Ser Pro Leu Leu Leu Ser Thr Thr Gln Trp Gln Val Leu Pro Cys Ser Phe Thr

2382/681
acc ctg cca gcc ttg tcc acc ggc ctc atc cac ctc cac cag aac att gtg gac gtg cag
Thr Leu Pro Ala Leu Ser Thr Gly Leu Ile His Leu His Gln Asn Ile Val Asp Val Gln

2442/701
tac ttg tac ggg gta ggg tca agc atc gcg tcc tgg gcc att aag tgg gag tac gtc gtt
Tyr Leu Tyr Gly Val Gly Ser Ser Ile Ala Ser Trp Ala Ile Lys Trp Glu Tyr Val Val

2502/721
ctc ctg ttc ctt ctg ctt gca gac gcg cgc gtc tgc tcc tgc ttg tgg atg atg tta ctc
Leu Leu Phe Leu Leu Leu Ala Asp Ala Arg Val Cys Ser Cys Leu Trp Met Met Leu Leu

2562/741                E2 <-|-> P7
ata tcc caa gcg gag gcg|gct ttg gag aac ctc gta ata ctc aat gca gca tcc ctg gcc
Ile Ser Gln Ala Glu Ala Ala Leu Glu Asn Leu Val Ile Leu Asn Ala Ala Ser Leu Ala

2622/761
ggg acg cac ggt ctt gtg tcc ttc ctc gtg ttc ttc tgc ttt gcg tgg tat ctg aag ggt
Gly Thr His Gly Leu Val Ser Phe Leu Val Phe Phe Cys Phe Ala Trp Tyr Leu Lys Gly

2682/781
agg tgg gtg ccc gga gcg gtc tac gcc ctc tac ggg atg tgg cct ctc ctc ctg ctc ctg
Arg Trp Val Pro Gly Ala Val Tyr Ala Leu Tyr Gly Met Trp Pro Leu Leu Leu Leu Leu

2742/801                            P7 <-|-> NS2
ctg gcg ttg cct cag cgg gca tac gca|ctg gac acg gag gtg gcc gcg tcg tgt ggc ggc
Leu Ala Leu Pro Gln Arg Ala Tyr Ala Leu Asp Thr Glu Val Ala Ala Ser Cys Gly Gly

2802/821
gtt gtt ctt gtc ggg tta atg gcg ctg act ctg tcg cca tat tac aag cgc tat atc agc
Val Val Leu Val Gly Leu Met Ala Leu Thr Leu Ser Pro Tyr Tyr Lys Arg Tyr Ile Ser

2862/841
tgg tgc atg tgg tgg ctt cag tat ttt ctg acc aga gta gaa gcg caa ctg cac gtg tgg
Trp Cys Met Trp Trp Leu Gln Tyr Phe Leu Thr Arg Val Glu Ala Gln Leu His Val Trp

2922/861
gtt ccc ccc ctc aac gtc cgg ggg ggg cgc gat gcc gtc atc tta ctc atg tgt gta gta
Val Pro Pro Leu Asn Val Arg Gly Gly Arg Asp Ala Val Ile Leu Leu Met Cys Val Val
```

```
2982/881
cac ccg acc ctg gta ttt gac atc acc aaa cta ctc ctg gcc atc ttc gga ccc ctt tgg
His Pro Thr Leu Val Phe Asp Ile Thr Lys Leu Leu Leu Ala Ile Phe Gly Pro Leu Trp

3042/901
att ctt caa gcc agt ttg ctt aaa gtc ccc tac ttc gtg cgc gtt caa ggc ctt ctc cgg
Ile Leu Gln Ala Ser Leu Leu Lys Val Pro Tyr Phe Val Arg Val Gln Gly Leu Leu Arg

3102/921
atc tgc gcg cta gcg cgg aag ata gcc gga ggt cat tac gtg caa atg gcc atc atc aag
Ile Cys Ala Leu Ala Arg Lys Ile Ala Gly Gly His Tyr Val Gln Met Ala Ile Ile Lys

3162/941
tta ggg gcg ctt act ggc acc tat gtg tat aac cat ctc acc cct ctt cga gac tgg gcg
Leu Gly Ala Leu Thr Gly Thr Tyr Val Tyr Asn His Leu Thr Pro Leu Arg Asp Trp Ala

3222/961
cac aac ggc ctg cga gat ctg gcc gtg gct gtg gaa cca gtc gtc ttc tcc cga atg gag
His Asn Gly Leu Arg Asp Leu Ala Val Ala Val Glu Pro Val Val Phe Ser Arg Met Glu

3282/981
acc aag ctc atc acg tgg ggg gca gat acc gcc gcg tgc ggt gac atc atc aac ggc ttg
Thr Lys Leu Ile Thr Trp Gly Ala Asp Thr Ala Ala Cys Gly Asp Ile Ile Asn Gly Leu

3342/1001
ccc gtc tct gcc cgt agg ggc cag gag ata ctg ctt ggg cca gcc gac gga atg gtc tcc
Pro Val Ser Ala Arg Arg Gly Gln Glu Ile Leu Leu Gly Pro Ala Asp Gly Met Val Ser

                            NS2<-|->NS3
3402/1021
aag ggg tgg agg ttg ctg gcg|ccc atc acg gcg tac gcc cag cag acg aga ggc ctc cta
Lys Gly Trp Arg Leu Leu Ala Pro Ile Thr Ala Tyr Ala Gln Gln Thr Arg Gly Leu Leu

3462/1041
ggg tgt ata atc acc agc ctg act ggc cgg gac aaa aac caa gtg gag ggt gag gtc cag
Gly Cys Ile Ile Thr Ser Leu Thr Gly Arg Asp Lys Asn Gln Val Glu Gly Glu Val Gln

3522/1061
atc gtg tca act gct acc caa acc ttc ctg gca acg tgc atc aat ggg gta tgc tgg act
Ile Val Ser Thr Ala Thr Gln Thr Phe Leu Ala Thr Cys Ile Asn Gly Val Cys Trp Thr

3682/1081
gtc tac cac ggg gcc gga acg agg acc atc gca tca ccc aag ggt cct gtc atc cag atg
Val Tyr His Gly Ala Gly Thr Arg Thr Ile Ala Ser Pro Lys Gly Pro Val Ile Gln Met

3642/1101
tat acc aat gtg gac caa gac ctt gtg ggc tgg ccc gct cct caa ggt tcc cgc tca ttg
Tyr Thr Asn Val Asp Gln Asp Leu Val Gly Trp Pro Ala Pro Gln Gly Ser Arg Ser Leu
```

```
3702/1121
aca ccc tgt acc tgc ggc tcc tcg gac ctt tac ctg gtc acg agg cac gcc gat gtc att
Thr Pro Cys Thr Cys Gly Ser Ser Asp Leu Tyr Leu Val Thr Arg His Ala Asp Val Ile

3762/1141
ccc gtg cgc cgg cga ggt gat agc agg ggt agc ctg ctt tcg ccc cgg ccc att tcc tac
Pro Val Arg Arg Arg Gly Asp Ser Arg Gly Ser Leu Leu Ser Pro Arg Pro Ile Ser Tyr

3822/1161
ttg aaa ggc tcc tcg ggg ggt ccg ctg ttg tgc ccc gcg gga cac gcc gtg ggc cta ttc
Leu Lys Gly Ser Ser Gly Gly Pro Leu Leu Cys Pro Ala Gly His Ala Val Gly Leu Phe

3882/1181
agg gcc gcg gtg tgc acc cgt gga gtg gct aaa gcg gtg gac ttt atc cct gtg gag aac
Arg Ala Ala Val Cys Thr Arg Gly Val Ala Lys Ala Val Asp Phe Ile Pro Val Glu Asn

3942/1201
cta ggg aca acc atg aga tcc ccg gtg ttc acg gac aac tcc tct cca cca gca gtg ccc
Leu Gly Thr Thr Met Arg Ser Pro Val Phe Thr Asp Asn Ser Ser Pro Pro Ala Val Pro

4002/1221
cag agc ttc cag gtg gcc cac ctg cat gct ccc acc ggc agc ggt aag agc acc aag gtc
Gln Ser Phe Gln Val Ala His Leu His Ala Pro Thr Gly Ser Gly Lys Ser Thr Lys Val

4062/1241
ccg gct gcg tac gca gcc cag ggc tac aag gtg ttg gtg ctc aac ccc tct gtt gct gca
Pro Ala Ala Tyr Ala Ala Gln Gly Tyr Lys Val Leu Val Leu Asn Pro Ser Val Ala Ala

4122/1261
acg ctg ggc ttt ggt gct tac atg tcc aag gcc cat ggg gtt gat cct aat atc agg acc
Thr Leu Gly Phe Gly Ala Tyr Met Ser Lys Ala His Gly Val Asp Pro Asn Ile Arg Thr

4182/1281
ggg gtg aga aca att acc act ggc agc ccc atc acg tac tcc acc tac ggc aag ttc ctt
Gly Val Arg Thr Ile Thr Thr Gly Ser Pro Ile Thr Tyr Ser Thr Tyr Gly Lys Phe Leu

4242/1301
gcc gac ggc ggg tgc tca gga ggt gct tat gac ata ata att tgt gac gag tgc cac tcc
Ala Asp Gly Gly Cys Ser Gly Gly Ala Tyr Asp Ile Ile Ile Cys Asp Glu Cys His Ser

4302/1321
acg gat gcc aca tcc atc ttg ggc atc ggc act gtc ctt gac caa gca gag act gcg ggg
Thr Asp Ala Thr Ser Ile Leu Gly Ile Gly Thr Val Leu Asp Gln Ala Glu Thr Ala Gly
```

4362/1341
gcg aga ctg gtt gtg ctc gcc act gct acc cct ccg ggc tcc gtc act gtg tcc cat cct
Ala Arg Leu Val Val Leu Ala Thr Ala Thr Pro Pro Gly Ser Val Thr Val Ser His Pro 4422/1361
aac atc gag gag gtt gct ctg tcc acc acc gga gag atc ccc ttt tac ggc aag gct atc
Asn Ile Glu Glu Val Ala Leu Ser Thr Thr Gly Glu Ile Pro Phe Tyr Gly Lys Ala Ile 4482/1381
ccc ctc gag gtg atc aag ggg gga aga cat ctc atc ttc tgc cac tca aag aag aag tgc
Pro Leu Glu Val Ile Lys Gly Gly Arg His Leu Ile Phe Cys His Ser Lys Lys Lys Cys 4542/1401
gac gag ctc gcc gcg aag ctg gtc gca ttg ggc atc aat gcc gtg gcc tac tac cgc ggt
Asp Glu Leu Ala Ala Lys Leu Val Ala Leu Gly Ile Asn Ala Val Ala Tyr Tyr Arg Gly 4602/1421
ctt gac gtg tct gtc atc ccg acc agc ggc gat gtt gtc gtc gtg tcg acc gat gct ctc
Leu Asp Val Ser Val Ile Pro Thr Ser Gly Asp Val Val Val Val Ser Thr Asp Ala Leu 4662/1441
atg act ggc ttt acc ggc gac ttc gac tct gtg ata gac tgc aac acg tgt gtc act cag
Met Thr Gly Phe Thr Gly Asp Phe Asp Ser Val Ile Asp Cys Asn Thr Cys Val Thr Gln 4722/1461
aca gtc gat ttc agc ctt gac cct acc ttt acc att gag aca acc acg ctc ccc cag gat
Thr Val Asp Phe Ser Leu Asp Pro Thr Phe Thr Ile Glu Thr Thr Thr Leu Pro Gln Asp 4782/1481
gct gtc tcc agg act caa cgc cgg ggc agg act ggc agg ggg aag cca ggc atc tat aga
Ala Val Ser Arg Thr Gln Arg Arg Gly Arg Thr Gly Arg Gly Lys Pro Gly Ile Tyr Arg 4842/1501
ttt gtg gca ccg ggg gag cgc ccc tcc ggc atg ttc gac tcg tcc gtc ctc tgt gag tgc
Phe Val Ala Pro Gly Glu Arg Pro Ser Gly Met Phe Asp Ser Ser Val Leu Cys Glu Cys 4902/1521
tat gac gcg ggc tgt gct tgg tat gag ctc acg ccc gcc gag act aca gtt agg cta cga
Tyr Asp Ala Gly Cys Ala Trp Tyr Glu Leu Thr Pro Ala Glu Thr Thr Val Arg Leu Arg 4962/1541
gcg tac atg aac acc ccg ggg ctt ccc gtg tgc cag gac cat ctt gaa ttt tgg gag ggc
Ala Tyr Met Asn Thr Pro Gly Leu Pro Val Cys Gln Asp His Leu Glu Phe Trp Glu Gly 5022/1561
gtc ttt acg ggc ctc act cat ata gat gcc cac ttt tta tcc cag aca aag cag agt ggg
Val Phe Thr Gly Leu Thr His Ile Asp Ala His Phe Leu Ser Gln Thr Lys Gln Ser Gly

```
5082/1581
gag aac ttt cct tac ctg gta gcg tac caa gcc acc gtg tgc gct agg gct caa gcc cct
Glu Asn Phe Pro Tyr Leu Val Ala Tyr Gln Ala Thr Val Cys Ala Arg Ala Gln Ala Pro

5142/1601
ccc cca tcg tgg gac cag atg tgg aag tgt ttg atc cgc ctt aaa ccc acc ctc cat ggg
Pro Pro Ser Trp Asp Gln Met Trp Lys Cys Leu Ile Arg Leu Lys Pro Thr Leu His Gly

5202/1621
cca aca ccc ctg cta tac aga ctg ggc gct gtt cag aat gaa gtc acc ctg acg cac cca
Pro Thr Pro Leu Leu Tyr Arg Leu Gly Ala Val Gln Asn Glu Val Thr Leu Thr His Pro

                                                                NS3 <-|-> NS4A
5262/1641
atc acc aaa tac atc atg aca tgc atg tcg gcc gac ctg gag gtc gtc acg|agc acc tgg
Ile Thr Lys Tyr Ile Met Thr Cys Met Ser Ala Asp Leu Glu Val Val Thr Ser Thr Trp

5322/1661
gtg ctc gtt ggc ggc gtc ctg gct gct ctg gcc gcg tat tgc ctg tca aca ggc tgc gtg
Val Leu Val Gly Gly Val Leu Ala Ala Leu Ala Ala Tyr Cys Leu Ser Thr Gly Cys Val

5382/1681
gtc ata gtg ggc agg atc gtc ttg tcc ggg aag ccg gca att ata cct gac agg gag gtt
Val Ile Val Gly Arg Ile Val Leu Ser Gly Lys Pro Ala Ile Ile Pro Asp Arg Glu Val

                                          NS4A <-|-> NS4B
5442/1701
ctc tac cag gag ttc gat gag atg gaa gag tgc|tct cag cac tta ccg tac atc gag caa
Leu Tyr Gln Glu Phe Asp Glu Met Glu Glu Cys Ser Gln His Leu Pro Tyr Ile Glu Gln

5502/1721
ggg atg atg ctc gct gag cag ttc aag cag aag gcc ctc ggc ctc ctg cag acc gcg tcc
Gly Met Met Leu Ala Glu Gln Phe Lys Gln Lys Ala Leu Gly Leu Leu Gln Thr Ala Ser

5562/1741
cgc cat gca gag gtt atc acc cct gct gtc cag acc aac tgg cag aaa ctc gag gtc ttt
Arg His Ala Glu Val Ile Thr Pro Ala Val Gln Thr Asn Trp Gln Lys Leu Glu Val Phe

5622/1761
tgg gcg aag cac atg tgg aat ttc atc agt ggg ata caa tac ttg gcg ggc ctg tca acg
Trp Ala Lys His Met Trp Asn Phe Ile Ser Gly Ile Gln Tyr Leu Ala Gly Leu Ser Thr

5682/1781
ctg cct ggt aac ccc gcc att gct tca ttg atg gct ttt aca gct gcc gtc acc agc cca
Leu Pro Gly Asn Pro Ala Ile Ala Ser Leu Met Ala Phe Thr Ala Ala Val Thr Ser Pro
```

```
5742/1801
cta acc act ggc caa acc ctc ctc ttc aac ata ttg ggg ggg tgg gtg gct gcc cag ctc
Leu Thr Thr Gly Gln Thr Leu Leu Phe Asn Ile Leu Gly Gly Trp Val Ala Ala Gln Leu

5802/1821
gcc gcc ccc ggt gcc gct act gcc ttt gtg ggt gct ggc cta gct ggc gcc gcc atc ggc
Ala Ala Pro Gly Ala Ala Thr Ala Phe Val Gly Ala Gly Leu Ala Gly Ala Ala Ile Gly

5862/1841
agc gtt gga ctg ggg aag gtc ctc gtg gac att ctt gca ggg tat ggc gcg ggc gtg gcg
Ser Val Gly Leu Gly Lys Val Leu Val Asp Ile Leu Ala Gly Tyr Gly Ala Gly Val Ala

5922/1861
gga gct ctt gta gca ttc aag atc atg agc ggt gag gtc ccc tcc acg gag gac ctg gtc
Gly Ala Leu Val Ala Phe Lys Ile Met Ser Gly Glu Val Pro Ser Thr Glu Asp Leu Val

5982/1881
aat ctg ctg ccc gcc atc ctc tcg cct gga gcc ctt gta gtc ggt gtg gtc tgc gca gca
Asn Leu Leu Pro Ala Ile Leu Ser Pro Gly Ala Leu Val Val Gly Val Val Cys Ala Ala

6042/1901
ata ctg cgc cgg cac gtt ggc ccg ggc gag ggg gca gtg caa tgg atg aac cgg cta ata
Ile Leu Arg Arg His Val Gly Pro Gly Glu Gly Ala Val Gln Trp Met Asn Arg Leu Ile

6102/1921
gcc ttc gcc tcc cgg ggg aac cat gtt tcc ccc acg cac tac gtg ccg gag agc gat gca
Ala Phe Ala Ser Arg Gly Asn His Val Ser Pro Thr His Tyr Val Pro Glu Ser Asp Ala

6162/1941
gcc gcc cgc gtc act gcc ata ctc agc agc ctc act gta acc cag ctc ctg agg cga ctg
Ala Ala Arg Val Thr Ala Ile Leu Ser Ser Leu Thr Val Thr Gln Leu Leu Arg Arg Leu

                                               NS4B<-|->NS5A
6222/1961
cat cag tgg ata agc tcg gag tgt acc act cca tgc|tcc ggt tcc tgg cta agg gac atc
His Gln Trp Ile Ser Ser Glu Cys Thr Thr Pro Cys Ser Gly Ser Trp Leu Arg Asp Ile

6282/1981
tgg gac tgg ata tgc gag gtg ctg agc gac ttt aag acc tgg ctg aaa gcc aag ctc atg
Trp Asp Trp Ile Cys Glu Val Leu Ser Asp Phe Lys Thr Trp Leu Lys Ala Lys Leu Met

6342/2001
cca caa ctg cct ggg att ccc ttt gtg tcc tgc cag cgc ggg tat agg ggg gtc tgg cga
Pro Gln Leu Pro Gly Ile Pro Phe Val Ser Cys Gln Arg Gly Tyr Arg Gly Val Trp Arg

6402/2021
gga gac ggc att atg cac act cgc tgc cac tgt gga gct gag atc act gga cat gtc aaa
Gly Asp Gly Ile Met His Thr Arg Cys His Cys Gly Ala Glu Ile Thr Gly His Val Lys
```

```
6462/2041
aac ggg acg atg agg atc gtc ggt cct agg acc tgc agg aac atg tgg agt ggg acg ttc
Asn Gly Thr Met Arg Ile Val Gly Pro Arg Thr Cys Arg Asn Met Trp Ser Gly Thr Phe
6522/2061
ccc att aac gcc tac acc acg ggc ccc tgt act ccc ctt cct gcg ccg aac tat aag ttc
Pro Ile Asn Ala Tyr Thr Thr Gly Pro Cys Thr Pro Leu Pro Ala Pro Asn Tyr Lys Phe
6582/2081
gcg ctg tgg agg gtg tct gca gag gaa tac gtg gag ata agg cgg gtg ggg gac ttc cac
Ala Leu Trp Arg Val Ser Ala Glu Glu Tyr Val Glu Ile Arg Arg Val Gly Asp Phe His
6642/2101
tac gta tcg ggt atg act act gac aat ctt aaa tgc ccg tgc cag atc cca tcg ccc gaa
Tyr Val Ser Gly Met Thr Thr Asp Asn Leu Lys Cys Pro Cys Gln Ile Pro Ser Pro Glu
6702/2121
ttt ttc aca gaa ttg gac ggg gtg cgc cta cac agg ttt gcg ccc cct tgc aag ccc ttg
Phe Phe Thr Glu Leu Asp Gly Val Arg Leu His Arg Phe Ala Pro Pro Cys Lys Pro Leu
6762/2141
ctg cgg gag gag gta tca ttc aga gta gga ctc cac gag tac ccg gtg ggg tcg caa tta
Leu Arg Glu Glu Val Ser Phe Arg Val Gly Leu His Glu Tyr Pro Val Gly Ser Gln Leu
6822/2161
cct tgc gag ccc gaa ccg gac gta gcc gtg ttg acg tcc atg ctc act gat ccc tcc cat
Pro Cys Glu Pro Glu Pro Asp Val Ala Val Leu Thr Ser Met Leu Thr Asp Pro Ser His
6882/2181
ata aca gca gag gcg gcc ggg aga agg ttg gcg aga ggg tca ccc cct tct atg gcc agc
Ile Thr Ala Glu Ala Ala Gly Arg Arg Leu Ala Arg Gly Ser Pro Pro Ser Met Ala Ser
6942/2201
tcc tcg gct agc cag ctg tcc gct cca tct ctc aag gca act tgc acc gcc aac cat gac
Ser Ser Ala Ser Gln Leu Ser Ala Pro Ser Leu Lys Ala Thr Cys Thr Ala Asn His Asp
7002/2221
tcc cct gac gcc gag ctc ata gag gct aac ctc ctg tgg agg cag gag atg ggc ggc aac
Ser Pro Asp Ala Glu Leu Ile Glu Ala Asn Leu Leu Trp Arg Gln Glu Met Gly Gly Asn
7062/2241
atc acc agg gtt gag tca gag aac aaa gtg gtg att ctg gac tcc ttc gat ccg ctt gtg
Ile Thr Arg Val Glu Ser Glu Asn Lys Val Val Ile Leu Asp Ser Phe Asp Pro Leu Val
```

```
7122/2261
gca gag gag gat gag cgg gag gtc tcc gta cct gca gaa att ctg cgg aag tct cgg aga
Ala Glu Glu Asp Glu Arg Glu Val Ser Val Pro Ala Glu Ile Leu Arg Lys Ser Arg Arg

7182/2281
ttc gcc cgg gcc ctg ccc gtc tgg gcg cgg ccg gac tac aac ccc ccg cta gta gag acg
Phe Ala Arg Ala Leu Pro Val Trp Ala Arg Pro Asp Tyr Asn Pro Pro Leu Val Glu Thr

7242/2301
tgg aaa aag cct gac tac gaa cca cct gtg gtc cat ggc tgc ccg cta cca cct cca cgg
Trp Lys Lys Pro Asp Tyr Glu Pro Pro Val Val His Gly Cys Pro Leu Pro Pro Pro Arg

7302/2321
tcc cct cct gtg cct ccg cct cgg aaa aag cgt acg gtg gtc ctc acc gaa tca acc cta
Ser Pro Pro Val Pro Pro Pro Arg Lys Lys Arg Thr Val Val Leu Thr Glu Ser Thr Leu

7362/2341
tct act gcc ttg gcc gag ctt gcc acc aaa agt ttt ggc agc tcc tca act tcc ggc att
Ser Thr Ala Leu Ala Glu Leu Ala Thr Lys Ser Phe Gly Ser Ser Ser Thr Ser Gly Ile

7422/2361
acg ggc gac aat acg aca aca tcc tct gag ccc gcc cct tct ggc tgc ccc ccc gac tcc
Thr Gly Asp Asn Thr Thr Thr Ser Ser Glu Pro Ala Pro Ser Gly Cys Pro Pro Asp Ser

7482/2381
gac gtt gag tcc tat tct tcc atg ccc ccc ctg gag ggg gag cct ggg gat ccg gat ctc
Asp Val Glu Ser Tyr Ser Ser Met Pro Pro Leu Glu Gly Glu Pro Gly Asp Pro Asp Leu

                                                                   NS5A<-->NS5B
7542/2401
agc gac ggg tca tgg tcg acg gtc agt agt ggg gcc gac acg gaa gat gtc gtg tgc tgc
Ser Asp Gly Ser Trp Ser Thr Val Ser Ser Gly Ala Asp Thr Glu Asp Val Val Cys Cys

7602/2421
tca atg tct tat tcc tgg aca ggc gca ctc gtc acc ccg tgc gct gcg gaa gaa caa aaa
Ser Met Ser Tyr Ser Trp Thr Gly Ala Leu Val Thr Pro Cys Ala Ala Glu Glu Gln Lys

7662/2441
ctg ccc atc aac gca ctg agc aac tcg ttg cta cgc cat cac aat ctg gtg tat tcc acc
Leu Pro Ile Asn Ala Leu Ser Asn Ser Leu Leu Arg His His Asn Leu Val Tyr Ser Thr

7722/2461
act tca cgc agt gct tgc caa agg cag aag aaa gtc aca ttt gac aga ctg caa gtt ctg
Thr Ser Arg Ser Ala Cys Gln Arg Gln Lys Lys Val Thr Phe Asp Arg Leu Gln Val Leu

7782/2481
gac agc cat tac cag gac gtg ctc aag gag gtc aaa gca gcg gcg tca aaa gtg aag gct
Asp Ser His Tyr Gln Asp Val Leu Lys Glu Val Lys Ala Ala Ala Ser Lys Val Lys Ala
```

```
7842/2501
aac ttg cta tcc gta gag gaa gct tgc agc ctg acg ccc cca cat tca gcc aaa tcc aag
Asn Leu Leu Ser Val Glu Glu Ala Cys Ser Leu Thr Pro Pro His Ser Ala Lys Ser Lys
7902/2521
ttt ggc tat ggg gca aaa gac gtc cgt tgc cat gcc aga aag gcc gta gcc cac atc aac
Phe Gly Tyr Gly Ala Lys Asp Val Arg Cys His Ala Arg Lys Ala Val Ala His Ile Asn
7962/2541
tcc gtg tgg aaa gac ctt ctg gaa gac agt gta aca cca ata gac act acc atc atg gcc
Ser Val Trp Lys Asp Leu Leu Glu Asp Ser Val Thr Pro Ile Asp Thr Thr Ile Met Ala
8022/2561
aag aac gag gtt ttc tgc gtt cag cct gag aag ggg ggt cgt aag cca gct cgt ctc atc
Lys Asn Glu Val Phe Cys Val Gln Pro Glu Lys Gly Gly Arg Lys Pro Ala Arg Leu Ile
8082/2581
gtg ttc ccc gac ctg ggc gtg cgc gtg tgc gag aag atg gcc ctg tac gac gtg gtt agc
Val Phe Pro Asp Leu Gly Val Arg Val Cys Glu Lys Met Ala Leu Tyr Asp Val Val Ser
8142/2601
aag ctc ccc ctg gcc gtg atg gga agc tcc tac gga ttc caa tac tca cca gga cag cgg
Lys Leu Pro Leu Ala Val Met Gly Ser Ser Tyr Gly Phe Gln Tyr Ser Pro Gly Gln Arg
8202/2621
gtt gaa ttc ctc gtg caa gcg tgg aag tcc aag aag acc ccg atg ggg ttc tcg tat gat
Val Glu Phe Leu Val Gln Ala Trp Lys Ser Lys Lys Thr Pro Met Gly Phe Ser Tyr Asp
8262/2641
acc cgc tgt ttt gac tcc aca gtc act gag agc gac atc cgt acg gag gag gca att tac
Thr Arg Cys Phe Asp Ser Thr Val Thr Glu Ser Asp Ile Arg Thr Glu Glu Ala Ile Tyr
8322/2661
caa tgt tgt gac ctg gac ccc caa gcc cgc gtg gcc atc aag tcc ctc act gag agg ctt
Gln Cys Cys Asp Leu Asp Pro Gln Ala Arg Val Ala Ile Lys Ser Leu Thr Glu Arg Leu
8382/2681
tat gtt ggg ggc cct ctt acc aat tca agg ggg gaa aac tgc ggc tac cgc agg tgc cgc
Tyr Val Gly Gly Pro Leu Thr Asn Ser Arg Gly Glu Asn Cys Gly Tyr Arg Arg Cys Arg
8442/2701
gcg agc ggc gta ctg aca act agc tgt ggt aac acc ctc act tgc tac atc aag gcc cgg
Ala Ser Gly Val Leu Thr Thr Ser Cys Gly Asn Thr Leu Thr Cys Tyr Ile Lys Ala Arg
```

8502/2721
gca gcc tgt cga gcc gca ggg ctc cag gac tgc acc atg ctc gtg tgt ggc gac gac tta
Ala Ala Cys Arg Ala Ala Gly Leu Gln Asp Cys Thr Met Leu Val Cys Gly Asp Asp Leu 8562/2741
gtc gtt atc tgt gaa agt gcg ggg gtc cag gag gac gcg gcg agc ctg aga gcc ttc acg
Val Val Ile Cys Glu Ser Ala Gly Val Gln Glu Asp Ala Ala Ser Leu Arg Ala Phe Thr 8622/2761
gag gct atg acc agg tac tcc gcc ccc ccc ggg gac ccc cca caa cca gaa tac gac ttg
Glu Ala Met Thr Arg Tyr Ser Ala Pro Pro Gly Asp Pro Pro Gln Pro Glu Tyr Asp Leu 8682/2781
gag ctt ata aca tca tgc tcc tcc aac gtg tca gtc gcc cac gac ggc gct gga aag agg
Glu Leu Ile Thr Ser Cys Ser Ser Asn Val Ser Val Ala His Asp Gly Ala Gly Lys Arg 8742/2801
gtc tac tac ctt acc cgt gac cct aca acc ccc ctc gcg aga gcc gcg tgg gag aca gca
Val Tyr Tyr Leu Thr Arg Asp Pro Thr Thr Pro Leu Ala Arg Ala Ala Trp Glu Thr Ala 8802/2821
aga cac act cca gtc aat tcc tgg cta ggc aac ata atc atg ttt gcc ccc aca ctg tgg
Arg His Thr Pro Val Asn Ser Trp Leu Gly Asn Ile Ile Met Phe Ala Pro Thr Leu Trp 8862/2841
gcg agg atg ata ctg atg acc cat ttc ttt agc gtc ctc ata gcc agg gat cag ctt gaa
Ala Arg Met Ile Leu Met Thr His Phe Phe Ser Val Leu Ile Ala Arg Asp Gln Leu Glu 8922/2861
cag gct ctt aac tgt gag atc tac gga gcc tgc tac tcc ata gaa cca ctg gat cta cct
Gln Ala Leu Asn Cys Glu Ile Tyr Gly Ala Cys Tyr Ser Ile Glu Pro Leu Asp Leu Pro 8982/2881
cca atc att caa aga ctc cat ggc ctc agc gca ttt tca ctc cac agt tac tct cca ggt
Pro Ile Ile Gln Arg Leu His Gly Leu Ser Ala Phe Ser Leu His Ser Tyr Ser Pro Gly 9042/2901
gaa atc aat agg gtg gcc gca tgc ctc aga aaa ctt ggg gtc ccg ccc ttg cga gct tgg
Glu Ile Asn Arg Val Ala Ala Cys Leu Arg Lys Leu Gly Val Pro Pro Leu Arg Ala Trp 9102/2921
aga cac cgg gcc cgg agc gtc cgc gct agg ctt ctg tcc aga gga ggc agg gct gcc ata
Arg His Arg Ala Arg Ser Val Arg Ala Arg Leu Leu Ser Arg Gly Gly Arg Ala Ala Ile 9162/2941
tgt ggc aag tac ctc ttc aac tgg gca gta aga aca aag ctc aaa ctc act cca ata gcg
Cys Gly Lys Tyr Leu Phe Asn Trp Ala Val Arg Thr Lys Leu Lys Leu Thr Pro Ile Ala

```
9222/2961
gcc gct ggc cgg ctg gac ttg tcc ggt tgg ttc acg gct ggc tac agc ggg gga gac att
Ala Ala Gly Arg Leu Asp Leu Ser Gly Trp Phe Thr Ala Gly Tyr Ser Gly Gly Asp Ile
9282/2981
tat cac agc gtg tct cat gcc cgg ccc cgc tgg ttc tgg ttt tgc cta ctc ctg ctc gct
Tyr His Ser Val Ser His Ala Arg Pro Arg Trp Phe Trp Phe Cys Leu Leu Leu Leu Ala
9342/3001                                NS5B <-> 3'NTR Variable Region
gca ggg gta ggc atc tac ctc ctc ccc aac cga tga agg ttg ggg taa aca ctc cgg cct
Ala Gly Val Gly Ile Tyr Leu Leu Pro Asn Arg *   Arg Leu Gly *   Thr Leu Arg Pro
9402/3021 -> EMCV IRES
ctt aag gtt att ttc cac cat att gcc gtc ttt tgg caa tgt gag ggc ccg gaa acc tgg
Leu Lys Val Ile Phe His His Ile Ala Val Phe Trp Gln Cys Glu Gly Pro Glu Thr Trp
9462/3041
ccc tgt ctt ctt gac gag cat tcc tag ggg tct ttc ccc tct cgc caa agg aat gca agg
Pro Cys Leu Leu Asp Glu His Ser *   Gly Ser Phe Pro Ser Arg Gln Arg Asn Ala Arg
9522/3061
tct gtt gaa tgt cgt gaa gga agc agt tcc tct gga agc ttc ttg aag aca aac aac gtc
Ser Val Glu Cys Arg Glu Gly Ser Ser Ser Ser Gly Ser Phe Leu Lys Thr Asn Asn Val
9582/3081
tgt agc gac cct ttg cag gca gcg gaa ccc ccc acc tgg cga cag gtg cct ctg cgg cca
Cys Ser Asp Pro Leu Gln Ala Ala Glu Pro Pro Thr Trp Arg Gln Val Pro Leu Arg Pro
9642/3101
aaa gcc acg tgt ata aga tac acc tgc aaa ggc ggc aca acc cca gtg cca cgt tgt gag
Lys Ala Thr Cys Ile Arg Tyr Thr Cys Lys Gly Gly Thr Thr Pro Val Pro Arg Cys Glu
9702/3121
ttg gat agt tgt gga aag agt caa atg gct ctc ctc aag cgt att caa caa ggg gct gaa
Leu Asp Ser Cys Gly Lys Ser Gln Met Ala Leu Leu Lys Arg Ile Gln Gln Gly Ala Glu
9762/3141
gga tgc cca gaa ggt acc cca ttg tat ggg atc tga tct ggg gcc tcg gtg cac atg ctt
Gly Cys Pro Glu Gly Thr Pro Leu Tyr Gly Ile *   Ser Gly Ala Ser Val His Met Leu
9822/3161
tac gtg tgt tta gtc gag gtt aaa aaa cgt cta ggc ccc ccg aac cac ggg gac gtg gtt
Tyr Val Cys Leu Val Glu Val Lys Lys Arg Leu Gly Pro Pro Asn His Gly Asp Val Val
```

```
                 9882/3181                     EMCV IRES
                 ttc ctt tga aaa aca cga tga taa t
                 Phe Lue *   Lys Thr Arg *   *
                 translation start by EMCV IRES
                 9907/1       tat coding sequence
                 atg agg cct atg gag cca gta gat cct aga cta gag ccc tgg aag cat cca gga agt cag
SEQ ID NO:21     Met Arg Pro Met Glu Pro Val Asp Pro Arg Leu Glu Pro Trp Lys His Pro Gly Ser Gln

                 9967/21
                 cct aaa act gct tgt acc aat tgc tat tgt aaa aag tgt tgc ttt cat tgc caa gtt tgt
                 Pro Lys Thr Ala Cys Thr Asn Cys Tyr Cys Lys Lys Cys Cys Phe His Cys Gln Val Cys

                 10027/41
                 ttc ata aca aaa gcc tta ggc atc tcc tat ggc agg aag aag cgg aga cag cga cga aga
                 Phe Ile Thr Lys Ala Leu Gly Ile Ser Tyr Gly Arg Lys Lys Arg Arg Gln Arg Arg Arg

                 10087/61
                 cct cct caa ggc agt cag act cat caa gtt tct cta tca aag caa ccc acc tcc caa tcc
                 Pro Pro Gln Gly Ser Gln Thr His Gln Val Ser Leu Ser Lys Gln Pro Thr Ser Gln Ser

                 10147/81                            TAT         FMDV2A
                 cga ggg gac ccg aca ggc ccg aag gaa gaa ttc gac ctt ctt aag ctt gcg gga gac gtc
                 Arg Gly Asp Pro Thr Gly Pro Lys Glu Glu Phe Asp Leu Leu Lys Leu Ala Gly Asp Val

                 10207/101               FMDV2A          Zeo
                 gag tcc aac cct ggg ccc gga tcc atg gcc aag ttg acc agt gcc gtt ccg gtg ctc acc
                 Glu Ser Asn Pro Gly Pro Gly Ser Met Ala Lys Leu Thr Ser Ala Val Pro Val Leu Thr

                 10267/121
                 gcg cgc gac gtc gcc gga gcg gtc gag ttc tgg acc gac cgg ctc ggg ttc tcc cgg gac
                 Ala Arg Asp Val Ala Gly Ala Val Glu Phe Trp Thr Asp Arg Leu Gly Phe Ser Arg Asp
```

```
10327/141
ttc gtg gag gac gac ttc gcc ggt gtg gtc cgg gac gac gtg acc ctg ttc atc agc gcg
Phe Val Glu Asp Asp Phe Ala Gly Val Val Arg Asp Asp Val Thr Leu Phe Ile Ser Ala

10387/161
gtc cag gac cag gtg gtg ccg gac aac acc ctg gcc tgg gtg tgg gtg cgc ggc ctg gac
Val Gln Asp Gln Val Val Pro Asp Asn Thr Leu Ala Trp Val Trp Val Arg Gly Leu Asp

10447/181
gag ctg tac gcc gag tgg tcg gag gtc gtg tcc acg aac ttc cgg gac gcc tcc ggg ccg
Glu Leu Tyr Ala Glu Trp Ser Glu Val Val Ser Thr Asn Phe Arg Asp Ala Ser Gly Pro

10507/201
gcc atg acc gag atc ggc gag cag ccg tgg ggg cgg gag ttc gcc ctg cgc gac ccg gcc
Ala Met Thr Glu Ile Gly Glu Gln Pro Trp Gly Arg Glu Phe Ala Leu Arg Asp Pro Ala

10567/221                                   Zeo
ggc aac tgc gtg cac ttc gtg gcc gag gag cag gac tga ctt aag cca ttt cct gtt ttt
Gly Asn Cys Val His Phe Val Ala Glu Glu Gln Asp *

10627/241
ttt ttt ttt ttt ttt ttt ttt ttc ttt ttt ttt ttc ttt cct ttc ctt ctt ttt ttc ctt

10687/261
tct ttt tcc ctt ctt taa tgg tgg ctc cat ctt agc cct agt cac ggc tag ctg tga aag

gtc cgt gac ccg cat gac tgc aga gag tgc tga tac tgg cct ctc tgc aga tca tgt
```

*Fig. 10h2*

```
                   |   10      |   20      |   30      |   40      |   50      |   60      |   70      |   80
SEQ ID NO:18    1 ACCTGGAAAA ACATGGAGCA ATCACAAGTA GCAATACAGC AGCTACCAAT GCTGCTTGTG CCTGGCTAGA AGCACAAGAG 80
               81 GAGGAGGAGG TGGGTTTTCC AGTCACACCT CAGGTACCTT TAAGACCAAT GACTTACAAG GCAGCTGTAG ATCTTAGCCA 160
              161 CTTTTTAAAA GAAAAGGGGG GACTGGAAGG GCTAATTCAC TCCCAAAGAA GACAAGATAT CCTTGATCTG TGGATCTACC 240
              241 ACACACAAGG CTACTTCCCT GATTAGCAGA ACTACACACC AGGGCCAGGG GTCAGATATC CACTGACCTT TGGATGGTGC 320
              321 TACAAGCTAG TACCAGTTGA GCCAGATAAG ATAGAAGAGG CCAATAAAGG AGAGAACACC AGCTTGTTAC ACCCTGTGAG 400
              401 CCTGCATGGG ATGGATGACC CGGAGAGAGA AGTGTTAGAG TGGAGGTTTG ACAGCCGCCT AGCATTTCAT CACGTGGCCC 480
              481 GAGAGCTGCA TCCGGAGTAC TTCAAGAACT GCTGACATCG AGCTTGCTAC AAGGGACTTT CCGCTGGGGA CTTTCCAGGG 560
              561 AGGCGTGGCC TGGGCGGGAC TGGGGAGTGG CGAGCCCTCA GATCCTGCAT ATAAGCAGCT GCTTTTTGCC TGTACTGGGT 640
              641 CTCTCTGGTT AGACCAGATC TGAGCCTGGG AGCTCTCTGG CTAACTAGGG AACCCACTGC TTAAGCCTCA ATAaagcttC 720
              721 TGCATGCTGC TGCTGCTGCT GCTGCTGGGC CTGAGGCTAC AGCTCTCCCT GGGCATCATC CCAGTTGAGG AGGAGAACCC 800
              801 GGACTTCTGG AACCGCGAGG CAGCCGAGGC CCTGGGTGCC GCCAAGAAGC TGCAGCCTGC ACAGACAGCC GCCAAGAACC 880
              881 TCATCATCTT CCTGGGCGAT GGGATGGGGG TGTCTACGGT GACAGCTGCC AGGATCCTAA AAGGGCAGAA GAAGGACAAA 960
              961 CTGGGGCCTG AGATACCCCT GGCCATGGAC CGCTTCCCAT ATGTGGCTCT GTCCAAGACA TACAATGTAG ACAAACATGT 1040
             1041 GCCAGACAGT GGAGCCACAG CCACGGCCTA CCTGTGCGGG GTCAAGGGCA ACTTCCAGAC CATTGGCTTG AGTGCAGCCG 1120
             1121 CCCGCTTTAA CCAGTGCAAC ACGACACGCG GCAACGAGGT CATCTCCGTG ATGAATCGGG CCAAGAAAGC AGGGAAGTCA 1200
             1201 GTGGGAGTGG TAACCACCAC ACGAGTGCAG CACGCCTCGC CAGCCGGCAC CTACGCCCAC ACGGTGAACC GCAACTGGTA 1280
             1281 CTCGGACGCC GACGTGCCTG CCTCGGCCCG CCAGGAGGGG TGCCAGGACA TCGCTACGCA GCTCATCTCC AACATGGACA 1360
             1361 TTGACGTGAT CCTAGGTGGA GGCCGAAAGT ACATGTTTCC CATGGGAACC CCAGACCCTG AGTACCCAGA TGACTACAGC 1440
             1441 CAAGGTGGGA CCAGGCTGGA CGGGAAGAAT CTGGTGCAGG AATGGCTGGC GAAGCGCCAG GGTGCCCGGT ATGTGTGGAA 1520
             1521 CCGCACTGAG CTCATGCAGG CTTCCCTGGA CCCGTCTGTG ACCCATCTCA TGGGTCTCTT TGAGCCTGGA GACATGAAAT 1600
             1601 ACGAGATCCA CCGAGACTCC ACACTGGACC CCTCCCTGAT GGAGATGACA GAGGCTGCCC TGCGCCTGCT GAGCAGGAAC 1680
             1681 CCCCGCGGCT TCTTCCTCTT CGTGGAGGGT GGTCGCATCG ACCATGGTCA TCATGAAAGC AGGGCTTACC GGGCACTGAC 1760
             1761 TGAGACGATC ATGTTCGACG ACGCCATTGA GAGGGCGGGC CAGCTCACCA GCGAGGAGGA CACGCTGAGC CTCGTCACTG 1840
             1841 CCGACCACTC CCACGTCTTC TCCTTCGGAG GCTACCCCCT GCGAGGGAGC TCCATCTTCG GGCTGGCCCC TGGCAAGGCC 1920
             1921 CGGGACAGGA AGGCCTACAC GGTCCTCCTA TACGGAAACG GTCCAGGCTA TGTGCTCAAG GACGGCGCCC GGCCGGATGT 2000
             2001 TACCGAGAGC GAGAGCGGGA GCCCCGAGTA TCGGCAGCAG TCAGCAGTGC CCCTGGACGA AGAGACCCAC GCAGGCGAGG 2080
             2081 ACGTGGCGGT GTTCGCGCGC GGCCCGCAGG CGCACCTGGT TCACGGCGTG CAGGAGCAGA CCTTCATAGC GCACGTCATG 2160
             2161 GCCTTCGCCG CCTGCCTGGA GCCCTACACC GCCTGCGACC TGGCGCCCCC CGCCGGCACC ACCGACGCCG CGCACCCGG  2239
                   |   10      |   20      |   30      |   40      |   50      |   60      |   70      |   80
```

*Fig. 12*

```
                                                           50
NNeo  SGSWLRDVWDWVCTVLSDFKTWLQSKLLPRLPGVPFLSCQRGYKGVWRGDGIMHTTCPCGAQIAGHVKNGSMRII
BNeo  ....................................F................Q.........T..........V

                          100                                                   150
NNeo  GPKTCSNTWHGTFPINAYTTGPCTPSPAPNYSKALWRVAAEEYVEVTRVGDFHYVTGITTDNVKCPCQVPAPEFF
BNeo  ..R.............................R........................M.................

                                                           200
NNeo  TEVDGVRLHRYAPVCKPLLRDEVVFQVGLNQYLVGSQLPCEPEPDVAVLTSMLTDPSHITAEAAKRRLARGSPPS
BNeo  .............A......E..T.L....................................T............

                                                                                300
NNeo  LASSSASQLSAPSLRATCTTHSSYNLDSPDVDLIAANLLWRQEMGGNITRVESENKVVVLDSFEPLRAEGDENEI
BNeo  ..............K.....R----H....A...E.......................I.......Q..E..R.V

                                                           350
NNeo  SIAAEILRKSKKFPAAIPIWARPDYNPPLLESWKNPDYVPPVVHGCPLPPVKAPPIPPPRRKRTVVLTDSTVSSV
BNeo  .VP.....R.R...R.M.................D...............A................SE.....A

                                                                                450
NNeo  LAELATKTFGSSELSAADSGTATAPPDQTSDNGGKDSDAESCSSMPPLEGEPGDPDLSDGSWSTVSEEAGESVVCC
BNeo  .............S..V.......S...P..D.DAG..V..Y...........................S.D....
```

*Fig. 15*

SEQ ID NO:35

```
GCCAGCCCCC TGATGGGGGC GACACTCCAC CATGAATCAC TCCCCTGTGA GGAACTACTG
TCTTCACGCA GAAAGCGTCT AGCCATGGCG TTAGTATGAG TGTCGTGCAG CCTCCAGGAC
CCCCCCTCCC GGGAGAGCCA TAGTGGTCTG CGGAACCGGT GAGTACACCG GAATTGCCAG
GACGACCGGG TCCTTTCTTG GATAAACCCG CTCAATGCCT GGAGATTTGG GCGTGCCCCC
GCAAGACTGC TAGCCGAGTA GTGTTGGGTC GCGAAAGGCC TTGTGGTACT GCCTGATAGG
GTGCTTGCGA GTGCCCCGGG AGGTCTCGTA GACCGTGCAC C
```

SEQ ID NO:38

```
     AGACC ACAACGGTTT CCCTCTAGCG GGATCAATTC CGCCCCTCTC CCTCCCCCCC
CCCTAACGTT ACTGGCCGAA GCCGCTTGGA ATAAGGCCGG TGTGCGTTTG TCTATATGTT
ATTTTCCACC ATATTGCCGT CTTTTGGCAA TGTGAGGGCC CGGAAACCTG GCCCTGTCTT
CTTGACGAGC ATTCCTAGGG GTCTTTCCCC TCTCGCCAAA GGAATGCAAG GTCTGTTGAA
TGTCGTGAAG GAAGCAGTTC CTCTGGAAGC TTCTTGAAGA CAAACAACGT CTGTAGCGAC
CCTTTGCAGG CAGCGGAACC CCCCACCTGG CGACAGGTGC CTCTGCGGCC AAAAGCCACG
TGTATAAGAT ACACCTGCAA AGGCGGCACA ACCCCAGTGC CACGTTGTGA GTTGGATAGT
TGTGGAAAGA GTCAAATGGC TCTCCTCAAG CGTATTCAAC AAGGGGCTGA AGGATGCCCA
GAAGGTACCC CATTGTATGG GATCTGATCT GGGGCCTCGG TGCACATGCT TTACATGTGT
TTAGTCGAGG TTAAAAAACG TCTAGGCCCC CCGAACCACG GGGACGTGGT TTTCCTTTGA
AAAACACGAT AATACC
```

*Fig. 24a*

SEQ ID NO:36

```
 ┌► Core                                            Core ◄──┬──► tat
 342/1                                             372/11      │                   402/21
 ATG AGC ACG AAT CCT AAA CCT CAA AGA AAA ACC AAA GTT CCT|ATG GAG CCA GTA GAT CCT AGA CTA GAG CCC TGG AAG CAT CCA GGA AGT
 M   S   T   N   P   K   P   Q   R   K   T   K   V   P   M   E   P   V   D   P   R   L   E   P   W   K   H   P   G   S
 432/31                                            462/41                                            492/51
 CAG CCT AAA ACT GCT TGT ACC AAT TGC TAT TGT AAA AAG TGT TGC TTT CAT TGC CAA GTT TGT TTC ATA ACA AAA GCC TTA GGC ATC TCC
 Q   P   K   T   A   C   T   N   C   Y   C   K   K   C   C   F   H   C   Q   V   C   F   I   T   K   A   L   G   I   S
 522/61                                            552/71                                            582/81
 TAT GGC AGG AAG AAG CGG AGA CAG CGA CGA AGA CCT CCT CAA GGC AGT CAG ACT CAT CAA GTT TCT CTA TCA AAG CAA CCC ACC TCC CAA
 Y   G   R   K   K   R   R   Q   R   R   R   P   P   Q   G   S   Q   T   H   Q   V   S   L   S   K   Q   P   T   S   Q
 612/91                                   tat ◄─┐ EcoRI                                          672/111     2A ◄──┐      HpaI
                                                642/101┌► 2A
 TCC CGA GGG GAC CCG ACA GGC CCG AAG GAA|GAA TTC GAC CTT CTT AAG CTT GCG GGA GAC GTC GAG TCC AAC CCT GGG CCC GGA TCT GTT
 S   R   G   D   P   T   G   P   K   E   E   F   D   L   L   K   L   A   G   D   V   E   S   N   P   G   P   G   S   V
 702/121►Neo                                       732/131                                           762/141
 AAC ATG ATT GAA CAA GAT GGA TTG CAC GCA GGT TCT CCG GCC GCT TGG GTG GAG AGG CTA TTC GGC TAT GAC TGG GCA CAA CAG ACA ATC
 N   M   I   E   Q   D   G   L   H   A   G   S   P   A   A   W   V   E   R   L   F   G   Y   D   W   A   Q   Q   T   I
 792/151                                           822/161                                           852/171
 GGC TGC TCT GAT GCC GCC GTG TTC CGG CTG TCA GCG CAG GGG CGC CCG GTT CTT TTT GTC AAG ACC GAC CTG TCC GGT GCC CTG AAT GAA
 G   C   S   D   A   A   V   F   R   L   S   A   Q   G   R   P   V   L   F   V   K   T   D   L   S   G   A   L   N   E
 882/181                                           912/191                                           942/201
 CTG CAG GAC GAG GCA GCG CGG CTA TCG TGG CTG GCC ACG ACG GGC GTT CCT TGC GCA GCT GTG CTC GAC GTT GTC ACT GAA GCG GGA AGG
 L   Q   D   E   A   A   R   L   S   W   L   A   T   T   G   V   P   C   A   A   V   L   D   V   V   T   E   A   G   R
 972/211                                           1002/221                                          1032/231
 GAC TGG CTG CTA TTG GGC GAA GTG CCG GGG CAG GAT CTC CTG TCA TCT CAC CTT GCT CCT GCC GAG AAA GTA TCC ATC ATG GCT GAT GCA
 D   W   L   L   L   G   E   V   P   G   Q   D   L   L   S   S   H   L   A   P   A   E   K   V   S   I   M   A   D   A
 1062/241                                          1092/251                                          1122/261
 ATG CGG CGG CTG CAT ACG CTT GAT CCG GCT ACC TGC CCA TTC GAC CAC CAA GCG AAA CAT CGC ATC GAG CGA GCA CGT ACT CGG ATG GAA
 M   R   R   L   H   T   L   D   P   A   T   C   P   F   D   H   Q   A   K   H   R   I   E   R   A   R   T   R   M   E
 1152/271                                          1182/281                                          1212/291
 GCC GGT CTT GTC GAT CAG GAT GAT CTG GAC GAA GAG CAT CAG GGG CTC GCG CCA GCC GAA CTG TTC GCC AGG CTC AAG GCG CGC ATG CCC
 A   G   L   V   D   Q   D   D   L   D   E   E   H   Q   G   L   A   P   A   E   L   F   A   R   L   K   A   R   M   P
 1242/301                                          1272/311                                          1302/321
 GAC GGC GAG GAT CTC GTC GTG ACC CAT GGC GAT GCC TGC TTG CCG AAT ATC ATG GTG GAA AAT GGC CGC TTT TCT GGA TTC ATC GAC TGT
 D   G   E   D   L   V   V   T   H   G   D   A   C   L   P   N   I   M   V   E   N   G   R   F   S   G   F   I   D   C
 1332/331                                          1362/341                                          1392/351
 GGC CGG CTG GGT GTG GCG GAC CGC TAT CAG GAC ATA GCG TTG GCT ACC CGT GAT ATT GCT GAA GAG CTT GGC GGC GAA TGG GCT GAC CGC
 G   R   L   G   V   A   D   R   Y   Q   D   I   A   L   A   T   R   D   I   A   E   E   L   G   G   E   W   A   D   R
 1422/361                                          1452/371                                          1482/381    Neo ◄┐
 TTC CTC GTG CTT TAC GGT ATC GCC GCT CCC GAT TCG CAG CGC ATC GCC TTC TAT CGC CTT CTT GAC GAG TTC TTC TGA
 F   L   V   L   Y   G   I   A   A   P   D   S   Q   R   I   A   F   Y   R   L   L   D   E   F   F   *
```

*Fig. 24b*

```
SEQ ID NO:37
                    tat
               342/1                                   372/11                                  402/21
               ATG GAG CCA GTA GAT CCT AGA CTA GAG CCC TGG AAG CAT CCA GGA AGT CAG CCT AAA ACT GCT TGT ACC AAT TGC TAT TGT AAA AAG TGT
               M   E   P   V   D   P   R   L   E   P   W   K   H   P   G   S   Q   P   K   T   A   C   T   N   C   Y   C   K   K   C
               432/31                                  462/41                                  492/51
               TGC TTT CAT TGC CAA GTT TGT TTC ATA ACA AAA GCC TTA GGC ATC TCC TAT GGC AGG AAG AAG CGG AGA CAG CGA CGA AGA CCT CCT CAA
               C   F   H   C   Q   V   C   F   I   T   K   A   L   G   I   S   Y   G   R   K   K   R   R   Q   R   R   R   P   P   Q
               522/61                                  552/71                                  582/81                  tat     EcoRI     2A
               GGC AGT CAG ACT CAT CAA GTT TCT CTA TCA AAG CAA CCC ACC TCC CAA TCC CGA GGG GAC CCG ACA GGC CCG AAG GAA GAA TTC GAC CTT
               G   S   Q   T   H   Q   V   S   L   S   K   Q   P   T   S   Q   S   R   G   D   P   T   G   P   K   E   E   F   D   L
               612/91                              2A  642/101         HpaI      Neo           672/111
               CTT AAG CTT GCG GGA GAC GTC GAG TCC AAC CCT GGG CCC GGA TCT GTT AAC ATG ATT GAA CAA GAT GGA TTG CAC GCA GGT TCT CCG GCC
               L   K   L   A   G   D   V   E   S   N   P   G   P   G   S   V   N   M   I   E   Q   D   G   L   H   A   G   S   P   A
               702/121                                 732/131                                 762/141
               GCT TGG GTG GAG AGG CTA TTC GGC TAT GAC TGG GCA CAA CAG ACA ATC GGC TGC TCT GAT GCC GCC GTG TTC CGG CTG TCA GCG CAG GGG
               A   W   V   E   R   L   F   G   Y   D   W   A   Q   Q   T   I   G   C   S   D   A   A   V   F   R   L   S   A   Q   G
               792/151                                 822/161                                 852/171
               CGC CCG GTT CTT TTT GTC AAG ACC GAC CTG TCC GGT GCC CTG AAT GAA CTG CAG GAC GAG GCA GCG CGG CTA TCG TGG CTG GCC ACG ACG
               R   P   V   L   F   V   K   T   D   L   S   G   A   L   N   E   L   Q   D   E   A   A   R   L   S   W   L   A   T   T
               882/181                                 912/191                                 942/201
               GGC GTT CCT TGC GCA GCT GTG CTC GAC GTT GTC ACT GAA GCG GGA AGG GAC TGG CTG CTA TTG GGC GAA GTG CCG GGG CAG GAT CTC CTG
               G   V   P   C   A   A   V   L   D   V   V   T   E   A   G   R   D   W   L   L   L   G   E   V   P   G   Q   D   L   L
               972/211                                 1002/221                                1032/231
               TCA TCT CAC CTT GCT CCT GCC GAG AAA GTA TCC ATC ATG GCT GAT GCA ATG CGG CGG CTG CAT ACG CTT GAT CCG GCT ACC TGC CCA TTC
               S   S   H   L   A   P   A   E   K   V   S   I   M   A   D   A   M   R   R   L   H   T   L   D   P   A   T   C   P   F
               1062/241                                1092/251                                1122/261
               GAC CAC CAA GCG AAA CAT CGC ATC GAG CGA GCA CGT ACT CGG ATG GAA GCC GGT CTT GTC GAT CAG GAT GAT CTG GAC GAA GAG CAT CAG
               D   H   Q   A   K   H   R   I   E   R   A   R   T   R   M   E   A   G   L   V   D   Q   D   D   L   D   E   E   H   Q
               1152/271                                1182/281                                1212/291
               GGG CTC GCG CCA GCC GAA CTG TTC GCC AGG CTC AAG GCG CGC ATG CCC GAC GGC GAG GAT CTC GTC GTG ACC CAT GGC GAT GCC TGC TTG
               G   L   A   P   A   E   L   F   A   R   L   K   A   R   M   P   D   G   E   D   L   V   V   T   H   G   D   A   C   L
               1242/301                                1272/311                                1302/321
               CCG AAT ATC ATG GTG GAA AAT GGC CGC TTT TCT GGA TTC ATC GAC TGT GGC CGG CTG GGT GTG GCG GAC CGC TAT CAG GAC ATA GCG TTG
               P   N   I   M   V   E   N   G   R   F   S   G   F   I   D   C   G   R   L   G   V   A   D   R   Y   Q   D   I   A   L
               1332/331                                1362/341                                1392/351
               GCT ACC CGT GAT ATT GCT GAA GAG CTT GGC GGC GAA TGG GCT GAC CGC TTC CTC GTG CTT TAC GGT ATC GCC GCT CCC GAT TCG CAG CGC
               A   T   R   D   I   A   E   E   L   G   G   E   W   A   D   R   F   L   V   L   Y   G   I   A   A   P   D   S   Q   R
               1422/361                        Neo     1452/371
               ATC GCC TTC TAT CGC CTT CTT GAC GAG TTC TTC TGA
               I   A   F   Y   R   L   L   D   E   F   F   *
```

SEQ ID NO:39

```
 Core
2077/1                                        2107/11                                       2137/21
atg AGC ACG AAT CCT AAA CCT CAA AGA AAA ACC AAA CGT AAC ACC AAC CGC CGC CCA CAG GAC GTC AAG TTC CCG GGC GGT GGT CAG ATC
M   S   T   N   P   K   P   Q   R   K   T   K   R   N   T   N   R   R   P   Q   D   V   K   F   P   G   G   G   Q   I
2167/31                                       2197/41                                       2227/51
GTT GGT GGA GTT TAC CTG TTG CCG CGC AGG GGC CCC AGG TTG GGT GTG CGC GCG ATC AGG AAG ACT TCC GAG CGG TCG CAA CCC CGT GGA
V   G   G   V   Y   L   L   P   R   R   G   P   R   L   G   V   R   A   I   R   K   T   S   E   R   S   Q   P   R   G
2257/61                                       2287/71                                       2317/81
AGG CGA CAG CCT ATC CCC AAG GCT CGC CGG CCC GAG GGC AGG GCC TGG GCT CAG CCC GGG TAT CCT TGG CCC CTC TAT GGC AAT GAG GGC
R   R   Q   P   I   P   K   A   R   R   P   E   G   R   A   W   A   Q   P   G   Y   P   W   P   L   Y   G   N   E   G
2347/91                                       2377/101                                      2407/111
ATG GGG TGG GCA GGA TGG CTC CTG TCA CCC CGC GGC TCC CGG CCT AGT TGG GGC CCC ACG GAC CCC CGG CGT AGG TCG CGT AAT TTG GGT
M   G   W   A   G   W   L   L   S   P   R   G   S   R   P   S   W   G   P   T   D   P   R   R   R   S   R   N   L   G
2437/121                                      2467/131                                      2497/141
AAG GTC ATC GAT ACC CTC ACA TGC GGC CTC GCC GAC CTC ATG GGG TAC ATT CCG CTC GTC GGC GGC CCC CTA GGG GGC GCT GCC AGG GCC
K   V   I   D   T   L   T   C   G   L   A   D   L   M   G   Y   I   P   L   V   G   G   P   L   G   G   A   A   R   A
2527/151                                      2557/161                                      2587/171
TTG GCA CAT GGT GTC CGG GTT CTG GAG GAC GGC GTG AAC TAT GCA ACA GGG AAC CTG CCC GGT TGC TCT TTT TCT ATC TTC CTC TTG GCT
L   A   H   G   V   R   V   L   E   D   G   V   N   Y   A   T   G   N   L   P   G   C   S   F   S   I   F   L   L   A
2617/181                              Core    2647/191  E1                                  2677/201
CTG CTG TCC TGT CTG ACC GTA CCA GCT TCC GCT|cat GAA GTG CGT AAC GCG TCC GGG GTA TAC CAT GTC ACG AAC GAC TGC TCC AAC TCA
L   L   S   C   L   T   V   P   A   S   A   H   E   V   R   N   A   S   G   V   Y   H   V   T   N   D   C   S   N   S
2707/211                                      2737/221                                      2767/231
AGC ATT GTG TTT GAG GCG GCG GAC TTG ATC ATG CAT ACT CCC GGG TGC GTG CCC TGC GTT CGG GAG GGT AAC TCC TCC CGC TGC TGG GTA
S   I   V   F   E   A   A   D   L   I   M   H   T   P   G   C   V   P   C   V   R   E   G   N   S   S   R   C   W   V
2797/241                                      2827/251                                      2857/261
GCG CTC ACT CCC ACG CTC GCG GCC AGG AAT GCT ACC ATC CCC ACT ACG ACA ATA CGA CAC CAC GTC GAT TTG CTC GTT GGG GCG GCT GCT
A   L   T   P   T   L   A   A   R   N   A   T   I   P   T   T   T   I   R   H   H   V   D   L   L   V   G   A   A   A
2887/271                                      2917/281                                      2947/291
CTC TGC TCC GCT ATG TAC GTG GGG GAC CTC TGC GGA TCT GTT TTC CTC GTC TCT CAG CTG TTC ACC TTC TCG CCC CGC CGG CAT GCG ACA
L   C   S   A   M   Y   V   G   D   L   C   G   S   V   F   L   V   S   Q   L   F   T   F   S   P   R   R   H   A   T
2977/301                                      3007/311                                      3037/321
TTG CAG GAC TGC AAT TGT TCG ATC TAC CCC GGC CAC GCG TCA GGT CAC CGC ATG GCC TGG GAC ATG ATG ATG AAC TGG TCA CCT ACA ACA
L   Q   D   C   N   C   S   I   Y   P   G   H   A   S   G   H   R   M   A   W   D   M   M   M   N   W   S   P   T   T
3067/331                                      3097/341                                      3127/351
GCC CTC GTA GTG TCG CAG TTA CTC CGG ATC CCA CAA GCC GTC ATC GAC ATG GTG GCG GGG GCC CAC TGG GGA GTC CTG GCG GGC CTT GCC
A   L   V   V   S   Q   L   L   R   I   P   Q   A   V   I   D   M   V   A   G   A   H   W   G   V   L   A   G   L   A
3157/361                                      3187/371                                      3217/381 E1    E2
TAC TAT TCC ATG GCG GGG AAC TGG GCT AAG GTT TTG ATT GTG ATG CTA CTT TTT GCC GGC GTT GAC GGG|cac ACC CTC ACA ACG GGG GGG
Y   Y   S   M   A   G   N   W   A   K   V   L   I   V   M   L   L   F   A   G   V   D   G   H   T   L   T   T   G   G
3247/391                                      3277/401                                      3307/411
CAC GCT GCC CGC CTC ACC AGC GGG TTC GCG GGC CTC TTT ACA CCT GGG CCG TCT CAG AGA ATC CAG CTT ATA AAC ACC AAT GGC AGT TGG
H   A   A   R   L   T   S   G   F   A   G   L   F   T   P   G   P   S   Q   R   I   Q   L   I   N   T   N   G   S   W
3337/421                                      3367/431                                      3397/441
CAC ATC AAC AGG ACT GCC CTG AAC TGC AAT GAC TCC CTC CAG ACT GGG TTT CTT GCC GCG CTG TTC TAC GCA CAT AGG TTC AAC TCG TCC
H   I   N   R   T   A   L   N   C   N   D   S   L   Q   T   G   F   L   A   A   L   F   Y   A   H   R   F   N   S   S
3427/451                                      3457/461                                      3487/471
GGA TGC CCG GAG CGC ATG GCC AGC TGC CGC TCC ATT GAC AAG TTC GAC CAG GGA TGG GGT CCT ATC ACT TAT GCT GAG CCT ACA AAA GAC
G   C   P   E   R   M   A   S   C   R   S   I   D   K   F   D   Q   G   W   G   P   I   T   Y   A   E   P   T   K   D
3517/481                                      3547/491                                      3577/501
CCG GAC CAG AGG CCT TAT TGC TGG CAC TAC CCA CCT CAA CAA TGT GGT ATC GTA CCT GCG TCG CAG GTG TGT GGT CCA GTG TAT TGC TTC
P   D   Q   R   P   Y   C   W   H   Y   P   P   Q   Q   C   G   I   V   P   A   S   Q   V   C   G   P   V   Y   C   F
```

SEQ ID NO:39

```
3607/511                                3637/521                                3667/531
ACC CCA AGT CCT GTT GTC GTG GGG ACA ACC GAT CGT CTC GGC AAC CCT ACG TAC AGC TGG GGG GAG AAC GAT ACT GAC GTG CTG CTC CTT
T   P   S   P   V   V   V   G   T   T   D   R   L   G   N   P   T   Y   S   W   G   E   N   D   T   D   V   L   L   L
3697/541                                3727/551                                3757/561
AAC AAC ACG CGG CCG CCG CAA GGC AAC TGG TTC GGC TGT ACA TGG ATG AAT AGC ACT GGG TTC ACC AAG ACG TGC GGG GCC CCC CCG TGT
N   N   T   R   P   P   Q   G   N   W   F   G   C   T   W   M   N   S   T   G   F   T   K   T   C   G   A   P   P   C
3787/571                                3817/581                                3847/591
AAC ATC GGG GGG GTC GGC AAT AAC ACC TTG ACC TGC CCC ACG GAC TGC TTC CGG AAG CAC CCC GAG GCC ACG TAC TCA AAA TGT GGC TCG
N   I   G   G   V   G   N   N   T   L   T   C   P   T   D   C   F   R   K   H   P   E   A   T   Y   S   K   C   G   S
3877/601                                3907/611                                3937/621
GGG CCT TGG TTG ACA CCT AGG TGC ATG GTT GAC TAC CCA TAC AGG CTC TGG CAC TAC CCC TGC ACT GTC AAC TTC TCC ATC TTT AAG GTT
G   P   W   L   T   P   R   C   M   V   D   Y   P   Y   R   L   W   H   Y   P   C   T   V   N   F   S   I   F   K   V
3967/631                                3997/641                                4027/651
AGG ATG TAT GTG GGG GGC GTG GAG CAC AGG CTT AAT GCT GCA TGC AAC TGG ACC CGA GGA GAG CGT TGC AAC TTG GAC GAC AGG GAC AGA
R   M   Y   V   G   G   V   E   H   R   L   N   A   A   C   N   W   T   R   G   E   R   C   N   L   D   D   R   D   R
4057/661                                4087/671                                4117/681
TCG GAG CTC AGC CCG CTG CTG CTC TCT ACA ACA GAG TGG CAG GTT CTG CCC TGC TCT TTC ACC ACC CTA CCG GCT CTG TCC ACT GGC TTG
S   E   L   S   P   L   L   L   S   T   T   E   W   Q   V   L   P   C   S   F   T   T   L   P   A   L   S   T   G   L
4147/691                                4177/701                                4207/711
ATC CAC CTC CAT CAG AAC ATC GTG GAC GTG CAA TAC CTG TAC GGT ATA GGG TCA GCG GTT GTC TCC TTT GCA ATC AAA TGG GAG TAT GTC
I   H   L   H   Q   N   I   V   D   V   Q   Y   L   Y   G   I   G   S   A   V   V   S   F   A   I   K   W   E   Y   V
4237/721                                4267/731                                4297/741                    E2 <-|-> P7
GTG TTG CTT TTC CTT CTC CTG GCG GAC GCG CGC GTC TGT GCC TGC TTG TGG ATG ATG CTG CTG ATA GCC CAG GCC GAG GCC|gcc TTA GAG
V   L   L   F   L   L   L   A   D   A   R   V   C   A   C   L   W   M   M   L   L   I   A   Q   A   E   A  |A   L   E
4327/751                                4357/761                                4387/771
AAC CTG GTG GCC CTC AAT GCA GCG TCC GTT GCC GGA GCG CAC GGC ATC CTC TCC TTC CTC GTG TTC TTC TGT GCC GCT TGG TAC ATC AAG
N   L   V   A   L   N   A   A   S   V   A   G   A   H   G   I   L   S   F   L   V   F   F   C   A   A   W   Y   I   K
4417/781                                4447/791                                4477/801                            P7
GGC AGG CTG GTC CCT GGG GCG GCA TAT GCT TTC TAT GGC GCA TGG CCG CTG CTC CTG CTC CTC TTG ACA TTA CCA CCA CGA GCT TAC GCC
G   R   L   V   P   G   A   A   Y   A   F   Y   G   A   W   P   L   L   L   L   L   L   T   L   P   P   R   A   Y   A
4507/811 NS2                            4537/821                                4567/831
atg GAC CGG GAG ATG GCT GCA TCG TGC GGA GGC GCG GTT TTT GTG GGT CTG GCA TTA TTG ACC TTG TCG CCA TAT TAC AAG GTG TTC CTC
M   D   R   E   M   A   A   S   C   G   G   A   V   F   V   G   L   A   L   L   T   L   S   P   Y   Y   K   V   F   L
4597/841                                4627/851                                4657/861
GCT AGG CTC CTA TGG TGG TTA CAA TAT CTT ATC ACC AGA GCT GAG GCG CAC TTG CAT GTG TGG GTT CCC CCC CTC AAC GTC CGG GGA GGC
A   R   L   L   W   W   L   Q   Y   L   I   T   R   A   E   A   H   L   H   V   W   V   P   P   L   N   V   R   G   G
4687/871                                4717/881                                4747/891
CGC GAT GCC ATC ATC CTC CTC ACG TGT GCA GTC CAC CCA GAG CTA ATC TTT GAT ATC ACC AAA CTT CTG ATT GCC ATA CTC GGA CCG CTC
R   D   A   I   I   L   L   T   C   A   V   H   P   E   L   I   F   D   I   T   K   L   L   I   A   I   L   G   P   L
4777/901                                4807/911                                4837/921
ATG GTG CTC CAA GCT GGC ATA ACT AGG GTG CCG TAC TTC GTA CGC GCT CAA GGG CTC ATT CGT GCA TGC ATG TTA GTG CGG AAA GTC GCT
M   V   L   Q   A   G   I   T   R   V   P   Y   F   V   R   A   Q   G   L   I   R   A   C   M   L   V   R   K   V   A
4867/931                                4897/941                                4927/951
GGG GGT CAT TAT GTC CAA ATG GCC TTC ATG AGA CTG GGC GCG CTG ACG GGC ACG TAC GTC TAT AAT CAC CTC ACC CCA CTG CGG GAT TGG
G   G   H   Y   V   Q   M   A   F   M   R   L   G   A   L   T   G   T   Y   V   Y   N   H   L   T   P   L   R   D   W
4957/961                                4987/971                                5017/981
GCC CAC GCC GGC CTA CGG GAC CTT GCG GTA GCA GTG GAG CCT GTC GTC TTC TCT GAC ATG GAG ACC AAG ATC ATC ACC TGG GGG GCG GAC
A   H   A   G   L   R   D   L   A   V   A   V   E   P   V   V   F   S   D   M   E   T   K   I   I   T   W   G   A   D
5047/991                                5077/1001                               5107/1011
ACC GCG GCG TGT GGG GAC ATC ATC CTG GGC CTA CCT GTC TCC GCC CGA AGG GGA AGG GAG ATA CTC CTG GGG CCG GCC GAT AGT CTA GTA
T   A   A   C   G   D   I   I   L   G   L   P   V   S   A   R   R   G   R   E   I   L   L   G   P   A   D   S   L   V
5137/1021                               5167/1031                               5197/1041
```

*Fig. 24d-1*

SEQ ID NO:39

```
                          NS2 <-|-> NS3
GGG CAG GGG TGG CGA CTC CTT|gcg CCC ATC ACG GCC TAC TCC CAA CAG ACC CGG GGC CTA CTT GGT TGC ATC ATC ACG AGT CTC ACA GGC
G   Q   G   W   R   L   L  |A   P   I   T   A   Y   S   Q   Q   T   R   G   L   L   G   C   I   I   T   S   L   T   G
5227/1051                  |            5257/1061                               5287/1071
CGG GAC AAG AAC CAG GTC GAG GGG GAG GTT CAA GTG GTC TCC ACC GCA ACA CAA TCT TTC CTG GCG ACC TGC GTC AAC GGC GTA TGT TGG
R   D   K   N   Q   V   E   G   E   V   Q   V   V   S   T   A   T   Q   S   F   L   A   T   C   V   N   G   V   C   W
5317/1081                               5347/1091                               5377/1101
ACT GTC TAC CAT GGT GCT GGC TCA AAG ACT CTA GCC GGC CCA AAA GGC CCA ATC GCC CAG ATG TAC ACT AAT GTA GAC CAG GAT CTC GTC
T   V   Y   H   G   A   G   S   K   T   L   A   G   P   K   G   P   I   A   Q   M   Y   T   N   V   D   Q   D   L   V
5407/1111                               5437/1121                               5467/1131
GGC TGG CCG GCG CCC CCC GGG GCG CGT TCC CTG ACA CCA TGC ACC TGT GGC AGC TCG GAC CTT TAC TTG GTT ACG AGA CAT GCA GAT GTT
G   W   P   A   P   P   G   A   R   S   L   T   P   C   T   C   G   S   S   D   L   Y   L   V   T   R   H   A   D   V
5497/1141                               5527/1151                               5557/1161
ATT CCG GTG CGC CGG CGG GGC GAC AAT AGA GGG AGC TTG CTC TCC CCC AGG CCT GTC TCC TAC TTG AAG GGC TCT TCG GGT GGC CCA CTG
I   P   V   R   R   R   G   D   N   R   G   S   L   L   S   P   R   P   V   S   Y   L   K   G   S   S   G   G   P   L
5587/1171                               5617/1181                               5647/1191
CTC TGC CCT TCG GGG CAC GCT GTG GGC GTC TTC CGG GCC GCT GTA TGC ACC CGG GGG GTT GCA AAG GCG GTG GAT TTT GTC CCC GTT GAG
L   C   P   S   G   H   A   V   G   V   F   R   A   A   V   C   T   R   G   V   A   K   A   V   D   F   V   P   V   E
5677/1201                               5707/1211                               5737/1221
TCC ATG GAA ACT ACT ATG CGG TCC CCG GTC TTC ACA GAC AAC TCA TCT CCC CCG GCC GTA CCG CAA ACA TTC CAA GTG GCC CAT CTA CAC
S   M   E   T   T   M   R   S   P   V   F   T   D   N   S   S   P   P   A   V   P   Q   T   F   Q   V   A   H   L   H
5767/1231                               5797/1241                               5827/1251
GCT CCC ACT GGC AGC GGC AAG AGC ACT AGA GTG CCG GCC GCA TAT GCG GCC CAA GGG TAC AAG GTG CTT GTC CTG AAC CCG TCT GTT GCC
A   P   T   G   S   G   K   S   T   R   V   P   A   A   Y   A   A   Q   G   Y   K   V   L   V   L   N   P   S   V   A
5857/1261                               5887/1271                               5917/1281
GCT ACC TTA GGT TTT GGG GCG TAT ATG TCT AAA GCA CAT GGT ACC GAC CCT AAC ATC AGG ACT GGG GTA AGG ACC ATT ACC ACG GGC GCC
A   T   L   G   F   G   A   Y   M   S   K   A   H   G   T   D   P   N   I   R   T   G   V   R   T   I   T   T   G   A
5947/1291                               5977/1301                               6007/1311
CCC ATT ACG TAC TCC ACC TAT GGC AAG TTC CTT GCC GAC GGT GGT TGC TCC GGG GGC GCT TAC GAC ATC ATA ATG TGC GAT GAG TGC CAC
P   I   T   Y   S   T   Y   G   K   F   L   A   D   G   G   C   S   G   G   A   Y   D   I   I   M   C   D   E   C   H
6037/1321                               6067/1331                               6097/1341
TCA ACT GAC TCA ACT ACT ATC TTG GGC ATC GGC ACA GTC CTG GAC CAA GCG GAG ACG GCT GGA GCG CGG CTT GTC GTG CTC GCC ACC GCT
S   T   D   S   T   T   I   L   G   I   G   T   V   L   D   Q   A   E   T   A   G   A   R   L   V   V   L   A   T   A
6127/1351                               6157/1361                               6187/1371
ACG CCT CCA GGA TCG GTC ACC GTG CCA CAC CCC AAT ATC GAG GAG GTG GCC CTG TCG AAC ACT GGA GAG ATC CCC TTC TAC GGC AAA GCC
T   P   P   G   S   V   T   V   P   H   P   N   I   E   E   V   A   L   S   N   T   G   E   I   P   F   Y   G   K   A
6217/1381                               6247/1391                               6277/1401
ATC CCC ATC GAA GCC ATC AAG GGG GGA AGG CAC CTC ATT TTC TGT CAC TCC AAG AAG AAG TGC GAC GAG CTT GCC GCA AAG CTG TCA GGC
I   P   I   E   A   I   K   G   G   R   H   L   I   F   C   H   S   K   K   K   C   D   E   L   A   A   K   L   S   G
6307/1411                               6337/1421                               6367/1431
CTC GGA ATC AAT GCT GTA GCG TAT TAC CGG GGT CTT GAT GTG TCC GTC ATA CCG ACC AGC GGA GAC GTC GTT GTC GTG GCA ACA GAC GCT
L   G   I   N   A   V   A   Y   Y   R   G   L   D   V   S   V   I   P   T   S   G   D   V   V   V   V   A   T   D   A
6397/1441                               6427/1451                               6457/1461
CTA ATG ACG GGC TAT ACC GGT GAC TTT GAT TCA GTG ATC GAC TGT AAT ACG TGT GTC ACC CAG ACA GTC GAC TTC AGC TTG GAC CCC ACC
L   M   T   G   Y   T   G   D   F   D   S   V   I   D   C   N   T   C   V   T   Q   T   V   D   F   S   L   D   P   T
6487/1471                               6517/1481                               6547/1491
TTC ACC ATT GAG ACG ACG ACC GTG CCC CAA GAC GCA GTG TCG CGC TCG CAG CGG CGG GGT AGG ACT GGC AGG GGC AGG GGG GGC ATA TAC
F   T   I   E   T   T   T   V   P   Q   D   A   V   S   R   S   Q   R   R   G   R   T   G   R   G   R   G   G   I   Y
6577/1501                               6607/1511                               6637/1521
AGG TTT GTA ACT CCG GGG GAA CGG CCC TCG GGC ATG TTC GAT TCC TCG GTC CTG TGC GAG TGC TAT GAC GCG GGC TGT GCT TGG TAC GAG
R   F   V   T   P   G   E   R   P   S   G   M   F   D   S   S   V   L   C   E   C   Y   D   A   G   C   A   W   Y   E
6667/1531                               6697/1541                               6727/1551
CTC ACC CCC GCT GAG ACC TCG GTT AGG TTG CGG GCT TAC CTA AAT ACA CCA GGA TTG CCC GTT TGC CAG GAC CAT CTG GAG TTC TGG GAG
```

*Fig. 24d-2*

SEQ ID NO:39

```
L   T   P   A   E   T   S   V   R   L   R   A   Y   L   N   T   P   G   L   P   V   C   Q   D   H   L   E   F   W   E
6757/1561                               6787/1571                               6817/1581
AGC GTC TTC ACA GGC CTC ACC CAT ATA GAT GCC CAC TTC CTG TCC CAG ACC AAG CAG GCA GGA GAT AAC TTC CCC TAC CTG GTG GCA TAC
S   V   F   T   G   L   T   H   I   D   A   H   F   L   S   Q   T   K   Q   A   G   D   N   F   P   Y   L   V   A   Y
6847/1591                               6877/1601                               6907/1611
CAA GCC ACA GTG TGC GCC AGG GCT CAG GCC CCA CCT CCA TCG TGG GAT CAA ATG TGG AAG TGT CTC ATA CGG CTA AAA CCC ACG CTG CAC
Q   A   T   V   C   A   R   A   Q   A   P   P   P   S   W   D   Q   M   W   K   C   L   I   R   L   K   P   T   L   H
6937/1621                               6967/1631                               6997/1641
GGG CCA ACG CCC CTG CTG TAT AGG CTA GGG GCC GTC CAA AAT GAG GTC ACC CTC ACA CAC CCC ATA ACC AAA TAC ATC ATG GCA TGC ATG
G   P   T   P   L   L   Y   R   L   G   A   V   Q   N   E   V   T   L   T   H   P   I   T   K   Y   I   M   A   C   M
7027/1651            NS3 <---->  NS4A7057/1661                                  7087/1671
TCG GCC GAC CTG GAA GTC GTC ACC|agc ACC TGG GTG CTG GTA GGC GGA GTC CTC GCA GCT CTG GCC GCA TAT TGC CTG ACA ACA GGC AGT
S   A   D   L   E   V   V   T  |S   T   W   V   L   V   G   G   V   L   A   A   L   A   A   Y   C   L   T   T   G   S
7117/1681                               7147/1691                               7177/1701
GTG GTT ATC GTG GGT AGG ATC ATC TTG TCC GGG AGG CCG GCT GTC GTT CCC GAT AGG GAA GTC CTC TAC CGG GAG TTC GAT GAA ATG GAA
V   V   I   V   G   R   I   I   L   S   G   R   P   A   V   V   P   D   R   E   V   L   Y   R   E   F   D   E   M   E
NS4A <-7207/1711 NS4B->                 7237/1721                               7267/1731
GAA TGC|gcc TCG CAC CTC CCT TAC ATC GAA CAG GGA ATG CAA CTC GCC GAG CAA TTC AAG CAG AAG GCG CTC GGG TTG TTG CAA ACA GCC
E   C  |A   S   H   L   P   Y   I   E   Q   G   M   Q   L   A   E   Q   F   K   Q   K   A   L   G   L   L   Q   T   A
7297/1741                               7327/1751                               7357/1761
ACC AAG CAG GCG GAG GCT GCC GCT CCC GTG GTG GAG TCC AAG TGG CGA GCT TTG GAG ACC TTC TGG GCA AAG CAC AAG TGG AAT TTC ATC
T   K   Q   A   E   A   A   A   P   V   V   E   S   K   W   R   A   L   E   T   F   W   A   K   H   K   W   N   F   I
7387/1771                               7417/1781                               7447/1791
AGC GGG ATA CAG TAC TTA GCG GGC TTA TCC ACC CTG CCT GGG AAC CCC GCG ATA GCA TCA CTG ATG GCA TTC ACA GCC TCT ATC ACC AGC
S   G   I   Q   Y   L   A   G   L   S   T   L   P   G   N   P   A   I   A   S   L   M   A   F   T   A   S   I   T   S
7477/1801                               7507/1811                               7537/1821
CCG CTC ACC ACC CAG AAC ACC CTC CTG TTT AAC ATC TTG GGG GGG TGG GTA GCC GCC CAA CTC GCT CCC CCC AGC GCT GCT TCG GCT TTC
P   L   T   T   Q   N   T   L   L   F   N   I   L   G   G   W   V   A   A   Q   L   A   P   P   S   A   A   S   A   F
7567/1831                               7597/1841                               7627/1851
GTG GGC GCT GGT ATC GCT GGT GCG GCT GTT GGC AGC ATA GGT CTT GGG AAG GTG CTA GTG GAC ATT CTG GCG GGC TAT GGG GCA GGG GTG
V   G   A   G   I   A   G   A   A   V   G   S   I   G   L   G   K   V   L   V   D   I   L   A   G   Y   G   A   G   V
7657/1861                               7687/1871                               7717/1881
GCT GGC GCG CTC GTG GCC TTC AAG GTC ATG AGC GGC GAG GCG CCC TCT GCC GAG GAC CTG ATC AAT TTG CTC CCT GCC ATC CTC TCT CCT
A   G   A   L   V   A   F   K   V   M   S   G   E   A   P   S   A   E   D   L   I   N   L   L   P   A   I   L   S   P
7747/1891                               7777/1901                               7807/1911
GGT GCC CTG GTC GTC GGA GTC GTG TGT GCA GCA ATA CTG CGT CGG CAT GTG GGC CCG GGA GAG GGG GCC GTG CAG TGG ATG AAC CGG CTG
G   A   L   V   V   G   V   V   C   A   A   I   L   R   R   H   V   G   P   G   E   G   A   V   Q   W   M   N   R   L
7837/1921                               7867/1931                               7897/1941
ATA GCG TTC GCT TCG CGG GGT AAC CAT GTC TCC CCC ACG CAC TAT GTG CCT GAG AGC GAC GCC GCA GCG CGT GTC ACT CAG GTC CTC TCC
I   A   F   A   S   R   G   N   H   V   S   P   T   H   Y   V   P   E   S   D   A   A   A   R   V   T   Q   V   L   S
7927/1951                               7957/1961                  NS4B <-7987/1971-> NS5A
AGC CTT ACC ATC ACC CAG CTG CTG AAG AGG CTC CAC CAG TGG ATT AAT GAG GAC TGT TCT ACG CCG TGT|tcc GGC TCG TGG CTG AGG GAT
S   L   T   I   T   Q   L   L   K   R   L   H   Q   W   I   N   E   D   C   S   T   P   C  |S   G   S   W   L   R   D
8017/1981                               8047/1991                               8077/2001
GTT TGG GAC TGG GTG TGC ACG GTG TTG AGT GAC TTC AAG ACC TGG CTC CAG TCC AAG CTC CTG CCG CGG TTA CCG GGT GTC CCT TTC CTC
V   W   D   W   V   C   T   V   L   S   D   F   K   T   W   L   Q   S   K   L   L   P   R   L   P   G   V   P   F   L
8107/2011                               8137/2021                               8167/2031
TCA TGC CAA CGT GGG TAC AAG GGA GTC TGG CGG GGG GAC GGC ATC ATG CAC ACC ACC TGC CCA TGT GGA GCA CAG ATC GCC GGA CAT GTC
S   C   Q   R   G   Y   K   G   V   W   R   G   D   G   I   M   H   T   T   C   P   C   G   A   Q   I   A   G   H   V
8197/2041                               8227/2051                               8257/2061
AAA AAC GGT TCC ATG AGG ATC ATC GGG CCG AAA ACC TGC AGC AAC ACG TGG CAT GGA ACA TTC CCC ATC AAC GCG TAC ACC ACG GGC CCC
K   N   G   S   M   R   I   I   G   P   K   T   C   S   N   T   W   H   G   T   F   P   I   N   A   Y   T   T   G   P
```

```
SEQ ID NO:39
8287/2071                                8317/2081                                8347/2091
TGC ACG CCT TCC CCG GCG CCA AAC TAT TCC AAG GCG CTG TGG CGG GTG GCT GCT GAG GAG TAC GTG GAG GTC ACG CGG GTG GGG GAT TTC
C   T   P   S   P   A   P   N   Y   S   K   A   L   W   R   V   A   A   E   E   Y   V   E   V   T   R   V   G   D   F
8377/2101                                8407/2111                                8437/2121
CAC TAC GTG ACG GGC ATA ACC ACC GAC AAC GTA AAG TGC CCA TGT CAG GTT CCA GCT CCT GAG TTT TTC ACG GAG GTG GAT GGG GTG CGG
H   Y   V   T   G   I   T   T   D   N   V   K   C   P   C   Q   V   P   A   P   E   F   F   T   E   V   D   G   V   R
8467/2131                                8497/2141                                8527/2151
TTG CAC AGG TAC GCC CCG GTG TGC AAA CCT CTC TTA CGG GAT GAG GTT GTA TTC CAG GTC GGG CTC AAT CAA TAC CTG GTT GGG TCA CAG
L   H   R   Y   A   P   V   C   K   P   L   L   R   D   E   V   V   F   Q   V   G   L   N   Q   Y   L   V   G   S   Q
8557/2161                                8587/2171                                8617/2181
CTC CCA TGC GAG CCC GAA CCG GAC GTA GCA GTG CTC ACT TCC ATG CTC ACC GAC CCC TCC CAC ATT ACA GCA GAG GCG GCT AAG CGT AGG
L   P   C   E   P   E   P   D   V   A   V   L   T   S   M   L   T   D   P   S   H   I   T   A   E   A   A   K   R   R
8647/2191                                8677/2201                                8707/2211
TTG GCC AGG GGG TCT CCC CCC TCC TTG GCC AGC TCT TCA GCT AGC CAG CTG TCT GCG CCC TCC TTG AGG GCG ACA TGC ACT ACC CAT TCT
L   A   R   G   S   P   P   S   L   A   S   S   S   A   S   Q   L   S   A   P   S   L   R   A   T   C   T   T   H   S
8737/2221                                8767/2231                                8797/2241
TCC TAT AAT CTT GAC TCT CCG GAC GTC GAC CTC ATT GCG GCC AAC CTC CTG TGG CGG CAG GAG ATG GGC GGA AAC ATC ACC CGC GTG GAG
S   Y   N   L   D   S   P   D   V   D   L   I   A   A   N   L   L   W   R   Q   E   M   G   G   N   I   T   R   V   E
8827/2251                                8857/2261                                8887/2271
TCG GAG AAC AAG GTG GTA GTC CTA GAC TCT TTC GAG CCG CTT CGA GCG GAG GGG GAT GAG AAT GAA ATA TCC ATT GCG GCG GAG ATC CTG
S   E   N   K   V   V   V   L   D   S   F   E   P   L   R   A   E   G   D   E   N   E   I   S   I   A   A   E   I   L
8917/2281                                8947/2291                                8977/2301
CGG AAG TCC AAG AAG TTC CCC GCG GCG ATA CCC ATA TGG GCA CGG CCG GAT TAC AAT CCT CCA TTG TTA GAG TCT TGG AAG AAC CCG GAC
R   K   S   K   K   F   P   A   A   I   P   I   W   A   R   P   D   Y   N   P   P   L   L   E   S   W   K   N   P   D
9007/2311                                9037/2321                                9067/2331
TAC GTC CCT CCG GTG GTA CAC GGG TGC CCA TTG CCA CCT GTC AAG GCC CCT CCA ATA CCA CCT CCA CGG AGA AAA AGG ACG GTT GTC CTG
Y   V   P   P   V   V   H   G   C   P   L   P   P   V   K   A   P   P   I   P   P   P   R   R   K   R   T   V   V   L
9097/2341                                9127/2351                                9157/2361
ACG GAC TCC ACC GTG TCT TCT GTT TTG GCG GAG CTC GCT ACC AAA ACC TTC GGC AGC TCC GAA TTG TCG GCC GCC GAC AGC GGC ACG GCG
T   D   S   T   V   S   S   V   L   A   E   L   A   T   K   T   F   G   S   S   E   L   S   A   A   D   S   G   T   A
9187/2371                                9217/2381                                9247/2391
ACC GCC CCT CCT GAC CAG ACC TCC GAC AAC GGC GGC AAA GAC TCC GAC GCT GAG TCA TGC TCC TCT ATG CCC CCC CTT GAG GGG GAG CCG
T   A   P   P   D   Q   T   S   D   N   G   G   K   D   S   D   A   E   S   C   S   S   M   P   P   L   E   G   E   P
9277/2401                                9307/2411                                9337/2421NS5A ←→ NS5B
GGG GAC CCC GAT CTC AGC GAC GGG TCT TGG TCT ACC GTG AGC GAG GAG GCT GGT GAG AGC GTC GTC TGC TGC|tca ATG TCC TAC ACA TGG
G   D   P   D   L   S   D   G   S   W   S   T   V   S   E   E   A   G   E   S   V   V   C   C  |S   M   S   Y   T   W
9367/2431                                9397/2441                                9427/2451
ACA GGT GCC CTG ATC ACG CCA TGC GCC GCG GAA GAA AGC AAG CTG CCC ATC AAC GCG TTG AGC AAC TCT TTG CTG CGC CAT CAC AAC ATG
T   G   A   L   I   T   P   C   A   A   E   E   S   K   L   P   I   N   A   L   S   N   S   L   L   R   H   H   N   M
9457/2461                                9487/2471                                9517/2481
GTC TAC GCC ACG ACA TCC CGC AGC GCG GGC CTG CGG CAG AAG AAG GTC ACC TTT GAC AGA CTG CAG GTC CTG GAT GAC CAT TAC CGG GAC
V   Y   A   T   T   S   R   S   A   G   L   R   Q   K   K   V   T   F   D   R   L   Q   V   L   D   D   H   Y   R   D
9547/2491                                9577/2501                                9607/2511
GTG CTT AAG GAG ATG AAG GCA AAG GCG TCC ACA GTC AAG GCT AAA CTT CTA TCC ATA GAA GAA GCC TGC CGC CTG ACG CCC CCA CAT TCG
V   L   K   E   M   K   A   K   A   S   T   V   K   A   K   L   L   S   I   E   E   A   C   R   L   T   P   P   H   S
9637/2521                                9667/2531                                9697/2541
GCC AAA TCC AAG TTT GGC TAT GGG GCA AAG GAC GTC CGG AAC CTA TCC AGC AGG GCC ATC AAC CAC ATC CGC TCC GTG TGG GAG GAC TTG
A   K   S   K   F   G   Y   G   A   K   D   V   R   N   L   S   S   R   A   I   N   H   I   R   S   V   W   E   D   L
9727/2551                                9757/2561                                9787/2571
CTG GAG GAC ACT GTG ACA CCA ATT GAC ACC ACC GTC ATG GCA AAG AAT GAG GTT TTC TGC GTC CAA CCA GAG AAG GGA GGC CGC AAG CCA
L   E   D   T   V   T   P   I   D   T   T   V   M   A   K   N   E   V   F   C   V   Q   P   E   K   G   G   R   K   P
9817/2581                                9847/2591                                9877/2601
```

SEQ ID NO:39

```
GCC CGC CTT ATC GTA TTC CCA GAT TTG GGA GTT CGT GTA TGC GAG AAG ATG GCT CTC TAC GAT GTG GTC TCC ACC CTT CCT CAA GCC GTG
A   R   L   I   V   F   P   D   L   G   V   R   V   C   E   K   M   A   L   Y   D   V   V   S   T   L   P   Q   A   V
9907/2611                               9937/2621                               9967/2631
ATG GGC TCC TCA TAC GGA TTC CAG TAC TCT CCC GGG CAG CGG GTC GAG TTC CTG GTA AAA GCC TGG AAA TCA AAG AAA AAC CCT ATG GGC
M   G   S   S   Y   G   F   Q   Y   S   P   G   Q   R   V   E   F   L   V   K   A   W   K   S   K   K   N   P   M   G
9997/2641                               10027/2651                              10057/2661
TTC TCA TAT GAC ACC CGC TGT TTT GAC TCA ACG GTC ACT GAG AAT GAC ATC CGT GTT GAG GAG TCA ATT TAC CAA TGT TGT GAC TTG GCC
F   S   Y   D   T   R   C   F   D   S   T   V   T   E   N   D   I   R   V   E   E   S   I   Y   Q   C   C   D   L   A
10087/2671                              10117/2681                              10147/2691
CCC GAA GCC AGA CAG GCT ATA AAA TCG CTC ACA GAG CGG CTT TAT ATC GGG GGT CCC CTG ACT AAT TCA AAA GGG CAG AGC TGT GGT TAT
P   E   A   R   Q   A   I   K   S   L   T   E   R   L   Y   I   G   G   P   L   T   N   S   K   G   Q   S   C   G   Y
10177/2701                              10207/2711                              10237/2721
CGC CGG TGC CGC GCG AGC GGC GTG CTG ACG ACT AGC TGC GGT AAT ACC CTC ACA TGT TAC TTG AAA GCC TCT GCC GCC TGT CGA GCT GCA
R   R   C   R   A   S   G   V   L   T   T   S   C   G   N   T   L   T   C   Y   L   K   A   S   A   A   C   R   A   A
10267/2731                              10297/2741                              10327/2751
AAG CTC CAG GAC TGC ACG ATG CTC GTG AAC GGG GAC GAC CTT GTC GTT ATC TGC GAA AGC GCG GGA ACC CAG GAG GAT GCG GCG AGC CTA
K   L   Q   D   C   T   M   L   V   N   G   D   D   L   V   V   I   C   E   S   A   G   T   Q   E   D   A   A   S   L
10357/2761                              10387/2771                              10417/2781
CGA GTC TTC ACG GAG GCT ATG ACT AGG TAC TCC GCC CCC CCC GGG GAC TTG CCC CAA CCA GAA TAC GAC TTG GAG TTG ATA ACA TCA TGT
R   V   F   T   E   A   M   T   R   Y   S   A   P   P   G   D   L   P   Q   P   E   Y   D   L   E   L   I   T   S   C
10447/2791                              10477/2801                              10507/2811
TCC TCC AAT GTG TCG GTC GCG CAC GAT GCA TCT GGC AAA AGG GTG TAC TAC CTC ACT CGC GAT CCC ACC ACC CCC ATC GCA CGG GCT GCG
S   S   N   V   S   V   A   H   D   A   S   G   K   R   V   Y   Y   L   T   R   D   P   T   T   P   I   A   R   A   A
10537/2821                              10567/2831                              10597/2841
TGG GAA ACA GCT AGA CAC ACT CCA GTT AAC TCC TGG CTA GGC AAC ATT ATC ATG TAT GCG CCC ACC TTA TGG GCA AGG ATG ATT CTG ATG
W   E   T   A   R   H   T   P   V   N   S   W   L   G   N   I   I   M   Y   A   P   T   L   W   A   R   M   I   L   M
10627/2851                              10657/2861                              10687/2871
ACC CAT TTC TTC TCC ATC CTT CTA GCT CAG GAG CAA CTT GAA AAA GCC CTG GAT TGC CAA ATC TAC GGG GCC TGT TAC TCC ATT GAG CCA
T   H   F   F   S   I   L   L   A   Q   E   Q   L   E   K   A   L   D   C   Q   I   Y   G   A   C   Y   S   I   E   P
10717/2881                              10747/2891                              10777/2901
CTT GAC CTA CCT CAG ATC ATT GAA gGA CTC CAT GGT CTT AGC GCA TTT TCA CTC CAT AGT TAC TCT CCA GGT GAG ATC AAT AGG GTG GCT
L   D   L   P   Q   I   I   E   G   L   H   G   L   S   A   F   S   L   H   S   Y   S   P   G   E   I   N   R   V   A
10807/2911                              10837/2921                              10867/2931
TCA TGC CTC AGG AAA CTT GGG GTA CCG CCC TTG CGA GTC TGG AGA CAT CGG GCC AGG GAC GTC CGC GCT AAA CTA CTG TCC CAG GGG GGG
S   C   L   R   K   L   G   V   P   P   L   R   V   W   R   H   R   A   R   D   V   R   A   K   L   L   S   Q   G   G
10897/2941                              10927/2951                              10957/2961
AGG GCC GCC ACT TGC GGC AAA TAC CTC TTC AAC TGG GCA GTA AAG ACC AAG CTC AAA CTC ACT CCA ATC CCG GCT GCG TCC CAG TTG GAC
R   A   A   T   C   G   K   Y   L   F   N   W   A   V   K   T   K   L   K   L   T   P   I   P   A   A   S   Q   L   D
10987/2971                              11017/2981                              11047/2991
TTA TCC GGC TGG TTC GTT GCT GGC TAC AGC GGG GGA GAC ATA TAT CAC AGC CTG TCT CGT GCC CGA CCC CGC TGG TTC ATG CTG TGC CTA
L   S   G   W   F   V   A   G   Y   S   G   G   D   I   Y   H   S   L   S   R   A   R   P   R   W   F   M   L   C   L
11077/3001                              11107/3011  NS5B ←|→ 3'NTR            11137/3021
CTC CTA CTT TCT GTA GGG GTA GGC ATC TAC TTG CTC CCC AAT CGA|tga ACG GGG AGC TAA ACA CTC CAG GCC AAT AGG CCA TTT CCT GTT
L   L   L   S   V   G   V   G   I   Y   L   L   P   N   R  |*   T   G   S   *   T   L   Q   A   N   R   P   F   P   V
11167/3031                              11197/3041                              11227/3051
TTT TTT TTT TTT TGG TTT TTT TTT TTT TTT TTT TTT TTT TTT TTT TTT TTT TTT CCT TTC CTT CTT TTT TTT TTT TTC CCT CTT TAT GGT
F   F   F   F   W   F   F   F   F   F   F   F   F   F   F   F   F   F   P   F   L   L   F   F   F   F   P   L   Y   G
11257/3061                              11287/3071                              11317/3081
GGC TCC GTC TTA GCC CTA GTC ACG GCT AGC TGT GAA AGG TCC GTG AGC CGC ATG ACT GCA GAG AGT GCT GAT ACT GGC CTC TCT GCA GAT
G   S   V   L   A   L   V   T   A   S   C   E   R   S   V   S   R   M   T   A   E   S   A   D   T   G   L   S   A   D
11347/3091
CAT|GT
3'NTR ←
```

Fig. 24d-5

SEQ ID NO:41

```
→ NS3
2119/1                                                      2149/11                                                     2179/21
ATG GCG CCT ATT ACG GCC TAC TCC CAA CAG ACG CGA GGC CTA CTT GGC TGC ATC ATC ACT AGC CTC ACA GGC CGG GAC AGG AAC CAG GTC
M   A   P   I   T   A   Y   S   Q   Q   T   R   G   L   L   G   C   I   I   T   S   L   T   G   R   D   R   N   Q   V
2209/31                                                     2239/41                                                     2269/51
GAG GGG GAG GTC CAA GTG GTC TCC ACC GCA ACA CAA TCT TTC CTG GCG ACC TGC GTC AAT GGC GTG TGT TGG ACT GTC TAT CAT GGT GCC
E   G   E   V   Q   V   V   S   T   A   T   Q   S   F   L   A   T   C   V   N   G   V   C   W   T   V   Y   H   G   A
2299/61                                                     2329/71                                                     2359/81
GGC TCA AAG ACC CTT GCC GGC CCA AAG GGC CCA ATC ACC CAA ATG TAC ACC AAT GTG GAC CAG GAC CTC GTC GGC TGG CAA GCG CCC CCC
G   S   K   T   L   A   G   P   K   G   P   I   T   Q   M   Y   T   N   V   D   Q   D   L   V   G   W   Q   A   P   P
2389/91                                                     2419/101                                                    2449/111
GGG GCG CGT TCC TTG ACA CCA TGC ACC TGC GGC AGC TCG GAC CTT TAC TTG GTC ACG AGG CAT GCC GAT GTC ATT CCG GTG CGC CGG CGG
G   A   R   S   L   T   P   C   T   C   G   S   S   D   L   Y   L   V   T   R   H   A   D   V   I   P   V   R   R   R
2479/121                                                    2509/131                                                    2539/141
GGC GAC AGC AGG GGG AGC CTA CTC TCC CCC AGG CCC GTC TCC TAC TTG AAG GGC TCT TCG GGC GGT CCA CTG CTC TGC CCC TCG GGG CAC
G   D   S   R   G   S   L   L   S   P   R   P   V   S   Y   L   K   G   S   S   G   G   P   L   L   C   P   S   G   H
2569/151                                                    2599/161                                                    2629/171
GCT GTG GGC ATC TTT CGG GCT GCC GTG TGC ACC CGA GGG GTT GCG AAG GCG GTG GAC TTT GTA CCC GTC GAG TCT ATG GAA ACC ACT ATG
A   V   G   I   F   R   A   A   V   C   T   R   G   V   A   K   A   V   D   F   V   P   V   E   S   M   E   T   T   M
2659/181                                                    2689/191                                                    2719/201
CGG TCC CCG GTC TTC ACG GAC AAC TCG TCC CCT CCG GCC GTA CCG CAG ACA TTC CAG GTG GCC CAT CTA CAC GCC CCT ACT GGT AGC GGC
R   S   P   V   F   T   D   N   S   S   P   P   A   V   P   Q   T   F   Q   V   A   H   L   H   A   P   T   G   S   G
2749/211                                                    2779/221                                                    2809/231
AAG AGC ACT AAG GTG CCG GCT GCG TAT GCA GCC CAA GGG TAT AAG GTG CTT GTC CTG AAC CCG TCC GTC GCC GCC ACC CTA GGT TTC GGG
K   S   T   K   V   P   A   A   Y   A   A   Q   G   Y   K   V   L   V   L   N   P   S   V   A   A   T   L   G   F   G
2839/241                                                    2869/251                                                    2899/261
GCG TAT ATG TCT AAG GCA CAT GGT ATC GAC CCT AAC ATC AGA ACC GGG GTA AGG ACC ATC ACC ACG GGT GCC CCC ATC ACG TAC TCC ACC
A   Y   M   S   K   A   H   G   I   D   P   N   I   R   T   G   V   R   T   I   T   T   G   A   P   I   T   Y   S   T
2929/271                                                    2959/281                                                    2989/291
TAT GGC AAG TTT CTT GCC GAC GGT GGT TGC TCT GGG GGC GCC TAT GAC ATC ATA ATA TGT GAT GAG TGC CAC TCA ACT GAC TCG ACC ACT
Y   G   K   F   L   A   D   G   G   C   S   G   G   A   Y   D   I   I   I   C   D   E   C   H   S   T   D   S   T   T
3019/301                                                    3049/311                                                    3079/321
ATC CTG GGC ATC GGC ACA GTC CTG GAC CAA GCG GAG ACG GCT GGA GCG CGA CTC GTC GTG CTC GCC ACC GCT ACG CCT CCG GGA TCG GTC
I   L   G   I   G   T   V   L   D   Q   A   E   T   A   G   A   R   L   V   V   L   A   T   A   T   P   P   G   S   V
3109/331                                                    3139/341                                                    3169/351
ACC GTG CCA CAT CCA AAC ATC GAG GAG GTG GCT CTG TCC AGC ACT GGA GAA ATC CCC TTT TAT GGC AAA GCC ATC CCC ATC GAG ACC ATC
T   V   P   H   P   N   I   E   E   V   A   L   S   S   T   G   E   I   P   F   Y   G   K   A   I   P   I   E   T   I
3199/361                                                    3229/371                                                    3259/381
AAG GGG GGG AGG CAC CTC ATT TTC TGC CAT TCC AAG AAG AAA TGT GAT GAG CTC GCC GCG AAG CTG TCC GGC CTC GGA CTC AAT GCT GTA
K   G   G   R   H   L   I   F   C   H   S   K   K   K   C   D   E   L   A   A   K   L   S   G   L   G   L   N   A   V
3289/391                                                    3319/401                                                    3349/411
GCA TAT TAC CGG GGC CTT GAT GTA TCC GTC ATA CCA ACT AGC GGA GAC GTC ATT GTC GTA GCA ACG GAC GCT CTA ATG ACG GGC TTT ACC
A   Y   Y   R   G   L   D   V   S   V   I   P   T   S   G   D   V   I   V   V   A   T   D   A   L   M   T   G   F   T
3379/421                                                    3409/431                                                    3439/441
GGC GAT TTC GAC TCA GTG ATC GAC TGC AAT ACA TGT GTC ACC CAG ACA GTC GAC TTC AGC CTG GAC CCG ACC TTC ACC ATT GAG ACG ACG
G   D   F   D   S   V   I   D   C   N   T   C   V   T   Q   T   V   D   F   S   L   D   P   T   F   T   I   E   T   T
3469/451                                                    3499/461                                                    3529/471
ACC GTG CCA CAA GAC GCG GTG TCA CGC TCG CAG CGG CGA GGC AGG ACT GGT AGG GGC AGG ATG GGC ATT TAC AGG TTT GTG ACT CCA GGA
T   V   P   Q   D   A   V   S   R   S   Q   R   R   G   R   T   G   R   G   R   M   G   I   Y   R   F   V   T   P   G
3559/481                                                    3589/491                                                    3619/501
GAA CGG CCC TCG GGC ATG TTC GAT TCC TCG GTT CTG TGC GAG TGC TAT GAC GCG GGC TGT GCT TGG TAC GAG CTC ACG CCC GCC GAG ACC
E   R   P   S   G   M   F   D   S   S   V   L   C   E   C   Y   D   A   G   C   A   W   Y   E   L   T   P   A   E   T
```

Fig. 24e

SEQ ID NO:41

```
    3649/511                                3679/521                                3709/531
    TCA GTT AGG TTG CGG GCT TAC CTA AAC ACA CCA GGG TTG CCC GTC TGC CAG GAC CAT CTG GAG TTC TGG GAG AGC GTC TTT ACA GGC CTC
    S   V   R   L   R   A   Y   L   N   T   P   G   L   P   V   C   Q   D   H   L   E   F   W   E   S   V   F   T   G   L
    3739/541                                3769/551                                3799/561
    ACC CAC ATA GAC GCC CAT TTC TTG TCC CAG ACT AAG CAG GCA GGA GAC AAC TTC CCC TAC CTG GTA GCA TAC CAG GCT ACG GTG TGC GCC
    T   H   I   D   A   H   F   L   S   Q   T   K   Q   A   G   D   N   F   P   Y   L   V   A   Y   Q   A   T   V   C   A
    3829/571                                3859/581                                3889/591
    AGG GCT CAG GCT CCA CCT CCA TCG TGG GAC CAA ATG TGG AAG TGT CTC ATA CGG CTA AAG CCT ACG CTG CAC GGG CCA ACG CCC CTG CTG
    R   A   Q   A   P   P   P   S   W   D   Q   M   W   K   C   L   I   R   L   K   P   T   L   H   G   P   T   P   L   L
    3919/601                                3949/611                                3979/621
    TAT AGG CTG GGA GCC GTT CAA AAC GAG GTT ACT ACC ACA CAC CCC ATA ACC AAA TAC ATC ATG GCA TGC ATG TCG GCT GAC CTG GAG GTC
    Y   R   L   G   A   V   Q   N   E   V   T   T   T   H   P   I   T   K   Y   I   M   A   C   M   S   A   D   L   E   V
NS3 4009/631  4A                              4039/641                                4069/651
    GTC ACG|AGC ACC TGG GTG CTG GTA GGC GGA GTC CTA GCA GCT CTG GCC GCG TAT TGC CTG ACA ACA GGC AGC GTG GTC ATT GTG GGC AGG
    V   T  |S   T   W   V   L   V   G   G   V   L   A   A   L   A   A   Y   C   L   T   T   G   S   V   V   I   V   G   R
    4099/661                                4129/671                                4159/681        4A      4B
    ATC ATC TTG TCC GGA AAG CCG GCC ATC ATT CCC GAC AGG GAA GTC CTT TAC CGG GAG TTC GAT GAG ATG GAA GAG TGC|GCC TCA CAC CTC
    I   I   L   S   G   K   P   A   I   I   P   D   R   E   V   L   Y   R   E   F   D   E   M   E   E   C  |A   S   H   L
    4189/691                                4219/701                                4249/711
    CCT TAC ATC GAA CAG GGA ATG CAG CTC GCC GAA CAA TTC AAA CAG AAG GCA ATC GGG TTG CTG CAA ACA GCC ACC AAG CAA GCG GAG GCT
    P   Y   I   E   Q   G   M   Q   L   A   E   Q   F   K   Q   K   A   I   G   L   L   Q   T   A   T   K   Q   A   E   A
    4279/721                                4309/731                                4339/741
    GCT GCT CCC GTG GTG GAA TCC AAG TGG CGG ACC CTC GAA GCC TTC TGG GCG AAG CAT ATG TGG AAT TTC ATC AGC GGG ATA CAA TAT TTA
    A   A   P   V   V   E   S   K   W   R   T   L   E   A   F   W   A   K   H   M   W   N   F   I   S   G   I   Q   Y   L
    4369/751                                4399/761                                4429/771
    GCA GGC TTG TCC ACT CTG CCT GGC AAC CCC GCG ATA GCA TCA CTG ATG GCA TTC ACA GCC TCT ATC ACC AGC CCG CTC ACC ACC CAA CAT
    A   G   L   S   T   L   P   G   N   P   A   I   A   S   L   M   A   F   T   A   S   I   T   S   P   L   T   T   Q   H
    4459/781                                4489/791                                4519/801
    ACC CTC CTG TTT AAC ATC CTG GGG GGA TGG GTG GCC GCC CAA CTT GCT CCT CCC AGC GCT GCT TCT GCT TTC GTA GGC GCC GGC ATC GCT
    T   L   L   F   N   I   L   G   G   W   V   A   A   Q   L   A   P   P   S   A   A   S   A   F   V   G   A   G   I   A
    4549/811                                4579/821                                4609/831
    GGA GCG GCT GTT GGC AGC ATA GGC CTT GGG AAG GTG CTT GTG GAT ATT TTG GCA GGT TAT GGA GCA GGG GTG GCA GGC GCG CTC GTG GCC
    G   A   A   V   G   S   I   G   L   G   K   V   L   V   D   I   L   A   G   Y   G   A   G   V   A   G   A   L   V   A
    4639/841                                4669/851                                4699/861
    TTT AAG GTC ATG AGC GGC GAG ATG CCC TCC ACC GAG GAC CTG GTT AAC CTA CTC CCT GCT ATC CTC TCC CCT GGC GCC CTA GTC GTC GGG
    F   K   V   M   S   G   E   M   P   S   T   E   D   L   V   N   L   L   P   A   I   L   S   P   G   A   L   V   V   G
    4729/871                                4759/881                                4789/891
    GTC GTG TGC GCA GCG ATA CTG CGT CGG CAC GTG GGC CCA GGG GAG GGG GCT GTG CAG TGG ATG AAC CGG CTG ATA GCG TTC GCT TCG CGG
    V   V   C   A   A   I   L   R   R   H   V   G   P   G   E   G   A   V   Q   W   M   N   R   L   I   A   F   A   S   R
    4819/901                                4849/911                                4879/921
    GGT AAC CAC GTC TCC CCC ACG CAC TAT GTG CCT GAG AGC GAC GCT GCA GCA CGT GTC ACT CAG ATC CTC TCT AGT CTT ACC ATC ACT CAG
    G   N   H   V   S   P   T   H   Y   V   P   E   S   D   A   A   A   R   V   T   Q   I   L   S   S   L   T   I   T   Q
    4909/931                                4939/941        4B      5A      4969/951
    CTG CTG AAG AGG CTT CAC CAG TGG ATC AAC GAG GAC TGC TCC ACG CCA TGC|TCC GGC TCG TGG CTA AGA GAT GTT TGG GAT TGG ATA TGC
    L   L   K   R   L   H   Q   W   I   N   E   D   C   S   T   P   C  |S   G   S   W   L   R   D   V   W   D   W   I   C
    4999/961                                5029/971                                5059/981
    ACG GTG TTG ACT GAT TTC AAG ACC TGG CTC CAG TCC AAG CTC CTG CCG CGA TTG CCG GGA GTC CCC TTC TTC TCA TGT CAA CGT GGG TAC
    T   V   L   T   D   F   K   T   W   L   Q   S   K   L   L   P   R   L   P   G   V   P   F   F   S   C   Q   R   G   Y
    5089/991                                5119/1001                               5149/1011
    AAG GGA GTC TGG CGG GGC GAC GGC ATC ATG CAA ACC ACC TGC CCA TGT GGA GCA CAG ATC ACC GGA CAT GTG AAA AAC GGT TCC ATG AGG
    K   G   V   W   R   G   D   G   I   M   Q   T   T   C   P   C   G   A   Q   I   T   G   H   V   K   N   G   S   M   R
```

*Fig. 24e-1*

SEQ ID NO:41

ATC GTG GGG CCT AGG ACC TGT AGT AAC ACG TGG CAT GGA ACA TTC CCC ATT AAC GCG TAC ACC ACG GGC CCC TGC ACG CCC TCC CCG GCG
I V G P R T C S N T W H G T F P I N A Y T T G P C T P S P A
5269/1051 5299/1061 5329/1071
CCA AAT TAT TCT AGG GCG CTG TGG CGG GTG GCT GCT GAG GAG TAC GTG GAG GTT ACG CGG GTG GGG GAT TTC CAC TAC GTG ACG GGC ATG
P N Y S R A L W R V A A E E Y V E V T R V G D F H Y V T G M
5359/1081 5389/1091 5419/1101
ACC ACT GAC AAC GTA AAG TGC CCG TGT CAG GTT CCG GCC CCC GAA TTC TTC ACA GAA GTG GAT GGG GTG CGG TTG CAC AGG TAC GCT CCA
T T D N V K C P C Q V P A P E F F T E V D G V R L H R Y A P
5449/1111 5479/1121 5509/1131
GCG TGC AAA CCC CTC CTA CGG GAG GAG GTC ACA TTC CTG GTC GGG CTC AAT CAA TAC CTG GTT GGG TCA CAG CTC CCA TGC GAG CCC GAA
A C K P L L R E E V T F L V G L N Q Y L V G S Q L P C E P E
5539/1141 5569/1151 5599/1161
CCG GAC GTA GCA GTG CTC ACT TCC ATG CTC ACC GAC CCC TCC CAC ATT ACG GCG GAG ACG GCT AAG CGT AGG CTG GCC AGG GGA TCT CCC
P D V A V L T S M L T D P S H I T A E T A K R R L A R G S P
5629/1171 5659/1181 5689/1191
CCC TCC TTG GCC AGC TCA TCA GCT AtC CAG CTG TCT GCG CCT TCC TTG AAG GCA ACA TGC ACT ACC CGT CAT GAC TCC CCG GAC GCT GAC
P S L A S S S A I Q L S A P S L K A T C T T R H D S P D A D
5719/1201 5749/1211 5779/1221
CTC ATC GAG GCC AAC CTC CTG TGG CGG CAG GAG ATG GGC GGG AAC ATC ACC CGC GTG GAG TCA GAA AAT AAG GTA GTA ATT TTG GAC TCT
L I E A N L L W R Q E M G G N I T R V E S E N K V V I L D S
5809/1231 5839/1241 5869/1251
TTC GAG CCG CTC CAA GCG GAG GAG GAT GAG AGG GAA GTA TCC GTT CCG GCG GAG ATC CTG CGG AGG TCC AGG AAA TTC CCT CGA GCG ATG
F E P L Q A E E D E R E V S V P A E I L R R S R K F P R A M
5899/1261 5929/1271 5959/1281
CCC ATA TGG GCA CGC CCG GAT TAC AAC CCT CCA CTG TTA GAG TCC TGG AAG GAC CCG GAC TAC GTC CCT CCA GTG GTA CAC GGG TGT CCA
P I W A R P D Y N P P L L E S W K D P D Y V P P V V H G C P
5989/1291 6019/1301 6049/1311
TTG CCG CCT GCC AAG GCC CCT CCG ATA CCA CCT CCA CGG AGG AAG AGG ACG GTT GTC CTG TCA GAA TCT ACC GTG TCT TCT GCC TTG GCG
L P P A K A P P I P P P R R K R T V V L S E S T V S S A L A
6079/1321 6109/1331 6139/1341
GAG CTC GCC ACA AAG ACC TTC GGC AGC TCC GAA TCG TCG GCC GTC GAC AGC GGC ACG GCA ACG GCC TCT CCT GAC CAG CCC TCC GAC GAC
E L A T K T F G S S E S S A V D S G T A T A S P D Q P S D D
6169/1351 6199/1361 6229/1371
GGC GAC GCG GGA TCC GAC GTT GAG TCG TAC TCC TCC ATG CCC CCC CTT GAG GGG GAG CCG GGG GAT CCC GAT CTC AGC GAC GGG TCT TGG
G D A G S D V E S Y S S M P P L E G E P G D P D L S D G S W
6259/1381 6289/1391 5A ←→ 5B 6319/1401
TCT ACC GTA AGC GAG GAG GCT AGT GAG GAC GTC GTC TGC TGC | TCG ATG TCC TAC ACA TGG ACA GGC GCC CTG ATC ACG CCA TGC GCT GCG
S T V S E E A S E D V V C C | S M S Y T W T G A L I T P C A A
6349/1411 6379/1421 6409/1431
GAG GAA ACC AAG CTG CCC ATC AAT GCA CTG AGC AAC TCT TTG CTC CGT CAC CAC AAC TTG GTC TAT GCT ACA ACA TCT CGC AGC GCA AGC
E E T K L P I N A L S N S L L R H H N L V Y A T T S R S A S
6439/1441 6469/1451 6499/1461
CTG CGG CAG AAG AAG GTC ACC TTT GAC AGA CTG CAG GTC CTG GAC GAC CAC TAC CGG GAC GTG CTC AAG GAG ATG AAG GCG AAG GCG TCC
L R Q K K V T F D R L Q V L D D H Y R D V L K E M K A K A S
6529/1471 6559/1481 6589/1491
ACA GTT AAG GCT AAA CTT CTA TCC GTG GAG GAA GCC TGT AAG CTG ACG CCC CCA CAT TCG GCC AGA TCT AAA TTT GGC TAT GGG GCA AAG
T V K A K L L S V E E A C K L T P P H S A R S K F G Y G A K
6619/1501 6649/1511 6679/1521
GAC GTC CGG AAC CTA TCC AGC AAG GCC GTT AAC CAC ATC CGC TCC GTG TGG AAG GAC TTG CTG GAA GAC ACT GAG ACA CCA ATT GAC ACC
D V R N L S S K A V N H I R S V W K D L L E D T E T P I D T
6709/1531 6739/1541 6769/1551
ACC ATC ATG GCA AAA AAT GAG GTT TTC TGC GTC CAA CCA GAG AAG GGG GGC CGC AAG CCA GCT CGC CTT ATC GTA TTC CCA GAT TTG GGG

*Fig. 24e-2*

SEQ ID NO:41

```
T   I   M   A   K   N   E   V   F   C   V   Q   P   E   K   G   G   R   K   P   A   R   L   I   V   F   P   D   L   G
6799/1561                               6829/1571                               6859/1581
GTT CGT GTG TGC GAG AAA ATG GCC CTT TAC GAT GTG GTC TCC ACC CTC CCT CAG GCC GTG ATG GGC TCT TCA TAC GGA TTC CAA TAC TCT
V   R   V   C   E   K   M   A   L   Y   D   V   V   S   T   L   P   Q   A   V   M   G   S   S   Y   G   F   Q   Y   S
6889/1591                               6919/1601                               6949/1611
CCT GGA CAG CGG GTC GAG TTC CTG GTG AAT GCC TGG AAA GCG AAG AAA TGC CCT ATG GGC TTC GCA TAT GAC ACC CGC TGT TTT GAC TCA
P   G   Q   R   V   E   F   L   V   N   A   W   K   A   K   K   C   P   M   G   F   A   Y   D   T   R   C   F   D   S
6979/1621                               7009/1631                               7039/1641
ACG GTC ACT GAG AAT GAC ATC CGT GTT GAG GAG TCA ATC TAC CAA TGT TGT GAC TTG GCC CCC GAA GCC AGA CAG GCC ATA AGG TCG CTC
T   V   T   E   N   D   I   R   V   E   E   S   I   Y   Q   C   C   D   L   A   P   E   A   R   Q   A   I   R   S   L
7069/1651                               7099/1661                               7129/1671
ACA GAG CGG CTT TAC ATC GGG GGC CCC CTG ACT AAT TCT AAA GGG CAG AAC TGC GGC TAT CGC CGG TGC CGC GCG AGC GGT GTA CTG ACG
T   E   R   L   Y   I   G   G   P   L   T   N   S   K   G   Q   N   C   G   Y   R   R   C   R   A   S   G   V   L   T
7159/1681                               7189/1691                               7219/1701
ACC AGC TGC GGT AAT ACC CTC ACA TGT TAC TTG AAG GCC GCT GCG GCC TGT CGA GCT GCG AAG CTC CAG GAC TGC ACG ATG CTC GTA TGC
T   S   C   G   N   T   L   T   C   Y   L   K   A   A   A   A   C   R   A   A   K   L   Q   D   C   T   M   L   V   C
7249/1711                               7279/1721                               7309/1731
GGA GAC GAC CTT GTC GTT ATC TGT GAA AGC GCG GGG ACC CAA GAG GAC GAG GCG AGC CTA CGG GCC TTC ACG GAG GCT ATG ACT AGA TAC
G   D   D   L   V   V   I   C   E   S   A   G   T   Q   E   D   E   A   S   L   R   A   F   T   E   A   M   T   R   Y
7339/1741                               7369/1751                               7399/1761
TCT GCC CCC CCT GGG GAC CCG CCC AAA CCA GAA TAC GAC TTG GAG TTG ATA ACA TCA TGC TCC TCC AAT GTG TCA GTC GCG CAC GAT GCA
S   A   P   P   G   D   P   P   K   P   E   Y   D   L   E   L   I   T   S   C   S   S   N   V   S   V   A   H   D   A
7429/1771                               7459/1781                               7489/1791
TCT GGC AAA AGG GTG TAC TAT CTC ACC CGT GAC CCC ACC ACC CCC CTT GCG CGG GCT GCG TGG GAG ACA GCT AGA CAC ACT CCA GTC AAT
S   G   K   R   V   Y   Y   L   T   R   D   P   T   T   P   L   A   R   A   A   W   E   T   A   R   H   T   P   V   N
7519/1801                               7549/1811                               7579/1821
TCC TGG CTA GGC AAC ATC ATC ATG TAT GCG CCC ACC TTG TGG GCA AGG ATG ATC CTG ATG ACT CAT TTC TTC TCC ATC CTT CTA GCT CAG
S   W   L   G   N   I   I   M   Y   A   P   T   L   W   A   R   M   I   L   M   T   H   F   F   S   I   L   L   A   Q
7609/1831                               7639/1841                               7669/1851
GAA CAA CTT GAA AAA GCC CTA GAT TGT CAG ATC TAC GGG GCC TGT TAC TCC ATT GAG CCA CTT GAC CTA CCT CAG ATC ATT CAA CGA CTC
E   Q   L   E   K   A   L   D   C   Q   I   Y   G   A   C   Y   S   I   E   P   L   D   L   P   Q   I   I   Q   R   L
7699/1861                               7729/1871                               7759/1881
CAT GGC CTT AGC GCA TTT TCA CTC CAT AGT TAC TCT CCA GGT GAG ATC AAT AGG GTG GCT TCA TGC CTC AGG AAA CTT GGG GTA CCG CCC
H   G   L   S   A   F   S   L   H   S   Y   S   P   G   E   I   N   R   V   A   S   C   L   R   K   L   G   V   P   P
7789/1891                               7819/1901                               7849/1911
TTG CGA GTC TGG AGA CAT CGG GCC AGA AGT GTC CGC GCT AGG CTA CTG TCC CAG GGG GGG AGG GCT GCC ACT TGT GGC AAG TAC CTC TTC
L   R   V   W   R   H   R   A   R   S   V   R   A   R   L   L   S   Q   G   G   R   A   A   T   C   G   K   Y   L   F
7879/1921                               7909/1931                               7939/1941
AAC TGG GCA GTA AGG ACC AAG CTC AAA CTC ACT CCA ATC CCG GCT GCG TCC CAG TTG GAT TTA TCC AGC TGG TTC GTT GCT GGT TAC AGC
N   W   A   V   R   T   K   L   K   L   T   P   I   P   A   A   S   Q   L   D   L   S   S   W   F   V   A   G   Y   S
7969/1951                               7999/1961                               8029/1971
GGG GGA GAC ATA TAT CAC AGC CTG TCT CGT GCC CGA CCC CGC TGG TTC ATG TGG TGC CTA CTC CTA CTT TCT GTA GGG GTA GGC ATC TAT
G   G   D   I   Y   H   S   L   S   R   A   R   P   R   W   F   M   W   C   L   L   L   L   S   V   G   V   G   I   Y
8059/1981  5B <---|---> 3'NTR               8089/1991                               8119/2001
CTA CTC CCC AAC CGA|TGA ACG GGG AGC TAA ACA CTC CAG GCC AAT AGG CCA TCC TGT TTT TTT CCC TTT TTT TTT TTC TTT TTT TTT TTT
L   L   P   N   R   *   T   G   S   *   T   L   Q   A   N   R   P   S   C   F   F   P   F   F   F   F   F   F   F   F
8149/2011                               8179/2021                               8209/2031
TTT TTT TTT TTT TTT TTT TTT TCT CCT TTT TTT TTC CTC TTT TTT TCC TTT TCT TTC CTT TGG TGG CTC CAT CTT AGC CCT AGT CAC GGC
F   F   F   F   F   F   F   S   P   F   F   F   L   F   F   S   F   S   F   L   W   W   L   H   L   S   P   S   H   G
8239/2041                               8269/2051                               8299/2061
TAG CTG TGA AAG GTC CGT GAG CCG CTT GAC TGC AGA GAG TGC TGA TAC TGG CCT CTC TGC AGA TCA AGT |
*   L   *   K   V   R   E   P   L   D   C   R   E   C   *   Y   W   P   L   C   R   S   S   |      END
                                                                                     3'NTR <-
```

Fig. 24e-3

REPLICATION COMPETENT HEPATITIS C VIRUS AND METHODS OF USE

CONTINUING APPLICATION DATA

This application claims priority to U.S. patent application Ser. No. 10/259,275, filed Sep. 27, 2002 now U.S. Pat. No. 6,921,634, which is a Continuation-In-Part of U.S. patent application Ser. No. 09/747,419, filed Dec. 23, 2000 now abanoned, which claims the benefit of U.S. Provisional Application Ser. No. 60/171,909, filed Dec. 23, 1999, each of which are incorporated by reference herein. This application also claims the benefit of U.S. Provisional Applications Ser. No. 60/325,236, filed Sep. 27, 2001, and Ser. No. 60/338,123, filed Nov. 13, 2001, each of which are incorporated by reference herein.

GOVERNMENT FUNDING

The present invention was made with government support under Grant No. U19-A140035, awarded by the National Institute of Allergy and Infectious Diseases. The Government has certain rights in this invention.

BACKGROUND

Hepatitis C virus is the most common cause of chronic viral hepatitis within the United States, infecting approximately 4 million Americans and responsible for the deaths of 8,000-10,000 persons annually due to progressive hepatic fibrosis leading to cirrhosis and/or the development of hepatocellular carcinoma. Hepatitis C virus is a single stranded, positive-sense RNA virus with a genome length of approximately 9.6 kb. It is currently classified within a separate genus of the flavivirus family, the genus *Hepacivirus*. The epatitis C virus genome contains a single large open reading frame (ORF) that follows a 5' non-translated RNA of approximately 342 bases containing an internal ribosome entry segment (IRES) directing cap-independent initiation of viral translation. The large ORF encodes a polyprotein which undergoes post-translational cleavage, under control of cellular and viral proteinases. This yields a series of structural proteins which include a core or nucleocapsid protein, two envelope glycoproteins, E1 and E2, and at least six nonstructural replicative proteins. These include NS2 (which with the adjacent NS3 sequence demonstrates cis-active metalloproteinase activity at the NS2/NS3 cleavage site), NS3 (a serine proteinase/NTPase/RNA helicase), NS4A (serine proteinase accessory factor), NS4B, NS5A, and NS5B (RNA-dependent RNA polymerase).

With the exception of the 5' non-translated RNA, there is substantial genetic heterogeneity among different stains of hepatitis C virus. Phylogenetic analyses have led to the classification of epatitis C virus strains into a series of genetically distinct "genotypes," each of which contains a group of genetically related viruses. The genetic distance between some of these genotypes is large enough to suggest that there may be biologically significant serotypic differences as well. There is little understanding of the extent to which infection with a virus of any one genotype might confer protection against viruses of a different genotype.

Several types of human interferon have proven effective in the treatment of infection by hepatitis C virus, either alone as monotherapy, or in combination with ribavirin. However, treatment with interferon-ribavirin carries a high risk of treatment failure, either primary failure of virus elimination, or relapse of the infection upon cessation of therapy. Moreover, these therapeutic agents are relatively toxic and are associated with a high frequency of adverse reactions. The development of better (more effective and safer) antiviral agents capable of suppressing or eliminating hepatitis C virus infection has been hindered by the fact that this virus replicates with very low efficiency, or not at all, in cultured cells. The absence of a highly permissive cell culture system that is capable of supporting robust replication of the virus has prevented the development of high throughput antiviral screens for use in the development of inhibitors of viral replication, and has delayed the investigation of the virus and relevant aspects of its molecular and cellular biology. It has also stymied efforts at vaccine development and the immunologic characterization of the virus, the human response to hepatitis C virus, and the diseases associated with infection. The development of infectious molecular cDNA clones of the viral genome has done little to solve this problem, since virus can be rescued from the RNA transcribed from such clones only by its injection into the liver of a living chimpanzee or other susceptible primate.

SUMMARY OF THE INVENTION

The present invention provides methods for identifying a compound that inhibits replication of an HCV RNA. The methods include contacting a cell that contains a replication competent HCV RNA with a compound. The replication competent HCV RNA includes a heterologous polynucleotide that contains a first coding sequence encoding a transactivator. The transactivator may inlcude an amino acid sequence having at least about 70% identity with the amino acid sequence SEQ ID NO:19 or amino acids 4-89 of SEQ ID NO:21. The cells are incubated under conditions where the replication competent HCV RNA replicates in the absence of the compound, and the replication competent HCV RNA is detected. A decrease the replication competent HCV RNA in the cell contacted with the compound compared to the replication competent HCV RNA in a cell not contacted with the compound indicates the compound inhibits replication of the replication competent HCV RNA.

The HCV RNA may include a second coding sequence encoding a hepatitis C virus polyprotein and a 3' non-translated RNA, and the heterologous polynucleotide may be present in the 3' non-translated RNA or 5' of the second coding sequence. Alternatively, the HCV RNA may include a 3' non-translated RNA and a second coding sequence encoding a subgenomic hepatitis C virus polyprotein, and the heterologous polynucleotide may be present in the 3' non-translated RNA or 5' of the second coding sequence.

The heterologous polynucleotide may include a second coding sequence encoding a selectable marker, and the first coding sequence and the second coding sequence together encode a fusion polypeptide. The heterologous polynucleotide may further include a third coding sequence encoding a cis-active proteinase present between the first coding sequence encoding the transactivator and the second coding sequence encoding the selectable marker. The first coding sequence, the third coding sequence, and the second coding sequence together encode a fusion polypeptide.

The cell may include a polynucleotide that includes a transactivated coding sequence encoding a detectable marker and an operator sequence operably linked to the transactivated coding sequence. The transactivator interacts with the operator sequence and alters expression of the transactivated coding sequence. Detecting the replication competent HCV RNA in the cell includes detecting the detectable marker encoded by the transactivated coding sequence. The present invention is also directed to the cell.

The present invention also provides a method for selecting a replication competent HCV RNA. The method includes incubating a vertebrate cell in the presence of a selecting agent, for instance, an antibiotic. The cell includes an HCV RNA that includes a first coding sequence encoding a hepatitis C virus polyprotein, and a heterologous polynucleotide, and the heterologous polynucleotide includes a second coding sequence encoding a selectable marker that confers resistance to the selecting agent. The selecting agent inhibits replication of a cell that does not express the selectable marker. A cell that replicates in the presence of the selecting agent is detected, and the presence of such a cell indicates the HCV RNA is replication competent.

The method may further include obtaining a virus particle produced by the first cell and exposing a second vertebrate cell to the isolated virus particle and incubating the second vertebrate cell in the presence of the selecting agent. A second cell that replicates in the presence of the selecting agent is detected, wherein the presence of such a cell indicates the HCV RNA present in the first cell produces an infectious virus particle.

The HCV RNA may include a 3' non-translated RNA, and the heterologous polynucleotide may be present in the 3' non-translated RNA or 5' of the first coding sequence.

The present invention also provides a method for detecting a replication competent HCV RNA. The method includes incubating a vertebrate cell comprising an HCV RNA. The HCV RNA includes a first coding sequence encoding a hepatitis C virus polyprotein, or a subgenomic hepatitis C virus polyprotein, and a heterologous polynucleotide includes a second coding sequence encoding a transactivator. The cell includes a transactivated coding region and an operator sequence operably linked to the transactivated coding region, where the transactivated coding region encodes a detectable marker and the transactivator alters transcription of the transactivated coding region. The detectable marker is detected, and the presence of the detectable marker indicates the cell contains a replication competent HCV RNA.

The heterologous polynucleotide may further include a third coding sequence encoding a selectable marker, and the second coding sequence and the third coding sequence together encode a fusion polypeptide. Alternatively, the heterologous polynucleotide may further include a fourth coding sequence encoding a cis-active proteinase present between the second coding sequence encoding the transactivator and the third coding sequence encoding the selectable marker, and the second coding sequence, the fourth coding sequence, and the third coding sequence together encode a fusion polypeptide.

The present invention further provides replication competent HCV polynucleotides that include a first coding sequence encoding a subgenomic hepatitis C virus polyprotein, and a heterologous polynucleotide containing a second coding sequence encoding a transactivator, wherein the heterologous polynucleotide is located 5' of the first coding sequence. In another aspect, the present invention provides a replication competent HCV polynucleotide containing a first coding sequence encoding a hepatitis C virus polyprotein, and a heterologous polynucleotide.

The present invention also provides kits. The kits include a replication competent HCV polynucleotide containing a heterologous polynucleotide that has a first coding sequence encoding a transactivator, and a vertebrate cell that includes a polynucleotide containing a transactivated coding sequence encoding a detectable marker and an operator sequence operably linked to the transactivated coding sequence. The transactivator interacts with the operator sequence and alters expression of the transactivated coding sequence.

Definitions

As used herein, the term "HCV" refers to a hepatitis C virus, e.g., a viral particle, or a polynucleotide that includes a hepatitis C viral genome or a portion thereof. Preferably, the polynucleotide is RNA.

As used herein, the term "replication competent" refers to an HCV RNA that replicates, e.g., HCV nucleic acid is synthesized, for instance synthesis of the negative-sense strand, in vitro or in vivo. As used herein, the term "replicates in vitro" indicates the HCV RNA replicates in a cell that is growing in culture. The cultured cell can be one that has been selected to grow in culture, including, for instance, an immortalized or a transformed cell. Alternatively, the cultured cell can be one that has been explanted from an animal. "Replicates in vivo" indicates the HCV RNA replicates in a cell within the body of an animal, for instance a primate (including a chimpanzee) or a human. In some aspects of the present invention, replication in a cell can include the production of infectious viral particles, i.e., viral particles that can infect a cell and result in the production of more infectious viral particles.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences and/or non-translated regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. The term "heterologous polynucleotide" refers to a polynucleotide that has been inserted into the HCV genome, typically by using recombinant DNA techniques, and is not naturally occurring.

The terms "3' non-translated RNA," "3' non-translated region," and "3' untranslated region" are used interchangeably, and are terms of art. The term refers to the nucleotides that are at the 3' end of the positive-sense strand of the HCV polynucleotide, the complement thereof (i.e., the negative-sense RNA), and the corresponding DNA sequences of the positive-sense and the negative-sense RNA sequences. The 3' non-translated RNA includes, from 5' to 3', nucleotides of variable length and sequence (referred to as the variable region), a poly-pyrimidine tract (the poly U-UC region), and a highly conserved sequence of about 100 nucleotides (the conserved region) (see FIG. 2). The variable region begins at the first nucleotide following the stop codon of the NS5B coding region, and ends immediately before the nucleotides of the poly U-UC region. The poly U-UC region is a stretch of predominantly U residues, CU residues, or C(U)n-repeats. When the nucleotide sequence of a variable region is compared between members of the same genotype, there is typically a great deal of similarity; however, there is typically very little similarity in the nucleotide sequence of the variable regions between members of different genotypes (see, for instance, Yamada et al., *Virology,* 223, 255-261 (1996)). The length of the variable region can vary.

The terms “5' non-translated RNA,” “5' non-translated region,” “5' untranslated region” and “5' noncoding region” are used interchangeably, and are terms of art (see Bukh et al., Proc. Nat. Acad. Sci. USA, 89, 4942-4946 (1992)). The term refers to the nucleotides that are at the 5' end of the positive-sense strand of the HCV polynucleotide, the complement thereof (i.e., the negative-sense RNA), and the corresponding DNA sequences of the positive-sense and the negative-sense RNA sequences. The 5' NTR includes about 341 nucleotides. The last nucleotide of the 5' NTR is immediately upstream and adjacent to the first nucleotide of the coding sequence encoding the hepatitis C virus polyprotein.

A “coding region” or “coding sequence” is a nucleotide region that encodes a polypeptide and, when placed under the control of appropriate regulatory sequences, expresses the encoded polypeptide. The boundaries of a coding region are generally determined by a translation start codon at its 5' end and a translation stop codon at its 3' end. A coding region can encode one or more polypeptides. For instance, a coding region can encode a polypeptide that is subsequently processed into several polypeptides. A regulatory sequence or regulatory region is a nucleotide sequence that regulates expression of a coding region to which it is operably linked. Nonlimiting examples of regulatory sequences include promoters, transcription initiation sites, translation start sites, internal ribosome entry sites, translation stop sites, and terminators. “Operably linked” refers to a juxtaposition wherein the components so described are in a relationship permitting them to function in their intended manner. A regulatory sequence is “operably linked” to a coding region when it is joined in such a way that expression of the coding region is achieved under conditions compatible with the regulatory sequence.

As used herein the term “marker” refers to a molecule, for instance, a polypeptide. A “selectable marker” is a polypeptide that inhibits a compound, for instance an antibiotic, from preventing cell growth. A “detectable marker” is a polypeptide that can be detected. A marker can be both selectable and detectable.

“Polypeptide” as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

As used herein a “fusion polypeptide” refers to a polypeptide encoded by a coding region that is made up of two coding regions that have been joined together in frame, typically using recombinant DNA techniques, such that the two coding regions now encode a single polypeptide.

As used herein, a “transactivator” is a polypeptide that affects in trans the expression of a transactivated coding region. A “transactivated coding region” is a coding region to which is operably linked an operator sequence. As used herein, the term “operator sequence” is a type of regulatory region and includes a polynucleotide with which a transactivator can interact to alter expression of an operably linked transactivated coding region.

An “isolated” virus means a virus that has been removed from its natural environment. For instance, a virus that has been removed from an animal is an isolated virus. Another example of an isolated virus is one that has been removed from the cultured cells in which the virus was propagated, for instance by removing media containing the virus. A virus of this invention may be purified, i.e., essentially free from any other associated cellular products or other impurities. The term “purified” is defined as encompassing preparations of a virus having less than about 50%, more preferable less than about 25% contaminating associated cellular products or other impurities.

As used herein, the phrase “selecting a replication competent HCV RNA” refers to identifying a cell that includes a replication competent HCV RNA under conditions that prevent the replication of cells that do not include a replication competent HCV RNA.

A “hepatitis C virus polyprotein” refers to a polypeptide that is post-translationally cleaved to yield more than one polypeptide. Unless noted otherwise, a hepatitis C virus polyprotein yields the polypeptides core (also referred to as nucleocapsid), E1, E2, P7, NS2, NS3, NS4A, NS4B, NS5A, and NS5B. Optionally, a hepatitis C virus polyprotein also yields protein F (see Xu et al., *EMBO J.,* 20, 3840-3848 (2001).

A “subgenomic” HCV polynucleotide, preferably an RNA, refers to an HCV RNA that does not include the entire HCV genome. A subgenomic HCV RNA typically includes a coding region encoding only a portion of a hepatitis C virus polyprotein, e.g., the nucleotides encoding one or more polypeptide is not present. Such a hepatitis C virus polyprotein is referred to as a “subgenomic hepatitis C virus polyprotein.” In some aspects of the invention, an HCV RNA contains a subgenomic hepatitis C virus polyprotein that does not include polypeptides encoded by the 5' end of the hepatitis C virus polyprotein. Thus, a subgenomic hepatitis C virus polyprotein may encode the polypeptides NS3, NS4A, NS4B, NS5A, and NS5B; NS2, NS3, NS4A, NS4B, NS5A, and NS5B; P7, NS2, NS3, NS4A, NS4B, NS5A, and NS5B; E2, P7, NS2, NS3, NS4A, NS4B, NS5A, and NS5B; or E1, E2, P7, NS2, NS3, NS4A, NS4B, NS5A, and NS5B. In other aspects of the invention, an HCV RNA contains a subgenomic hepatitis C virus polyprotein that does not include polypeptides persent in an internal portion of a hepatitis C virus polyprotein. Thus, a subgenomic hepatitis C virus polyprotein may encode, for instance, the polypeptides NS3, NS4A, NS4B, and NS5B. Replication of a subgenomic HCV RNA in a cell includes the synthesis of viral nucleic acid, for instance synthesis of the negative-sense strand, and typically does not include the production of infectious viral particles.

Unless otherwise specified, “a,” “an,” “the,” and “at least one” are used interchangeably and mean one or more than one.

BRIEF DESCRIPTION OF THE FIGURES

FIG. 12. Nucleotide sequence of HIVSEAP (SEQ ID NO:18). The HIV long terminal repeat (LTR) is depicted at nucleotides 1-719, and secretory alkaline phosphatase is encoded by the nucleotides 748-2239.

FIG. 15. Alignment of the amino acid sequences of the NS5A proteins encoded by NNeo/3-5B and Neo/3-5B. The ISDR is shaded, with the 4-amino-acid SSYN insertion in NNeo/3-5B shown in boldface type and enclosed in a box. Arrows indicate the location of single-base substitutions and insertions and the large 47-amino-acid deletion that has been shown previously to enhance the replication capacity of BNeo/3-5B (Blight et al., *Science,* 290, 1972-1974 (2000), Krieger et al., *J. Virol.,* 75, 4614-4624 (2001), Lohmann et al., *J. Virol.,* 75, 1437-1449 (2002)). The asterisk indicates the S20051 mutation.

FIG. 24. Nucleotide sequences of constructs described in FIG. 17. The nucleotide sequence of the 5' NTR is disclosed at SEQ ID NO:35, the nucleotide sequence of the ΔCtat2ANeo is disclosed at SEQ ID NO:36, the nucleotide sequence of the tat2ANeo is disclosed at SEQ ID NO:37, the nucleotide sequence of the EMCV IRES located between the two cistrons is disclosed at SEQ ID NO:38. The nucleotide sequence encoding hepatitis C virus polyprotein derived from HCV-N is disclosed at SEQ ID NO:39, and the amino acid sequence (SEQ ID NO:40) of the polyprotein encoded by the nucleotides 2077-11121 is also shown. The nucleotide sequence encoding hepatitis C virus polyprotein derived from Con1 is disclosed at SEQ ID NO:41, and the amino acid sequence (SEQ ID NO:42) of the polyprotein encoded by the nucleotides 2119-8073 is also shown. The nucleotide sequence of the 3NTR that is present in those replicons having an hepatitis C virus polyprotein derived from HCV-N is disclosed at nucleotides 11122-11349 of SEQ ID NO:39. The nucleotide sequence of the 3'NTR that is present in those replicons having an hepatitis C virus polyprotein derived from Con1 is disclosed at nucleotides 8074-8307 of SEQ ID NO:41.

DETAILED DESCRIPTION OF THE INVENTION

Hepatitis C Virus

Figure 1:
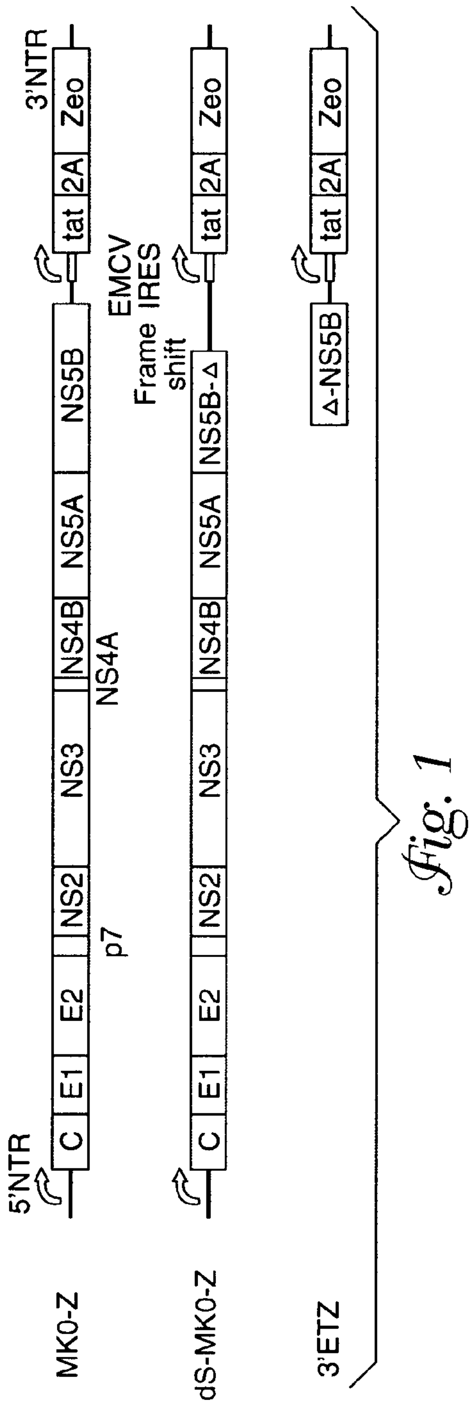
FIG. 1. Genomic organization of MK0-Z, ds-MK0-Z, and 3'ETZ. The rightward facing arrows, location and direction of transcription initiation; 5'NTR, 5' non-translated RNA; C, core protein; E1, envelope protein 1; E2, envelope protein 2; E2-p7, a polypeptide of about 7 kDa; NS2, non-structural protein 2; NS3, non-structural protein 3; NS4A, non-structural protein 4A; NS4B, non-structural protein 4B; NS5A, non-structural protein 5A; NS5B, non-structural protein 5B; EMCV IRES, encephalomyocarditis virus internal ribosome entry site; tat, portion of the human immunodeficiency virus I (HIV I) tat protein; 2A, 2A proteinase of foot-and-mouth disease virus (FMDV); Zeo, polypeptide encoding resistance to phleomycin; 3'NTR, 3' non-translated RNA.

The present invention provides HCV polynucleotides, preferably RNA, that include a heterologous polynucleotide. In some aspects of the invention, the HCV includes a coding sequence encoding an hepatitis C virus polyprotein, and in other aspects the HCV includes a coding region encoding a portion of an HCV polyprotein. Preferably, the HCV are replication competent. Preferably the HCV are isolated, more preferably, purified. Unless otherwise noted, HCV polynucleotide, and other terms that refer to all or a part of an HCV polynucleotide (including, for instance, "3' non-translated RNA") include an RNA sequence of the positive-sense genome RNA, the complement thereof (i.e., the negative-sense RNA), and the DNA sequences corresponding to the positive-sense and the negative-sense RNA sequences.

It is expected that HCV polynucleotides from different sources, including molecularly cloned laboratory strains, for instance cDNA clones of HCV, and clinical isolates can be used in the methods described below to yield replication competent HCV of the present invention. Examples of molecularly cloned laboratory strains include the HCV that is encoded by pCV-H77C (Yanagi et al., *Proc. Natl. Acad. Sci., USA,* 94, 8738-8743 (1997)), and pHCV-N as modified by Beard et al. (*Hepatol.,* 30, 316-324 (1999)). Clinical isolates can be from a source of infectious HCV, including tissue samples, for instance from blood, plasma, serum, liver biopsy, or leukocytes, from an infected animal, including a human or a primate.

It is expected that the HCV polynucleotides of the present invention are not limited to a specific genotype. For instance, an HCV of the present invention can be genotype 1a, 1b, 1c, 2a, 2b, 2c, 3a, 3b, 4, 5a, or 6a (as defined by Simmons, *Hepatology,* 21, 570-583 (1995)). It is also expected that HCV used in the methods described below can be prepared by recombinant, enzymatic, or chemical techniques. In some aspects, an HCV that is modified as described herein to include a heterologous polynucleotide is able to replicate in vivo, preferably in a chimpanzee, prior to inserting the heterologous polypeptide. Methods for determining whether an HCV is able to replicate in a chimpanzee are described herein.

In some aspects of the present invention, the nucleotide sequence of an HCV polynucleotide used in the methods of the present invention is similar to the nucleotide sequence of an HCV, preferable an HCV of genotype 1a, 1b, 2a, or 2b. An example of an HCV of genotype 1a is present at Genbank accession AF011751. Examples of an HCV of genotype 1b are present at Genbank accession AF139594, Genbank accession AJ238799, or the sequences present at FIG. 24. An example of an HCV of genotype 2a is present at Genbank accession AF238481. An example of an HCV of genotype 2b is present at Genbank accession AB030907. The similarity is referred to as structural similarity and may be determined by aligning the residues of the two polynucleotides (i.e., the nucleotide sequence of a candidate nucleotide sequence and the nucleotide sequence of HCV, or a portion thereof) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate nucleotide sequence is the nucleotide sequence being compared to the nucleotide sequence of the HCV, or a portion thereof. Two nucleotide sequences can be compared using standard software algorithms. Preferably, two nucleotide sequences are compared using the Blastn program of the BLAST 2 search algorithm, as described by Tatusova, et al. (*FEMS Microbiol Left* 1999, 174:247-250), and available at ncbi.nlm.nih.gov/gorf/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with the coding region of an HCV, or a portion thereof, of at least about 66%, at least about 77%, at least about 91%, at least about 94%, at least about 96%, or at least about 99% identity.

Specific mutations increasing the replicative capacity of HCV polynucleotides have been characterized for HCV 1b subgenomic RNA replicons (see, for instance, Blight et al., *Science,* 290, 1972-1975 (2000); Lohmann et al., "Adaptation of selectable HCV replicon to a human hepatoma cell line," Abstract P038, 7th International Meeting on Hepatitis C virus and Related viruses (Molecular Virology and Pathogenesis), The Marriott resort Hotel, Gold coast, Queensland, Australia, Dec. 3-7 (2000); and Guo et al., "Identification of a novel RNA species in cell lines expressing HCV subgenomic replicons," Abstract P045, 7th International Meeting on Hepatitis C virus and Related viruses (Molecular Virology and Pathogenesis), The Marriott resort Hotel, Gold coast, Queensland, Australia, Dec. 3-7 (2000)). Such mutations are referred to herein as "cell culture adaptive mutations." It is expected that the introduction of these individual mutations may enhance the replication capacity of an HCV of some aspects of the present invention. The approximate locations and types of some mutations are shown in Table 1. The precise location of these cell culture adaptive mutations can vary between members of different genotypes, and between members of the same genotype. For instance, with mutations 2442 and 2884 listed in Table 1, in HCV genotype 1a the locations of these mutations are 2443 and 2885, respectively. The location of a mutation introduced into an HCV of the present invention to enhance replication is expected to be within 4 amino acids, preferably within 3 amino acids, more preferably within 2 amino acids, most preferably within 1 amino acid of the positions listed in Table 1. Another example of an adaptive mutation of HCV-N is the insertion of amino acids SSYN present at position 2220-2223.

TABLE 1

Adaptive mutations in an HCV of genotype 1b.

| Amino acid position[1] | Mutation[2] |
|---|---|
| 1202 | E to G |
| 1281 | T to I |
| 1283 | R to G |
| 1383 | E to A |
| 1577 | K to R |
| 1609 | K to E |
| 1757 | L to I |
| 1936 | P to S |
| 2163 | E to G |
| 2177 | D to H, or D to N |
| 2189 | R to G |
| 2196 | P to S |
| 2197 | S to P, or S to C |
| 2199 | A to S, or A to T |
| 2201 | deletion of S |
| 2204[3] | S to I |
| 2207-2254 | Deletion of 48 amino acids |
| 2330 | K to E |
| 2442 | I to V |
| 2884[4] | R to G |

[1]Amino acid position refers to amino acid number where the first amino acid is the first amino acid of the polyprotein expressed by the HCV at Genbank Accession number AJ238799.
[2]Amino acids are listed in the single letter code. The first amino acid is the wild-type amino acid, and the second amino acid is the residue present in the mutant.
[3]Amino acid 2205 in the polyprotein expressed by the HCV at Genbank Accession number AF139594.
[4]Amino acid 2889 in the polyprotein expressed by the HCV at Genbank Accession number AF139594.

Cell culture adaptive mutations can be introduced into an HCV polynucleotide of the present invention by mutagenesis of the nucleotide sequence of the HCV in the form of plasmid DNA. Methods for targeted mutagenesis of nucleotide sequences are known to the art, and include, for instance, PCR mutagenesis.

In some aspects of the invention, the heterologous polynucleotide is present in the HCV 3' non-translated RNA, for instance, in the variable region of the 3' non-translated RNA. In some aspects of the invention, the heterologous polynucleotide is inserted into the variable region such that the variable region is not removed. Alternatively, deletions of the variable region can be made, in whole or in part, and replaced with the heterologous polynucleotide. Preferably, in some aspects of the invention, when the HCV has the genotype 1a, more preferably, the strain H77C, the heterologous polynucleotide is inserted in the variable region between nucleotides 5 and 6 of the sequence 5'CUCUUAAGC 3', where the sequence shown corresponds to the positive-strand.

A heterologous polynucleotide can include a non-coding region and/or a coding region, preferably a coding region. The coding region can encode a polypeptide including, for instance, a marker, including a detectable marker and/or a selectable marker. Examples of detectable markers include secretory alkaline phosphatase, green fluorescent protein, and molecules that can be detected by antibody. Examples of selectable markers include molecules that confer resistance to antibiotics, including the antibiotics kanamycin, ampicillin, chloramphenicol, tetracycline, neomycin, and formulations of phleomycin D1 including, for example, the formulation available under the trade-name ZEOCIN (Invitrogen, Carlsbad, Calif.). Other examples of polypeptides that can be encoded by the coding region include a transactivator, and/or a fusion polypeptide. Preferably, when the polypeptide is a fusion polypeptide, the coding region includes nucleotides encoding a marker, more preferably, nucleotides encoding a fusion between a transactivator and a marker. Optionally, the coding region can encode an immunogenic polypeptide. When the heterologous polynucleotide includes a coding region, the HCV is typically dicistronic, i.e., the coding region of the heterologous polynucleotide and the coding region encoding the HCV polyprotein or portion thereof are separate.

An "immunogenic polypeptide" refers to a polypeptide which elicits an immunological response in an animal. An immunological response to a polypeptide is the development in a subject of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed specifically to an epitope or epitopes of the polypeptide fragment.

A transactivator is a polypeptide that affects in trans the expression of a coding region, preferably a coding region integrated in the genomic DNA of a cell. Such coding regions are referred to herein as "transactivated coding regions." The cells containing transactivated coding regions are described in detail herein in the section "Methods of use." Transactivators useful in the present invention include those that can interact with a regulatory region, preferably an operator sequence, that is operably linked to a transactivated coding region. As used herein, the term "transactivator" includes polypeptides that interact with an operator sequence and either prevent transcription from initiating at, activate transcription initiation from, or stabilize a transcript from, a transactivated coding region operably linked to the operator sequence. Examples of useful transactivators include the HIV tat polypeptide (see, for example, the polypeptide SEQ ID NO:19, MEPVDPRLEPWKHPGSQP-KTACTNCYCKKCCFHCQVCFITKALGI-SYGRKKRRQRRRAHQNSQTHQASL-SKQPTSQPRGDPTGPKE which is encoded by nucleotides 5377 to 5591 and 7925 to 7970 of Genbank accession number AF033819), and MEPVDPRLEPWKHPGSQPK-TACTNCYCKKCCFHCQVCFITKALGI-SYGRKKRRQRRRPPQGSQTHQVSL-SKQPTSQSRGDPTGPKE, the polypeptide present at amino acids 4-89 of SEQ ID NO:21. The HIV tat polypeptide interacts with the HIV long terminal repeat. Other useful transactivators include human T cell leukemia virus tax polypeptide (which binds to the operator sequence tax response element, Fujisawa et al., *J. Virol.,* 65, 4525-4528 (1991)), and transactivating polypeptides encoded by spumaviruses in the region between env and the LTR, such as the bel-1 polypeptide in the case of human foamy virus (which binds the U3 domain of these viruses, Rethwilm et al., *Proc. Natl. Acad. Sci. USA,* 88, 941-945 (1991)). Alternatively, a post-transcriptional transactivator, such as HIV rev, can be used. HIV rev binds to a 234 nucleotide RNA sequence in the env gene (the rev-response element, or RRE) of HIV (Hadzopolou-Cladaras et al., *J. Virol.,* 63, 1265-1274 (1989)).

Other transactivators that can be used are those having similarity with the amino acid sequence of SEQ ID NO:19 or amino acids 4-89 of SEQ ID NO:21. The similarity is referred to as structural similarity and is generally determined by aligning the residues of the two amino acid sequences (i.e., a candidate amino acid sequence and the amino acid sequence of SEQ ID NO:19 or amino acids 4-89 of SEQ ID NO:21) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence is the amino acid sequence being compared to an amino acid sequence present in SEQ ID NO:19 or amino acids 4-89 of SEQ ID NO:21. A candidate amino acid sequence can be isolated from a virus, or can be produced using recombinant techniques, or chemically or enzymatically synthesized. Preferably, two amino acid sequences are compared using the Blast program of the BLAST 2 search algorithm, as described by Tatusova, et al. (*FEMS Microbiol Lett* 1999, 174: 247-250), and available at www.ncbi.nlm-.nih.gov/gorf/bl2.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identities." Preferably, a transactivator includes an amino acid sequence having a structural similarity with SEQ ID NO:19 or amino acids 4-89 of SEQ ID NO:21 of at least about 70%, at least about 80%, at least about 90%, at least about 94%, at least about 96%, or at least about 99% identity. Typically, an amino acid sequence having a structural similarity with SEQ ID NO:19 or amino acids 4-89 of SEQ ID NO:21 has tat activity. Whether such a polypeptide has activity can be evaluated by determining if the amino acid sequence can interact with an HIV LTR, preferably, alter transcription from a coding sequence operably linked to an HIV LTR.

Active analogs or active fragments of a transactivator can be used in the invention. An active analog or active fragment of a transactivator is one that is able to interact with an operator sequence and either prevent transcription from initiating at, activate transcription initiation from, or stabilize a transcript from, a transactivated coding region operably linked to the operator sequence.

Active analogs of a transactivator include polypeptides having conservative amino acid substitutions that do not eliminate the ability to interact with an operator and alter transcription. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, aspartate, and glutamate. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gin for Asn to maintain a free $NH_2$.

Active fragments of a transactivator include a portion of the transactivator containing deletions or additions of about 1, about 2, about 3, about 4, or at least about 5 contiguous or noncontiguous amino acids such that the resulting transactivator will alter expression of an operably linked transactivated coding region. A preferred example of an active fragment of the HIV tat polypeptide includes amino acids amino acids 1-48 of SEQ ID NO:19, or amino acids 4-51 of SEQ ID NO:21.

In those aspects of the invention where the heterologous polynucleotide includes a coding region that encodes a fusion polypeptide, the fusion polypeptide can further include amino acids corresponding to a cis-active proteinase. When the fusion polypeptide is a fusion between a transactivator and a marker, preferably the fusion polypeptide also includes amino acids corresponding to a cis-active proteinase. Preferably the amino acids corresponding to a cis-active proteinase are present between the amino acids corresponding to the transactivator and the marker. A cis-active proteinase in this position allows the amino acids corresponding to the transactivator and the marker to be physically separate from each other in the cell within which the HCV is present. Examples of cis-active proteinases that are useful in the present invention include the cis-active 2A proteinase of foot-and-mouth disease (FMDV) virus (see, for example, U.S. Pat. No. 5,846,767 (Halpin et al.) and U.S. Pat. No. 5,912,167 (Palmenberg et al.)), ubiquitin (see, for example, Tauz et al., *Virology,* 197, 74-85 (1993)), and the NS3 recognition site GADTEDVVCCSMSY (SEQ ID NO:31) (see, for example, Lai et al., *J. Virol.,* 74, 6339-6347 (2000)).

Active analogs and active fragments of cis-active proteinases can also be used. Active analogs of a cis-acting proteinase include polypeptides having conservative amino acid substitutions that do not eliminate the ability of the proteinase to catalyze cleavage. Active fragments of a cis-active proteinase include a portion of the cis-active proteinase containing deletions or additions of one or more contiguous or noncontiguous amino acids such that the resulting cis-active proteinase will catalyze the cleavage of the proteinase.

In some aspects of the invention, the heterologous polynucleotide may further include a regulatory region that is operably linked to the coding region of the heterologous polynucleotide. Preferably, a regulatory region located 5' of the operably linked coding region provides for the translation of the coding region.

A preferred regulatory region located 5' of an operably linked coding region is an internal ribosome entry site (IRES). An IRES allows a ribosome access to mRNA without a requirement for cap recognition and subsequent scanning to the initiator AUG (Pelletier, et al., *Nature,* 334, 320-325 (1988)). An IRES is located upstream of the translation initiation codon, e.g., ATG or AUG, of the coding sequence to which the IRES is operably linked. The distance between the IRES and the initiation codon is dependent on the type or IRES used, and is known to the art. For instance, poliovirus IRES initiates a ribosome translocation/scanning process to a downstream AUG codon. For other IRES elements, the initiator codon is generally located at the 3' end of the IRES sequence. Examples of an IRES that can be used in the invention include a viral IRES, preferably a picornaviral IRES or a flaviviral IRES. Examples of poliovirus IRES elements include, for instance, poliovirus IRES, encephalomyocarditis virus IRES, or hepatitis A virus IRES. Examples of preferred flaviviral IRES elements include hepatitis C virus IRES, GB virus B IRES, or a pestivirus IRES, including but not limited to bovine viral diarrhea virus IRES or classical swine fever virus IRES. Other IRES elements with similar secondary and tertiary structure and translation initiation activity can either be generated by mutation of these viral sequences, by cloning of analogous sequences from other viruses (including picornaviruses), or prepared by enzymatic synthesis techniques.

The size of the heterologous polynucleotide is not critical to the invention. It is expected there is no lower limit on the size of the heterologous polynucleotide. It is expected that there is an upper limit on the size of the heterologous polynucleotide. This upper limit can be easily determined by a person skilled in the art, as heterologous polynucleotides that are greater than this upper limit adversely affect replication of an HCV polynucleotide. In increasing order of preference, the heterologous polynucleotide is at least about 10 nucleotides, at least about 20 nucleotides, at least about 30 nucleotides, most preferably at least about 40 nucleotides.

In some aspects of the invention, the heterologous polynucleotide is present in an HCV downstream of the 5' NTR. For instance, the first nucleotide of the heterologous polynucleotide may be immediately downstream and adjacent to the last nucleotide of the 5' NTR. Alternatively, the first nucleotide of the heterologous polynucleotide may be about 33 to about 51 nucleotides, more preferably, about 36 to about 48 nucleotides, downstream of the last nucleotide of the 5' NTR. Typically, when the first nucleotide of the heterologous polynucleotide is not immediately downstream of the last nucleotide of the 5' NTR, the nucleotides in between the 5' NTR and the heterologous polynucleotide encode the amino terminal amino acids of the HCV core polypeptide.

In those aspects of the invention where the heterologous polynucleotide present in an HCV is inserted downstream of the 5' NTR and upstream of the coding region encoding the HCV polyprotein or a portion thereof, the heterologous polynucleotide typically includes a regulatory region operably linked to the downstream coding region. Preferably, the regulatory region provides for the translation of the downstream coding region. The size of the regulatory region may be from about 400 nucleotides to about 800 nucleotide, more preferably, about 600 nucleotides to about 700 nucleotides. Preferably, the regulatory region is an IRES. Examples of IRES elements are described herein.

In those aspects of the invention where the HCV polynucleotide includes a portion of the hepatitis C virus polyprotein, the 5' end of the coding region encoding the HCV polyprotein may further include about 33 to about 51 nucleotides, more preferably, about 36 to about 48 nucleotides, that encode the first about 11 to about 17, more preferably, about 12 to about 16, amino acids of the core polypeptide. The result is a fusion polypeptide between the amino terminal amino acids of the core polypeptide and the first polypeptide encoded by the heterologous polnucleotide.

The replication competent HCV polynucleotide of the invention can be present in a vector. When a replication competent HCV is present in a vector the HCV is DNA, including the 5' non-translated RNA and the 3' non-translated RNA. Methods for cloning an HCV and inserting it into a vector are known to the art (see, e.g., Yanagi et al., *Proc. Natl. Acad. Sci., USA,* 94, 8738-8743 (1997); and Rice et al., (U.S. Pat. No. 6,127,116)). Such constructs are often referred to as molecularly cloned laboratory strains, and an HCV that is inserted into a vector is typically referred to as a cDNA clone of the HCV. If the RNA encoded by the HCV is able to replicate in vivo, the HCV present in the vector is referred to as an infectious cDNA clone. A vector is a replicating polynucleotide, such as a plasmid, phage, cosmid, or artificial chromosome to which another polynucleotide may be attached so as to bring about the replication of the attached polynucleotide. A vector can provide for further cloning (amplification of the polynucleotide), i.e., a cloning vector, or for expression of the polypeptide encoded by the coding region, i.e., an expression vector. The term vector includes, but is not limited to, plasmid vectors, viral vectors, cosmid vectors, or artificial chromosome vectors. Preferably the vector is a plasmid. Preferably the vector is able to replicate in a prokaryotic host cell, for instance *Escherichia coli*. Preferably, the vector can integrate in the genomic DNA of a eukaryotic cell.

An expression vector optionally includes regulatory sequences operably linked to the HCV such that the HCV is transcribed to produce RNA molecules. These RNA molecules can be used, for instance, for introducing an HCV to a cell that is in an animal or growing in culture. The terms "introduce" and "introducing" refer to providing an HCV to a cell under conditions that the HCV is taken up by the cell in such a way that the HCV can then replicate. The HCV can be a virus particle, or a nucleic acid molecule, preferably RNA. The invention is not limited by the use of any particular promoter, and a wide variety are known. Promoters act as regulatory signals that bind RNA polymerase in a cell to initiate transcription of a downstream (3' direction) HCV. The promoter used in the invention can be a constitutive or an inducible promoter. A preferred promoter for the production of HCV is T7 promoter.

Figure 9A:
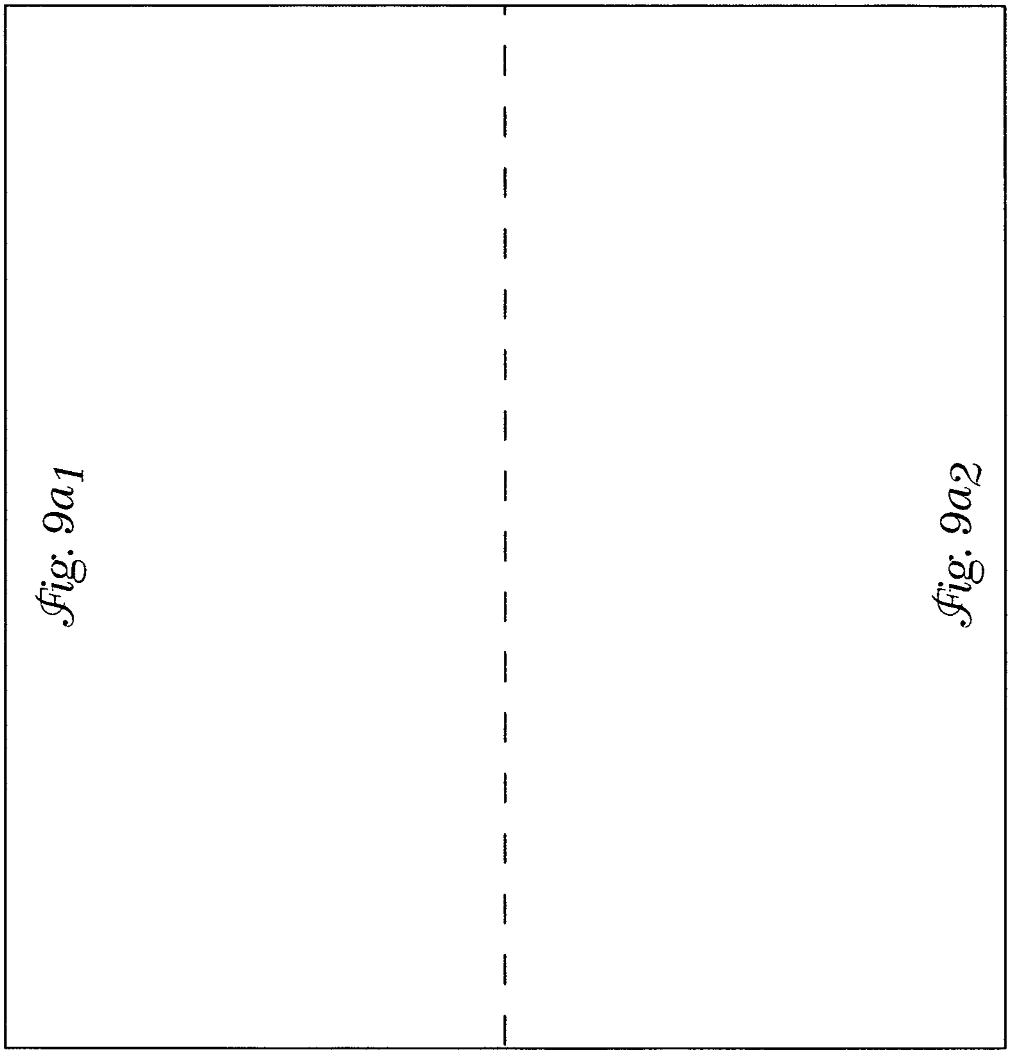
FIG. 9. Nucleotide sequence of MK0-Z (SEQ ID NO:17). The initiation codon of the viral polyprotein which undergoes post-translational cleavage is the ATG at nucleotides 342-344. The initiation codon of the inserted heterologous polynucleotide is the ATG at nucleotides 9907-9909.
Figure 9B:
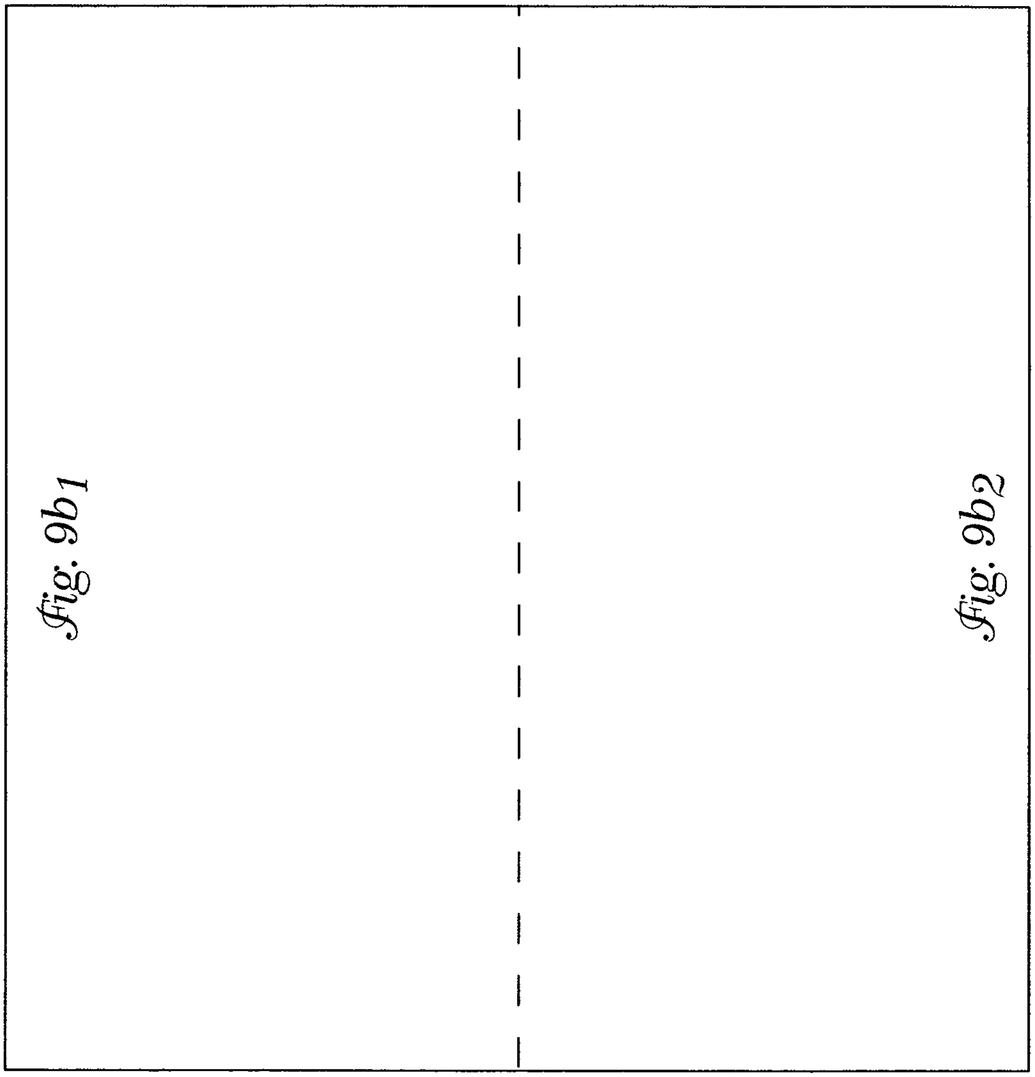
Figure 10A:
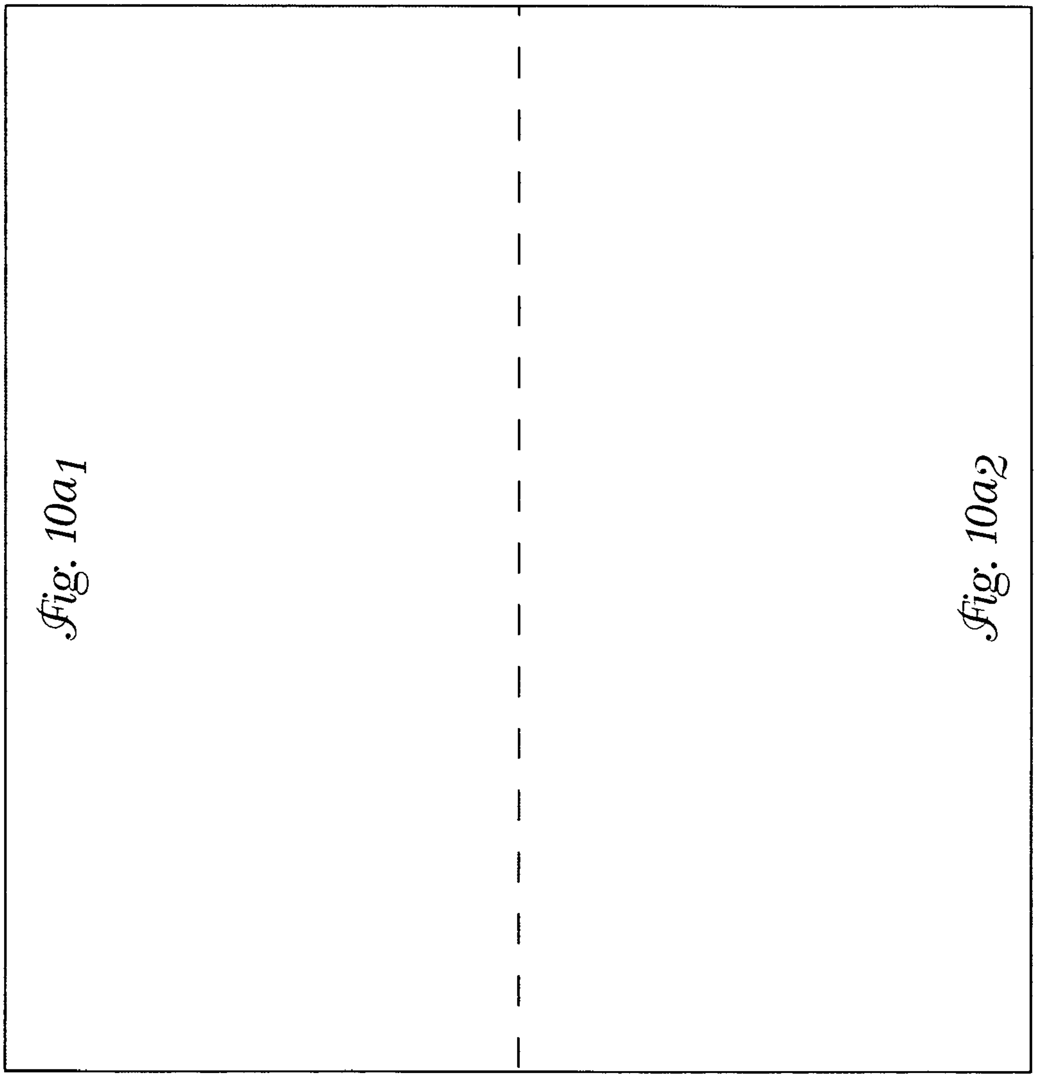
FIG. 10. Nucleotides 342-10,803 of SEQ ID NO:17, and the polyprotein (SEQ ID NO:20). The amino acid sequences SEQ ID NO:32, SEQ ID NO:33, and SEQ ID NO:34 encoded by nucleotides 9,390-9,485, nucleotides 9,489-9,794, and nucleotides 9,798-9,887 of SEQ ID NO:17, respectively, are shown. The amino acid sequence (SEQ ID NO:21) encoded by the heterologous polynucleotide (i.e., nucleotides 9907-10,602 of SEQ ID NO:17) is also shown.
Figure 10B:
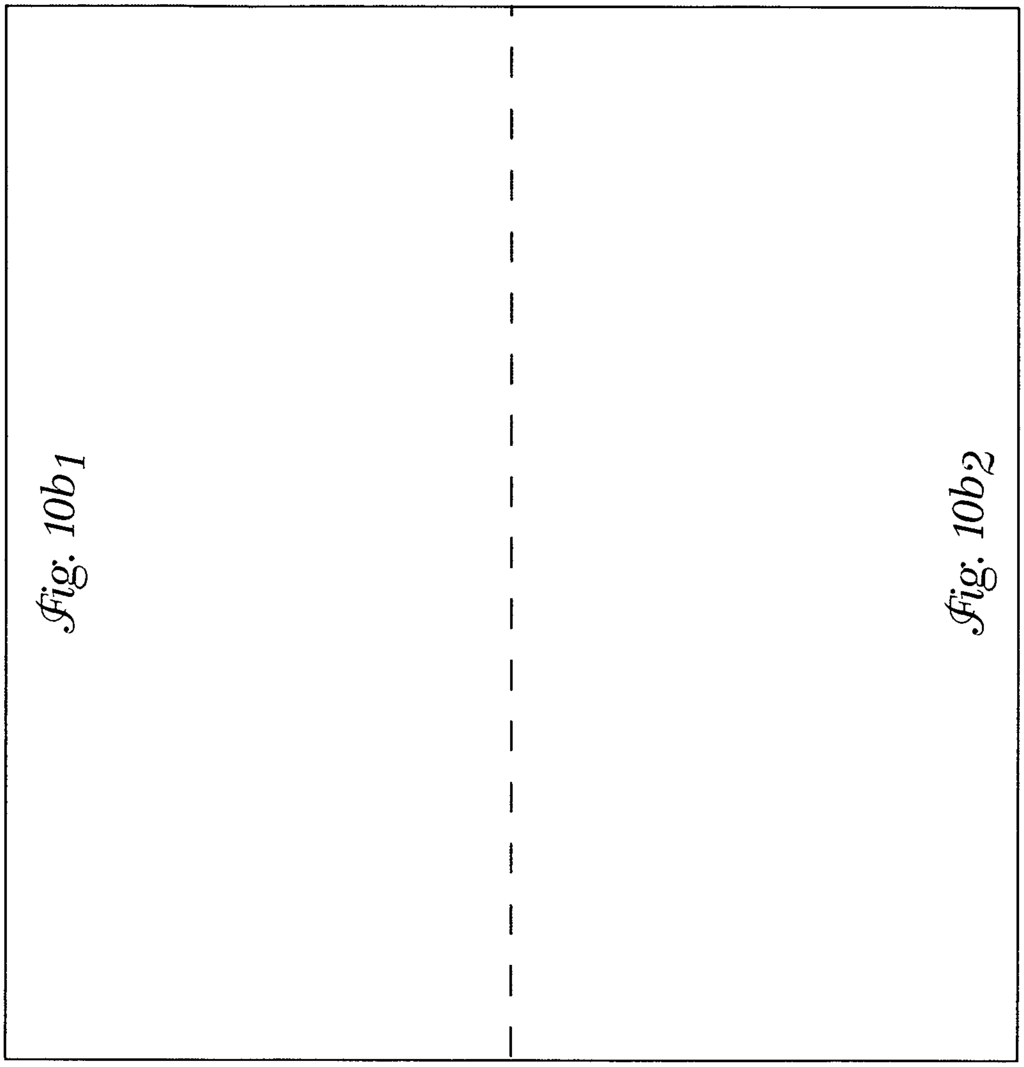
Figure 10C:
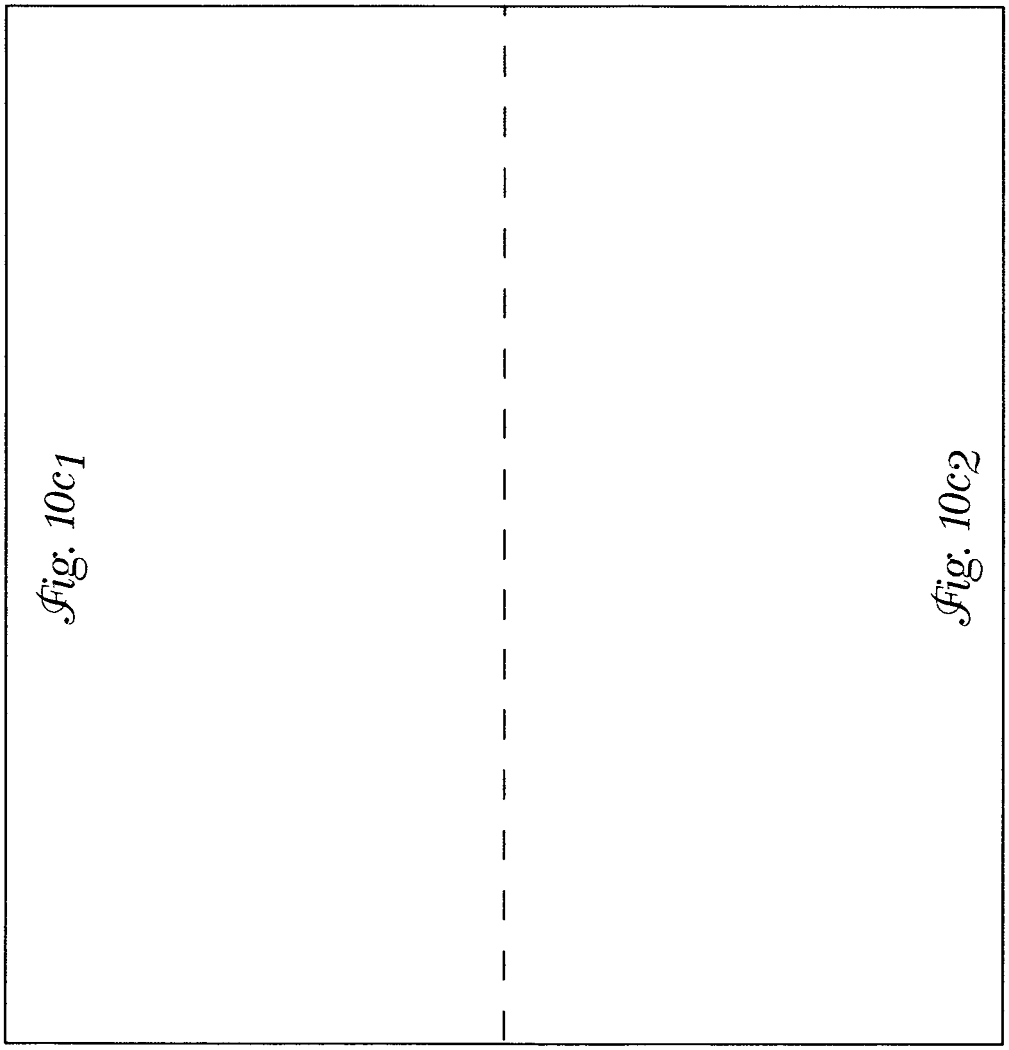
Figure 10D:
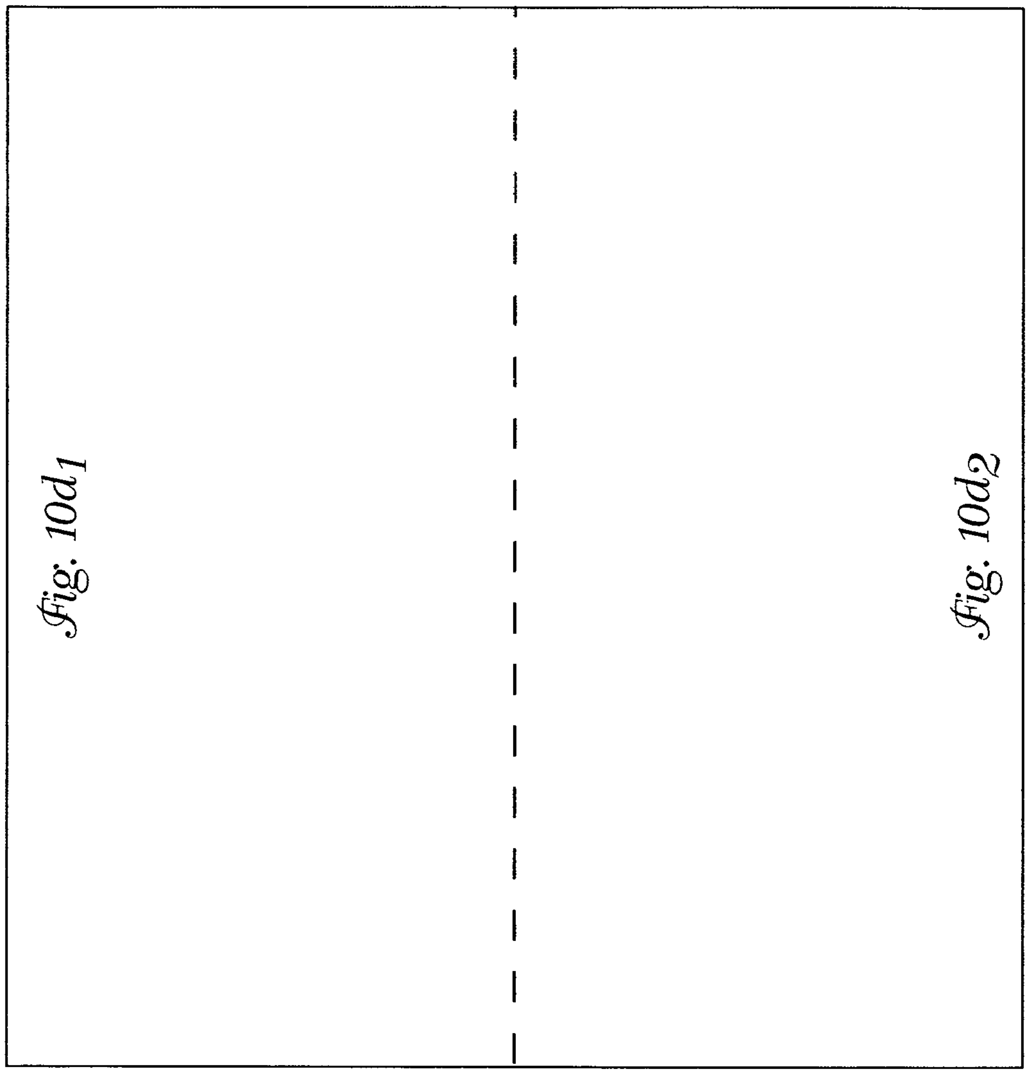
Figure 10E:
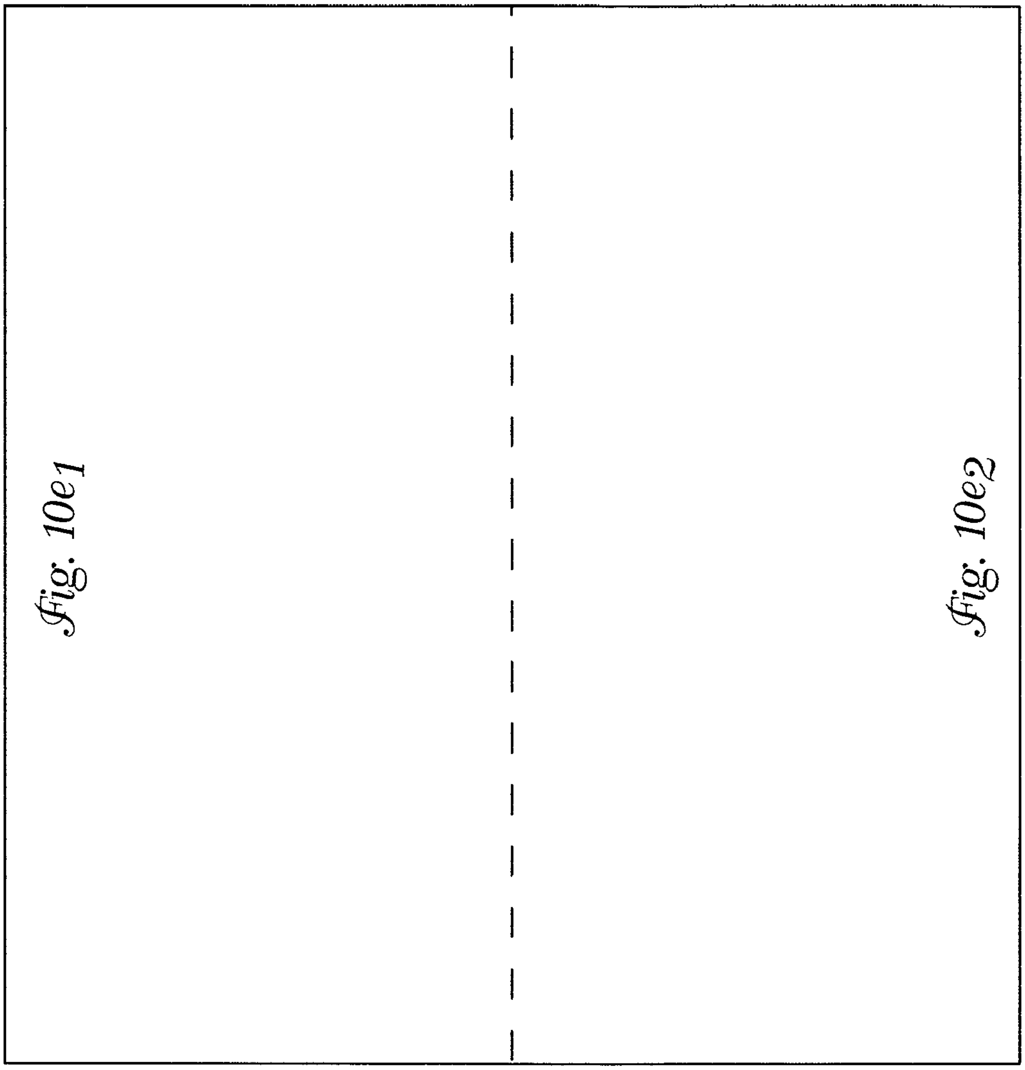
Figure 10F:
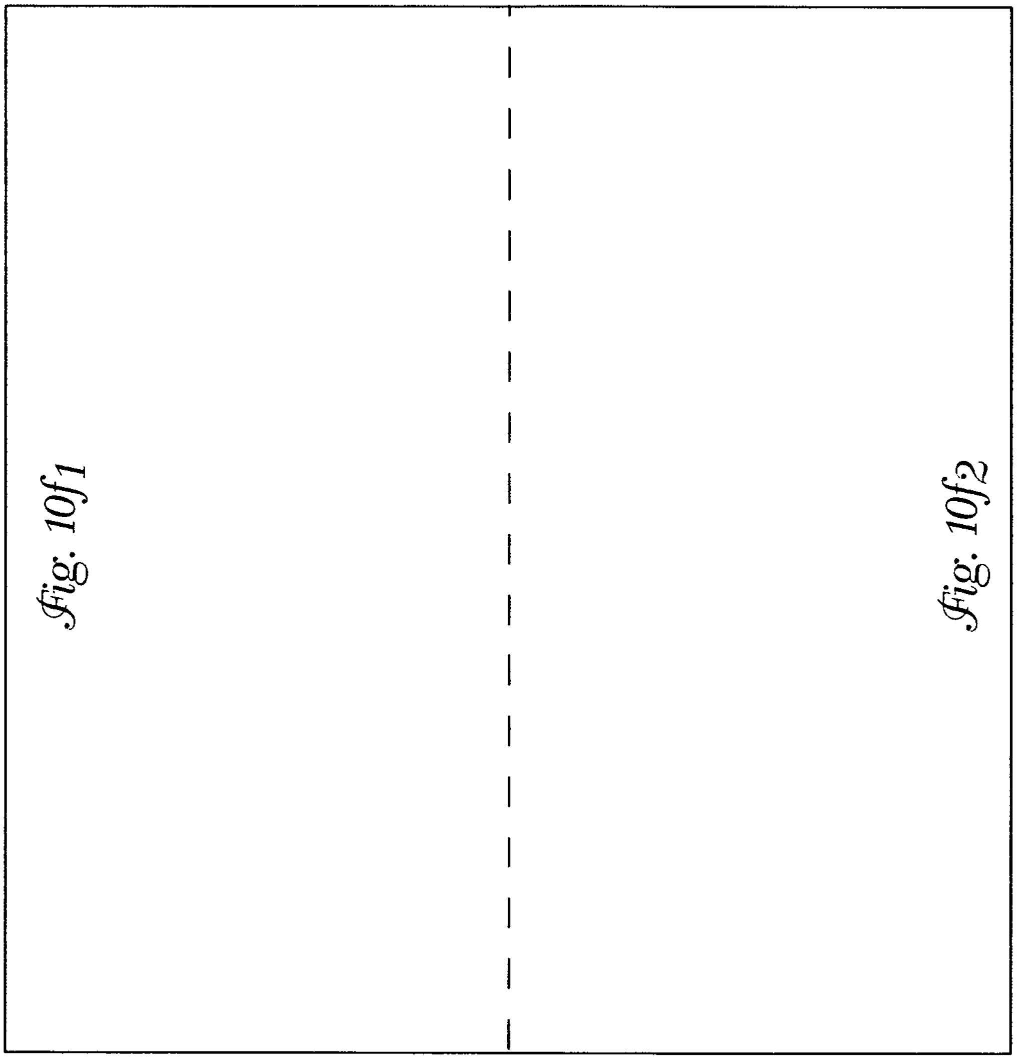
Figure 10G:
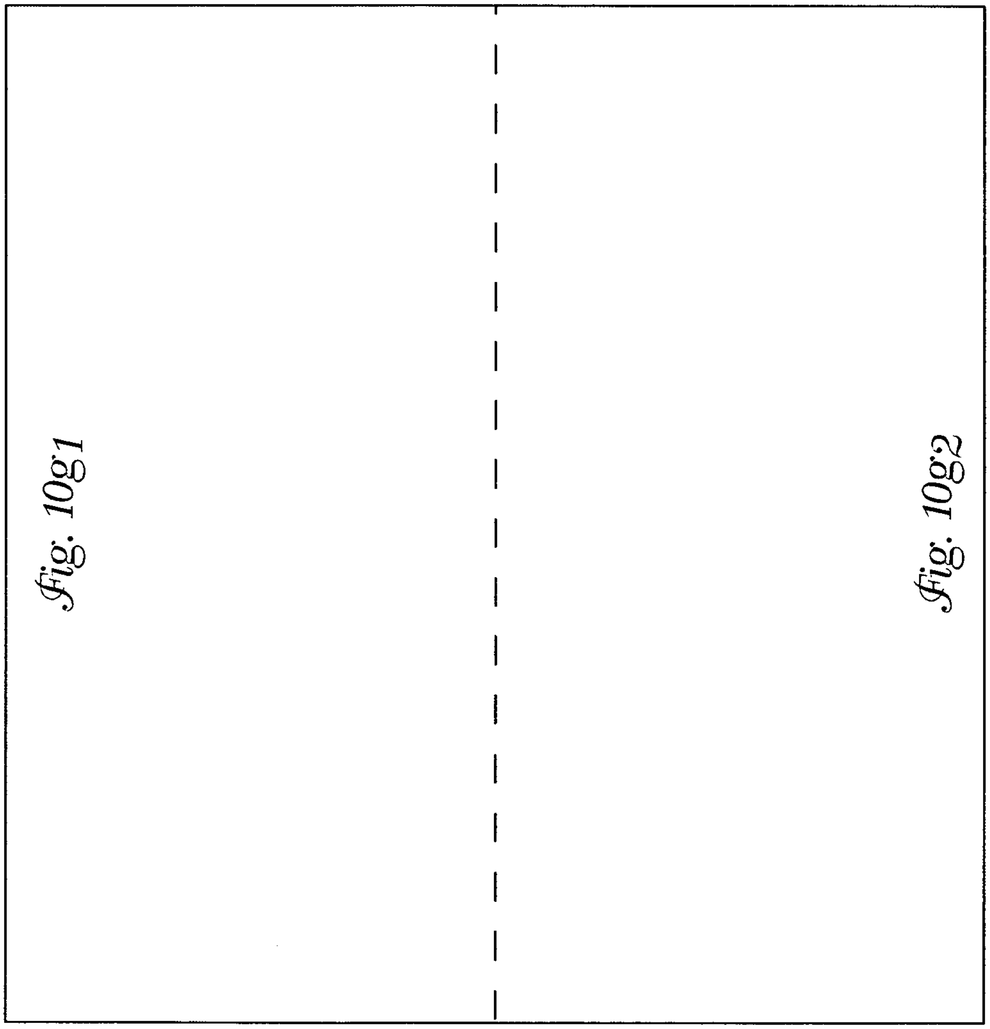
Figure 10H:
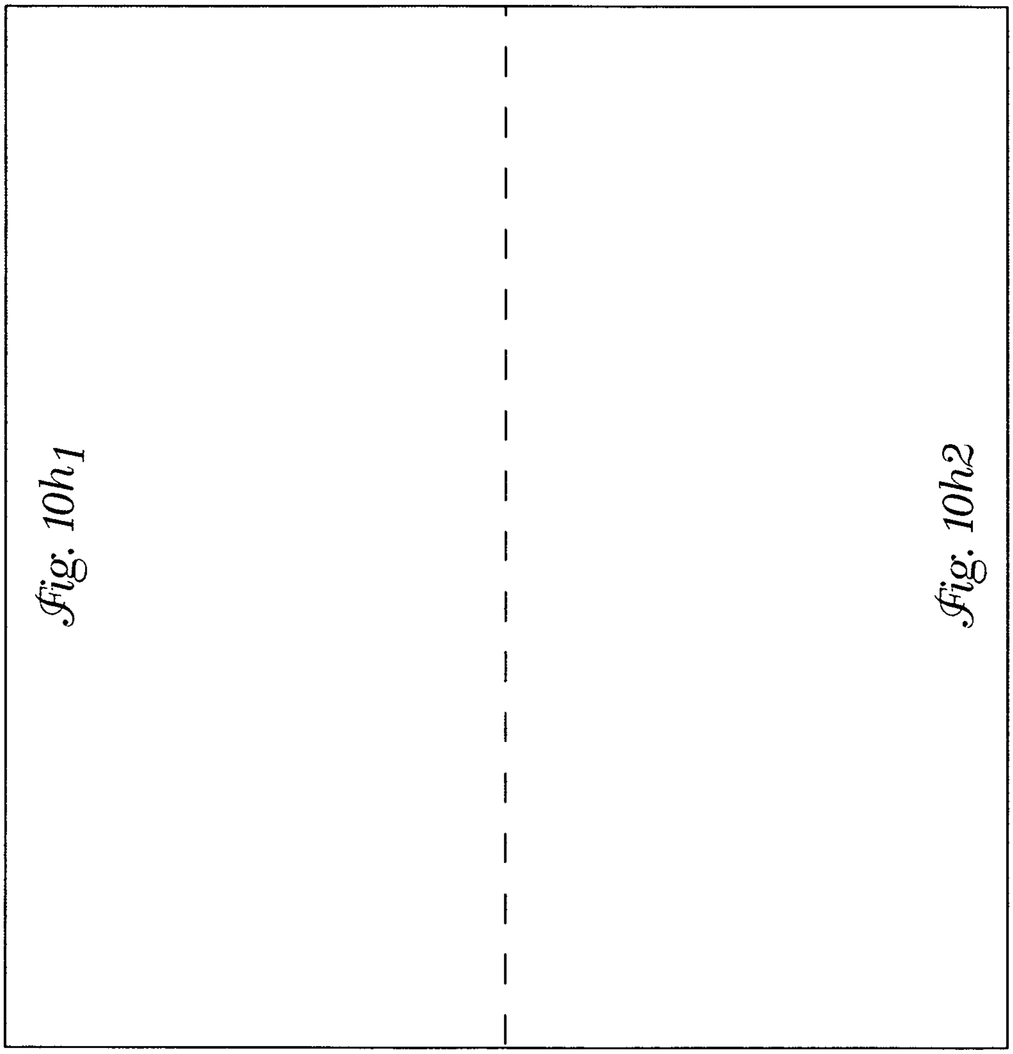
Figure 17A:
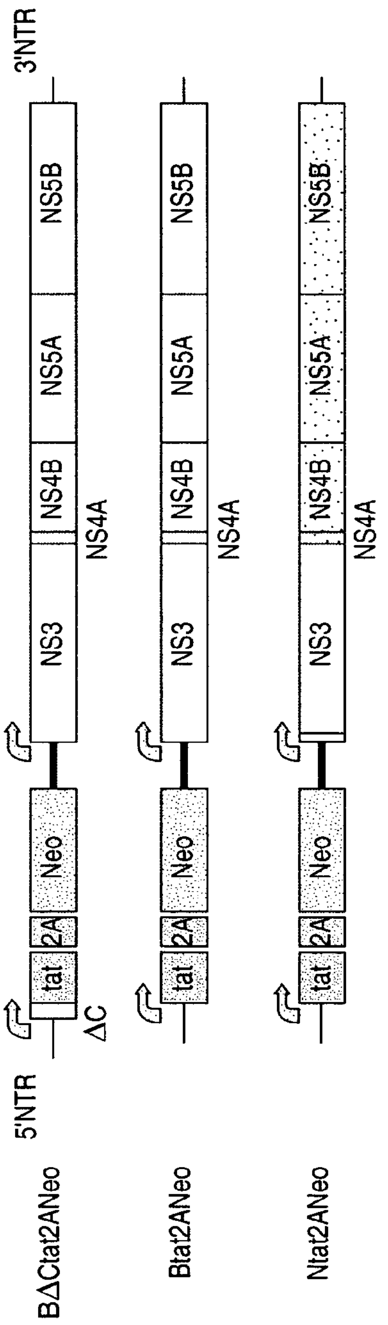
FIG. 17. (A) Organization of subgenomic HCV RNA replicons encoding tat. Open reading frames are depicted as boxes, and nontranslated segments of the dicistronic RNAs as solid lines. ΔC indicates the N-terminal 14 amino acid core protein segment. (B) Additional mutations engineered into the replicons.

Preferred examples of HCV polynucleotide of the present invention are shown in FIGS. 9, 10, and 17. It should be noted that while these sequences are DNA sequences, the present invention contemplates the corresponding RNA sequence, and RNA and DNA complements thereof, as well.

Methods of Use

The present invention is directed to methods for identifying a replication competent HCV polynucleotide, including detecting and/or selecting for cells containing a replication competent HCV polynucleotide. Typically, the cells used in this aspect of the invention are cells growing in culture. Useful cultured cells will support the replication of the HCV of the present invention, and include primary human or chimpanzee hepatocytes, peripheral mononuclear cells, cultured human lymphoid cell lines (for instance lines expressing B-cell and T-cell markers such as Bjab and Molt-4 cells), and continuous cell lines derived from such cells, including Huh-7, HepG2, and PH5CH-8. The cells may be primate or human cells, preferably human cells. In general, useful cells include those that support replication of HCV RNA, including, for instance, replication of the HCV encoded by pCV-$H_{77}$C, or replication of the HCV encoded by pHCV-N as modified by Beard et al. (*Hepatol.,* 30, 316-324 (1999)). A preferred cultured cell is HuH-7, which is known to workers in the field of HCV (see, for instance, Lohmann et al., *Science,* 285, 570-574 (1999)).

In some aspects of the invention, the cultured cell includes a polynucleotide that includes a coding region, the expression of which is controlled by a transactivator. Such a coding region is referred to herein as a transactivated coding region. A transactivated coding region encodes a marker, preferably a detectable marker, for example, secretory alkaline phosphatase. In some aspects of the invention, the detectable marker is secretory alkaline phospahtase (SEAP). An example of an SEAP is encoded by nucleotides 748-2239 of SEQ ID NO:18. Typically, a cultured cell that includes a polynucleotide having a transactivated coding region is used in conjunction with an HCV polynucleotide that includes a coding region encoding a transactivator.

The polynucleotide that includes the transactivated coding region can be present integrated into the genomic DNA of the cell, or present as part of a vector that is not integrated. Preferably, the polynucleotide is integrated into the genomic DNA of the cell. Methods of modifying a cell to contain an integrated DNA are known to the art. An example of making such a cell is described in Example 3 and Example 9.

Operably linked to the transactivated coding region is an operator sequence. The interaction of a transactivator can alter transcription of the operably linked transactivated coding region. In those aspects of the invention where a transactivator increases transcription, preferably there is low transcription of the transactivated coding region in the absence of a transactivator, more preferably, essentially no transcription. An operator sequence can be present upstream (5') or downstream (3') of a transactivated coding region. An operator sequence can be a promoter, or can be a nucleotide sequence that is present in addition to a promoter.

In some aspects of the invention, the operator sequence that is operably linked to a transactivated coding sequence is an HIV long terminal repeat (LTR). An example of an HIV LTR is depicted at nucleotides 1-719 of SEQ ID NO:18. Also included in the present invention are operator sequences having similarity to nucleotides 1-719 of SEQ ID NO:18. The similarity between two nucleotides sequences may be determined as described above, however, the candidate nucleotide sequence is compared to the nucleotides 1-719 of SEQ ID NO:18. Preferably, an operator sequence includes a nucleotide sequence having a structural similarity with the nucleotides 1-719 of SEQ ID NO:18 of at least about 80%, more preferably at least about 90%, most preferably at least about 95% identity. Typically, an operator sequence having structural similarity with the nucleotides 1-719 of SEQ ID NO:18 has transcriptional activity. Whether such an operator sequence has transcriptional activity can be determined by evaluating the ability of the operator sequence to alter transcription of an operably linked coding sequence in response to the presence of a polypeptide having tat activity, preferably, a polypeptide including the amino acids of SEQ ID NO:19 or amino acids 4-89 of SEQ ID NO:21.

In some aspects of the present invention, the replication of cultured cells may be inhibited by a selecting agent. Examples of selecting agents include antibiotics, including kanamycin, ampicillin, chloramphenicol, tetracycline, neomycin, and formulations of phleomycin D1. A selecting agent can act to prevent replication of a cell while the agent is present and the cell does not express a molecule that provides resistance to the selecting agent. Alternatively and preferably, a selecting agent can act to kill a cell that does not express a molecule that provides resistance to the selecting agent. Typically, the molecule providing resistance to a selecting agent is expressed in the cell by an HCV polynucleotide of the present invention. Alternatively, the molecule providing resistance to a selecting agent is expressed by the cell but the expression of the molecule is controlled by an HCV polynucleotide of the present invention that is present in the cell. The concentration of the selecting agent is typically chosen such that a cell that does not contain a molecule providing resistance to a selecting agent does not replicate. The appropriate concentration of a selecting agent varies depending on the particular selecting agent, and can be easily determined by one having ordinary skill in the art using known techniques.

When a polynucleotide that includes a replication competent HCV polynucleotide is introduced into a cell that is growing in culture, the polynucleotide can be introduced using techniques known to the art. Such techniques include, for instance, liposome and non-liposome mediated transfection. The Examples describe the use of one type of liposome mediated transfection. Non-liposome mediated transfection methods include, for instance, electroporation.

In some aspects of the invention, when a replication competent HCV polynucleotide is identified using cultured cells, its ability to replicate may be verified by introducing the HCV to a cell present in an animal, preferably a chimpanzee. When the cell is present in the body of an animal, the polynucleotide that includes a replication competent HCV can be introduced by, for instance, subcutaneous, intramuscular, intraperitoneal, intravenous, or percutaneous intrahepatic administration, preferably by percutaneous intrahepatic administration. Methods for determining whether an HCV polynucleotide is able to replicate in a chimpanzee are known to the art (see, for example, Yanagi et al., *Proc. Natl. Acad. Sci. USA,* 94, 8738-8743 (1997), and Example 2). In general, the demonstration of infectivity is based on the appearance of the virus in the circulation (blood) of the chimpanzee over the days and weeks following the intrahepatic injection of the HCV. The presence of the virus can be confirmed by reverse transcription-polymerase chain reaction (RT-PCR) detection of the viral RNA, by inoculation of a second chimpanzee with transfer of the hepatitis C virus infection as indicated by the appearance of liver disease and seroconversion to hepatitis C virus in ELISA tests, or possibly by the immunologic detection of components of the hepatitis C virus (e.g., the core protein) in the circulation of the inoculated animal. It should be noted that seroconversion by itself would not be a useful indicator of infection in an animal injected with a viral RNA produced using a molecularly cloned laboratory strain, as this RNA may have immunizing properties and be capable of inducing HCV-specific antibodies to proteins translated from an input RNA that is non-replicating. Similarly, the absence of seroconversion does not exclude the possibility of viral replication and infection of a chimpanzee with HCV.

Whether an HCV polynucleotide of the present invention is replication competent can be determined using methods known to the art, including methods that use nucleic acid amplification to detect the result of increased levels of HCV replication. In some aspects of the invention, another method for detecting a replication competent HCV polynucleotide includes measuring the production of viral particles by a cell. The measurement of viral particles can be accomplished by passage of supernatant from media containing a cell culture that may contain a replication competent HCV, and using the supernatant to infect a second cell. Detection of HCV in the second cell indicates the initial cell contains a replication competent HCV. The production of infectious virus particles by a cell can also be measured using antibody that specifically binds to an HCV viral particle. As used herein, an antibody that can "specifically bind" an HCV viral particle is an antibody that interacts only with the epitope of the antigen (e.g., the viral particle or a polypeptide that makes up the particle) that induced the synthesis of the antibody, or interacts with a structurally related epitope. "Epitope" refers to the site on an antigen to which specific B cells and/or T cells respond so that antibody is produced. An epitope could includes about 3 amino acids in a spatial conformation which is unique to the epitope. Generally an epitope includes at least about 5 such amino acids, and more usually, consists of at least about 8-10 such amino acids. Antibodies to HCV viral particles can be produced as described herein.

In another aspect, identifying a replication competent HCV polynucleotide includes incubating a cultured cell that includes an HCV of the present invention. In those aspects of the invention where the heterologous polynucleotide encodes a detectable marker, cells containing a replication competent HCV can be identified by observing individual cells that contain the detectable marker. Alternatively, if the detectable marker is secreted by the cell, the presence of the marker in the medium in which the cell is incubated can be detected. Methods for observing the presence or absence of a detectable marker in a cell or in liquid media are known to the art.

Another aspect of the invention provides for the positive selection of cells that include a replication competent HCV polynucleotide. The marker expressed by the HCV is a selectable marker, and the cell, which includes the HCV, is incubated in the presence of a selecting agent. Those cells that can replicate in the presence of the selecting agent contain an HCV that is replication competent. Typically, the cells that can replicate are detected by allowing resistant cells to grow in the presence of the selecting agent.

In some aspects, the method may further include isolating virus particles from the cells that contain a replication competent HCV polynucleotide and exposing a second cell to the isolated virus particle under conditions such that the virus particle is introduced to the cell. After providing time for expression of the selectable marker, the second cell is then incubated with the selecting agent. The presence of a cell that replicates indicates the replication competent HCV produces infectious virus particles. Preferably, virus particles are isolated by removing a volume of the media in which the first cells are incubated.

In another aspect, the invention provides a method for detecting a replication competent HCV polynucleotide. The method includes incubating a cell that contains an HCV of the present invention. The cell includes a transactivated coding region and an operator sequence operably linked to the transactivated coding region. The transactivated coding region encodes a detectable marker.

The heterologous polynucleotide present in the HCV polynucleotide encodes a transactivator that interacts with the operator sequence present in the cell. The interaction of the transactivator to the operator sequence can decrease transcription or increase transcription of the operably linked transactivated coding region. Preferably, binding of the transactivator to the operator sequence increases transcription. Preferably, the HCV also encodes a marker, more preferably, a fusion polypeptide that includes a transactivator and a marker. Most preferably, the fusion polypeptide further includes a cis-acting proteinase located between the nucleotides encoding the transactivator and the nucleotides encoding the marker.

The method further includes detecting the presence or absence of the detectable marker encoded by the transactivated coding region present in the cell. The presence of the detectable marker indicates the cell includes a replication competent HCV. Preferably, the detectable marker is one that is secreted by the cell, for instance secretory alkaline phosphatase.

The methods described above for identifying replication competent HCV polynucleotide can also be used for identifying a variant HCV polynucleotide, i.e., an HCV that is derived from a replication competent HCV of the present invention. Preferably, a variant HCV has a faster replication rate than the parent or input HCV. The method takes advantage of the inherently high mutation rate of RNA replication. It is expected that during continued culture of a replication competent HCV in cultured cells, the HCV of the present invention may mutate, and some mutations will result in HCV with greater replication rates. The method includes identifying a cell that has greater expression of a polypeptide encoded by a replication competent HCV. An HCV of the present invention that replicates at a faster rate will result in more of the polypeptide(s) that is encoded by the heterologous polynucleotide present in the HCV. For instance, when an HCV encodes a selectable marker, a cell containing a variant HCV having a greater replication rate will be resistant to higher levels of an appropriate selecting agent. When an HCV encodes a transactivator, a cell containing a variant HCV having a greater replication rate than the parent or input HCV will express higher amounts of the transactivated coding region that is present in the cell. The observed increases in resistance to phleomycin D1 (for instance, ZEOCIN) suggest the accumulation of mutations that allow increased rates of replication.

A cDNA molecule of a variant HCV polynucleotide can be cloned using methods known to the art (see, for instance, Yanagi et al., *Proc. Natl. Acad. Sci., USA,* 94, 8738-8743 (1997)). The nucleotide sequence of the cloned cDNA can be determined using methods known to the art, and compared with that of the input RNA. This allows identification of mutations that have occurred in association with passage of the HCV in cell culture. For example, using methods known to the art, including longrange RT-PCR, extended portions of a variant HCV genome can be obtained. Multiple clones could be obtained from each segment of the genome, and the dominant sequence present in the culture determined. Mutations that are identified by this approach can then be reintroduced into the background of the HCV cDNA encoding the parent or input HCV. This may be used to produce a replication competent HCV that does not contain a heterologous polynucleotide. Such an HCV would have superior replication properties in cell culture compared to the parent HCV and the variant HCV because it would not carry the burden of an additional coding region within its 3' non-translated RNA.

The present invention also provides methods for identifying a compound that inhibits replication of an HCV polynucleotide, preferably a replication competent HCV as described herein in the section "Hepatitis C Virus." The method includes contacting a cell containing a replication competent HCV polynucleotide with a compound and incubating the cell under conditions that permit replication of the replication competent HCV polynucleotide in the absence of the compound. After a period of time sufficient to allow replication of the HCV polynucleotide, the replication competent HCV polynucleotide is detected. A decrease in the presence of replication competent HCV polynucleotide in the cell contacted with the compound relative to the presence of replication competent HCV polynucleotide in a cell not contacted by the compound indicates the compound inhibits replication of a replication competent HCV. A compound that inhibits replication of an HCV includes compounds that completely prevent replication, as well as compounds that decrease replication. Preferably, a compound inhibits replication of a replication competent HCV by at least about 50%, more preferably at least about 75%, most preferably at least about 95%.

The compounds added to a cell can be a wide range of molecules and is not a limiting aspect of the invention. Compounds include, for instance, a polyketide, a non-ribosomal peptide, a polypeptide, a polynucleotide (for instance an antisense oligonucleotide or ribozyme), or other organic molecules. The sources for compounds to be screened include, for example, chemical compound libraries, fermentation media of *Streptomycetes*, other bacteria and fungi, and extracts of eukaryotic or prokaryotic cells. When the compound is added to the cell is also not a limiting aspect of the invention. For instance, the compound can be added to a cell that contains a replication competent HCV. Alternatively, the compound can be added to a cell before or at the same time that the replication competent HCV is introduced to the cell.

Typically, the ability of a compound to inhibit replication of a replication competent HCV polynucleotide is measured using methods described herein. For instance, methods that use nucleic acid amplification to detect the amount of HCV nucleic acid in a cell can be used. Alternatively, methods that detect or select for a marker encoded by a replication competent HCV or encoded by a cell containing a replication competent HCV can be used.

In some aspects of the invention, the replication competent HCV polynucleotide of the invention can be used to produce infectious viral particles. For instance, a cell that includes a replication competent HCV can be incubated under conditions that allow the HCV to replicate, and the infectious viral particles that are produced can be isolated, preferably purified. The infectious viral particles can be used as a source of virus particles for various assays, including evaluating methods for inactivating particles, excluding particles from serum, identifying a neutralizing compound, and as an antigen for use in detecting anti-HCV antibodies in an animal. An example of using a viral particle as an antigen includes use as a positive-control in assays that test for the presence of anti-HCV antibodies.

For instance, the activity of compounds that neutralize or inactivate the particles can be evaluated by measuring the ability of the molecule to prevent the particles from infecting cells growing in culture or in cells in an animal. Inactivating compounds include detergents and solvents that solubilize the envelope of a viral particle. Inactivating compounds are often used in the production of blood products and cell-free blood products. Examples of compounds that can be neutralizing include a polyketide, a non-ribosomal peptide, a polypeptide (for instance, an antibody), a polynucleotide (for instance, an antisense oligonucleotide or ribozyme), or other organic molecules. Preferably, a neutralizing compound is an antibody, including polyclonal and monoclonal antibodies, as well as variations thereof including, for instance, single chain antibodies and Fab fragments.

Viral particles produced by replication competent HCV polynucleotide of the invention can be used to produce antibodies. Laboratory methods for producing polyclonal and monoclonal antibodies are known in the art (see, for instance, Harlow E. et al. *Antibodies: A laboratory manual* Cold Spring Harbor Laboratory Press, Cold Spring Harbor (1988) and Ausubel, R. M., ed. *Current Protocols in Molecular Biology* (1994)), and include, for instance, immunizing an animal with a virus particle. Antibodies produced using the viral particles of the invention can be used to detect the presence of viral particles in biological samples. For instance, the presence of viral particles in blood products and cell-free blood products can be determined using the antibodies.

The present invention further includes methods of treating an animal including administering neutralizing antibodies. The antibodies can be used to prevent infection (prophylactically) or to treat infection (therapeutically), and optionally can be used in conjunction with other molecules used to prevent or treat infection. The neutralizing antibodies can be mixed with pharmaceutically acceptable excipients or carriers. Suitable excipients include but are not limited to water, saline, dextrose, glycerol, ethanol, or the like and combinations thereof. In addition, if desired, neutralizing antibodies and pharmaceutically acceptable excipients or carriers may contain minor amounts of auxiliary substances such as wetting or emulsifying agents, pH buffering agents, and/or adjuvants which enhance the effectiveness of the neutralizing antibodies. Such additional formulations and modes of administration as are known in the art may also be used.

The virus particles produced by replication competent HCV polynucleotide of the invention can be used as a source of viral antigen to measure the presence and amount of antibody present in an animal. Assays are available that measure the presence in an animal of antibody directed to HCV, and include, for instance, ELISA assays, and recombinant immunoblot assay. These types of assays can be used to detect whether an animal has been exposed to HCV, and/or whether the animal may have an active HCV infection. However, these assays do not use virus particles, but rather individual or multiple viral polypeptides expressed from recombinant cDNA that are not in the form of virus particles. Hence they are unable to detect potentially important antibodies directed against surface epitopes of the envelope polypeptides, nor are they measures of functionally important viral neutralizing antibodies. Such antibodies could only be detected with the use of infectious virus particles, such as those that are produced in this system. The use of infectious viral particles as antigen in assays that detect the presence of specific antibodies by virtue of their ability to block the infection of cells with HCV viral particles, or that possibly bind to whole virus particles in an ELISA assay or radioimmunoassay, will allow the detection of functionally important viral neutralizing antibodies.

The present invention also provides a kit for identifying a compound that inhibits replication of a replication competent HCV polynucleotide. The kit includes a replication competent HCV polynucleotide as described herein, and a cell that contains a polynucleotide including a transactivated coding sequence encoding a detectable marker and an operator sequence operably linked to the transactivated coding sequence in a suitable packaging material. Optionally, other reagents such as buffers and solutions needed to practice the invention are also included. Instructions for use of the packaged materials are also typically included.

As used herein, the phrase "packaging material" refers to one or more physical structures used to house the contents of the kit. The packaging material is constructed by well known methods, preferably to provide a sterile, contaminant-free environment. The packaging material may include a label which indicates that the replication competent HCV polynucleotide can be used for identifying a compound that inhibits replication of an HCV. In addition, the packaging material may contain instructions indicating how the materials within the kit are employed. As used herein, the term "package" refers to a solid matrix or material such as glass, plastic, and the like, capable of holding within fixed limits the replication competent virus and the vertebrate cell.

The present invention is illustrated by the following examples. It is to be understood that the particular examples, materials, amounts, and procedures are to be interpreted broadly in accordance with the scope and spirit of the invention as set forth herein.

EXAMPLES

Example 1

Construction of the Infectious MK0-Z RNA

Figure 2:
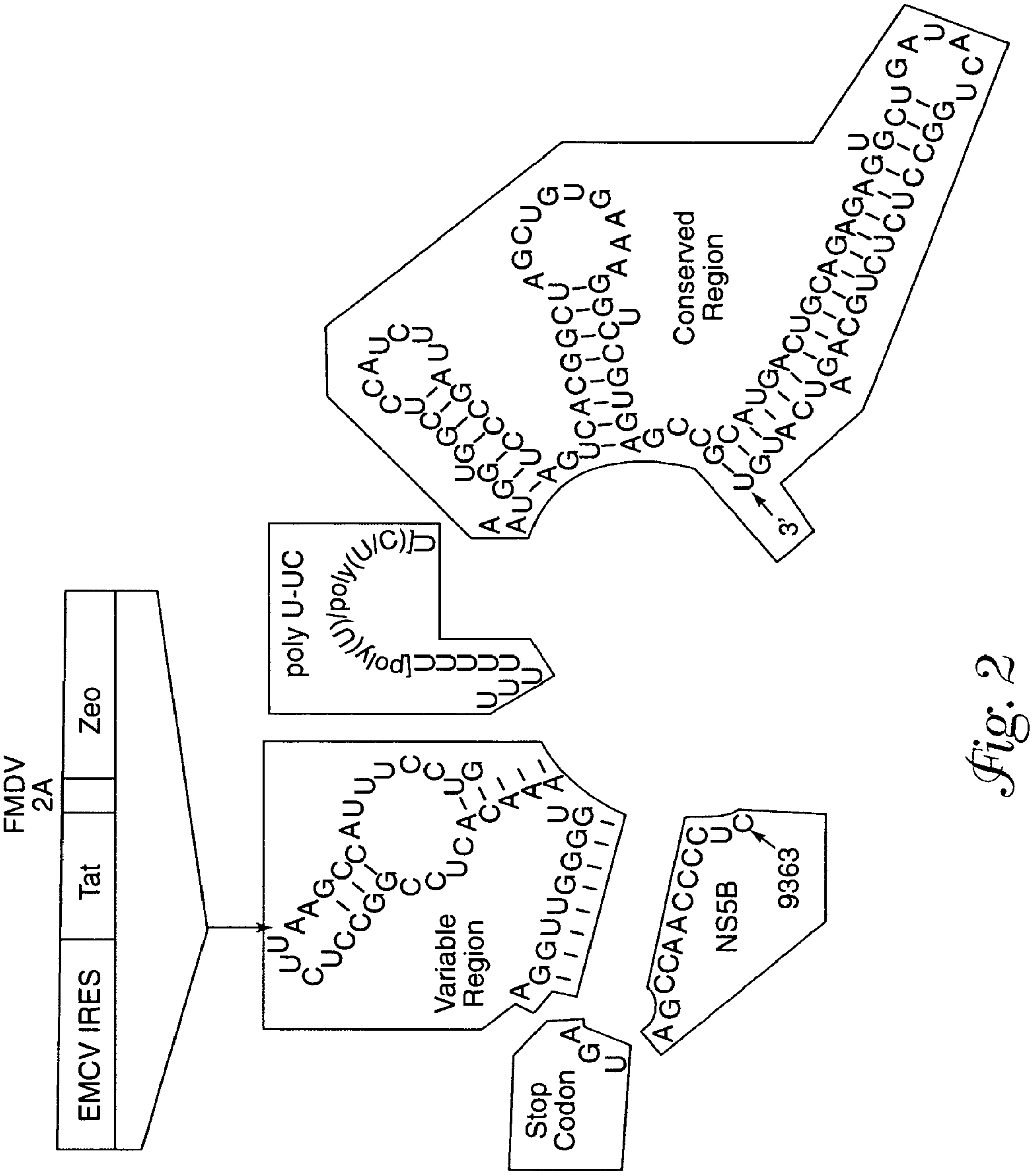
FIG. 2. Site of insertion of heterologous sequence within the 3'NTR (3' non-translated RNA) of H77C strain (pCV-H77C). Variable region, poly U-UC, and Conserved region refer to regions of the 3' non-translated RNA; EMCV IRES, tat, FMDV 2A, and Zeo, see legend to FIG. 1; NS5B refers to the last 12 nucleotides that encode NS5B.

FIG. 1 shows the full-length modified HCV cDNA (MK0-Z) that was constructed by modification of pCV-H77C. The nucleotide sequence of MK0-Z is shown in FIG. 9. A coding region encoding a polypeptide conferring resistance to neomycin has been expressed under control of the EMCV IRES from a second reading frame inserted within the 3' non-translated RNA in subgenomic Kunjin virus replicons. However, the specific placement of the foreign sequence could not be used as a guide for the placement of a coding region in HCV since the 3' non-translated RNA of these viruses share no sequence identity. In the case of MK0-Z, the heterologous sequence functions as a unique 3' cistron, with the internal ribosome entry site (IRES) of encephalomyocarditis virus (EMCV) directing the cap independent translation of a novel polyprotein composed of Tat and the ZEOCIN (phleomycin, Invitrogen) resistance protein, Zeo, separated by the cis-active 2A proteinase of foot-and-mouth disease (FMDV) virus. The Asn-Pro-Gly sequence at the carboxy terminus of FMDV 2A mediates proteolytic cleavage at the 2AZeo junction, effectively separating the upstream Tat and downstream Zeo polypeptides (Ryan et al., *EMBO J*, 13, 928-933 (1994)). The heterologous sequence is placed within the 3'NTR of HCV, a genomic region that contains highly conserved sequences that cannot be deleted without loss of infectivity. More specifically, the heterologous sequence was placed within the variable region of the 3'NTR (FIG. 2). As a control, a replication-incompetent variant of MK0-Z, dS-MK0-Z, was constructed by opening the clone at two closely positioned Sma I sites within the NS5B coding region, then religating the plasmid. This resulted in a frame-shift deletion in the HCV sequence, upstream of the GDD motif in the polymerase encoded by the NS5B coding region, that is lethal to viral replication. The novel 3' reading frame in MK0-Z, has been shown to be active translationally in in vitro translation reactions carried out in rabbit reticulocyte lysates. These experiments also demonstrated that the 2A proteinase effectively cleaved the resulting polyprotein, releasing Tat-2A from the Zeo protein.

a. Construction of pUC HCV3'-EMCV-tat-2A-Zeo

To make pHCV3', full length HCV 1a (present on the plasmid pCV-H77C) (provided by Dr. Purcell at NIH) was digested with HindIII-XbaI. A DNA fragment of about 1.7 kilobases, corresponding to nucleotides 7861-9599 of the HCV nucleotide sequence available at Genbank Accession number AF011751, was isolated and ligated into the vector pBluescript (Stratagene) that had been digested with HindIII and XbaI. The resulting plasmid was designated pHCV3'.

A DNA fragment containing the EMCV IRES was generated by the polymerase chain reaction (PCR). The plasmid pEMCV-CAT, described in Whetter et al., (*Arch. Virol. Suppl.* 9, 291-298 (1994)) was amplified using the sense primer 5'-GGCCTCTTAAGGTTATTTTCCACCATATTG-CC (SEQ ID NO:22) which contained a BfrI site, and the anti-sense primer 5'-TCCCCGCGGAAGGCCTCATATT-ATCATCGTGTTTTTC (SEQ ID NO:23) which contained a SacI and StuI site. The italicized nucleotides are those which are not present in the DNA to be amplified, and the underlined nucleotides indicate a restriction endonuclease site. The PCR conditions were: 94° C. for 30 seconds, 55° C. for 30 seconds, and 72° C. for 1 minute, for 35 cycles.

pHCV3'-EMCV was generated by ligating EMCV IRES fragment digested with BfrI-SacI and vector from pHCV3' digested with same enzymes.

A DNA fragment containing the nucleotides encoding 85 amino acids from the HIV I Tat protein was generated by PCR. The amino acid sequence of the HIV I Tat protein is shown at amino acids 4-89 of SEQ ID NO:21 The plasmid used was pCTAT (provided by Dr. Bryan Cullen, Duke University, Durham, N.C. Dept. of Microbiology) (see Bieniasz et al., *Molecular Cellular Biology,* 19, 4592-4599); was amplified using the sense primer 5'-GA AGGCCTATGGAGCCAGTAGATCCTAGA (SEQ ID NO:28), which contained a StuI site, and and anti-sense primer 5'-CGGAATTCTTCCTTCGGGCCTGTCGGGTCC (SEQ ID NO:29), which contained an EcoRI site. The italicized nucleotides are those which are not present in the DNA to be amplified, and the underlined nucleotides indicate a restriction endonuclease site. The PCR conditions were: 94° C. for 30 seconds, 55° C. for 30 seconds, and 72° C. for 1 minute, for 35 cycles.

A DNA fragment containing the nucleotides encoding 15 amino acids of FMDV 2A was generated by annealing 51 mer primer set; sense primer 5'-AATTCGACCTTCTTAA-GCTTGCGGGAGACGTCGAGTCCAACCCTGGGCC-CG (SEQ ID NO:24) and anti-sense primer 5'-GATCCG-GGCCCAGGGTTGGACTCGACGTCTCCCGCAAGCT-TAAGAAGGTCG (SEQ ID NO:25) with putative digested form of EcoRI and BamHI site at its 5' and 3' end, respectively. The result was a DNA fragment encoding the 15 amino acids of FMDV 2A. The amino acid sequence encoded by the DNA fragment was FDLLKLAGDVESNPG (SEQ ID NO:30).

A DNA fragment containing the coding region encoding resistance to phleomycin was generated by the polymerase chain reaction (PCR). The plasmid pZeoSV (Invitrogen) was amplified using the sense primer 5'-CCGCTCGAGGCCT GGATCCATGGCCAAGTTGACCAGTGCC (SEQ ID NO:26) which contained a BamHI site, and anti-sense primer 5'-GGCCTCTTAAGTCAGTCCTGCTCCTCGGC-CACG (SEQ ID NO:27) which contained a BfrI site. The italicized nucleotides are those which are not present in the DNA to be amplified, and the underlined nucleotides indicate a restriction endonuclease site. The PCR conditions were: 94° C. for 30 seconds, 55° C. for 30 seconds, and 72° C. for 1 minute, for 35 cycles.

pΔHCV3'-2A-Zeo was generated by digesting the DNA fragment containing the coding region encoding resistance to phleomycin with BfrI-BamHI, and pHCV3' was with EcoRI-BfrI. These two fragments and the FMDV 2A fragment (which contains an EcoRI site with staggered ends and a BamH site with staggered ends) were then ligated to form pΔHCV3'-2A-Zeo.

pUC HCV3'-EMCV-tat-2A-Zeo was generated by ligating 4 fragments together. A DNA fragment containing the EMCV IRES was obtained by digesting pHCV3'-EMCV with SphI-StuI. The amplified DNA fragment encoding a portion of the HIV I Tat protein was digested with StuI-EcoRI. pΔHCV3'-2A-Zeo was digested with EcoRI and XbaI to yield a DNA fragment containing the nucleotides encoding the FMVD 2A and phleomycin resistance. pUC20 vector digested with SphI-XbaI. These were ligated together and the resulting plasmid was designated pUC HCV3'-EMCV-tat-2A-Zeo.

b. Construction of pUC HCV3'-EMCV-tat-2A Containing New HCV 3'Fragment

Original full length HCV 1a (present on the plasmid pCV-H77C) was digested with SphI-BfrI and a 342 nucleotide fragment (corresponding to nucleotides 9060-9427 of HCV) was isolated. pUC HCV3'-EMCV-tat-2A-Zeo was digested StuI-BamHI and a fragment of 317 nucleotides containing tat-2A was isolated. The remaining portion of the plasmid was digested with BfrI, and a 508 nucleotide BfrI-StuI fragment containing the EMCV IRES was isolated. The remaining 361 nucleotide fragment, which contained the nucleotides encoding phleomycin resistance was isolated and reserved for later use in the construction of pUC Zeo-HCV3'NTR containing new HCV3'NTR fragment (see section c below).

pUC HCV3'-EMCV-tat-2A was generated by ligating the 3 fragments described above, i.e., the 342 nucleotide SphI-BfrI fragment corresponding to nucleotides 9060-9427 of HCV, the 508 nucleotide BfrI-StuI fragment containing the EMCV IRES, and the 317 nucleotide StuI-BamHI fragment containing tat-2A, with the vector pUC20 that had been digested with SphI-BamHI. The resulting plasmid was designated pUC HCV3'-EMCV-tat-2A.

c. Construction of pUC Zeo-HCV3'NTR Containing New HCV3'NTR Fragment pUC Zeo-HCV3'NTR was constructed by ligating the 361 nucleotide BamHI-BfrI fragment encoding phleomycin resistance (see above), a 198 nucleotide fragment (corresponding to nucleotides 9427-9625 of HCV) generated by digesting original full length HCV 1a with BfrI-XbaI, and the vector pUC20 that had been digested with BamHI-XbaI.

d. Construction of MK0-Z RNA

Steps b and c above were repeated to produce a second pUC HCV3'-EMCV-tat-2A and a second pUC Zeo-HCV3'NTR containing new HCV3'NTR fragment for use in the construction of MK0-Z RNA.

MK0-Z was generated by the ligation of 4 fragments. Full length HCV was digested with HindIII-SphI and a 1,199 nucleotide fragment (corresponding to nucleotides 7861-9060 of HCV) was isolated. A SphI-BamHI DNA fragment containing HCV3'-EMCV-tat-2A was isolated from pUC HCV3'-EMCV-tat-2A. A BamHI-XbaI DNA fragment containing Zeo-HCV3'NTR was isolated from pUC Zeo-HCV3'NTR. Nucleotides corresponding to nucleotides 1-7860 were isolated from pCV-H77C by digestion with HindIII-XbaI. Ligation of these 4 fragments resulted in MK0-Z.

e. Construction of ds-MK0-Z RNA

The plasmid pHCV3' was digested with SmaI and ligated under conditions to result in self-ligation. The result of the self ligation was loss of the nucleotides corresponding to nucleotides 8497-8649 of HCV. The resulting plasmid was designated pds-HCV3'.

ds-MK0-Z was generated by ligation of 4 DNA fragments. pds-HCV3' was digested with HindIII-SphI to yield a DNA fragment corresponding to nucleotides 7861-9060 of HCV and containing the SmaI fragment deletion. pUC HCV3'-EMCV-tat-2A was digested with SphI-BamHI to yield a fragment containing HCV3'-EMCV-tat-2A. pUC Zeo-HCV3'NTR was digested with BamHI-XbaI to yield a fragment containing the nucleotides encoding Zeo-HCV3'NTR. Nucleotides corresponding to nucleotides 1-7860 were isolated from pCV-H77C by digestion with HindIII-XbaI. Ligation of these 4 fragments resulted in ds-MK0-Z.

Example 2

Production of the Virus by Chimpanzee

This demonstrates the insertion of a heterologous sequence into an HCV does not destroy the ability of the HCV to replicate and produce infectious virus.

MK0-Z plasmid was linearized with XbaI and RNA was synthesized with T7 mega transcription kit from Ambion. The reaction was analysed by gel electrophoresis before injecting into the liver of an HCV-naive Chimpanzee. RNA was frozen at −70° C. overnight before used. About 300 μg of RNA was injected. When injecting, the RNA, which was in 100 ml of transcription reaction mixture, was diluted in 1 ml PBS. The RNA was administered to a Chimpanzee by percutaneous intrahepatic injection guided by ultrasound. Several sites and injections were done in single day. The levels of ALT in the chimpanzee were monitored and were in normal ranges throughout the experiment. Sera from the chimpanzee were collected weekly, and the presence of HCV in each 1 ml of those sera, were checked by RT-PCR, using either the TaqMan or Light Cycler RT-PCR methods.

The primers and probe used for the TaqMan RT-PCR were sense primer, AAGACTGCTAGCCGAGTAGTGTT nt 243 to 265 (SEQ ID NO:1); anti-sense primer: GGTTGGTGTTACGTTTGGTTT nt 390 to 370 (SEQ ID NO:2); and probe: TGCACCATGAGCACGAATCCTAAA nt 336 to 359 (SEQ ID NO:3), where "nt 243 to 265," "nt 390 to 370," and "nt 336 to 359" refers to the HCV nucleotides (at Genbank Accession number AF011751) to which the primers hybridize. All single-tube EZ RT-PCR reactions were carried out in optical MicroAmp reaction tubes with optical lids in 50 microliter (μl) volume (96 well format). The RNA amplification was done using the TaqMan EZ RT-PCR Kit. Briefly, reactions contained 1× amplification buffer (TaqMan EZ Buffer), 3 mM manganese, 0.5 U AmpErase uracil-N-glycosylate, 7.5 U rTth DNA polymerase, RNA, 200 nM forward and reverse primers, 200 μM each dNTP, and 500 uM of dUTP. Thermocycling conditions were one cycle at 50° C. for 2 minutes, one cycle at 60° C. for 30 minutes, one cycle at 95° C. for 5 minutes, and 40 cycles of 95° C. for 20 seconds, 60° C. for 1 minute. Amplifications were evaluated by ABI7700 Sequence Detector version 1.6.3 software (Applied Biosystems), as suggested by the manufacturer.

The primers and probe used for Light Cycler RT-PCR were forward primer, ACACTCCACCATGAATCACTC, nt 22 to 41, (SEQ ID NO:4); reverse primer, GATCGGGCTCATCACAACCC, nt 268 to 250, (SEQ ID NO:5); fluor probe, GCGTCTAGCCATGGCGTTAGTATGAGT(fluor), nt 75 to 101 (SEQ ID NO:6); and red probe, (LC640) TCGTGCAGCCTCCAGGACCCC(phosphate), nt 103 to 123 (SEQ ID NO:7). The terms "nt 22 to 41," "nt 268 to 250," "nt 75 to 101" and "nt 103 to 123" refer to the HCV nucleotides (at Genbank Accession number AF011751) to which the primers hybridize. The "fluor probe" is labeled at the 3' end with fluorescein, and the "red probe" is labeled at the 5' with LightCycler Red 640 dye.

Single-tube RT-PCR reactions were carried out in capillary tubes in a reaction volume of 20 μl using the core reagents of RNA Amplification Kit Hybridization Probes (Roche) as suggested by the manufacturer. A master mix was made according to the manufacturer's suggestions, containing Lightcycler-RT-PCR Reaction Mix Hybridization probe solution, LightCycler RT-PCR Enzyme mix, 7 mM $MgCl_2$, 0.5 μM of forward primer, 0.9 μM of reverse primer and 0.5 μM of fluor probe, 0.9 μM of red probe, and $H_2O$ is added to make it total 20 μL. This master mix was added directly to the RNA pellet and after dissolve the RNA, it was loaded into glass capillary tube. After adding the 5 ul wash, the tube was snap sealed with a plastic cap. The RT-PCR conditions were 55° C. for 15 minutes, 95° C. for 30 seconds, and 40 cycles of 94° C. for 0 seconds, 60° C. annealing for 15 seconds, and 72° C. extension for 15 seconds.

The signal acquisition was at the end of the annealing step for 100 milliseconds (ms). After amplification was complete, a melting curve was performed by cooling to 55° C., holding at 55° C. for 30 seconds, and then heating slowly at the rate of 0.2 C/second until 90° C. Signal was collected continuously during this melting to monitor the dissociation of the 5'-LC640-labeled probe. The signal was the result of fluorescence resonance energy transfer (FRET) between the fluor probe and the red probe. These probes hybridize to an internal sequence of the amplified fragment during the annealing phase of the PCR cycle. One probe is labeled at the 5' end with a LightCycler-Red fluorophore (LC-Red 640 or LC-Red 705), and to avoid extension, modified at the 3' end by phosphorylation. The other probe is labeled at the 3' end with fluorescein. Only after hybridization to the template, do the two probes come in close proximity, resulting in FRET between the two fluorophores. During FRET, fluorescein, the donor fluorophore, is excited by the light source of the LightCycler Instrument. Part of the excitation energy is transferred to LightCycler-Red, the acceptor fluorophore. The emitted fluorescence of the LightCycler-Red fluorophore is measured. The melting curves were then displayed as –dF/d T vs T plots as calculated by LightCycler software version 3.

Figure 11:
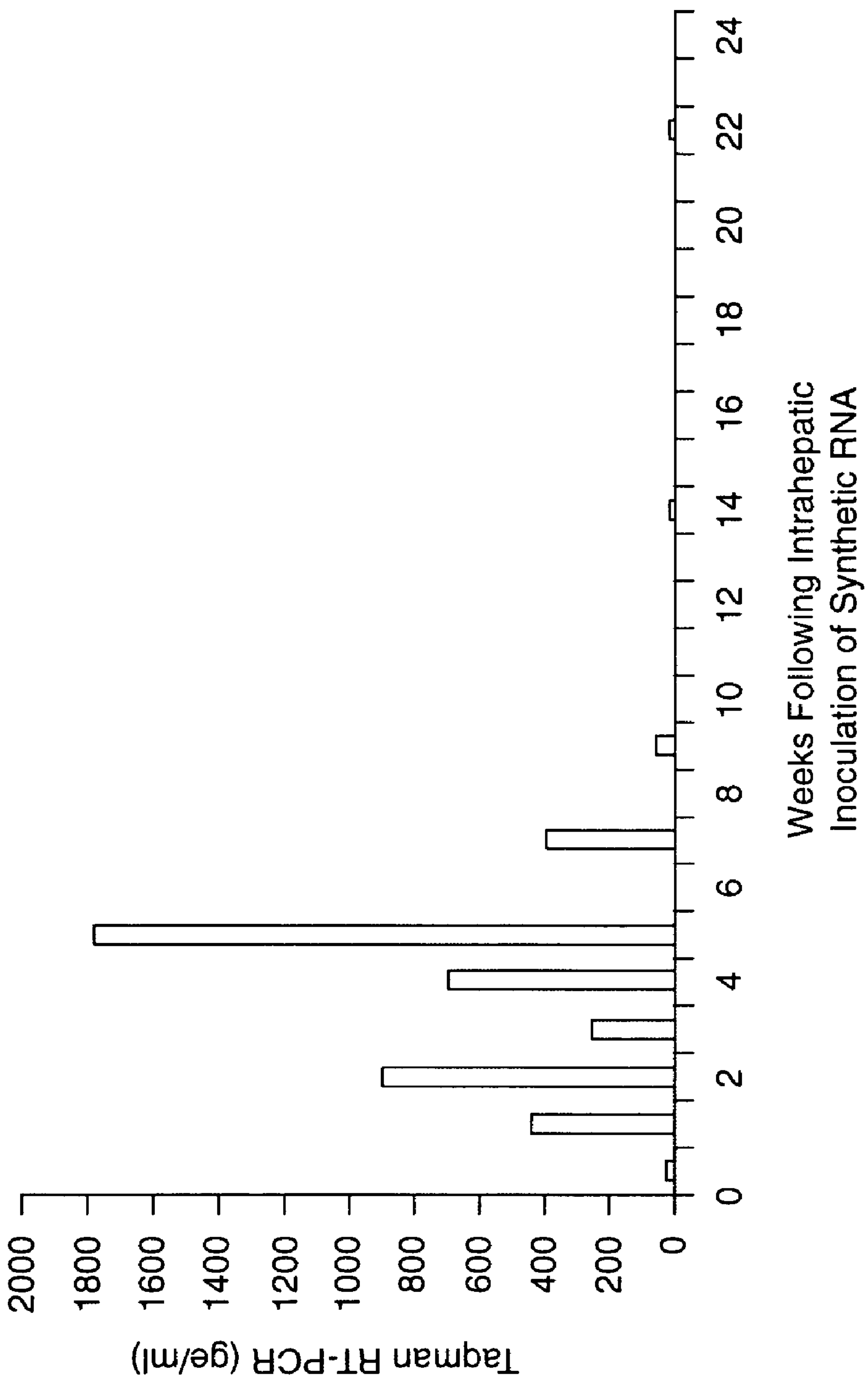
FIG. 11. The results of Taqman RT-PCR of a chimpanzee inoculated with MK0-Z RNA. The term ge/ml refers to genomic equivalents per milliliter.

The results of TaqMan RT-PCR are shown in FIG. 11. They demonstrate that MK0-Z RNA is infectious in a chimpanzee.

Example 3

Construction of a Cellular Enzyme Reporter System for Detection of Replicating HCV A major difficulty in evaluating the outcome of experiments in which cultured cells are transfected with candidate infectious RNAs lies in the detection of newly synthesized viral RNAs against the large background of transfected input RNA. While this is less of a problem with very robustly replicating viral RNAs, only Lohmann et al. (*Science,* 285, 110-113 (1999)) and Blight et al. (*Science,* 290, 1972-1975 (2000)) have thus far reported levels of replication detectable by northern analysis, using subgenomic RNA replicons that are not capable of producing infectious virus. Moreover, these authors observed such replication only in a small number of cell clones that were isolated over a period of weeks by a stringent antibiotic selection protocol. RT-PCR is difficult to use to detect newly replicated nucleic acid in recently transfected cells due to the persistence of input RNA (in our experience, RNA transfected by liposome-mediated methods remains detectable for weeks). The use of a negative-strand "specific" assay reduces, but does not eliminate this problem, since such assays have no more than a ~1,000-fold relative specificity for detection of the negative strand vs. detection of the positive-strand (see, for instance, Lanford et al., *J. Virol.,* 69, 8079-8083 (1995)).

Figure 3:
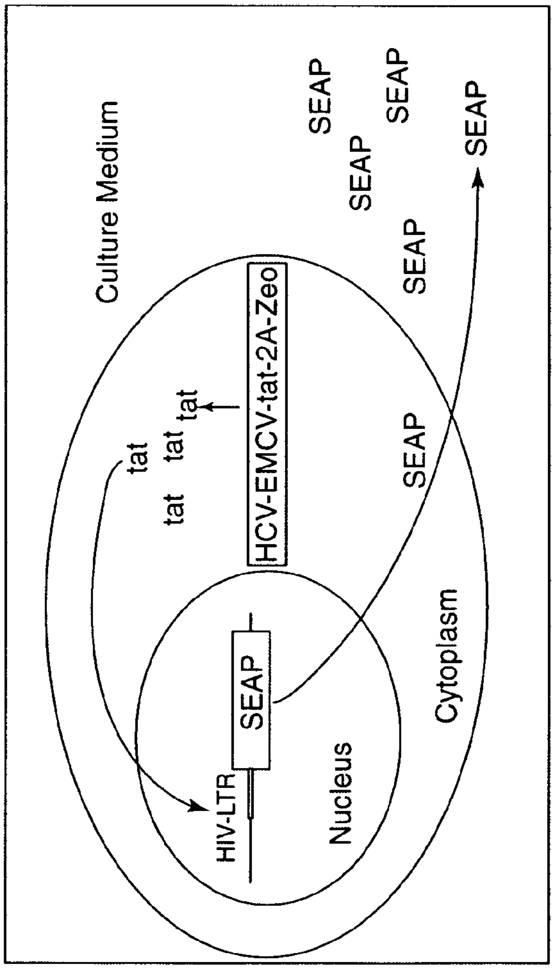
FIG. 3. Schematic depicting release of SEAP from a reporter cell line by expression of Tat from a modified HCV RNA. EMCV, tat, 2A, and Zeo, see legend to FIG. 1; HIV-LTR, HIV I long terminal repeat transcriptional regulator; SEAP, secretory alkaline phosphatase.

This Example details the construction of a cell line that allows the detection of replicating synthetic HCV RNA. The detection is based on the detection of a protein product expressed from the RNA. The system uses the incorporation of the sequence encoding the HIV I Tat protein within modified viral RNAs (see FIG. 1). The Tat protein is a strong transactivator of the HIV I long terminal repeat (LTR) transcriptional regulator. For use as cell substrates in this system, multiple stably transformed cell lines were established. The transformed cell lines were derived from Huh-7 cells that express secretory alkaline phosphatase (SEAP) under transcriptional control of the HIV I LTR. These cell lines were established using either Neomycin or Blastocidin selection, so that either of these antibiotics or Zeocin can be used for subsequent selection of replicating full-length HCV RNAs. The expression of Tat within these cells leads to measurable increases in SEAP activity within the culture medium, as depicted schematically in FIG. 3.

For establishment of neomycin resistant SEAP cell lines, the HIV-SEAP sequence was PCR amplified from pBCHIVSEAP plasmid (provided by Dr. Bryan Cullen, Duke University, Durham, N.C. Dept. of Microbiology) (see Cullen, *Cell,* 46, 973-982 (1986), and Berger et al., *Gene,* 66, 1-10 (1988)) using the primer pairs 5'-CTAGCTAGCCTCGAGACCTGGAAAAACATGGAG (SEQ ID NO:8) and 5'-ATAAGAATGCGGCCGCTTAACCCGGGTGCGCGG (SEQ ID NO:9). The non-italicized nucleotides in SEQ ID NOs:8 and 9 hybridize with nucleotides present in the target DNA, and the italicized nucleotides in SEQ ID NO:9 represent additional nucleotides that do not hybridize with the target DNA. The underlined nucleotides indicate introduced restriction endonuclease sites. The nucleotide sequence of the amplified fragment is shown in FIG. 12 (SEQ ID NO:18).

After filling in to repair the possible PCR overhang, this fragment was digested with NotI and ligated to vector derived from pRcCMV (Invitrogen) digested with NruI-NotI removing CMV promoter. The resulting plasmid was designated pRcHIVSEAP The nucleotide sequence of the pRcHIVSEAP was used to transfect Huh-7 cells using a non-liposomal transfection reagent commercially available under the trade name FUGENE (Boerhinger Manheim). Tranfectants were selected using G418 (neomycin). The ability of a cell to express SEAP in the presence of tat was tested by transfecting cells with the plasmid pCTAT, which expresses the tat protein. Two resulting cell lines which expressed high levels of SEAP were designated Huh-o10

(also referred to as Huh7-SEAP-o10) and Huh7-SEAP-N7, and were used for subsequent experiments.

A Blasticidin resistant SEAP cell line was constructed as follows. pcDNA6/V5-His (Invitrogen) was digested with BglII-BamHI to remove the CMV promoter. The vector was then self-ligated and subsequently digested with EcoRV-NotI and ligated to the HIV-SEAP DNA fragment that was PCR amplified from pBCHIVSEAP fragment mentioned. The resulting plasmid was used to transfect Huh-7 cells using a non-liposomal transfection reagent commercially available under the trade name FUGENE (Boerhinger Manheim). Tranfectants were selected using Blastocidin (Invitrogen). A blastocidin resistant cell was selected and designated Huh-SEAP-Bla-EN.

Example 4

Evaluation of the Cellular Enzyme Reporter System for Detection of Replicating HCV This Example demonstrates the feasibility and utility of the SEAP cellular reporter system, and demonstrates the expression of Tat by the genetically modified HCV RNA.

To test the SEAP cellular reporter system, MK0-Z RNA was synthesized and transfected into two different SEAP reporter cell lines, Huh7-SEAPo10 and Huh7-SEAP-N7 (another cell line that resulted from neomycin selection), on the same day. To provide adequate controls for this experiment, cells from both cell lines were transfected with RNAs synthesized from each of the plasmid DNAs shown in FIG. 1. These include MK0-Z, its replication incompetent control dS-MK0-Z, and a subgenomic transcript, 3'ETZ, each of which encode the novel polyprotein consisting of Tat and Zeo separated by the 19 amino acid 2A proteinase from FMDV 4. Fifteen of the amino acids were the FMDV 2A sequence, and 4 additional amino acids were encoded by nucleotides present to introduce restriction endonuclease sites. In each of the transfected RNAs, this polyprotein is under the translational control of the EMCV IRES.

DNA was linearized with Xba I and RNA was synthesized with T7 mega transcription kit (Ambion, Madison, Wis.). Transfection of RNA was done using Lipofectin (Gibco BRL, Rockville, Md.). Briefly, about 5 μg of RNA was added to a mixture (1 hour incubation prior to transfection) of 15 μl of Lipofectin and 200 μl OPTIMEM (Gibco BRL), incubated for 15 min, and applied to cells. The cells were in 6 well plates which had been plated one day before transfection. The cells were washed two times with OPTIMEM before addition of the RNA, followed by the addition of 1 ml of OPTIMEM. After overnight incubation, cells were washed with PBS two times and growth medium (DMEM with 2% FBS as above) was added.

Transfection of these RNAs was associated with striking increases in SEAP secreted into the cell culture supernatant, as measured by assay of SEAP. SEAP was assayed using Tropix Phospha-Light Chemiluminescent Reporter Assay for secreted Alkine Phosphatase reagent (Tropix, Foster City, Calif.), according to the manufacturer's suggested protocol, but reduced ⅓ in scale. Luminescent signal detected by a TD-20/20 Luminometer (Turner Design).

The increase in SEAP occurred as a result of transfection with either MK0-Z or the replication deficient dS-MK0-Z RNA, indicating that the SEAP released in the initial weeks after transfection was expressed from the input RNA, not newly replicated RNA. High expression of SEAP was observed from 3'ETZ, reflecting greater transfection efficiency of this small RNA transcript. This experiment demonstrates the feasibility and utility of the SEAP cellular reporter system, and demonstrates the expression of Tat by the genetically modified HCV RNA.

Figure 4A:
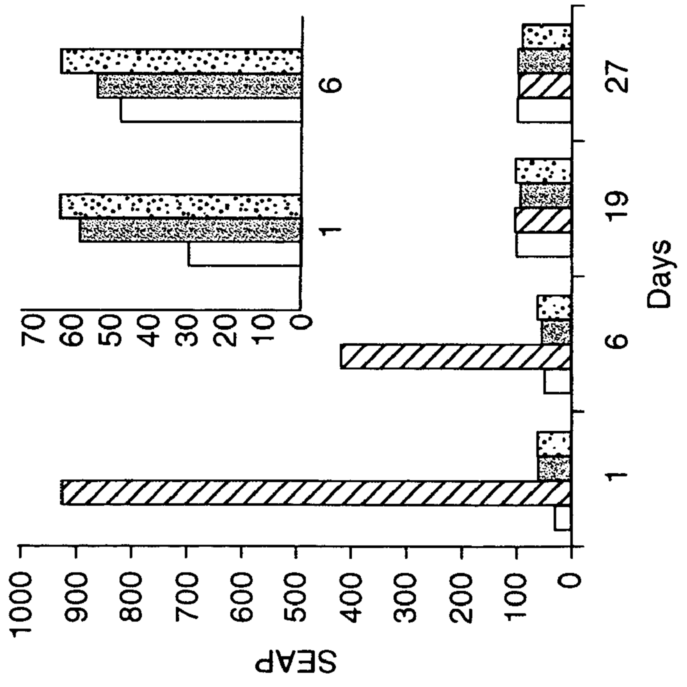
FIG. 4. SEAP activity in medium collected from cells following transfection with RNAs. (A) Huh7-SEAP-o10 cells. (B) Huh7-SEAP-N7 cells. The smaller graph A and B each depict days 1 and 6, but use different scales. Mock, cells exposed to transfection conditions but not RNA; 3'ETZ, MK0-Z, and dS-MK0-Z, the constructs shown in FIG. 1; y-axis, units of secretory alkaline phosphatase activity measured by luminescent signal detected by a TD-20/20 Luminometer (Turner Design, Sunnyvale, Calif.).
Figure 4B:
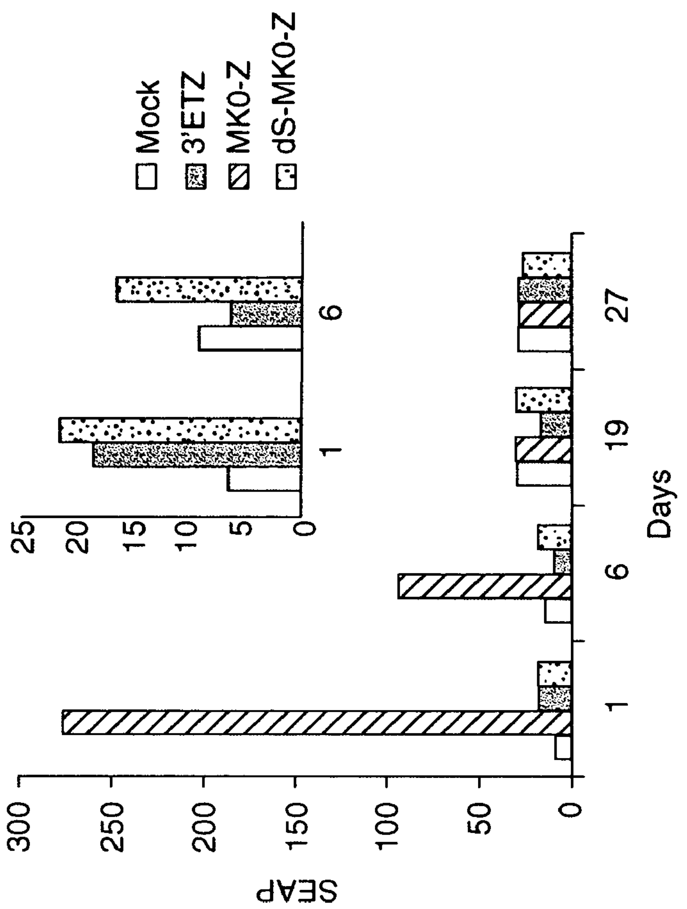
Figure 5:
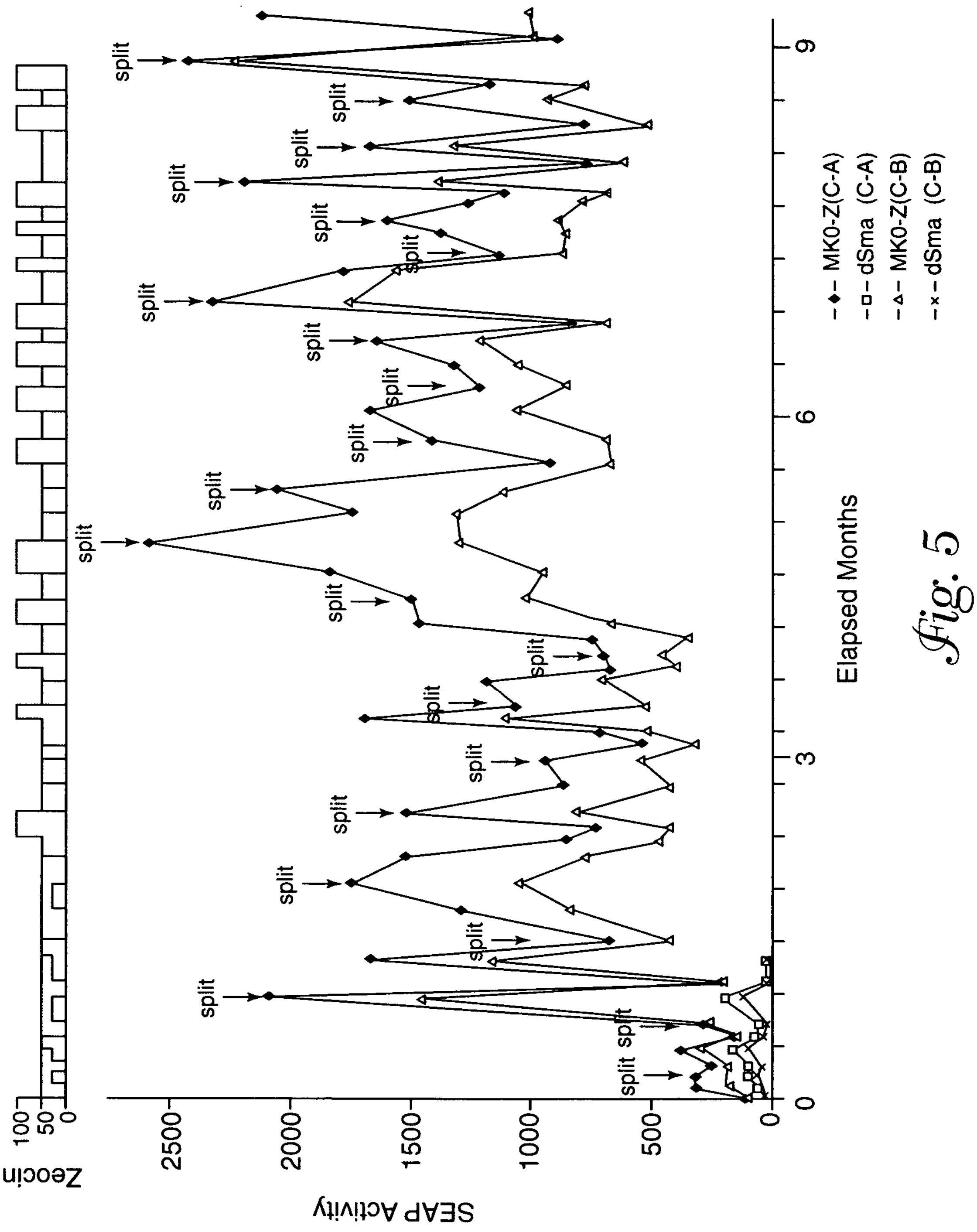
FIG. 5. The passage history of two Huh-SEAP-o10 cell sublines (MK0-Z.C-A and MK0-Z.C-B) that were infected with MK0-K and the secretory alkaline phosphatase (SEAP) activity in supernatant media collected at approximately weekly intervals from both surviving cell lines. dSma (C-A) and dSma (C-B) are two Huh-SEAP-o10 cell sublines infected with supernatant fluids collected from cells transfected in parallel with dS-MK0-Z (NS5B-deletion mutant) RNA. Split, points at which the cultures were split are indicated by arrows. The top panel shows the timing and magnitude of Zeocin selection pressure (top panel, mg/ml).

Proof that infection had been accomplished by the transfection of MK0-Z RNA and that virus adaptation to replication in cultured cells had occurred under antibiotic selection pressure accumulated over the ensuring several months, as follows. FIG. 4 (left panel) shows the results of SEAP assays on media harvested from these cells during the first month after transfection with MK0-Z, and the pol(−) mutant dSMk0-Z. These cells were subsequently maintained in medium with a low concentration of fetal calf serum (2%) over the ensuing 3 months, during which the cells were split periodically and intermittently exposed to low concentrations of the antibiotic Zeocin as tolerated (about 10 to 25 μg/ml). There was no significant difference in cell survival in the presence of Zeo between cells transfected with MK0-Z, and those transfected with dSMK0-Z, but the former usually expressed somewhat higher levels of SEAP in the media (about 1.5 times to about 2 times higher than the control cells). At approximately 3 months, these cells (both MK0Z and ds-MKM0-Z transfected cells) underwent a spontaneous crisis with loss of viability. The supernatant fluids were collected and placed on replicate cultures of fresh Huh-SEAPo 10 cells in an attempt at blind passage of virus. Antibiotic selection was continued intermittently, with gradually intensifying Zeocin selection (intermittent exposure ultimately to 50 μg/ml). With the increase to 50 μg/ml Zeocin, sudden marked increases in SEAP expression were noted from replicate cultures of cells that had been inoculated with medium from the MK0-Z transfected cells, but not cells inoculated with the pol(−) mutant, dS-MK0-Z. This occurred about 7 months after the original transfection, and 4 months after the attempt at cell-free passage of virus. All cells were unable to survive the higher concentration of Zeo, however and the cultures were lost at this point. However, cells that had been previously frozen from the putative passage were recovered from the freezer, and subjected to intermittent concentrations of Zeocin ranging from 25-50 μg/ml. Results are shown in FIG. 5, and summarized in Table 2.

TABLE 2

Passage history of vMK0-Z-infected Huh-SEAP-o10 C-A and C-B sublines.[1]

| Passage | Approximate elapsed time (days) | Comments |
|---|---|---|
| P1 | 1 | Huh-SEAP-o10 cells transfected with MK0-Z RNA, maintained in the absence of antibiotic selection. |
| | 33 | Start intermittent Zeocin selection pressure, 10-25 mg/ml. |
| | 75 | Cells entered crisis and were lost |
| P2 | 68 | Fresh Huh-SEAP-o10 cells infected with P1 day 68 supernatant, and maintained in intermittent Zeocin 25 mg/ml. |
| | 190 | Increase Zeocin to 25-50 mg/ml, with resulting increase in SEAP expression. |
| | 197 | Cells frozen (continuously cultured cells lost within about 1.5 months) |
| | 283 | Cells frozen on P2 day 197 were replated, cultured in intermittent Zeocin 50-100 mg/ml, with marked increase in SEAP expression. P2 cells infected with P1 supernatant from control dS-MK0-Z did not survive. |
| | 547 | Two cell lines (C-A and C-B), both established on P2 day 283, maintained in intermittent Zeocin 50-100 mg/ml with high SEAP. |

TABLE 2-continued

Passage history of vMK0-Z-infected Huh-SEAP-o10 C-A and C-B sublines.[1]

| Passage | Approximate elapsed time (days) | Comments |
| --- | --- | --- |
| P3 | 514 | Fresh Huh-SEAP-o10 cells infected with 0.45 m-filtered supernatant media from P2 C-A and C-B cell lines on day 544, maintained in intermittent Zeocin 25 mg/ml. |

[1]The term "vMK0-Z" is used to refer to the viral form of MK0-Z after passage.

As observed previously, striking increases occurred in the level of SEAP secreted from 12 of 12 replicate cultures of cells infected with medium from the MK0-Z-transfected cells, but not from any cultures of cells infected in parallel with medium from dS-MK0-Z transfected cells. Moreover, all of the control cell cultures were lost under exposure to 50 μg/ml Zeocin, while each of the cultures infected with MK0-Z material remained viable. Significantly, there was no increase in SEAP released into the medium from the dying cell lines (FIG. 5, dSma (C-A) and dSma (C-B)), consistent with the fact that all SEAP produced is actively secreted from the cells into the medium. This result confirms that cell death does not result in a false elevation of SEAP activity in culture supernatant fluids. The Zeocin resistance and SEAP expression displayed by these cells cannot be explained by fortuitous integration of DNA from the transfected material, since the cells shown in FIG. 5 were never transfected, only exposed to medium from transfected cells. Cell survival and SEAP expression also cannot be explained by cellular mutations in these experiments, as these events have occurred in multiple cultures exposed to the supernatant fluid of MK0-Z transfected cells, but not in related control cell cultures that were similarly exposed to media from dS-MK0-Z transfected cells.

Fluctuations in SEAP activity correlated in part with cell density, and cell viability. At times, these cultures demonstrated considerable cytopathology. However, it was demonstrated that there was minimal intracellular SEAP activity and that most SEAP is actively secreted from the cells. Thus, peaks of SEAP activity reflect peaks of SEAP synthesis, not release from dying cells.

The results shown in FIG. 5 indicate that these cells express two heterologous proteins encoded by MK0-Z, RNA. The Huh-SEAPo10 cells have acquired relative Zeocin resistance, indicating the expression of the Zeocin resistance protein, and they secrete 5- to 10-fold greater quantities of SEAP than control cells, indicating the expression of Tat. Moreover, RT-PCR has been used to successfully detect the presence of HCV RNA in samples of the supernatant fluids collected from these cells, using a primer set derived from the viral 5'NTR (see Example 5). Detection of the signal was dependent on Southern blotting of first round RT-PCR products, and amplification was dependent upon the inclusion of reverse transcriptase in the reaction. The results suggest that only small quantities of RNA are present, but confirm that the RT-PCR products are amplified from RNA and not contaminating DNA. The sequence of the amplified product was identical to the H77C strain 5NTR, the virus from which the MK0-Z clone was derived. These results thus represent the first successful attempt at recovery of HCV from cells transfected with synthetic RNA.

One of the more important features of the experiment depicted in FIG. 5 is the significant change in the behavior of these HCV infected cells over the months of observation, both in terms of their increasing Zeocin resistance and increasing SEAP secretion. This is consistent with adaptation of the viral RNA to more efficient replication within these cells, as would be expected for a positive-strand RNA virus. Furthermore, since at this point all of the cells exposed to medium from cells transfected with the pol(−) mutant dS-MK0-7 have failed to survive Zeocin selection, it can now be assumed that all of the surviving cells harbor viral RNA. Thus, any further increases in SEAP expression must be indicative of greater abundance of the RNA and enhanced replication of the virus.

In summary, these two cell lines continue to demonstrate substantial Zeocin resistance and high level SEAP activity, two independent measures of protein expression from the second open reading frame of the modified vMK0-Z genome, more than 12 months after their infection with supernatant fluids taken from RNA-transfected cells. This is strong evidence of continued replication of the viral RNA in these cells.

Example 5

Passage of vMK0-Z to Fresh Huh-SEAP-o10 Cells

A third passage of vMK0-Z was carried out using supernatant media collected from the C-A and C-B cell lines on P2 day 540 (see Table 2). These media samples were passed through a 0.45μ filter and then used to feed fresh Huh-SEAP-o10 cells. Control cell cultures (n=6) were mock infected with normal media. One hundred and twenty hours after inoculation, these cells were exposed to intermittent Zeocin selection pressure (25 μg/ml). When treated with high concentrations of drug, or when maintained in continuous drug condition, these cells tend to die. Accordingly, drug exposure was intermittent, and not at high concentrations. The mock-infected cells were lost due to Zeocin toxicity by about day 546 (relative SEAP activity of infected to control cells at this point was 42658 and 31510, respectively, and is not shown in FIG. 6).

Figure 6B:
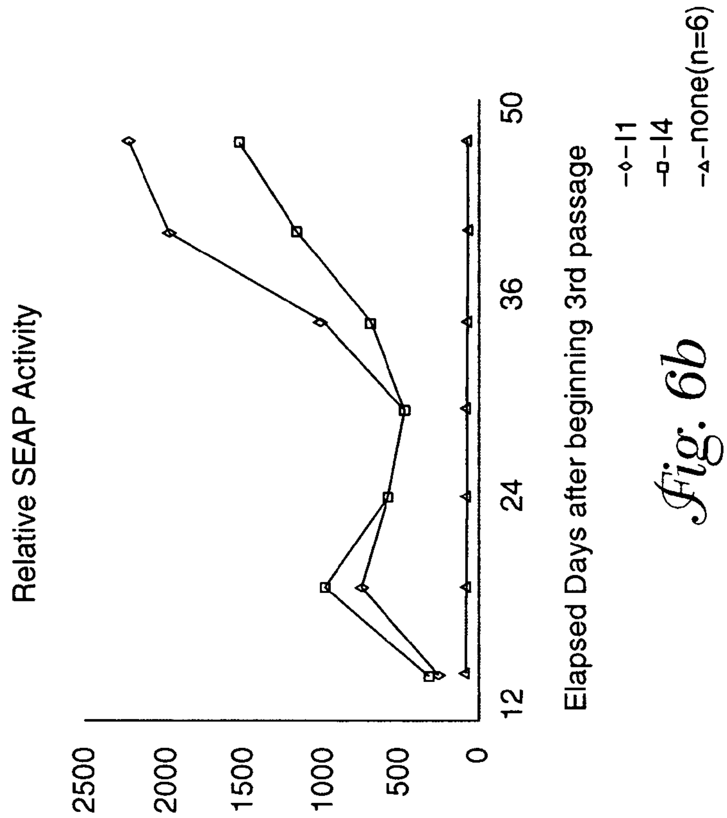
FIG. 6. SEAP expression profiles of Huh-SEAP-o10 cells. (A) Absolute SEAP activities of supernatant media from cells inoculated with supernatant fluids of C-A and C-B MK0-Z infected cell lines. "I1" inoculum=media from C-A subline, "I4" inoculum=media from C-B subline. None=mock infections. (B) SEAP activity relative to SEAP activity of mock-infected control Huh-SEAP-o10 cells (lost during Zeocin selection).
Figure 6A:
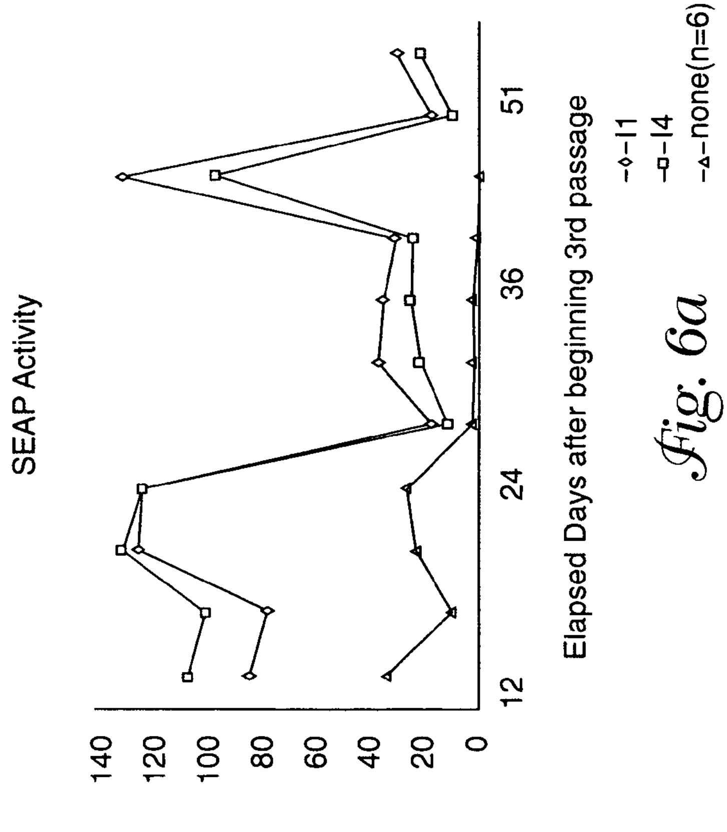

The results shown in FIG. 6 demonstrate the passage of SEAP expression activity and Zeocin resistance to fresh Huh-SEAPo10 cells following inoculation of these cells with supernatant medium collected from vMK0-Z-infected cells.

Example 6

Detection of Viral RNA in Huh-SEAPo10 Cell Lines

Despite the results described above, and the demonstration of viral antigen in MK0-Z infected cells (see Example 7), it has proven difficult to consistently demonstrate viral RNA in these cells. This Example describes methods for detecting the presence of viral RNA in Huh-SEAPo10 cell lines.

Two different quantitative RT-PCR assays (LightCycler and TaqMan) have been used in recent efforts to detect viral RNA in lysates of the cells or in supernatant media. Greatest consistency of success has been in detection of viral RNA in supernatant media following PEG precipitation. This technique works very well, allowing concentration of 130 genome copies equivalent from 1 milliliter (ml) supernatant with 80% recovery. Viral RNA has been reproducibly but intermittently detected in the supernatant fluids; however, reliable detection of viral RNA in cell lysates has not been possible.

The primers and probes that have been used for these assays were as follows:

Lightcycler RT-PCR

This method used the Lightcycler thermal cycler manufactured by Roche.

Primers:

```
Forward
5'-GACACTCCACCATGAATCACT,      (SEQ ID NO:10)
nt 21 to 41,

Reverse
5'-GTTCCGCAGACCACTATGG,        (SEQ ID NO:11)
nt 156 to 139,
```

Probes for Fluorescence Resonance Energy Transfer (FRET):

```
5'-AGAAAGCGTCTAGCCATGGCGTTAG      (SEQ ID NO:12)
(Fluor)

5'(LC640)ATGAGTGTCGTGCAGCCTCCAG   (SEQ ID NO:13)
(phosphate)
```

Briefly, the HCV virus was precipitated with PEG (Sigma, St. Louis, Mo.) prior to extraction with QIAamp serum kit Qiagen, Valencia, Calif.). Supernatant (1.3 ml) was mixed with 0.3 ml of 40% PEG and was placed in an ice bath for 4 hours. The mixture was then centrifuged at 10000×g for 30 minutes at 4° C. The supernatant was removed from the white pellet and 140 μl of TE was added to it. The RNA was then extracted from the viral pellet by following the manufacturers instructions. The eluate was treated with Dnase I as was instructed by the T7 mega transcription kit (Ambion), precipitated with 60 μg glycogen in 130 μl IPA, and stored at −80° C. The positive serum control was a volume of serum containing 5000 genome equivalents, added to media (1.3 ml TE) before precipitation with 0.3 ml PEG and extraction as discussed above. The HCV genome equivalents were determined by National Genetics Institute (Los Angeles, Calif.). The negative serum control was 1 μl of serum from an uninfected volunteer. The serum was treated in the same way as the positive control serum.

The single-tube RT-PCR reactions were carried out in capillary tubes in a reaction volume of 20 μl using the core reagents of RNA Amplification Kit Hybridization Probes (Roche). A 20 μl RT-PCR mixture contained 0.05 μM forward primer, 0.9 μM of reverse primer, RNA sample and 5 ul tube wash of purified sample RNA. The precipitated RNA was first reconstituted with RT-PCR master mix then was loaded into a glass capillary tube, after adding the 5 μl wash the tube was snap sealed with a plastic cap. The RT-PCR conditions were 55° C. for 15 minutes, 95° C. for 30 seconds, and 40 cycles of 94° C. for 0 seconds, 60° C. annealing for 15 seconds, and 72° C. extension for 15 seconds. The signal acquisition was at the end of the annealing step for 100 ms. After amplification was complete, a melting curve was performed by cooling to 55°, holding at 55° C. for 30 seconds, and then heating slowly at 0.2 C/seconds until 90° C. Signal was collected continuously during this melting to monitor the dissociation of the 5'-LC640-labeled probe. The melting curves were then displayed as −dF/d T vs T plots by Lightcycler software version 3.

Figure 7:
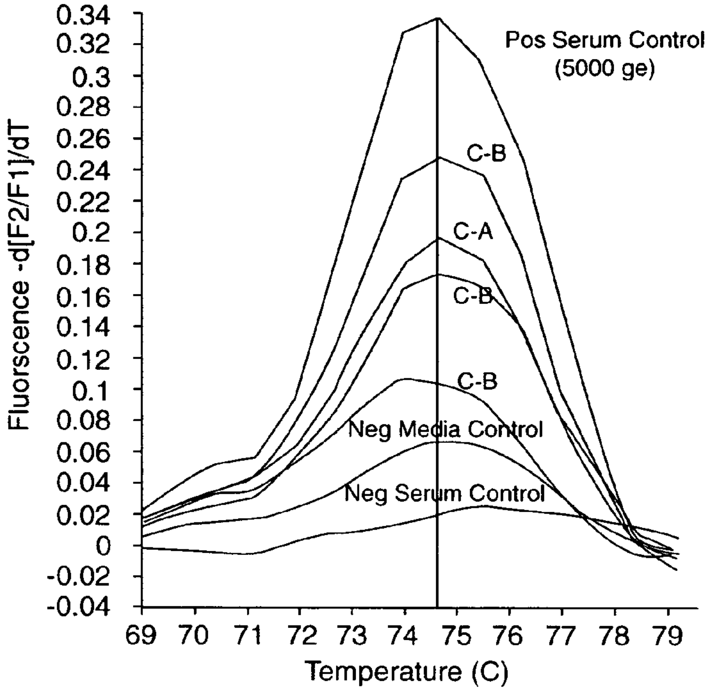
FIG. 7. LightCycler RT-PCR detection of viral RNA in supernatant fluids of C-A and C-B cells. The plot demonstrates the melting curves of the fluorescence resonance energy transfer signal from products generated from the cell culture samples and associated controls. Fluorescence −d[F2/F1]/dT, the melting curve as calculated by the LightCycler thermal cycler.

Results obtained in the LightCycler assay with PEG-precipitated supernatant media collected from the C-A and C-B cell sublines are shown in FIG. 7, which shows the melting curve detected by the FRET method. The melting curve indicates the specificity of product. Both C-A and C-B's curve matches that of positive control. The height of the curve correlates with the amount of the product produced. The negative media control was cell culture media maintained in the isolation room in which the C-A and C-B cell sublines are maintained. The negative serum control was contributed by a volunteer.

TaqMan RT-PCR

Primers (see Takeuchi et al., *Gastroenterol.,* 116, 636-642 (1999)):

```
Forward   5'-CGGGAGAGCCATAGTGG      (SEQ ID NO:14)

Reverse   5'-AGTACCACAAGGCCTTTCG    (SEQ ID NO:15)
```

TaqMan Probe:

```
5'-(FAM)-CTGCGGAACCGGTGAGTACAC    (SEQ ID NO:16)
(TAMRA)-3'
```

RNA was obtained from cells as described above for PCR with the Lightcycler thermal cycler. This experiment was set up according to the protocol provided in TaqMan EZ RT-PCR Core Reagents Protocol (product number 402877, Applied Biosystems, Foster City, Calif.). Briefly, All single-tube EZ RT-PCR reactions were carried out in optical MicroAmp reaction tubes with optical lids and in 50 μl volume in a 96-well format. The RNA amplification contained 1× amplification buffer, 3 mM manganese, 0.5 Units (U) AmpErase uracil-N-glycosylate, 7.5 U rTth DNA polymerase, RNA, 200 nM forward and reverse primers, 200 μM each dNTP, 500 μM of d UTP. AB17700 Sequence Detector version 1.6.3 software was used for sample analysis. Thermocycling conditions were one cycle at 50° C. for 2 minutes, one cycle at 60° C. for 30 minutes, one cycle at 95° C. for 5 minutes, 40 cycles at 95° C. for 20 seconds and 60° C. for 1 minutes.

Figure 8:
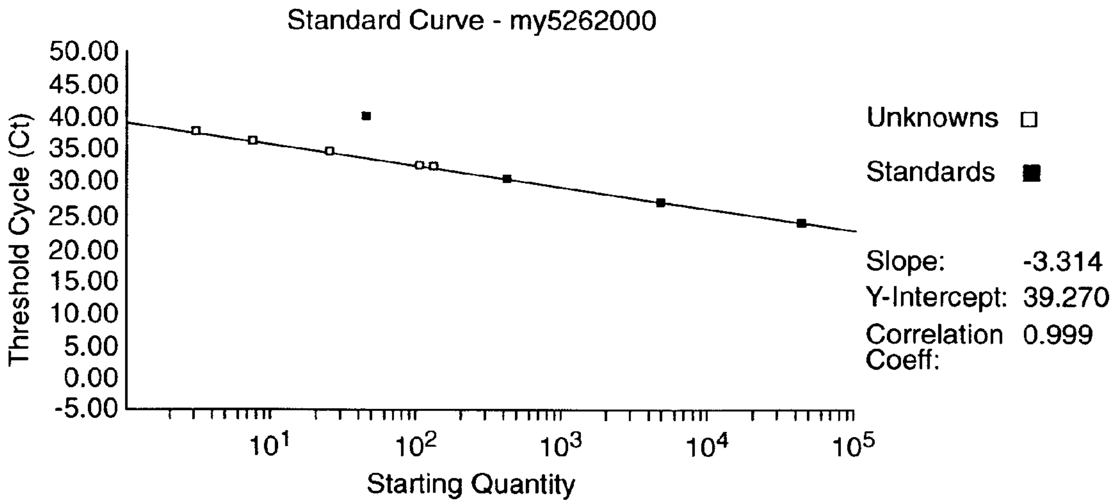
FIG. 8. TaqMan RT-PCR detection of HCV RNA in C-A and C-B cell culture supernatants.

FIG. 8 shows results of TaqMan RT-PCR The C-A and C-B product as detected according to program is aligned along with a known concentration of positive control HCV. The approximate number of HCV protracted from this graph is shown in Table 3.

TABLE 3

TaqMan quantitation of HCV RNA in supernatant media.

| Supernatant from: | Number of genome equivalents |
|---|---|
| Positive serum control (5000 ge[1]) | 4188 |
| C-B | 109 |
| C-A | 136 |
| C-B (unhealthy culture)[2] | 3 |
| C-A (unhealthy culture)[2] | 7 |
| Negative control media | 24[3] |
| Medium | 0 |
| Negative control | 0 |

[1]ge, genome equivalents.
[2]Cultures were losing viability.
[3]This is believed to be the result of contamination.

There was good correlation between the TaqMan and LightCycler results on these specimens.

Example 7

Demonstration of Viral Antigens in vMK0-Z-Infected Huh-SEAPo10 Cell Lines

Viral antigens expressed from both coding regions (i.e., the coding region encoding the viral polypeptides and the coding region inserted in the 3' NTR) in the modified HCV genome have been demonstrated in vMK0-Z infected Huh-SEAP-o10 cells by indirect immunofluorescence. Negative controls for these experiments were uninfected Huh-SEAPo10 cells. Cells were grown in tissue culture chamber slides and fixed in acetone-methanol at room temperature prior to staining. Cells were fixed in 50% methanol/50% Acetone for 10 minutes. Blocking agent was 3% BSA in PBS. The primary antibodies used were a mouse monoclonal antibody against HCV core protein, (anti-core antibody, provided by Johnson Lau, Schering-Plough Research Institute, Kennilworth, N.J.) used at a dilution of 1:100, a rabbit polyclonal antibody raised against Sh Ble protein (anti-Zeo antibody, CAYLA, France) used at a dilution of 1:250. The secondary antibodies were fluorescene conjugated anti-mouse or anti-rabbit. Antibodies were incubated with cells for 1 hour each. Between each incubation, the cells were washed three times for 5 minutes each with PBS. Nuclear counterstain was done using DAPI. Dapi staining to detect nucleus was done in 1:10,000 dilution in PBS. It was incubated for 5 minutes, followed by three washes for 5 minutes each in PBS. Photographic exposure times and contrast enhancements were identical for the infected cells and control cell images.

Exposure of cells to an anti-core antibody demonstrated the presence of HCV core protein in vMK0-Z infected cells. Exposure of cell to an anti-zeocin resistance protein demonstrated the presence of the Zeocin resistance protein in vMK0-Z infected cells.

Example 8

Construction of Subgenomic and Genome-Length Dicistronic RNAs

This example demonstrates the successful construction of replication competent, selectable dicistronic replicons from an infectious clone of a Japanese genotype 1b HCV virus (HCV-N) (Beard et al., *Hepatol.,* 30, 316-324, (1999)). Unlike other replicons, adaptive mutations are not required for efficient replication of these HCV-N replicons in Huh7 cells or for the selection of Huh7 clones under G418 selection. We also demonstrate the replication competence of similar selectable, dicistronic RNAs incorporating the NS2-NS5B, E1-NS5B, or complete core-NS5B sequences of this virus. Our findings extend the range of replication competent HCV replicons to a second, genotype 1b virus and show that a natural 4-amino-acid insertion within the NS5A protein of the wild-type HCV-N virus has a controlling role in determining the replication capacity of this RNA in cultured Huh7 cells.

MATERIALS AND METHODS

Plasmids.

The plasmid pBNeo/3-5B (FIG. 13) contains the Con1 sequence of the $I_{377}$neo/NS3-3' replicon of Lohmann et al. (Lohmann et al., *Science,* 285, 110-113 (1999), GenBank accession no. AJ242652) downstream of the T7 promoter which is present in the vector upstream of the 5' untranslated region (FIG. 13) (obtained from M. Murray, Schering-Plough Research Institute, Kenilworth, N.J.). pNNeo/3-5B (FIG. 13) contains the sequence of a similar HCV replicon in which almost all of the NS3-NS5B sequence of the 3' cistron is derived from an infectious molecular clone of the genotype 1b virus, HCV-N (GenBank accession no. AF139594) (Beard et al., *Hepatol.,* 30, 316-324, (1999)). It was constructed by replacing the large BsrGI-XbaI fragment of pBNeo/3-5B with the analogous HCV sequence derived from the plasmid pHCV-N. This fragment swap results in the NS3-NS5B sequence in pNNeo/3-5B being identical to that of HCV-N, with the exception of substitutions at 2 amino acid residues that retain the Con1 sequence: a Lys-to-Arg substitution at residue 1053 and an Ala-to-Thr substitution at residue 1099 (where the numbering system is based on the location within the original full length polyprotein as described at GenBank AF139594), near the N-terminus (proteinase domain) of the NS3 protein. The 5' untranslated region ('UTR) and N-terminal core protein sequences of HCV-N and the BNeo/3-5B replicon are identical.

The mutant pNNeo/3-5BΔi5A (FIG. 13) was derived from pNNeo/3-5B by an in-frame deletion removing a unique 4-amino-acid insertion that is present in the NS5A sequence of HCV-N in comparison to the consensus genotype 1b sequence (Beard et al., *Hepatol.,* 30, 316-324, (1999)). This was accomplished by QuickChange mutagenesis (Stratagene, La Jolla, Calif.). By similar methods, additional mutations were created within the background of pNNeo/3-5B and pNNeo/3-5BΔi5A incorporating single-amino-acid substitutions within NS5A or NS5B that have previously been reported to enhance the replication capacity of the 1377/NS3-3' replicon (BNeo/3-5B) by others: the R2884G mutation described by Lohmann et al. (*J. Virol.,* 75, 1437-1449 (2001)), and the S11791 mutation described by Blight et al. (Blight et al., *Science,* 290, 1972-1974 (2000)). These mutations are referred to as R2889G and S2005I, respectively, for the purposes of this study, according to the location of these residues within the original full-length HCV-N polyprotein sequence. The resulting mutants were designated NNeo/3-5B(RG) and NNeo/3-5B(SI). Similar substitutions were introduced into the background of pBNeo/3-5B to generate BNeo/3-5B(RG) and BNeo/3-5B (SI). Two additional mutants, NNeo/3-5BΔGDD and BNeo/3-5BΔGDD, each possess an in-frame deletion of 10 amino acids (MLVNGDDLVV) spanning the GDD motif (underlined) within the NS5B RNA-dependent RNA polymerase of both wild-type replicons. DNA sequencing of the manipulated regions of the plasmids verified all mutations.

Figure 14:
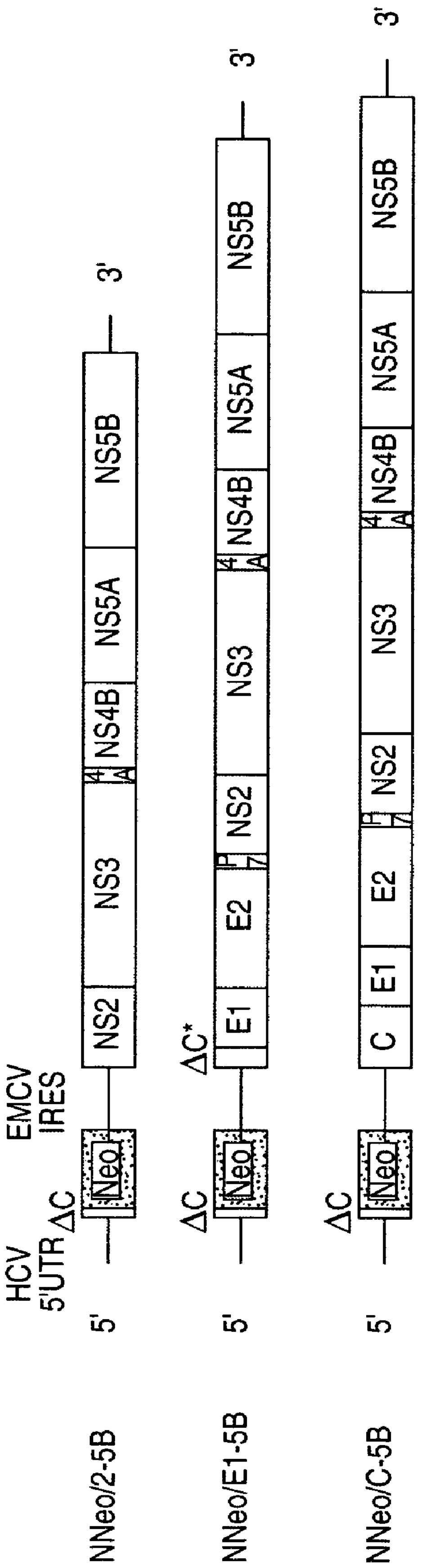
FIG. 14. Organization of selectable dicistronic RNAs containing HCV-N sequence encoding NS2, the envelope proteins E1 and E2, and/or the core protein within the 3' cistron. NTR, nontranslated region.

Selectable, dicistronic replicons containing part or all of the HCV-N structural protein-coding sequence within the 3' cistron were generated as follows. The plasmid pNNeo/C-5B contains the full-length HCV-N polyprotein-coding sequence downstream of the EMCV IRES (see FIG. 14). To construct it, DNA fragments representing the EMCV IRES and HCV core protein-coding sequence were fused by overlapping PCR. Briefly, the primer set to amplify the EMCVIRES-core fusion were as follows. For EMCV and part of core sequence containing fragment, sense primer, 5'-TCCCTCTAGA CGGACCGCTA TCAGGACATA GC (SEQ ID NO:43) (which corresponds to nucleotides 1030-1051 of 1377/NS3-3'UTR (AJ242652), within the EMCV coding region, and italics indicate non HCV replicon sequence) and antisense primer, 5'-ATTCGTGCTC ATGG-TATTAT CGTGTTTTTC AAAGG (SEQ ID NO:44) (where the italicized nucleotides correspond to nucleotides 342-353 of HCV-N, and the remainder correspond to nucleotides 1778-1800 of 1377/NS3-3'UTR. For part of the EMCV and core containing fragment; the sense primer was 5'-CACGATAATA CCATGAGCAC GAATCCTAAA CCTC (SEQ ID NO:45), which corresponds to nucleotides 1789-1800 of 1377/NS3-3'UTR (AJ242652) within EMCV coding region, and italics indicate HCV N core coding region nucleotides 342-363) and antisense primer, 5'-CCGCTCGAGG CAGTCGTTCG TGACATGGTA TACC (SEQ ID NO:46) (italics indicate non HCV replicon nucleotides, and the remainder correspond to nucleotides 938-962 of HCV-N). The resulting DNA was digested with RsrII and BstZ17I and then ligated with the XbaI-RsrII fragment of pBNeo/3-5B and the BstZ17I-XbaI fragment of pHCV-N.

pNNeo/E1-5B contains sequence encoding the C-terminal 22 amino acids of the core protein, the downstream E1 and E2 sequences and the remainder of the HCV-N polyprotein coding sequence. To construct it, a DNA fragment containing the EMCV sequence was fused to the E1 sequence by an overlapping PCR. Briefly, the primer set to amplify the EMCVIRES-E1 fusion were as follows. For EMCV and part of the E1 containing fragment, the sense primer was 5'-TCCCTCTAGA CGGACCGCTA TCAGGACATA GC (SEQ ID NO:47) (which corresponds to nucleotides 1030-1051 of 1377/NS3-3'UTR (AJ242652), within EMCV coding region, and italics indicate non HCV replicon nucleotides) and antisense primer, 5'-AGAGCAACCG GGCATGGTAT TATCGTGTTT TTCAAAGG (SEQ ID NO:48) (where italics correspond to E1 sequence (nucleotides 849-861 of HCV-N) and the remaining nucleotides correspond to nucleotides 1778-1803 of 1377/NS3-3'UTR. For part of the EMCV and E1 containing fragment; the sense primer was 5'-CACGATAATA CCATGCCCGG TTGCTCTTTT TCTATCTTCC (SEQ ID NO:49) (which corresponds to nucleotides 1789-1803 of 1377/NS3-3'UTR (AJ242652), within EMCV coding region, and italics indicate nucleotides 849-873 of the HCV N E1) and antisense primer, 5'-ATGTACAGCC GAACCAGTTG CC (SEQ ID NO:50) (which corresponds to nucleotides 1983-2004 of HCV-N). The resulting DNA was digested with RsrII and NotI, and then ligated to the XbaI-RsrII fragment of pBNeo/3-5B and NotI-XbaI fragment of pHCV-N.

The 3' cistron of pNNeo/2-5B contains sequence encoding the NS2-NS5B proteins of HCV-N, immediately downstream of the EMCV IRES. It was constructed in a fashion similar to pNNeo/C-5B and pNNeo/E1-5B, with fusion of the EMCV and NS2 sequences by an overlapping PCR. Briefly, the primer set to amplify the EMCVIRES-NS2 fusion were as follows. For EMCV and part of the NS2 sequence containing fragment, the sense primer was 5'-TCCCTCTAGA CGGACCGCTA TCAGGACATA GC (SEQ ID NO:51) (which corresponds to nucleotides 1030-1051 of 1377/NS3-3'UTR (AJ242652), within EMCV coding region, and italics indicate non HCV replicon sequence) and antisense primer, 5'-CTCCCGGTCCATGGTATTAT CGTGTTTTTC AAAGG (SEQ ID NO:52) (where the italics indicate NS2 sequence of HCV-N (nucleotides 2772-2783) and the remainder of the sequence corresponds to nucleotides 1778-1800 of 1377/NS3-3'UTR. For part of the EMCV and NS2 containing fragment; the sense primer was 5'-CACGATAATA CCATGGACCG GGAGATGGCT GC (SEQ ID NO:53) (which corresponds to nucleotides 1789-1800 of 1377/NS3-3'UTR (AJ242652), within EMCV coding region, and italics indicate nucleotides 2772-2791 of the HCV-N NS2) and antisense primer, 5'-GAGCGGTCCG AGTATGGCAA TCAG (SEQ ID NO:54) (which corresponds to nucleotides 3018-3041 of HCV-N). The resulting DNA was digested with RsrII and EcoRV, and ligated to the XbaI-RsrII fragment of pBNeo/3-5B and EcoRV-XbaI fragment from pHCV-N.

Cells

Huh7 cells were cultured in Dulbecco's modified Eagle's medium (Gibco-BRL, Invitrogen Life Technologies, Carlsbad, Calif.) supplemented with 10% fetal calf serum, penicillin, and streptomycin. Transfected cells supporting the replication of HCV replicons were maintained in the presence of 1 mg of G418 (Geneticin) per ml and passaged two or three times per week at a 4:1 split ratio.

In Vitro Transcription and Transfection of Synthetic RNA.

Plasmid DNAs were linearized by XbaI and purified by passage through a column (PCR Purification Kit; Qiagen, Valencia, Calif.) prior to transcription. RNA was synthesized with T7 MEGAScript reagents (Ambion, Austin, Tex.) following the manufacturer's suggested protocol, and the reaction was stopped by digestion with RNase-free DNase. Following precipitation with lithium chloride, RNA was washed with 75% ethanol and dissolved in RNase-free water. For electroporation, Huh7 cells were washed twice with ice-cold phosphate-buffered saline (PBS) and resuspended at $10^7$ cells/ml in PBS. RNA (1 to 10 μg) was mixed with 500 μl of the cell suspension in a cuvette with a gap width of 0.2 cm (GenePulser II System; Bio-Rad, Hercules, Calif.). The mixture was immediately subjected to two pulses of current at 1.5 kV, 25 μF, and maximum resistance. Following 10 minutes (min) of incubation at room temperature, the cells were transferred into 9 ml of growth medium and the number of viable cells assessed by staining with trypan blue. Cells were seeded into 10-cm-diameter cell culture dishes. For selection of Neo-expressing cells, the medium was replaced with fresh medium containing 1 mg of G418 per ml after 24 to 48 hours (h) in culture.

Indirect Immunofluorescence.

Cells were grown on chamber slides until 70 to 80% confluent, washed three times with PBS, and fixed in methanol-acetone (1:1 [vol/vol]) for 10 min at room temperature. Dilutions of primary, murine monoclonal antibodies to residues 1 to 61 of the core protein (MAB7013; Maine Biotechnology Services, Portland) (1:25), E2 (obtained from Y. Matsuura and T. Miyamura, National Institute of Health, Tokyo, Japan) (1:400), or NS5A (MAB7022P; Maine Biotechnology Services) (1:10) were prepared in PBS containing 3% bovine serum albumin and incubated with fixed cells for 2 h at room temperature. After additional washes with PBS, specific antibody binding was detected with a goat anti-mouse immunoglobulin G-fluorescein isothiocyanate-conjugated secondary antibody (Sigma-Aldrich, St. Louis, Mo.) diluted 1:70. Cells were washed with PBS, counterstained with 4,6-diamidino-2-phenylindole (DAPI), and mounted in Vectashield mounting medium (Vector Laboratories, Burlingame, Calif.) prior to examination by a Zeiss AxioPlan2 fluorescence microscope.

Northern Analysis.

To minimize potential variation in the intracellular abundance of HCV RNAs that might occur due to variation in the growth status of cells, RNA was extracted from freshly plated cultures after cells had reached 70 to 80% confluence. Total cellular RNAs were extracted with TRIzol reagent (Gibco-BRL) and quantified by spectrophotometry at 260 nm. RNAs were separated by denaturing agarose-formaldehyde gel electrophoresis and transferred to positively charged Hybond-N+ nylon membranes (Amersham-Pharmacia Biotec, Piscataway, N.J.) with reagents provided with the NorthernMax kit (Ambion) and the manufacturer's suggested protocol. RNAs were immobilized on the membranes by UV cross-linking (Stratagene) and stained with ethidium bromide to locate 28S rRNA on the membrane. The upper part of the membrane containing HCV replicon RNA (size greater than 28S) was hybridized with a digoxigenin-labeled, negative-sense RNA riboprobe complementary to the NS5B sequence of HCV-N, while the lower part of the membrane containing P-actin mRNA was hybridized with a digoxigenin-labeled, P-actin-specific riboprobe. For detection of the bound riboprobes, membranes were incubated with antidigoxigenin-alkaline phosphatase conjugate, reacted with CSPD (Roche Molecular Biochemicals, Indianapolis, Ind.), and exposed to X-ray film.

RT-PCR Amplification and Sequencing of cDNA from Replicating HCV RNAs.

Total cellular RNA was extracted from replicon-bearing cell lines as described above and used as a template for the amplification of cDNA fragments spanning the NS3-NS5B segment of the NNeo/3-5B replicon. Reverse transcription (RT) was carried out with 1 μg of RNA, 200 U of SuperScript II reverse transcriptase (Gibco-BRL), and two HCV-specific primers (N6700R, 5'-AGCCTCTTCAGC AGCTG (SEQ ID NO:55) and N9411R 5'-AGGAAATGGCCTATTGGC (SEQ ID NO:56), 1 μM), complementary to sequence in the NS4B and 3'UTR segments of the genome, in a total reaction volume of 10 μl for 60 min at 42° C. cDNAs were subsequently amplified with Pfu Turbo DNA polymerase (Stratagene) by 30 PCR cycles involving annealing at 60° C. for 60 seconds (s), extension at 72° C. for 120 s, and denaturation at 95° C. for 30 s, followed by a final extension reaction at 72° C. for 2 min. Eight separate PCR primer sets were used to amplify nested segments spanning the NS3-NS5B region of the genome (see Table 4). The sequence of each amplified cDNA segment was determined directly with an ABI 9600 automatic DNA sequencer. The existence of mutations was confirmed by sequencing the products of at least two separate RT-PCRs.

Results

Autonomous Replication of Subgenomic HCV Replicons Derived from HCV-N

Figure 13A:
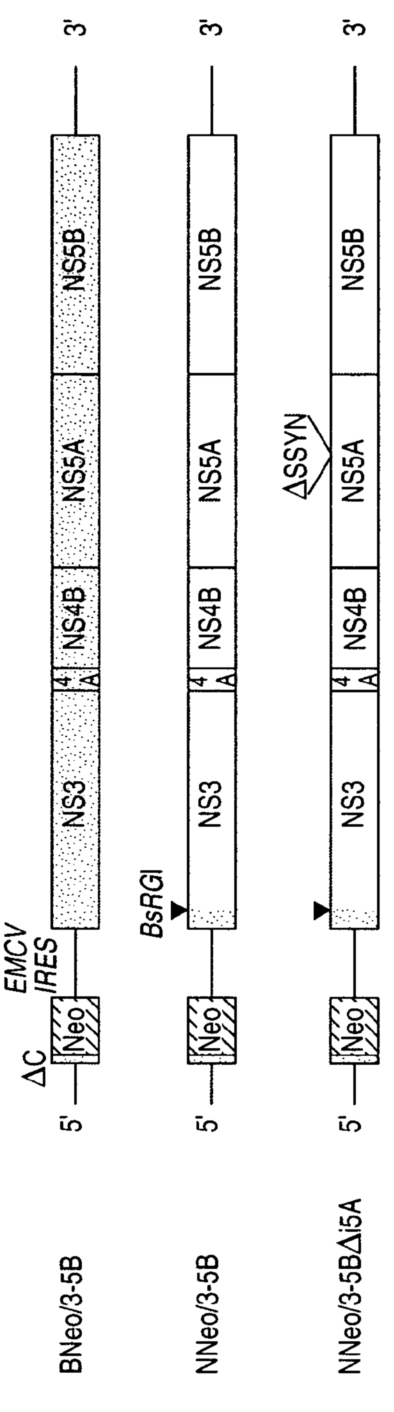
FIG. 13. (A) Organization of the subgenomic HCV RNA replicons. Open reading frames are depicted as boxes, and untranslated segments of the dicistronic RNAs are depicted as solid lines. The sequence of BNeo/3-5B (shaded box) is identical to that of 1377NS3-3/wt, described previously by Lohmann et al. (*Science,* 285, 110-113 (1999)). NNeo/3-5B contains mostly HCV-N-derived sequence (open boxes). The amino acid sequence of NS3 in NNeo/3-5B differs from that of HCV-N at only 2 amino acid residues while the 5'- and 3' UTR sequences are identical. "ΔC" indicates the N-terminal segment of the HCV core protein that is expressed as a fusion with Neo in these replicons. (B) Locations of the S2205I and R2889G BNeo/3-5B-adaptive mutations and the MLVNGDDLVV deletion introduced into the replicons shown in panel A.
Figure 13B:
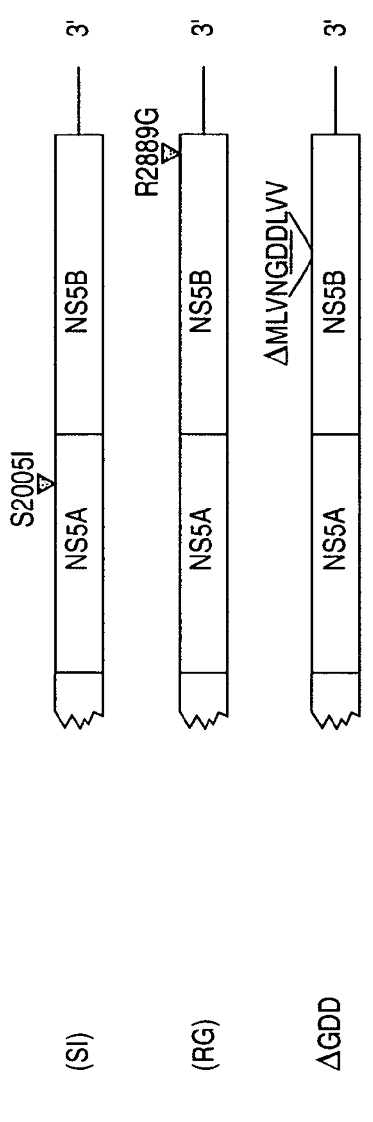

HCV-N is a genotype 1b virus (Beard et al., *Hepatol.,* 30, 316-324, (1999)) that shares only about 90% nucleotide identity in the NS3-NS5B region with the Con1 sequence present in the replicon RNAs described by Lohmann et al. (Lohmann et al., *Science,* 285, 110-113 (1999)) and Blight et al. (*Science,* 290, 1972-1974 (2000)). To determine whether subgenomic RNAs derived from a previously constructed molecular clone of this virus are capable of replication in Huh7 cells, a plasmid was constructed with a T7 transcriptional unit containing the sequence of a candidate replicon, NNeo/3-5B (FIG. 13). The organization of RNA transcripts generated from this plasmid is identical to that of the $I_{377}$neo/NS3-3' replicon of Lohmann et al. (Lohmann et al., *Science,* 285, 110-113 (1999)) (designated BNeo/3-5B in this study), with the 5'UTR of HCV and immediately downstream sequence encoding the N-terminal 12 amino acids of the core protein fused in-frame to the selectable marker, Neo, followed by the IRES of EMCV fused to the NS3-coding sequence and downstream regions of the HCV genome, including the 3'UTR (FIG. 13). The sequences of the proteins expressed by both the 5' and 3' cistrons of NNeo/3-5B are identical to those of HCV-N, with the exception of substitutions at 2 amino acid residues near the amino terminus of NS3, a Lys-to-Arg substitution at residue

TABLE 4

Primer pairs.

| Primer sequence | | Corresponds to: |
|---|---|---|
| TTTCCACCATATTGCCGTC | (SEQ ID NO:57) | nucleotides 1307-1325 of 1377/NS3-3'UTR |
| TTGACGCAGGTCGCCAGG | (SEQ ID NO:58) | nucleotides 3551-3568 of HCV-N |
| GAACCAGGTCGAGGGGGAGG | (SEQ ID NO:59) | nucleotides 3499-3519 of HCV-N |
| TCGATGGGGATGGCTTTGCC | (SEQ ID NO:60) | nucleotides 4473-4492 of HCV-N |
| CTCGCCACCGCTACGCCTCC | (SEQ ID NO:61) | nucleotides 3551-3568 of HCV-N |
| ACTCCGCCTACCAGCACCC | (SEQ ID NO:62) | nucleotides 5323-5341 of HCV-N |
| ACCCCATAACCAAATACATC | (SEQ ID NO:63) | nucleotides 5260-5279 of HCV-N |
| AGCCTCTTCAGCAGCTG | (SEQ ID NO:64) | nucleotides 6207-6223 of HCV-N |
| TATGTGCCTGAGAGCGACGC | (SEQ ID NO:65) | nucleotides 6144-6163 of HCV-N |
| TATGTGCCTGAGAGCGACGC | (SEQ ID NO:66) | nucleotides 7116-7132 of HCV-N |
| AACCTTCTGTGGCGGCAGG | (SEQ ID NO:67) | nucleotides 7044-7062 of HCV-N |
| CTGGTTGGACGCAGAAAACC | (SEQ ID NO:68) | nucleotides 8042-8061 of HCV-N |
| AACCACATCCGCTCCGTGTG | (SEQ ID NO:70) | nucleotides 7962-7981 of HCV-N |
| TGGCTCAATGGAGTAACAGG | (SEQ ID NO:71) | nucleotides 8962-8981 of HCV-N |
| TTCTCCATCCTTCTAGCT | (SEQ ID NO:72) | nucleotides 8901-8918 of HCV-N |
| AACAGGAAATGGCCTATTG | (SEQ ID NO:73) | nucleotides 9412-9431 of HCV-N |

1053 and an Ala-to-Thr substitution at residue 1099. These substitutions derive from the Con1 sequence employed in construction of this plasmid.

In initial experiments, NNeo/3-5B transcripts were transfected into Huh7 cells, and the cells were grown in the presence of G418 to select cells with active expression of Neo from replicon RNAs undergoing amplification. BNeo/3-5B transcripts were transfected in parallel. Numerous G418-resistant cell colonies survived the selection process in Huh7 cultures transfected with NNeo/3-5B RNA, with the number of cell colonies isolated proportional to the quantity of RNA electroporated into the cells. However, there were no surviving G418-resistant cell colonies following transfection of NNeo/3-5BΔGDD, a mutated replicon containing an in-frame deletion spanning the GDD motif in the NS5B RNA-dependent RNA polymerase. The absence of surviving cell colonies following transfection of this RNA indicates that amplification of the NNeo/3-5B replicon is essential for G418 resistance. Despite reproducible isolation of greater than 1,000 colonies from cultures transfected with 1 μg of NNeo/3-5B RNA, we were unable to isolate any colonies from cells transfected with an equivalent quantity of either BNeo/3-5B or BNeo/ΔGDD RNA. The failure to recover G418-resistant colonies following transfection of BNeo/3-5B suggests strongly that this previously described RNA replicates significantly less efficiently than NNeo/3-5B in these Huh7 cells.

To confirm the presence of replicating subgenomic RNAs in cells selected for G418 resistance following transfection with NNeo/3-5B, three G418-resistant cell colonies were selected at random and clonally isolated. These clonal cell lines were then examined for the presence of HCV RNA by Northern analysis. The presence of a substantial abundance of HCV-specific RNA with a length approximating 8 kb was detected in extracts of total cellular RNA prepared from each of these stable cell lines (data shown only for clones 1 and 2). Although the abundance of the replicon RNA was significantly greater in the BNeo/3-5B(RG) cell line than in other cell lines studied in this particular experiment, we noted no consistent trends in the abundance of replicon RNA among cell lines derived with different replicon constructs. Abundant NS5A protein was also demonstrated in each of the cell lines by indirect immunofluorescence. These data confirm the ability of wild-type HCV-N subgenomic replicons to undergo autonomous replication in Huh7 cells and represent an important confirmation of the results of Lohmann et al. (Lohmann et al., *Science,* 285, 110-113 (1999)) with a second, independent isolate of HCV.

Adaptive Mutations are not Required for Efficient Replication of NNeo/3-5B RNA.

Data reported both by Lohmann et al. (*J. Virol.,* 75, 1437-1449 (2002)) and by Blight et al. (*Science,* 290, 1972-1974 (2000)) suggest that spontaneously arising, cell culture-adaptive mutations are required for efficient replication of BNeo/3-5B in Huh7 cells. Such mutations appear to be present within each replicon-bearing cell line that has been clonally isolated and characterized in detail (Blight et al., *Science,* 290, 1972-1974 (2000), Krieger et al., *J. Virol.,* 75, 4614-4624 (2001), Lohmann et al., *J. Virol.,* 75, 1437-1449 (2002)). Cell culture-adaptive mutations have been identified within NS3, NS5A, and NS5B and have been shown to dramatically increase the efficiency of colony formation when cells are transfected and subjected to G418 selection. To determine whether such adaptive mutations are also required with NNeo/3-5B replicons derived from HCV-N, we determined the nucleotide sequences of the NS3-NS5B segment of the replicons present in the three clonal cell lines described in the preceding section. RNA extracted from these cells were reverse transcribed into cDNA and amplified by RT-PCR for direct DNA sequencing as described in Materials and Methods.

Replicon RNAs in two of the three cell lines contained single-amino-acid mutations: a 3-base insertion resulting in a new Lys residue at position 2040 (NS5A) in clone 2, and a single-base change leading to a Cys-to-Ser substitution at residue 1519 (NS3 helicase domain) in clone 3. Remarkably, there were no mutations identified in the amino acid sequence of the nonstructural proteins in clone 1, despite the fact that the replicon RNA abundance in these cells was approximately equivalent to that in other G418-resistant cell lines, including clone 2, in which there was the insertion of an additional residue in NS5A. These results confirm that NNeo/3-5B RNA is capable of efficient autonomous replication in the absence of adaptive mutations and suggest that the two mutations may have relatively little impact on the replication of this RNA.

Effect of BNeo/3-5B Adaptive Mutations on Replication of NNeo/3-5B.

To determine whether mutations in NS5A or NS5B that have been reported previously to enhance the replication of BNeo/3-5B would further enhance the replication of NNeo/3-5B replicons, we constructed NNeo/3-5B-derived replicons with a Ser-to-Ile substitution at residue 2005, NNeo/3-5B(SI), comparable to the Con1 replicons containing the S117931 mutation in NS5A described by Blight et al. (*Science,* 290, 1972-1974 (2000)), or an Arg-to-Gly substitution at residue 2889, NNeo/3-5B(RG), comparable to the replicon containing the R2884G mutation in NS5B reported by Lohmann et al. (*J. Virol.,* 75, 1437-1449 (2002)). Identical mutations were also introduced into BNeo/3-5B, leading to the creation of BNeo/3-5B(SI) and BNeo/3-5B(RG), respectively, and the modified NNeo/3-5B and BNeo/3-5B RNAs were transfected into Huh7 cells in parallel experiments.

The results of these experiments confirmed the cell culture adaptive activities of these NS5A and NS5B mutations on Con1-derived replicons. The introduction of S2005I into the background of BNeo/3-5B increased the efficiency of G418-resistant colony formation substantially more than the introduction of R2884G. The number of colonies generated following transfection of Huh7 cells with BNeo/3-5B(SI) RNA approximated that obtained with NNeo/3-5B RNA. These results thus confirmed the importance of the S2005I substitution for replication of the BNeo/3-5B replicon, as reported previously (Blight et al., *Science,* 290, 1972-1974 (2000)). However, they also demonstrated that the wild-type NNeo/3-5B RNA is comparable to BNeo/3-5B RNAs containing adaptive mutations such as S2005I in terms of its ability to replicate in Huh7 cells and lead to the selection of G418-resistant colonies. In fact, there was no apparent difference in the abundance of HCV RNA in cell lines selected following transfection of BNeo/3-5B(SI) and NNeo/3-5B (clone 1, which contains no adaptive mutations). Interestingly, however, a cell line selected following transfection with BNeo/3-5B(RG) had a greater abundance of viral RNA despite the substantially lower number of G418-resistant cell colonies generated with this RNA. We did not determine whether this particular cell line contained additional adaptive mutations.

The introduction of either of these two mutations into the background of NNeo/3-5B also resulted in an increase in the number of G418-resistant colonies, but proportionately this increase was much less than that observed with the introduction of these mutations into the BNeo/3-5B background. The S2005I and R2889G mutations resulted in comparable increases in the numbers of G418-resistant colonies, although the density of colony formation made their enumeration difficult even when only 1 μg of RNA was transfected per culture dish. However, we also compared the effects of these two mutations when introduced into the background of a similar subgenomic HCV-N replicon containing blastocidin rather than Neo as a selection marker (NBla/3-5B). In this case, where blastocidin is generally less efficient than Neo as a selectable marker, the introduction of R2889G was shown to result in an ~5-fold higher number of G418-resistant cell colonies than the introduction of S2005I. Importantly, the introduction of these mutations increased the number of G418-resistant colonies obtained with NNeo/3-5B replicons no more than severalfold, and far less than the 1,000-fold or greater increases seen with the comparable BNeo/3-5B replicons. Neither mutation resulted in an increase in the abundance of replicon RNA in G418-resistant cell lines selected following transfection with NNeo/3-5B RNAs.

Enhanced Replication Capacity of HCV-N RNA is Due to a Natural 4-amino-acid Insertion in NS5A.

As mentioned above, the sequence of the infectious HCV-N cDNA clone contains a unique 4-amino-acid insertion (-Ser-Ser-Tyr-Asn-) within the ISDR segment of the NS5A protein in alignments with other HCV sequences (Beard et al., *Hepatol.,* 30, 316-324, (1999)). This insertion includes amino acid residues 2220 to 2223 in the HCV-N polyprotein and, although unique in the database, was present in cDNA cloned directly from the Japanese patient who served as the source of the HCV-N isolate (Hayashi et al., *J. Hepatol.,* 17, S94-S107 (1993)). It is thus representative of the wild-type sequence of this virus. Since mutations that enhance the replication of the BNeo/3-5B replicon have been suggested to cluster near the ISDR of NS5, we questioned whether the presence of this unique insertion in the ISDR might contribute to the ability of NNeo/3-5B replicons to replicate efficiently in the absence of additional cell culture-adaptive mutations. To address this question, we deleted the 4-amino-acid insertion from NNeo/3-5B (generating NNeo/3-5BΔi5A) and assessed the ability of this NS5A deletion mutant to support the selection of 6418-resistant colonies following transfection of Huh7 cells. Additional deletion mutants were generated by removal of the 4-amino-acid insertion from NNeo/3-5B(SI) and NNeo/3-5B(RG), designated NNeo/3-5B(SI) i5A and NNeo/3-5B (RG) i5A, respectively.

The number of G418-resistant colonies selected following transfection with NNeo/3-5BΔi5A was much lower than after transfection with NNeo/3-5B. Only a small number of colonies were generated following transfection with a large amount of RNA (20 μg per culture dish), confirming the importance of this insertion to replication of this RNA in Huh7 cells. In contrast, the deletion of these 4 amino acids from the NS5A sequences of NNeo/3-5B(SI) resulted in only a modest decrease in the efficiency of colony formation, with large numbers of G418-resistant colonies selected after transfection of relatively small amounts of NNeo/3-5B(SI) i5A RNA (1 μg/culture dish). Similar results were obtained with the NNeo/3-5B(RG) i5A replicon, although the number of surviving G418-resistant colonies was less than that with NNeo/3-5B(SI). The fact that efficient G418-resistant colony-forming activity could be preserved by either of these previously described cell culture adaptive mutations in the absence of the 4-amino-acid insertion in NS5A provides further evidence that the 4-amino-acid insertion is responsible for the inherent ability of NNeo/3-5B RNA to replicate efficiently in Huh7 cells.

Since many of the mutations that enhance the replication of BNeo/3-5B have been localized to the NS5A sequence (Blight et al., *Science,* 290, 1972-1974 (2000), we compared the NS5A sequences of NNeo/3-5B and BNeo/3-5B. The proteins are predicted to differ at 49 of 451 (11%) amino acid residues (FIG. 15). Amino acid differences are scattered across the length of the protein sequence, although they are somewhat more frequent within the ISDR and C-terminal half of the protein. Interestingly, there are no differences at any of the residues at which single-amino-acid substitutions have previously been reported to enhance the replication capacity of BNeo/3-5B.

The most striking difference in the NS5A sequences of these replicons is the presence of the 4-amino-acid insertion within the ISDR of NNeo/3-5B. This insertion and, in fact, the entire ISDR are within a 47-amino-acid segment that was shown to have been spontaneously deleted in a cell line bearing a BNeo/3-5B replicon isolated by Blight et al. (*Science,* 290, 1972-1974 (2000)). This large deletion mutation significantly increased the numbers of G418-resistant cell colonies selected following transfection of BNeo/3-5B RNA (Blight et al., *Science,* 290, 1972-1974 (2000)). When the 4-amino-acid insertion was deleted from NNeo/3-5B, its capacity to generate G418-resistant colonies was substantially, although not completely, eliminated. However, the ability of the RNA to efficiently generate G418-resistant colonies was preserved by introduction of the BNeo/3-5B-adaptive S2005I mutation in NS5A and, to a slightly lesser extent, the R2889G mutation in NS5B. The 4-amino-acid insertion in NS5A thus accounts, at least in part, for the unique ability of the wild-type HCV-N RNA to replicate in these cells. It thus represents a natural cell culture-adaptive mutation. Although present in the synthetic HCV-N RNA that gave rise to infection in a chimpanzee, as described above (Beard et al., *Hepatol.,* 30, 316-324, (1999)), the persistence of this sequence polymorphism was not studied in this animal. Thus, it is not possible to comment further on its contribution to replication in vivo.

Replication Competence of Selectable Dicistronic HCV-N RNAs Encoding the Structural Proteins of HCV Lohmann et al. (Lohmann et al., *Science,* 285, 110-113 (1999)) demonstrated that subgenomic Con1 replicons containing the NS2-NS5B segment of HCV also were capable of autonomous replication in Huh7 cells, although the number of G418-resistant colonies selected was somewhat less than that obtained after transfection of cells with replicon RNA containing only the NS3-NS5B segment. To determine whether the replication capacity of the HCV-N RNA would be influenced by the inclusion of NS2-coding sequence or sequences encoding the envelope and core proteins of HCV-N, we constructed a series of plasmids with transcriptional units encoding the selectable, dicistronic RNAs shown in FIG. 14. In addition to the NS3-NS5B coding sequence present in NNeo/3-5B, the 3' cistrons of these dicistronic RNAs contain upstream wild-type HCV-N sequence encoding NS2 (NNeo/2-5B), the envelope proteins as well as NS2 (NNeo/E1-5B), or the entire polyprotein (NNeo/C-5B). RNA transcripts prepared from these plasmids were transfected into Huh7 cells, as described above, and in each case gave rise to G418-resistant colonies after several weeks of culture in G418-containing media. The number of colonies produced from each RNA diminished with the increasing length of the second cistron, with ~160 colonies obtained with NNeo/2-5B, ~60 colonies with NNeo/E11-5B, and only 22 colonies from NNeo/C-5B. However, stable G418-resistant cell lines were clonally isolated from transfections with each of these RNAs, indicating that the RNA remained replication competent despite the inclusion of the additional sequence.

Total cellular RNA extracted from these G418-resistant cell lines was analyzed by Northern analysis for HCV RNA. Each cell line contained HCV-specific RNA of the appropriate length, confirming the ongoing replication of HCV RNA in cell lines selected after transfection with each of the RNAs shown in FIG. 14. However, cells selected following transfection with NNeo/C-5B contained a demonstrably lower abundance of replicon RNA than cells selected following transfection with NNeo/2-5B or NNeo/E1-5B. These latter cell lines were comparable in replicon abundance to cells selected following transfection with NNeo/3-5B. Furthermore, G418-resistant cells selected with the NNeo/C-5B replicon grew slowly and failed to become completely confluent after several weeks in culture. Colonies of cells selected from one of the NNeo/C-5B cell lines were subcloned and, after passage for an additional month, demonstrated improved growth properties. Northern analysis of total cellular RNA extracted from three of these NNeo/C-5B subclones contained viral RNA of the appropriate length, with an abundance approximating that of replicon RNA in cell lines selected following transfection with NNeo/3-5B.

G418-resistant cell lines selected following transfection with NNeo/E1-5B or NNeo/C-5B were examined for the presence of structural protein antigens by indirect immunofluorescence. In addition to NS5A antigen, cells selected following transfection with NNeo/E1-5B contained detectable E2 antigen, while cells selected following transfection with NNeo/C-5B RNA stained positively for core antigen. In both cases, only a proportion of the cells present in the clonally isolated cell lines contained a detectable abundance of these antigens at any single point in time. This result was different from what was observed with G418-resistant cell lines selected following transfection with NNeo/3-5B, in which almost all cells contained detectable NS5A antigen. It is possible that this may reflect cell cycle dependence of the replication of these RNAs (Pietschmann et al., J. Virol., 75, 1252-1264 (2001)), because the cell lines were clonally derived and stable. Together, however, these data provide strong confirmatory evidence of the replication competence of genome-length, selectable, dicistronic HCV-N RNAs in Huh7 cells.

Example 9

Subgenomic Hepatitis C Virus Replicons Inducing Expression of a Secreted Enzymatic Reporter Protein This Example describes a useful refinement of these subgenomic replicons that simplifies detection of HCV RNA replication in both transiently-transfected cells and established cell clones selected under antibiotic pressure. By modifying the upstream cistron so that it expresses the tat protein of human immunodeficiency virus (HIV) in addition to the Neo resistance marker, replicon RNAs were developed that are capable of signaling their presence and abundance in cells by the secretion of placental alkaline phosphatase (SEAP), expressed under transcriptional control of the HIV LTR. This system permits the autonomous replication of the viral RNA to be monitored in intact cells by an enzymatic assay of SEAP activity in the media bathing the cells. Using these novel reporter replicons, we show the effect of interferon-α on the replication of RNAs derived from two different strains of HCV in stably transformed cell cultures.

Materials and Methods

Cells. En5-3 cells are a clonal cell line derived from Huh7 cells by stable transformation with the plasmid pLTR-SEAP (see below). These cells were cultured in Dulbecco's modified Eagle's medium (Gibco BRL) supplemented with 10% fetal calf serum, 2 μg/ml blasticidin (Invitrogen), penicillin and streptomycin. Following transfection with replicon RNAs, cells supporting replicon amplification were selected and maintained in the above media containing in addition 400 μg/ml G418 (geneticin). Cell lines were passaged once or twice per week.

Plasmids. The plasmid pLTR-SEAP was generated as follows. pcDNA6/V5-His (Invitrogen) was digested with BglII-BamHI to remove the CMV promoter. The vector was then self-ligated, digested with EcoRV-NotI, and religated to a DNA fragment encoding SEAP under transcriptional control of the HIV LTR that was amplified from pBCHIVSEAP (obtained from B. Cullen, Duke University, Durham, N.C.) using the oligonucleotide primer pairs; 5'-CTAGCTAGCCTCGAGACCTGGAAAAACATGGAG (SEQ ID NO:8) and 5'-ATAAGAATGCGGCCGCTTAACCCGGGTGCGCGG (SEQ ID NO:9). The resulting plasmid was transfected into Huh7 cells using a non-liposomal transfection reagent (FUGENE, Boerhinger Manheim), and stably resistant cells were selected in the presence of blasticidin (Invitrogen). Blasticidin-resistant cell colonies were clonally selected and subjected to further characterization. One, designated En5-3, was selected for subsequent use due to a low basal level of SEAP activity and efficient induction of SEAP following expression of the HIV tat protein.

To construct the plasmid pEt2AN, a DNA fragment containing the EMCV IRES was amplified by PCR from pEMCV-CAT (Whetter et al., *Arch Viol.,* 136, 291-298 (1994)) using paired primers containing HindIII and StuI sites, respectively. DNA encoding the tat protein was similarly amplified from pCTAT (also a generous gift of Dr. Cullen) with paired primers containing StuI and EcoRI sites, respectively. Finally, a DNA fragment encoding 15 amino acids of the foot-and-mouth disease virus (FMDV) 2A protein was generated by annealing the complementary primers 5'-AATTCGACCTTCTTAAGCTTGCGGGAGACGTCGAGTCCAACCCTGGGCCCG (SEQ ID NO:24) and 5'-GATCCGGGCCCAGGGTTGGACTCGACGTCTCCCGCAAGCTTAAGAAGGCG (SEQ ID NO:69) to form a duplex DNA molecule with EcoRI and BamHI sticky ends, respectively. The neo sequence was amplified from pRcCMV (Invitrogen) with primer pairs containing BglII and NotI. These fragments were ligated to pcDNA6/V5-His (Invitrogen) diggested with HindIII and NotI to generate pEt2AN.

To construct the replicon plasmid pBΔCtat2Aneo, the genotype 1a infectious clone, pCV-H77c (generously provided by Dr. Robert Purcell, National Institutes of Health, Bethesda, Md.) was digested with SphI and the small fragment was religated. A single T to A nucleotide change was engineered in this plasmid at nucleotide 444 of the HCV sequence of H77c (GenBank accession number AF011751) using QuickChange (Statagene) mutagenesis, generating a novel HpaI site at this position. This resulting plasmid was digested with HpaI and XbaI to generate a DNA fragment representing the HCV 1a 5'NTR and immediately downstream sequence encoding the first 14 amino acids of the HCV polyprotein. A second DNA fragment representing the tat, 2A, and partial neo sequence was excised from pEt2AN by digestion with StuI and SphI. Finally, the plasmid pBNeo/wt (FIG. 16), containing the sequence of the 1377neo/NS3-3' replicon of Lohmann et al. (obtained form Michael Murray, Schering-Plough Research Institute) was digested with SphI and XbaI to generate a fragment representing the C-terminal neo sequence, EMCV IRES, and downstream elements of the HCV replicon. These three fragments were ligated to generate pBΔCtat2Aneo (FIG. 16), which contains the 5'NTR and downstream 42 nts of core-coding sequence of the H77 strain of HCV (genotype 1a) and the NS3-5B and 3'NTR sequence of the Con1 strain of HCV (genotype 1b). The plasmid pBtat2Aneo was generated by QuickChange mutagenesis of pBΔCtat2Aneo, with deletion of the 42 nucleotides of core-coding sequence and fusion of the tat sequence directly downstream of 5'NTR of HCV. pNtat2Aneo was constructed by exchanging the large BsrGI-XbaI fragment of pBtat2Aneo with the analogous HCV sequence derived from the plasmid pHCV-N resulting in replacment of most of the NS3-NS5B and 3'NTR sequence. A similar strategy was employed for the construction of variants of these replicon plasmids containing various cell culture-adaptive mutations or a deletion of the GDD motif in the NS5B protein, as described in Example 8.

RNA transcription and transfection. RNA was synthesized with T7 MEGAScript reagents (Ambion), after linearizing plasmids with XbaI. Following treatment with RNase-free Dnase to remove template DNA and precipitation of the RNA with lithium chloride, the RNA was transfected into En5-3 cells. Transfection was done by electroporation, as described previously. Briefly, 10 μg RNA was mixed with $5\times10^6$ cells suspended in 500 μl phosphate buffered saline, in a cuvette with a gap width of 0.2 cm (Bio-Rad). Electroporation was with two pulses of current delivered by the Gene Pulser II electoporation device (Bio-Rad), set at 1.5 kV, 25 μF, and maximum resistance.

In vitro translation. In vitro transcribed RNA, prepared as described above, was used to program in vitro translation reactions in rabbit reticulocyte lysate (Promega). About 1 mg of each RNA, 2 μl of [$^{35}$S]-methionine (1,000 Ci/mmol at 10 mCi/ml), and 1 ml of an amino acid mixture lacking methionine were included in each 50 ml reaction mixture. Translation was carried out at 30° C. for 90 min. Translation products were separated by SDS-PAGE followed by autoradiography or PhosphorImager (Molecular Dynamics) analysis.

Northern analysis for HCV RNA. We seeded replicon-bearing cells into 6 well plates at a density of $2\times10^5$ cells/well, and harvested the RNA from individual wells at daily intervals. Total cellular RNAs were extracted with TRizol reagent (Gibco-BRL) and quantified by spectrophotometry at 260 nm. One half of the total RNA extracted from each well was loaded onto a denaturing agarose-formaldehyde gel, subjected to electrophoresis and transferred to positively-charged Hybond-N+ nylon membranes (Amersham-Pharmacia Biotec) using reagents provided with the NorthernMax Kit (Ambion). RNAs were immobilized on the membranes by UV-crosslinking. The membrane was hybridized with a [$^{32}$P]-labeled antisense riboprobe complementary to the 3'-end of NS5B sequence (HCV nucleotides 8990-9275 corresponding to GenBank accession number AF139594), and the hybridized probe was detected by exposure to X-ray film.

Indirect immunofluorescence analysis. Cells were grown on chamber slides until 70-80% confluent, washed 3 times with PBS, and fixed in methanol/acetone (1:1 V/V) for 10 min at room temperature. A 1:10 dilution of a primary, murine monoclonal antibody to NS5A (MAB7022P, Maine Biotechnology Services) was prepared in PBS containing 3% bovine serum albumin, and incubated with the fixed cells for 1 hr at room temperature. Following additional washes with PBS, specific antibody binding was detected with a goat anti-mouse IgG FITC-conjugated secondary antibody (Sigma) diluted 1:70. Cells were washed with PBS, counterstained with DAPI, and mounted in Vectashield mounting medium (Vector Laboratories) prior to examination by a Zeiss AxioPlan2 fluorescence microscope.

Alkaline phosphatase assay. SEAP activity was measured in 20 μl aliquots of the supernatant culture fluids using the Phospha-Light Chemiluminescent Reporter Assay (Tropix), and the manufacturer's suggested protocol reduced ⅓ in scale. The luminescent signal was read using a TD-20/20 Luminometer (Turner Designs, Inc.). In most time course experiments, the culture medium was replaced every 24 hrs. Thus, the SEAP activity measured in these fluids reflected the daily production of SEAP by the cells.

Real-time quantitative RT-PCR analysis of HCV RNA. Quantitative RT-PCR assays were carried out using TaqMan chemistry on a PRISM 7700 instrument (ABI). For detection and quantitation of HCV RNA, we used primers complementary to the 5'NTR region of HCV (Takeuchi et al., *Gastroenterology,* 116, 636-642 (1999)), with in vitro transcribed HCV RNA included in the assays as a standard. Results were normalized to the estimated total RNA content of the sample, as determined by the abundance of cellular GAPDH mRNA detected in a similar real-time RT-PCR assay using reagents provided with Taqman GAPDH Control Reagents (Human) (Applied Biosystems).

Sequence analysis of cDNA from replicating HCV RNAs. HCV RNA was extracted from cells, converted to cDNA and amplified by PCR as described previously (see Example 8). First-strand cDNA synthesis was carried out with Superscript II reverse transcriptase (Gibco-BRL), and pfu-Turbo DNA polymerase (Stratagene) was used for PCR amplification of the DNA. The amplified DNAs were subjected to direct sequencing using an ABI 9600 automatic DNA sequencer.

Interferon treatment of cell cultures. Selected replicon-bearing cell lines were seeded into 12 well plates. The media was replaced 24 hrs later with fresh, G418 free media containing various concentrations of recombinant interferon-α2B ranging from 0 to 100 units/ml. The medium was subsequently completely removed every 24 hrs, the cells washed, and refed with fresh interferon-containing media. SEAP activity was measured in the media removed from the cells as described above.

Results

Figure 16A:
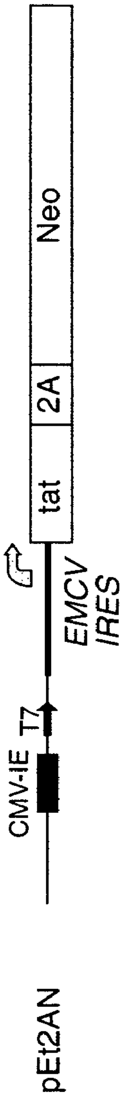
FIG. 16. Enzyme reporter system. (A) Organization of pEt2AN. A solid square represents the CMV promoter region; a solid arrow the T7 promoter; a thick line the EMCV IRES and the open box for the open reading frame encoding the fusion polypeptide tat-2A-Neo. (B) SEAP expression following pEt2AN DNA transfection into En5-3 cells (▲). The expression of tat from this plasmid is dependent on the CMV promoter. Note that SEAP activity is reported in arbitrary units. SEAP expression from En5-3 cells without DNA transfection was also shown (■). (C) SEAP expression following electroporation of En5-3 cells with RNA transcribed in vitro from pEt2AN (▲). SEAP expression from En5-3 cells without RNA transfection was also shown (■).

Tat-SEAP enzyme reporter system. The HIV tat protein is a potent transcriptional transactivator of its LTR promoter element. Unlike most known eukaryotic transcriptional transactivators, tat functions via an interaction with an RNA structure, the transactivation responsive element (TAR), rather than through interaction with DNA (Naryshkin et al., *Biochemistry,* 63, 189-503 (1998); Cullen, *Cell,* 93, 685-692 (1998)). In the absence of tat, almost all RNA transcripts initiated by the LTR promoter are terminated prematurely within ~60-70 nucleotides of the start site. Tat acts to promote the efficient elongation of premature transcripts, thereby transactivating the transcription of functional mRNAs from sequences placed under control of the HIV LTR promoter. We have taken advantage of the small size of the tat protein, and the manner in which it functionally regulates the LTR promoter, to develop a system in which a replication-competent, subgenomic HCV RNA expressing tat induces the expression of secreted alkaline phosphatase (SEAP) placed under transcriptional control of the LTR in stably transformed liver cells.

pEt2AN is an expression plasmid in which the HIV tat coding sequence is fused to sequence encoding the FMDV 2A proteinase and the positive, selectable marker neomycin phosphotransferase (Neo) (FIG. 16A). The small FMDV 2A polypeptide sequence possesses autocatalytic activity (Ryan et al., *EMBO J.,* 13, 928-933 (1994)), resulting in the scission of the peptide backbone at its C-terminus and the release of Neo. The translation of this minipolyprotein is driven by the EMCV IRES sequence located just upstream of the protein coding sequence (FIG. 16A), while transcription is directed by a composite CMV/T7 promoter. We used this plasmid to determine the level of SEAP expressed by stably transformed Huh7 cells (selected for blasticidin resistance) in which the SEAP sequence had been integrated under transcriptional control of the HIV LTR. SEAP activity was measured in the supernatant culture medium before and after transfection of the cells with pEt2AN. Results obtained with one clonally-isolated cell line, En5-3, are shown in FIG. 16B.

Figure 16B:
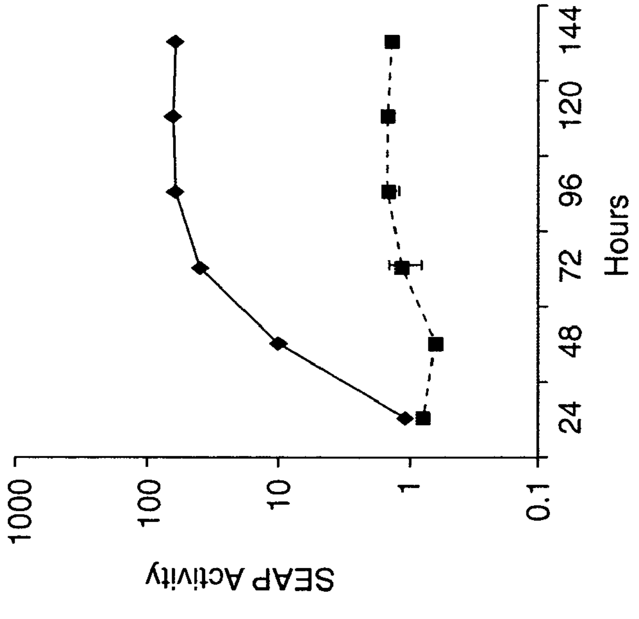
Figure 16C:
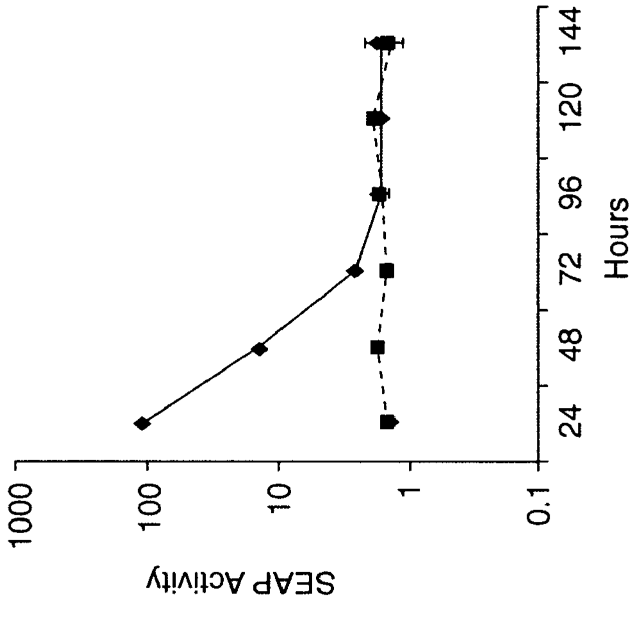

This cell line produced a minimal basal level of SEAP activity, while transfection of the cells with pEt2AN DNA led to an approximately 100 fold increase in the secretion of SEAP into the medium in response to tat expression (FIG. 16B). The secretion of SEAP from En5-3 cells began to increase between 24 and 48 hrs after DNA transfection, and reached maximal levels at 72 to 96 hrs. In contrast, the transfection of En5-3 cells with RNA transcribed in vitro from pEt2AN led to an immediate increase in SEAP activity that was maximal when first assayed at 24 hrs post-transfection and subsequently decreased over time, reaching background levels 72 hours later (FIG. 16C). Since the cell culture medium bathing these transfected cells was replaced at 24 hr intervals in these experiments (see Materials and Methods), the SEAP activity measured at each time point reflected the amount of the reporter protein secreted into the medium over the preceding 24 hr period. The delay in SEAP secretion following DNA versus RNA transfection is likely to represent the time required for RNA transcription to occur, while the rapid decline of SEAP following RNA transfection reflects degradation of the transfected RNA and the tat protein translated from it. These encouraging results suggested that the expression of tat from a replicating subgenomic HCV RNA could provide a simple and useful approach to monitoring the presence and abundance of replicon RNA in En5-3 cells.

Subgenomic HCV replicons expressing tat. To test this hypothesis, we constructed a plasmid with a transcriptional unit containing a dicistronic, subgenomic HCV replicon similar to that reported originally by Lohmann et al. (*Science,* 285, 110-113 (1999)), but in which the 5' cistron encodes the tat-2A-Neo minipolyprotein present in pEt2AN (FIG. 16), fused in frame downstream of the N-terminal 14 amino acid residues of the HCV core protein sequence (FIG. 17, BΔCtat2ANeo). The second cistron in this replicon contained the NS3-5B segment of the Con1 HCV sequence placed under the translational control of the ECMV IRES, as in the original HCV replicons (Lohmann et al., *Science,* 285, 110-113 (1999)). We also constructed a variant in which the 5' cistron contained no HCV protein-coding sequence, and in which HCV IRES-directed translation initiated at the tat coding sequence (FIG. 17, Btat2ANeo). To enhance the potential replication of these replicons in Huh7 cells, additional variants were engineered to contain the S2205I (SI) cell culture-adaptive mutation described by Blight et al. (*Science,* 290, 1972-1974 (2000)), and the R2889G (RG) mutation described by Krieger et al. (*J. Virol,* 75, 4614-4624 (2001)), respectively (these mutations are numbered according to the location of the cognate residue within the HCV-N sequence) (see Example 8) (FIG. 17).

Figure 18B:
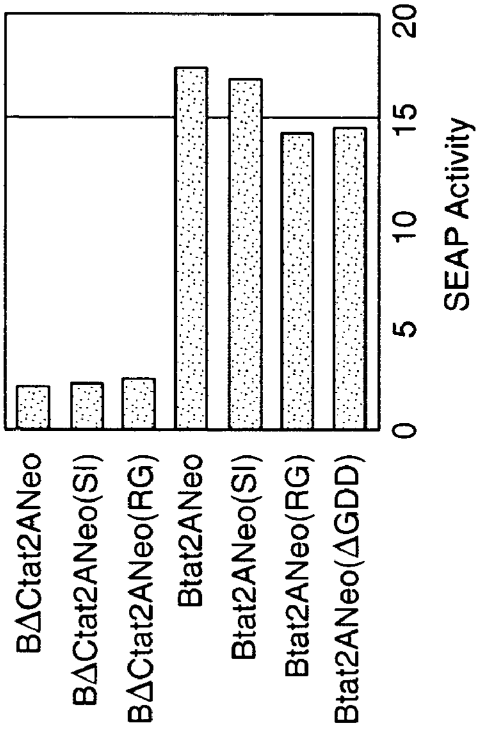
FIG. 18. (A) Product of in vitro translation reactions programmed with the indicated RNAs. (*) indicates the expected positions of the major protein products anticipated to be produced from the dicistronic RNAs. (B) SEAP activity present in tissue culture media 72 hrs following transient transfection with synthetic RNAs transcribed from the indicated plasmids.
Figure 18A:
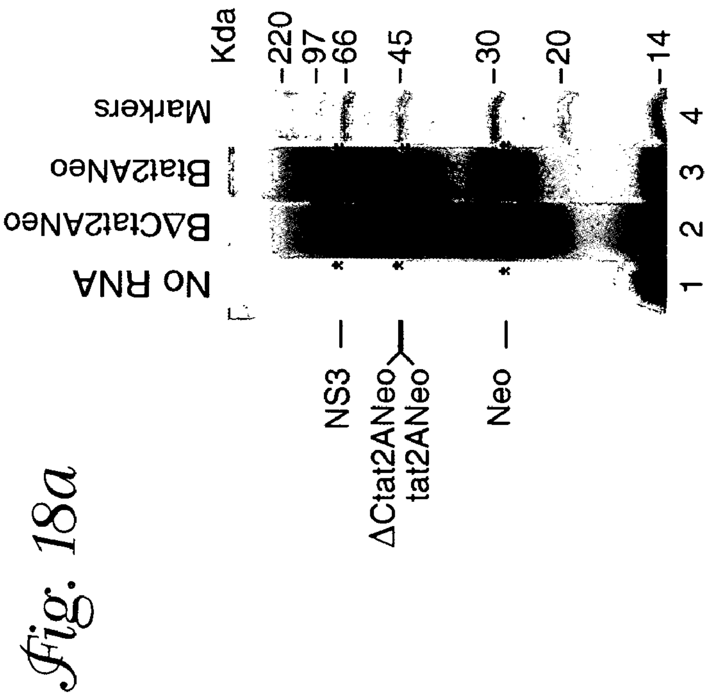

Since the fusion of heterologous sequence directly downstream of the HCV IRES may reduce the ability of the HCV IRES to direct the internal initiation of translation on a hybrid RNA (Reynolds et al., *EMBO J.,* 14, 6010-6020 (1995); Rijinbrand et al., *RNA,* 7, 585-597 (2001)), we evaluated the translational activity of these replicons by programming rabbit reticulocyte lysates for translation with RNAs transcribed from these plasmids. The results of these experiments confirmed the activity of the FMDV 2A proteinase within the minipolyprotein, as protein species migrating with the mobilities expected for both the unprocessed DCtat2ANeo and tat2ANeo precursor proteins, and the fully processed Neo protein, were evident in SDS-PAGE gels of the translation products from BΔCtat2ANeo and Btat2ANeo, respectively (FIG. 18A, lanes 2 and 3). The tat2A cleavage product was not observed due to its small size. The results also suggested that the absence of the core protein-coding sequence in Btat2ANeo did in fact result in a significant reduction in translation of the upstream cistron, as reflected in reduced quantities of Neo and the tat2ANeo precursor protein in lysate programmed with Btat2ANeo RNA (FIG. 18A, compare lane 3 with lane 2). In contrast, the quantity of NS3 produced from the downstream cistron was relatively increased in lysates programmed with Btat2ANeo RNA compared to BΔCtat2ANeo, suggesting that the reduction in the activity of the HCV IRES in the former RNA may have a complementary, beneficial effect on the downstream EMCV IRES. This suggests that there may be intercistronic competition for translation factors between the HCV and EMCV IRES elements in these replicon RNAs, as noted previously with other dicistronic RNAs (Whetter et al., *J. Virol.,* 68, 5253-5263 (1994)).

Figure 17B:
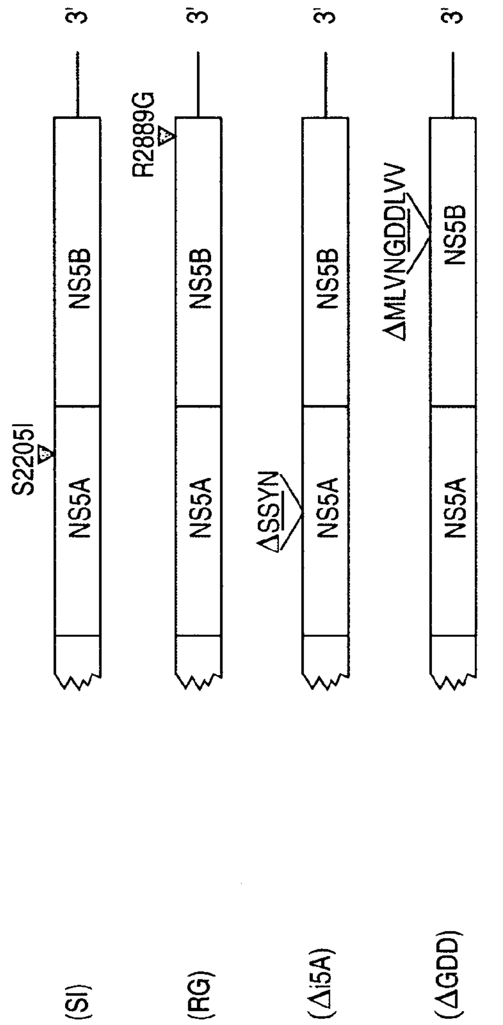

We next assessed the activities of tat proteins expressed from the upstream cistron in the BΔCtat2ANeo and Btat2ANeo replicons (FIG. 17) in transient transfections of these replicon RNAs in En5-3 cells. SEAP activity was monitored in the supernatant media at 72 hrs post-transfection, in the absence of Neo selection. The results of these experiments indicated that the tat protein was significantly less active when expressed as a fusion protein with the N-terminal 14 amino acid segment of core (FIG. 18B, compare BΔCtat2ANeo, BΔCtat2ANeo(SI) and BΔCtat2ANeo(RG), with Btat2ANeo, Btat2ANeo(SI) and Btat2ANeo(RG) RNAs). Although the tat proteins expressed from these RNAs also have a C-terminal fusion with the FMDV 2A proteinase, this C-terminal fusion does not abrogate the transactivating activity of tat, as evidenced in the experiments shown in FIGS. 16B and 16C. Replication of the RNAs did not contribute to the expression of SEAP in the transient transfection experiment shown in FIG. 18B, as the amount of SEAP induced by transfection of an NS5B deletion mutant, Btat2ANeo(ΔGDD), was only slightly less than that induced by its parent, Btat2ANeo. Similarly, the cell culture-adaptive NS5A S2205I and NS5B R2889G mutations (FIG. 17) engineered into these RNAs had no effect on the level of SEAP expression under these conditions (FIG. 18B).

Stable cell lines expressing SEAP under control of replicon-mediated tat expression. Efforts to select stable, G418-resistant colonies following transfection of En5-3 cells with Btat2ANeo or BΔCtat2ANeo were unsuccessful. These results are consistent with the very low frequency of colony formation with the unmodified Con1 NS3-5B sequence, as reported by Lohmann and others (Lohmann et al., *Science,* 285, 110-113 (1999); Blight et al., *Science,* 290, 1972-1974 (2000)).

However, it was possible to select G418-resistant En5-3 clones following transfection of the modified Btat2ANeo containing the adaptive S2205I mutation and BΔCtat2ANeo RNAs containing the adaptive S2205I and R2889G mutations in NS5A and NS5B (FIG. 17), respectively. The efficiency of colony formation was substantially lower with these replicons, even with the adaptive mutations, than what has been reported in the literature (Lohmann et al., *J. Virol.,* 75, 1437-1449 (2001); Blight et al., *Science,* 290, 1972-1974 (2000)) or what we have observed previously (see Example 8) with dicistronic, subgenomic HCV replicons. This may reflect the use of the clonal, blastocidin-resistant En5-3 cell line rather than the parental Huh7 cells. Moreover, the number of colonies selected with Btat2ANeo(SI) RNA was approximately 10-fold lower than with BΔCtat2ANeo(SI), suggesting that the absence of the short, ΔC core protein-coding sequence in Btat2ANeo(SI) decreases the efficiency of colony selection. This could be due to the lower level of Neo expressed from this RNA (FIG. 18), or potentially to other effects on replication of the subgenomic RNA.

Because replicons containing the genotype 1b, HCV-N sequence have proven to be substantially superior to Con1 replicons in their ability to induce the selection of G418-resistant Huh7 cell clones (see Example 8), we constructed a parallel series of replicons containing the tat2ANeo sequence in the upstream cistron with the downstream cistron, NS3-NS5B sequence derived from HCV-N: Ntat2ANeo, Ntat2ANeo(SI) and Ntat2ANeo(RG) (FIG. 17). Transfection with each of these RNAs led to the selection of stable, G418-resistant colonies. The number of G418-resistant colonies selected with Ntat2ANeo(RG) was at least 100-fold higher than with Btat2ANeo(SI). Overall, the efficiency of colony selection observed with replicon RNAs that lacked any core protein coding sequence (FIG. 17) could be ordered as follows, from high to low: Ntat2ANeo(SI), Ntat2ANeo(RG), Ntat2ANeo, Btat2ANeo(SI). This is consistent with our previous observations with subgenomic HCV replicons expressing only Neo from the upstream cistron (see Example 8).

Figure 19B:
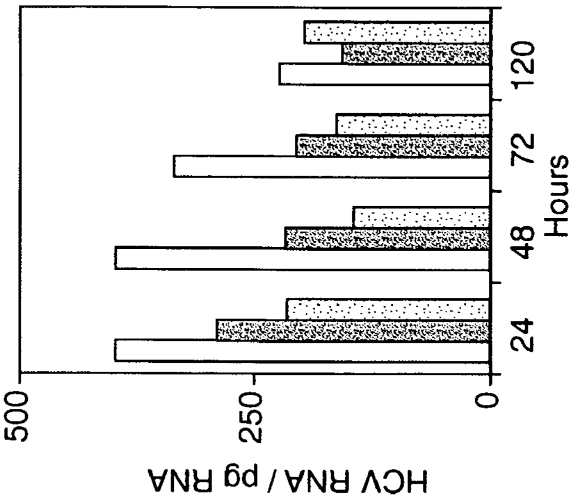
FIG. 19. (A) Northern Blot analysis of replicon RNAs following passage of stable G418-resistant cell clones. (B) HCV RNA abundance detected by TaqMan RT-PCR, normalized to a total cellular RNA standard, and presented as copies of HCV RNA per pg total cellular RNA. The same RNA samples were used as in northern blot analysis in FIG. 19A. Open bar represents BΔCtat2ANeo(SI), solid bar represents Btat2ANeo(SI); gray bar, for Ntat2ANeo(RG).
Figure 19A:
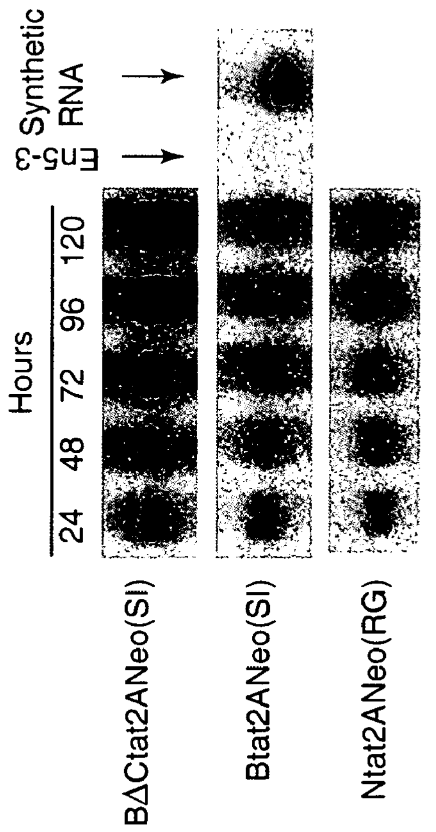

Replicon RNA was readily detected by northern analysis of G418-resistant cell lines selected following transfection with BΔCtat2ANeo(SI), Btat2ANeo(SI) and Ntat2ANeo (RG) (FIG. 19A). The abundance of the viral RNA was significantly greater in the BΔCtat2ANeo(SI) cell line selected for testing, than in cell lines supporting replication of Btat2ANeo(SI) and Ntat2ANeo(RG). While the total abundance of the replicon RNAs (see Materials and Methods) increased in each of the cell lines studied over a 120 hr period following passage of the cells (FIG. 19A), quantitative real-time RT-PCR assays showed a trend toward a reduction in the intracellular abundance of the replicon RNA relative to the abundance of GAPDH mRNA as the cells approached confluence at 120 hrs (FIG. 19B). This is similar to the reduction in intracellular abundance of replicon RNAs reported recently by Pietschmann et al. (*J. Virol.,* 75, 1252-1264 (2001)). Once confluent, the intracellular abundance of the replicon RNAs appeared to be similar in all three cell lines studied. These results confirm that there is no requirement for core-protein coding sequence for replication of these dicistronic, subgenomic viral RNAs.

Figure 20A:
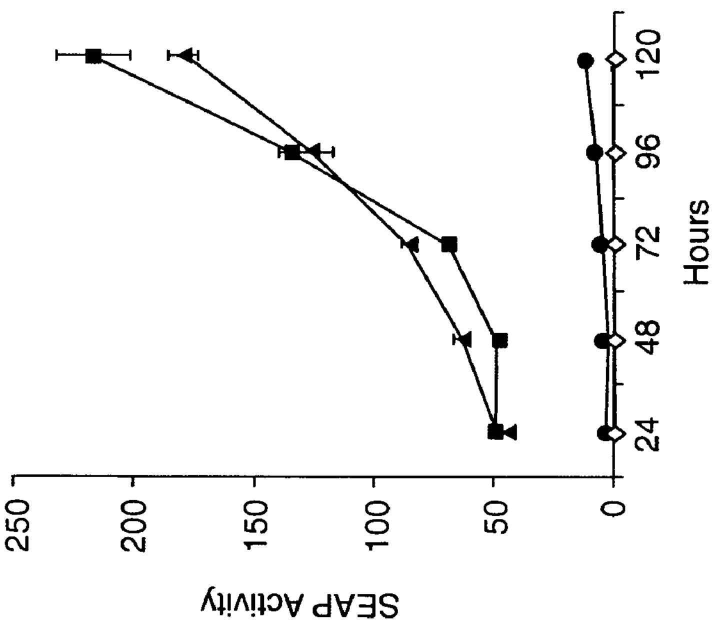
FIG. 20. (A) SEAP activity present in supernatant culture media at various time point following passage of stable cell lines. Btat2ANeo(SI) (▲), Ntat2ANeo(RG) (■), BCtat2ANeo(SI) (●), En5-3 (◇). Bars show the range of SEAP activity from duplicate experiments. (B) Linear regression analysis of SEAP activity vs. abundance of replicon RNA in the culture, as determined by densitometry of northern blots. Btat2ANeo(SI) (▲- - - ), Ntat2ANeo(RG) (■- - - ).

We also examined the cell lines shown in FIG. 19 for viral protein expression as well as secretion of SEAP. NS5A antigen was readily detected within the cytoplasm in each cell line, while no NS5A antigen was detectable in normal En5-3 cells stained in parallel. The abundance of the viral protein was significantly greater in cells containing BΔCtat2ANeo(SI) than Btat2ANeo(SI) or Ntat2ANeo(RG), consistent with the greater abundance of replicon RNA detected in the former by northern analysis (FIG. 19A). In contrast, the SEAP activities expressed by these cell lines showed a very different relationship to the abundance of the replicon RNA. Each of the cell lines secreted increased amounts of SEAP that were detectable above the low background activity present in En5-3 media (FIG. 20A). However, the level of SEAP activity expressed by the BΔCtat2A(SI) cell line was minimally above background and much lower than that secreted by the Btat2ANeo(SI) or Ntat2ANeo(RG) cell lines, despite a higher abundance of viral RNA and viral proteins in the former. Sequencing of cDNA amplified by RT-PCR from the replicon RNAs present in the BΔCtat2A(SI) cells did not identify any mutations within the upstream, ΔCtat2ANeo cistron, ruling out adventitious mutations as a potential cause for the minimal level of SEAP expressed by these cells. The Btat2ANeo(SI) and Ntat2ANeo(RG) cell lines demonstrated robust secretion of the reporter protein, reaching levels at least 100-fold above background after 5 days in culture (FIG. 20A). These results are consistent with the results of the transient transfections presented above (FIG. 18B), and serve to confirm that the fusion of tat to the N-terminal segment of the core protein sharply diminishes its ability to functionally transactivate the HIV LTR.

Figure 20B:
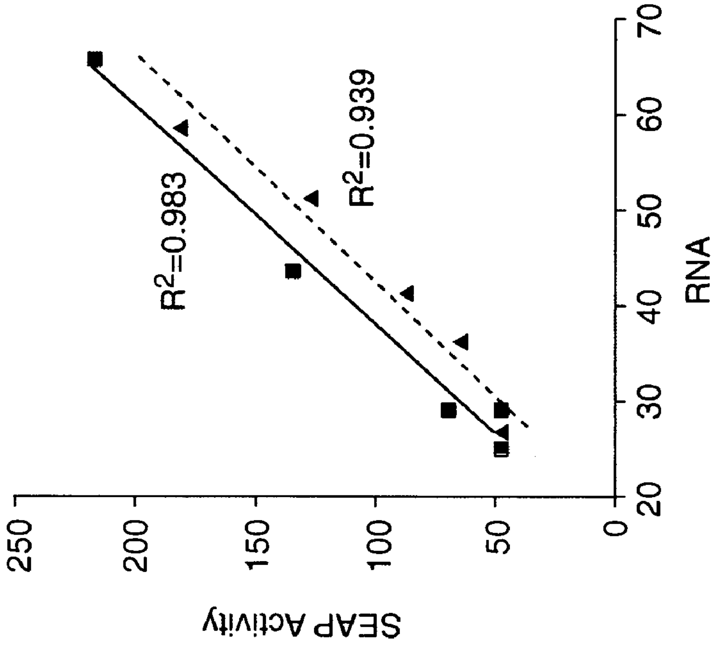

In the experiment shown in FIG. 20A, it is important to note that the media was completely replaced at 24 hr intervals, and that the cells were thoroughly washed before being refed with fresh media. Thus, the results shown represent the quantity of SEAP secreted by the Btat2ANeo (SI) and Ntat2ANeo(RG) cells during successive 24 hr periods. The secretion of SEAP correlated closely with the abundance of replicon RNA in the Btat2ANeo(SI) and Ntat2ANeo(RG) cells as determined by densitometry of northern blots (FIG. 20B, R2=0.983 and 0.939 by linear regression analysis, respectively). In aggregate, these results demonstrate that the expression of tat from subgenomic HCV RNAs that are replicating in En5-3 cells effectively signals the secretion of SEAP, thereby providing an easily measurable and accurate marker of viral RNA replication that does not require lysis or destruction of the cell monolayer.

Impact of cell culture-adaptive mutations on the replication of tat-expressing HCV replicons in transient transfection assays. Further studies of these replicons focused on those with no core protein sequence fused to tat, since the fusion with the core sequence effectively inactivated the transactivating function of tat. To determine whether the activation of SEAP expression in En5-3 cells by tat was sufficiently sensitive for detection of the replication of subgenomic RNAs in transient transfection assays, replicon RNAs were transfected into En5-3 cells using electroporation, and the cells were followed for a period of 20 days in the absence of G418 selection. Included in this experiment were the Btat2ANeo and Ntat2ANeo replicons, and mutants containing cell culture-adaptive mutations that were derived from them, as shown schematically in FIG. 17B. The supernatant media bathing the transfected cells was removed and replaced with fresh media at 24 hr intervals, as in the experiment shown in FIG. 20A, and the cells were collected by trypsinization and passaged into fresh culture vessels at 7 and 14 days. The levels of SEAP activity present in the media that was removed from cells transfected with the replicon RNAs based on the Btat2ANeo (Con1) sequence (FIG. 17) are shown in FIG. 21A, while FIG. 21B shows SEAP activities in media collected from cells transfected with replicons derived from the HCV-N sequence.

Figure 21B:
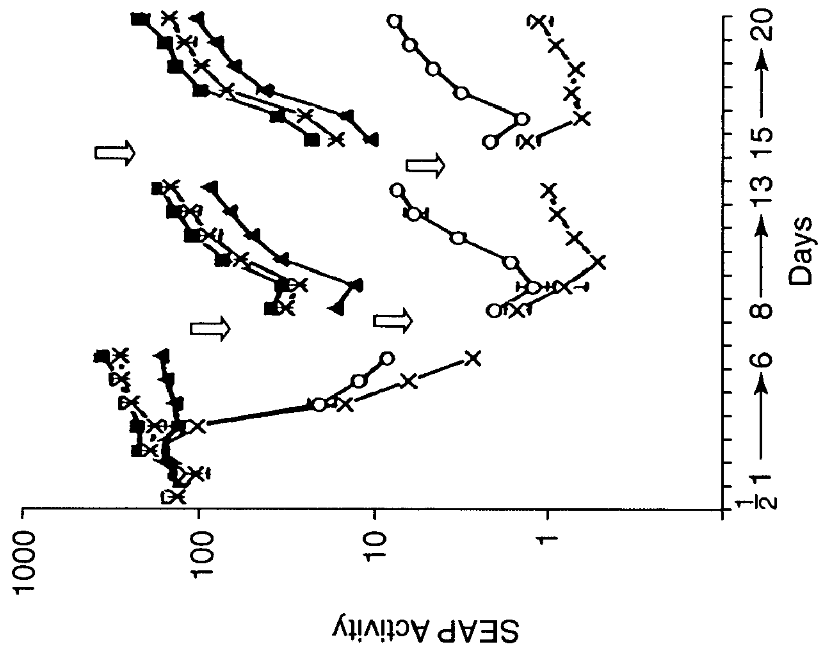
FIG. 21. SEAP activity following transient transfection of En5-3 cells with (A) Btat2Aneo and (B) Ntat2Aneo with various mutations. Wt(○), SI (■), RG (▲), GDD (X), N-Δ5ASI (*). Arrow indicates trypsinization and passage of cells.
Figure 21A:
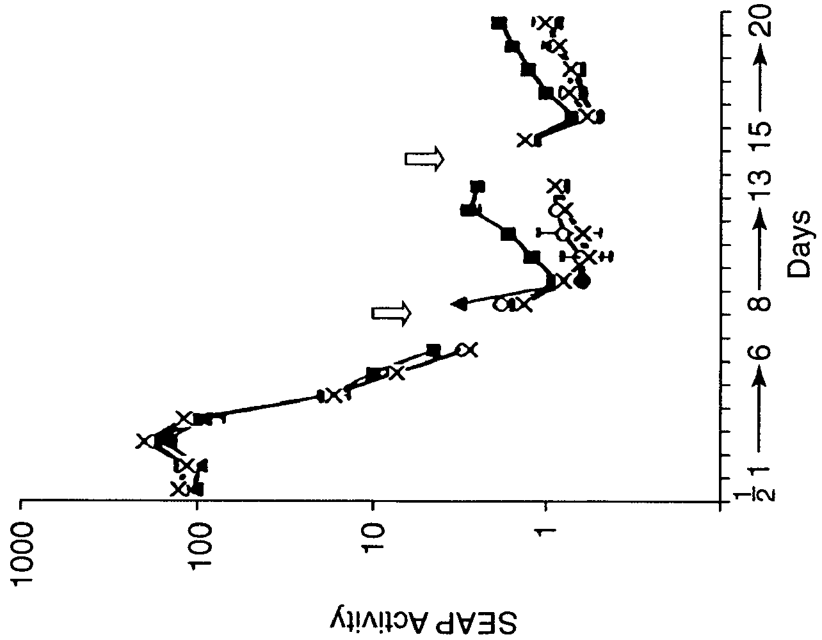

The transfection of any of these replicon RNAs into En5-3 cells resulted in a high initial level of SEAP expression that was present in the culture media as early as 12 hrs after electroporation (FIGS. 21A and 21B). This early, high level of SEAP secretion persisted for approximately 3 days, and was due to translation of the transfected input RNA, as in the experiment shown in FIG. 18C. This high initial SEAP level was also observed with replication-defective mutants containing a deletion in the NS5B sequence involving the GDD polymerase motif (ΔGDD mutants) (FIGS. 21A and 21B). The SEAP activity secreted into the media of cells transfected with Btat2ANeo(ΔGDD) and Ntat2ANeo (ΔGDD) began to decrease by day 4, and reached baseline values similar to those observed with normal En5-3 cells by 8 days after electroporation (FIGS. 21A and 21B). In contrast, other, replication competent RNAs, particularly those derived from the HCV-N sequence, demonstrated increased levels of SEAP expression at later time points that were significantly above the En5-3 cell background and thus indicative of replication of the transfected RNA.

In experiments with replicon RNAs derived from the Con1 sequence, significant increases in SEAP activity above that observed with the Btat2ANeo(ΔGDD) mutant were seen only in cells transfected with Btat2ANeo(SI). There was no apparent difference in the levels of SEAP expressed by cells transfected with the Btat2ANeo and Btat2ANeo(RG) replicons. Cells transfected with Btat2ANeo(SI) demonstrated a low level but sustained increase in SEAP activity above background beginning about 10 days after transfection (FIG. 21A). However, the secretion of SEAP was modest in magnitude, and never more than several-fold above background. In sharp contrast, the HCV-N based replicons were remarkably more potent in terms of their abilities to elicit sustained increases in SEAP expression (FIG. 21B). Levels of SEAP secretion up to 100-fold above background were observed with Ntat2ANeo(SI) and Ntat2ANeo(RG), as well as Ntat2ANeo(SIΔi5A). This latter replicon contains both the S2205I substitution in NS5A as well as the deletion of a natural 4 amino acid insertion that is present in the NS5A sequence of HCV-N (FIG. 17B). This natural insertion in NS5A, which was present in cDNA cloned from human serum (Beard et al., *Hepatology,* 30, 316-324 (1999)), has been shown to contribute substantially to the replication capacity of replicons containing the wild-type HCV-N sequence in Huh7 cells (Example 8). The results shown in FIG. 21 are consistent with those disclosed in Example 8 concerning the relative abilities of subgenomic RNAs containing the Con1 and HCV-N NS3-NS5B sequences (with or without cell culture adaptive mutations in NS5A and NS5B) to transduce the selection of G418-resistant cell clones. These results also provide independent confirmation of the ability of the S2205I and R2889G mutations to enhance the replication capacity of subgenomic, genotype 1b RNAs in cultured cells (Blight et al., *Science,* 290, 1972-1974 (2000); Krieger et al., *J. Virol.,* 75, 4614-4624 (2001); Example 8).

We also examined transiently transfected cells for expression of NS5A antigen at 12 and 19 days after electroporation. These studies demonstrated that the proportion of cells containing a detectable abundance of NS5A was significantly greater following transfection with Ntat2ANeo(RG) and Ntat2ANeo(SI), than Ntat2ANeo or Btat2ANeo(SI). Thus, these results parallel closely the results of the SEAP assays shown in FIG. 21. Interestingly, the intensity of staining of individual positive cells appeared similar with each of the replicon RNAs, suggesting that the level of SEAP expression may correlate with the proportion of cells in which replicon amplification is occurring, rather than the intracellular abundance of the replicon under these conditions. As this experiment was carried out in the absence of G418 selection, it is uncertain whether those cells that did not stain positively for NS5A antigen contained levels of the viral protein that were below the threshold of detection or, alternatively, none at all.

Figure 22B:
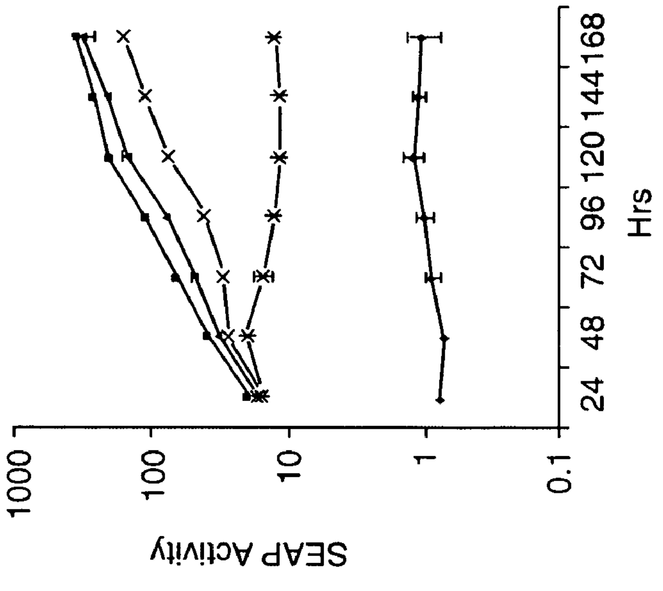
FIG. 22. Suppression of HCV replicon amplification by interferon-α2b. (A) SEAP activity secreted from cells supporting replication of Btat2ANeo(SI) over successive 24 hr intervals following addition of interferon to the medium. (B) SEAP secretion from Ntat2ANeo(RG) cells. Interferon concentrations were: (*) 100 units/ml; (X) 10 units/ml; (▲) 1 unit/ml; (■) no interferon. SEAP expression from En5-3 cells without interferon treatment was also shown (♦). SEAP expression from En5-3 cells was not affected by interferon treatment.

Interferon suppression of HCV RNA replication. To demonstrate the utility of the tat-expressing HCV replicons, we assessed the ability of recombinant interferon-α2b to suppress the replication of Btat2ANeo(SI) and Ntat2ANeo(RG) in stable, G418 resistant cell clones. Recently seeded cell cultures were fed with media containing various concentrations of recombinant interferon-α2B ranging from 0 to 100 units/ml. The medium was subsequently removed completely at 24 hr intervals, and the cells were washed thoroughly and refed with fresh interferon-containing media. Results are shown in FIG. 22 and demonstrate dose-dependent inhibition of SEAP secretion in both cell lines. As shown, cells cultured in the absence of interferon, or at the lowest concentration of interferon, showed an increasing level of SEAP secretion over successive 24 hr intervals, consistent with the growth of the cells. At the highest concentration of interferon tested (100 units/ml), this trend was reversed and SEAP expression declined over time in the absence of demonstrable cellular cytotoxicity. Independent quantitative RT-PCR assays for HCV RNA demonstrated that the decline in SEAP secretion was closely matched by similar decreases in the intracellular abundance of RNA (compare FIG. 22 and FIG. 23). The decline in intracellular RNA preceded the decreases in SEAP secretion by approximately 24 hrs, most likely reflecting the kinetic delay in tat signaling of SEAP secretion.

Figure 22A:
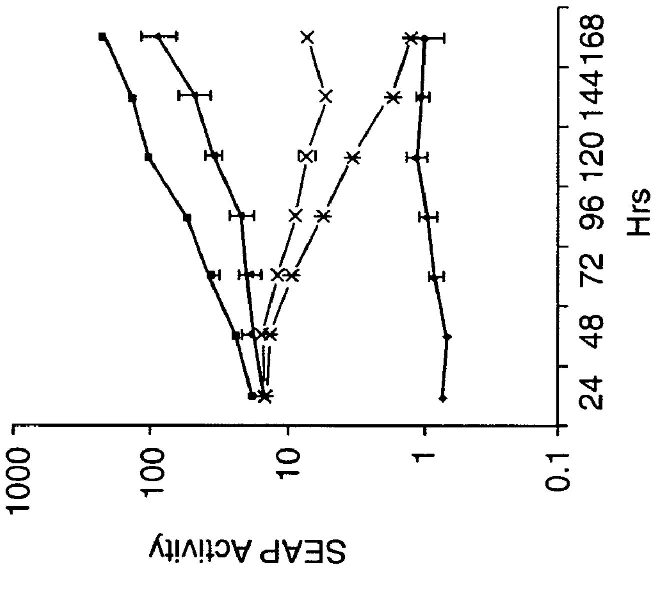
Figure 23A:
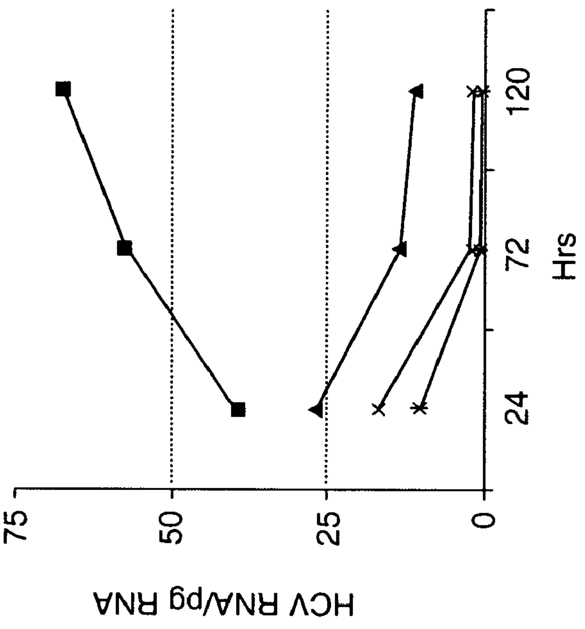
FIG. 23. Suppression of HCV replicon RNA abundance by interferon-α2b in the cell cultures depicted in FIG. 22. (A) Intracellular abundance of HCV RNA in cells supporting replication of Btat2ANeo(SI) at 24, 72 and 120 hrs following addition of interferon to the medium. (B) RNA abundance in Ntat2ANeo(RG) cells under similar conditions. HCV RNA was quantified by RT-PCR analysis, and normalized to a total cellular RNA standard (see legend to FIG. 19B). Interferon concentrations were: (*) 100 units/ml; (X) 10 units/ml; (▲) 1 unit/ml; (■) no interferon.
Figure 23B:
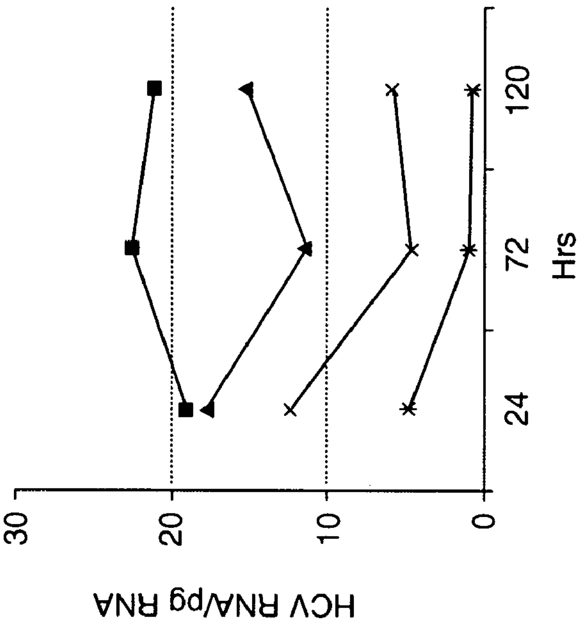

Surprisingly, the Ntat2ANeo(RG) replicon (FIG. 22B) was approximately 10-fold more resistant to interferon than the Btat2ANeo(SI) replicon (FIG. 22A). This relative interferon resistance was reflected also in differences in the degree of suppression of the intracellular abundance of HCV RNA following interferon treatment of these cells (compare the decrease in Btat2ANeo(SI) RNA abundance at different interferon concentrations in FIG. 23A, with the decreases in Ntat2ANeo(RG) RNA abundance shown in FIG. 23B). A similar level of interferon resistance was observed in separate experiments with an independently selected, G418-resistant clone supporting the replication of the Ntat2ANeo (RG) replicon, suggesting that the resistance observed in FIGS. 22B and 23B was not an idiosyncratic feature of the particular cell clone tested. Studies are currently in progress to determine the molecular basis of this difference in the response of the two replicons to interferon-α2b.

Discussion

We have described here an enzymatic reporter system that permits the detection and quantitation of HCV RNA replication in intact cell monolayers. The system is based on the expression of the tat transactivator protein by replicating subgenomic RNA replicons, and the subsequent induction of SEAP synthesis in En5-3 cells that contain the SEAP gene under transcriptional control of the HIV LTR promoter.

SEAP is secreted efficiently into the medium bathing these cells, where it is readily quantified as an accurate marker of viral RNA abundance. We adapted both Con-1 and HCV-N replicons for use in this system, and have shown that the induction of SEAP is a useful measure of the replicon RNA abundance in stable, G418-resistant cell lines (FIG. 20), as well as in cells that have been transiently transfected by these RNAs (FIG. 21). Parallel measurements of RNA abundance and SEAP expression in two separate stable cell lines demonstrated a remarkable degree of correlation (FIG. 20B), providing strong validation of the system.

We have utilized this system to document the inhibition of HCV-N and Con-1HCV RNA replication in En5-3 cells following treatment with recombinant interferon-α2B (FIG. 22 and FIG. 23). We found Ntat2ANeo(RG) to be about 10-fold less sensitive to interferon than Btat2ANeo(SI). These results differ from those reported recently by Guo et al. (*J. Virol.,* 75, 8516-8523 (2001)), who found comparable interferon sensitivities with simple subgenomic dicistronic replicons constructed from these two viral sequences. We are currently investigating the molecular basis of the difference we observed in the interferon responsiveness of these replicons. Using the tat-expressing replicons, we have also been able to demonstrate the inhibition of viral RNA replication by prototype antiviral compounds that have activity against the viral NS3 proteinase or NS5B RNA-dependent, RNA polymerase. Thus, we believe that this unique and simple system for monitoring viral RNA replication is likely to prove useful in future antiviral drug discovery efforts.

Because measurements of SEAP are technically simpler and considerably less expensive than quantitative RT-PCR assays for viral RNA, this system is likely to prove advantageous for high throughput screening for compounds with antiviral activity. An additional technical advantage over HCV replicons that express luciferase or most other conventional reporter proteins is that SEAP activity is measured in supernatant culture fluids and does not require the lysis of cells. This permits serial measurements of the kinetics of RNA amplification in single cultures of cells (FIG. 21). One potential drawback of this system is that suppression of SEAP activity by candidate antiviral compounds could result from inhibition of the activity of either the 2A protease or tat, or even (as with other published dicistronic HCV replicons) the EMCV IRES. To address this issue, we established a stably transformed cell line that constitutively expresses the tat2ANeo polyprotein under the translational control of the EMCV IRES. This cell line (Et2AN) was established by transfection of pEt2AN DNA (FIG. 16) into En5-3 cells, followed by selection with G418. In contrast to the results shown in FIG. 22, where interferon-α2B suppressed the secretion of SEAP from the replicon-bearing cell lines, there was no suppression of the secretion of SEAP by the Et2AN cell line at comparable concentrations of interferon. This indicates that the effect of interferon-α2B on SEAP secretion from the replicon cell line was due to specific suppression of the replication of HCV RNA, and not the fortuitious suppression of 2A, tat, or EMCV IRES activity. It also demonstrates the absence of nonspecific toxicity at the concentrations of interferon tested, and is consistent with the suppression of HCV RNA abundance in these cells shown in FIG. 23.

In developing these replicons, we have shown that none of the viral core protein-coding sequence is required for replication of HCV RNA. There has been considerable controversy over the role of this sequence in viral translation since Reynolds et al. (*RNA,* 2, 867-878 (1996)) first suggested that the 5' proximal 33 nts of the core sequence were an integral part of the viral IRES and required for efficient cap-independent translation. Recently, however, Rijinbrand et al. (*RNA,* 7, 585-597 (2001)) demonstrated that the requirement is not for any specific sequence, but rather for a lack of secondary RNA structure within the core-coding sequence immediately downstream of the initiator AUG. This is consistent with prior work by Honda et al. (*RNA,* 2, 955-968 (1996)) that indicated that stable RNA structure within the vicinity of the AUG is very detrimental to IRES-directed translation. Because of concerns that the 5' proximal core coding sequence might be required for optimal activity of the HCV IRES, the original dicistronic, subgenomic HCV replicons that were constructed by Lohmann et al. (*Science,* 285, 110-113 (1999)) contained RNA encoding 12 or 16 amino acids of the core protein fused in-frame to the Neo gene in the upstream cistron. We found that replicons in which the tat sequence was fused directly to the HCV IRES had reduced translation of the upstream tat2ANeo mini-polyprotein (FIG. 17A), but were nonetheless capable of replication and the transduction of G418-resistant cell lines. These results demonstrate that none of the core coding sequence is required for viral RNA replication. Other subgenomic HCV replicons have recently been described in which all core protein sequence had been removed, but in these replicons translation of the upstream cistron was driven by a picornaviral IRES and the HCV 5'NTR sequence functioned only in template recognition by the RNA replicase complex (Kim et al., *Biochem Biophys Res Commun,* 290, 105-112 (2002)).

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the beading, unless so specified.

What is claimed is:

1. A method for detecting a replication competent HCV RNA, the method comprising:

incubating a vertebrate cell comprising an HCV RNA, wherein:

the HCV RNA comprises a first coding sequence encoding a hepatitis C virus polyprotein, and a heterologous polynucleotide comprising a second coding sequence encoding a transactivator;

the cell comprises a transactivated coding region and an operator sequence operably linked to the transactivated coding region; and the transactivated coding region encodes a detectable marker, wherein the transactivator alters transcription of the transactivated coding region; and detecting the detectable marker, wherein the presence of the detectable marker indicates the cell comprises a replication competent HCV RNA.

2. The method of claim 1 wherein the HCV RNA comprises a 3' non-translated RNA, and wherein the heterologous polynucleotide is present in the 3' non-translated RNA or 5' of the first coding sequence.

3. The method of claim 1 wherein the heterologous polynucleotide further comprises a third coding sequence encoding a selectable marker, wherein the second coding sequence and the third coding sequence together encode a fusion polypeptide.

4. The method of claim 3 wherein the heterologous polynucleotide further comprises a fourth coding sequence encoding a cis-active proteinase present between the second coding sequence encoding the transactivator and the third coding sequence encoding the selectable marker, wherein the second coding sequence, the fourth coding sequence, and the third coding sequence together encode a fusion polypeptide.

5. A method for detecting a replication competent HCV RNA, the method comprising:

incubating a vertebrate cell comprising an HCV RNA, wherein:

the HCV RNA comprises a first coding sequence encoding a subgenomic hepatitis C virus polyprotein, and a heterologous polynucleotide comprising a second coding sequence encoding a transactivator;

the cell comprises a transactivated coding region and an operator sequence operably linked to the transactivated coding region; and the transactivated coding region encodes a detectable marker, wherein the transactivator alters transcription of the transactivated coding region; and detecting the detectable marker, wherein the presence of the detectable marker indicates the cell comprises a replication competent HCV RNA.

6. The method of claim 5 wherein the heterologous polynucleotide further comprises a third coding sequence encoding a selectable marker, wherein the second coding sequence and the third coding sequence together encode a fusion polypeptide.

7. The method of claim 5 wherein the heterologous polynucleotide further comprises a fourth coding sequence encoding a cis-active proteinase present between the second coding sequence encoding the transactivator and the third coding sequence encoding the selectable marker, wherein the second coding sequence, the fourth coding sequence, and the third coding sequence together encode a fusion polypeptide.

8. The method of claim 5 wherein the transactivator comprises an amino acid sequence comprising at least about 70% identity with an amino acid sequence selected from the group consisting of SEQ ID NO:19 and amino acids 4-89 of SEQ ID NO:21, and wherein the transactivator has tat activity.

9. A method for detecting a replication competent HCV RNA, the method comprising:

incubating a vertebrate cell comprising an HCV RNA, wherein:

the HCV RNA comprises a first coding sequence, and a heterologous polynucleotide comprising a second coding sequence encoding a transactivator;

the cell comprises a transactivated coding region and an operator sequence operably linked to the transactivated coding region; and the transactivated coding region encodes a detectable marker, wherein the transactivator alters transcription of the transactivated coding region; and detecting the detectable marker, wherein the presence of the detectable marker indicates the cell comprises a replication competent HCV RNA.

10. The method of claim 9 wherein the first coding sequence encodes a subgenomic hepatitis C virus polyprotein.

11. The method of claim 9 wherein the first coding sequence encodes a hepatitis C virus polyprotein.

* * * * *

UNITED STATES PATENT AND TRADEMARK OFFICE

CERTIFICATE OF CORRECTION

PATENT NO. : 7,288,369 B2
APPLICATION NO. : 11/006313
DATED : October 30, 2007
INVENTOR(S) : Lemon et al.

It is certified that error appears in the above-identified patent and that said Letters Patent is hereby corrected as shown below:

Column 1, line 21, delete “U19-A140035” and insert --U19-AI40035--;

Column 9, line 7, delete “GDD (X)” and insert --ΔGDD (X)--;

Column 14, line 24, delete “Gin” and insert --Gln--;

Column 46, line 55, delete “diggested” and insert --digested--;

Column 47, line 49, delete “Phosphorlmager” and insert --PhosphorImager--.

Signed and Sealed this

Eighth Day of April, 2008

JON W. DUDAS
*Director of the United States Patent and Trademark Office*

SEQUENCE LISTING

<160> NUMBER OF SEQ ID NOS: 73

<210> SEQ ID NO 1
<211> LENGTH: 23
<212> TYPE: DNA
<213> ORGANISM: Artificial

-continued

<220> FEATURE:
<223> OTHER INFORMATION: Primer

<400> SEQUENCE: 1
aagactgcta gccgagtagt gtt 23

<210> SEQ ID NO 2
<211> LENGTH: 21
<212> TYPE: DNA
<213> ORGANISM: artificial
<220> FEATURE:
<223> OTHER INFORMATION: Primer

<400> SEQUENCE: 2
ggttggtgtt acgtttggtt t 21

<210> SEQ ID NO 3
<211> LENGTH: 24
<212> TYPE: DNA
<213> ORGANISM: artificial
<220> FEATURE:
<223> OTHER INFORMATION: Probe

<400> SEQUENCE: 3
tgcaccatga gcacgaatcc taaa 24

<210> SEQ ID NO 4
<211> LENGTH: 21
<212> TYPE: DNA
<213> ORGANISM: artificial
<220> FEATURE:
<223> OTHER INFORMATION: Primer

<400> SEQUENCE: 4
acactccacc atgaatcact c 21

<210> SEQ ID NO 5
<211> LENGTH: 20
<212> TYPE: DNA
<213> ORGANISM: artificial
<220> FEATURE:
<223> OTHER INFORMATION: Primer

<400> SEQUENCE: 5
gatcgggctc atcacaaccc 20

<210> SEQ ID NO 6
<211> LENGTH: 27
<212> TYPE: DNA
<213> ORGANISM: artificial
<220> FEATURE:
<223> OTHER INFORMATION: Fluor probe
<220> FEATURE:
<221> NAME/KEY: misc_difference
<222> LOCATION: (27)..(27)
<223> OTHER INFORMATION: Labeled with fluorescein

<400> SEQUENCE: 6
gcgtctagcc atggcgttag tatgagt 27

<210> SEQ ID NO 7
<211> LENGTH: 21
<212> TYPE: DNA
<213> ORGANISM: artificial
<220> FEATURE:
<223> OTHER INFORMATION: Red probe
<220> FEATURE:

-continued

<221> NAME/KEY: misc_difference
<222> LOCATION: (1)..(1)
<223> OTHER INFORMATION: LC640 labeled

<400> SEQUENCE: 7
tcgtgcagcc tccaggaccc c 21

<210> SEQ ID NO 8
<211> LENGTH: 33
<212> TYPE: DNA
<213> ORGANISM: artificial
<220> FEATURE:
<223> OTHER INFORMATION: Primer

<400> SEQUENCE: 8
ctagctagcc tcgagacctg gaaaaacatg gag 33

<210> SEQ ID NO 9
<211> LENGTH: 33
<212> TYPE: DNA
<213> ORGANISM: artificial
<220> FEATURE:
<223> OTHER INFORMATION: Primer

<400> SEQUENCE: 9
ataagaatgc ggccgcttaa cccgggtgcg cgg 33

<210> SEQ ID NO 10
<211> LENGTH: 21
<212> TYPE: DNA
<213> ORGANISM: artificial
<220> FEATURE:
<223> OTHER INFORMATION: Primer

<400> SEQUENCE: 10
gacactccac catgaatcac t 21

<210> SEQ ID NO 11
<211> LENGTH: 19
<212> TYPE: DNA
<213> ORGANISM: artificial
<220> FEATURE:
<223> OTHER INFORMATION: Primer

<400> SEQUENCE: 11
gttccgcaga ccactatgg 19

<210> SEQ ID NO 12
<211> LENGTH: 25
<212> TYPE: DNA
<213> ORGANISM: artificial
<220> FEATURE:
<223> OTHER INFORMATION: Probe
<220> FEATURE:
<221> NAME/KEY: misc_difference
<222> LOCATION: (25)..(25)
<223> OTHER INFORMATION: Labeled with fluorescein

<400> SEQUENCE: 12
agaaagcgtc tagccatggc gttag 25

<210> SEQ ID NO 13
<211> LENGTH: 22
<212> TYPE: DNA
<213> ORGANISM: artificial
<220> FEATURE:
<223> OTHER INFORMATION: Probe -continued
<220> FEATURE:
<221> NAME/KEY: misc_difference
<222> LOCATION: (1)..(1)
<223> OTHER INFORMATION: LC640 labeled
<220> FEATURE:
<221> NAME/KEY: misc_difference
<222> LOCATION: (22)..(22)
<223> OTHER INFORMATION: phosphate

<400> SEQUENCE: 13
atgagtgtcg tgcagcctcc ag 22

<210> SEQ ID NO 14
<211> LENGTH: 17
<212> TYPE: DNA
<213> ORGANISM: artificial
<220> FEATURE:
<223> OTHER INFORMATION: Primer

<400> SEQUENCE: 14
cgggagagcc atagtgg 17

<210> SEQ ID NO 15
<211> LENGTH: 19
<212> TYPE: DNA
<213> ORGANISM: artificial
<220> FEATURE:
<223> OTHER INFORMATION: Primer

<400> SEQUENCE: 15
agtaccacaa ggcctttcg 19

<210> SEQ ID NO 16
<211> LENGTH: 21
<212> TYPE: DNA
<213> ORGANISM: artificial
<220> FEATURE:
<223> OTHER INFORMATION: Probe
<220> FEATURE:
<221> NAME/KEY: misc_difference
<222> LOCATION: (21)..(21)
<223> OTHER INFORMATION: Labeled with TAMRA

<400> SEQUENCE: 16
ctgcggaacc ggtgagtaca c 21

<210> SEQ ID NO 17
<211> LENGTH: 10803
<212> TYPE: DNA
<213> ORGANISM: artificial
<220> FEATURE:
<223> OTHER INFORMATION: Nucleotide sequence of MK0-Z

<400> SEQUENCE: 17
gccagccccc tgatgggggc gacactccac catgaatcac tcccctgtga ggaactactg 60
tcttcacgca gaaagcgtct agccatggcg ttagtatgag tgtcgtgcag cctccaggac 120 ccccccctccc gggagagcca tagtggtctg cggaaccggt gagtacaccg gaattgccag 180
gacgaccggg tcctttcttg gataaacccg ctcaatgcct ggagatttgg gcgtgccccc 240
gcaagactgc tagccgagta gtgttgggtc gcgaaaggcc ttgtggtact gcctgatagg 300
gtgcttgcga gtgccccggg aggtctcgta gaccgtgcac catgagcacg aatcctaaac 360
ctcaaagaaa aaccaaacgt aacaccaacc gtcgcccaca ggacgtcaag ttcccgggtg 420
gcggtcagat cgttggtgga gtttacttgt tgccgcgcag gggccctaga ttgggtgtgc 480

-continued

```
gcgcgacgag gaagacttcc gagcggtcgc aacctcgagg tagacgtcag cctatcccca    540
aggcacgtcg gcccgagggc aggacctggg ctcagcccgg gtacccttgg cccctctatg    600
gcaatgaggg ttgcgggtgg gcgggatggc tcctgtctcc ccgtggctct cggcctagct    660
ggggccccac agacccccgg cgtaggtcgc gcaatttggg taaggtcatc gataccctta    720
cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaactc gagtattgtg tacgaggcgg ccgatgccat cctgcacact ccggggtgtg   1020
tcccttgcgt tcgcgagggt aacgcctcga ggtgttgggt ggcggtgacc cccacggtgg   1080
ccaccaggga cggcaaactc cccacaacgc agcttcgacg tcatatcgat ctgcttgtcg   1140
ggagcgccac cctctgctcg gccctctacg tgggggacct gtgcgggtct gtctttcttg   1200
ttggtcaact gtttaccttc tctcccaggc gccactggac gacgcaagac tgcaattgtt   1260
ctatctatcc cggccatata acgggtcatc gcatggcatg ggatatgatg atgaactggt   1320
cccctacggc agcgttggtg gtagctcagc tgctccggat cccacaagcc atcatggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aaatgccggc cgcaccacgg ctgggcttgt tggtctcctt acaccaggcg   1560
ccaagcagaa catccaactg atcaacacca acggcagttg gcacatcaat agcacggcct   1620
tgaattgcaa tgaaagcctt aacaccggct ggttagcagg gctcttctat caacacaaat   1680
tcaactcttc aggctgtcct gagaggttgg ccagctgccg acgccttacc gattttgccc   1740
agggctgggg tcctatcagt tatgccaacg gaagcggcct cgacgaacgc ccctactgct   1800
ggcactaccc tccaagacct tgtggcattg tgcccgcaaa gagcgtgtgt ggcccggtat   1860
attgcttcac tcccagcccc gtggtggtgg gaacgaccga caggtcgggc gcgcctacct   1920
acagctgggg tgcaaatgat acggatgtct tcgtccttaa caacaccagg ccaccgctgg   1980
gcaattggtt cggttgtacc tggatgaact caactggatt caccaaagtg tgcggagcgc   2040
cccctgtgt catcggaggg gtgggcaaca acaccttgct ctgccccact gattgcttcc   2100
gcaaacatcc ggaagccaca tactctcggt gcggctccgg tccctggatt acacccaggt   2160
gcatggtcga ctacccgtat aggctttggc actatccttg taccatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580
ctttggagaa cctcgtaata ctcaatgcag catccctggc cgggacgcac ggtcttgtgt   2640
ccttcctcgt gttcttctgc tttgcgtggt atctgaaggg taggtgggtg cccggagcgg   2700
tctacgccct ctacgggatg tggcctctcc tcctgctcct gctggcgttg cctcagcggg   2760
catacgcact ggacacggag gtggccgcgt cgtgtggcgg cgttgttctt gtcgggttaa   2820
tggcgctgac tctgtcgcca tattacaagc gctatatcag ctggtgcatg tggtggcttc   2880
```

-continued

```
agtattttct gaccagagta gaagcgcaac tgcacgtgtg ggttcccccc ctcaacgtcc   2940
gggggggcg cgatgccgtc atcttactca tgtgtgtagt acacccgacc ctggtatttg   3000
acatcaccaa actactcctg gccatcttcg gacccctttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttaggggcg cttactggca   3180
cctatgtgta taaccatctc acccctcttc gagactgggc gcacaacggc ctgcgagatc   3240
tggccgtggc tgtggaacca gtcgtcttct cccgaatgga gaccaagctc atcacgtggg   3300
gggcagatac cgccgcgtgc ggtgacatca tcaacggctt gcccgtctct gcccgtaggg   3360
gccaggagat actgcttggg ccagccgacg gaatggtctc caaggggtgg aggttgctgg   3420
cgcccatcac ggcgtacgcc cagcagacga gaggcctcct agggtgtata atcaccagcc   3480
tgactggccg ggacaaaaac caagtggagg gtgaggtcca gatcgtgtca actgctaccc   3540
aaaccttcct ggcaacgtgc atcaatgggg tatgctggac tgtctaccac ggggccggaa   3600
cgaggaccat cgcatcaccc aagggtcctg tcatccagat gtataccaat gtggaccaag   3660
accttgtggg ctggcccgct cctcaaggtt cccgctcatt gacaccctgt acctgcggct   3720
cctcggacct ttacctggtc acgaggcacg ccgatgtcat tcccgtgcgc cggcgaggtg   3780
atagcagggg tagcctgctt tcgccccggc ccatttccta cttgaaaggc tcctcggggg   3840
gtccgctgtt gtgccccgcg ggacacgccg tgggcctatt cagggccgcg gtgtgcaccc   3900
gtggagtggc taaagcggtg gactttatcc ctgtggagaa cctagggaca accatgagat   3960
ccccggtgtt cacggacaac tcctctccac cagcagtgcc ccagagcttc caggtggccc   4020
acctgcatgc tcccaccggc agcggtaaga gcaccaaggt cccggctgcg tacgcagccc   4080
agggctacaa ggtgttggtg ctcaacccct ctgttgctgc aacgctgggc tttggtgctt   4140
acatgtccaa ggcccatggg gttgatccta atatcaggac cggggtgaga acaattacca   4200
ctggcagccc catcacgtac tccacctacg gcaagttcct tgccgacggc gggtgctcag   4260
gaggtgctta tgacataata atttgtgacg agtgccactc cacggatgcc acatccatct   4320
tgggcatcgg cactgtcctt gaccaagcag agactgcggg ggcgagactg gttgtgctcg   4380
ccactgctac ccctccgggc tccgtcactg tgtcccatcc taacatcgag gaggttgctc   4440
tgtccaccac cggagagatc cccttttacg gcaaggctat ccccctcgag gtgatcaagg   4500
ggggaagaca tctcatcttc tgccactcaa agaagaagtg cgacgagctc gccgcgaagc   4560
tggtcgcatt gggcatcaat gccgtggcct actaccgcgg tcttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcaac   4800
gccggggcag gactggcagg gggaagccag gcatctatag atttgtggca ccgggggagc   4860
gcccctccgg catgttcgac tcgtccgtcc tctgtgagtg ctatgacgcg ggctgtgctt   4920
ggtatgagct cacgcccgcc gagactacag ttaggctacg agcgtacatg aacaccccgg   4980
ggcttcccgt gtgccaggac catcttgaat tttgggaggg cgtctttacg ggcctcactc   5040
atatagatgc ccacttttta tcccagacaa agcagagtgg ggagaacttt ccttacctgg   5100
tagcgtacca agccaccgtg tgcgctaggg ctcaagcccc tcccccatcg tgggaccaga   5160
tgtggaagtg tttgatccgc cttaaaccca ccctccatgg gccaacaccc ctgctataca   5220
```

-continued gactgggcgc tgttcagaat gaagtcaccc tgacgcaccc aatcaccaaa tacatcatga 5280
catgcatgtc ggccgacctg gaggtcgtca cgagcacctg ggtgctcgtt ggcggcgtcc 5340
tggctgctct ggccgcgtat tgcctgtcaa caggctgcgt ggtcatagtg ggcaggatcg 5400
tcttgtccgg gaagccggca attatacctg acagggaggt tctctaccag gagttcgatg 5460
agatggaaga gtgctctcag cacttaccgt acatcgagca agggatgatg ctcgctgagc 5520
agttcaagca gaaggccctc ggcctcctgc agaccgcgtc ccgccatgca gaggttatca 5580
cccctgctgt ccagaccaac tggcagaaac tcgaggtctt ttgggcgaag cacatgtgga 5640
atttcatcag tgggatacaa tacttggcgg gcctgtcaac gctgcctggt aaccccgcca 5700
ttgcttcatt gatggctttt acagctgccg tcaccagccc actaaccact ggccaaaccc 5760
tcctcttcaa catattgggg gggtgggtgg ctgcccagct cgccgccccc ggtgccgcta 5820
ctgcctttgt gggtgctggc ctagctggcg ccgccatcgg cagcgttgga ctggggaagg 5880
tcctcgtgga cattcttgca gggtatggcg cgggcgtggc gggagctctt gtagcattca 5940
agatcatgag cggtgaggtc ccctccacgg aggacctggt caatctgctg cccgccatcc 6000
tctcgcctgg agcccttgta gtcggtgtgg tctgcgcagc aatactgcgc cggcacgttg 6060
gcccgggcga gggggcagtg caatggatga accggctaat agccttcgcc tcccggggga 6120
accatgtttc ccccacgcac tacgtgccgg agagcgatgc agccgcccgc gtcactgcca 6180
tactcagcag cctcactgta acccagctcc tgaggcgact gcatcagtgg ataagctcgg 6240
agtgtaccac tccatgctcc ggttcctggc taagggacat ctgggactgg atatgcgagg 6300
tgctgagcga ctttaagacc tggctgaaag ccaagctcat gccacaactg cctgggattc 6360
cctttgtgtc ctgccagcgc gggtataggg ggtctggcg aggagacggc attatgcaca 6420
ctcgctgcca ctgtggagct gagatcactg gacatgtcaa aaacgggacg atgaggatcg 6480
tcggtcctag gacctgcagg aacatgtgga gtgggacgtt ccccattaac gcctacacca 6540
cgggcccctg tactcccctt cctgcgccga actataagtt cgcgctgtgg agggtgtctg 6600
cagaggaata cgtggagata aggcgggtgg gggacttcca ctacgtatcg ggtatgacta 6660
ctgacaatct taaatgcccg tgccagatcc catcgcccga atttttcaca gaattggacg 6720
gggtgcgcct acacaggttt gcgcccccctt gcaagccctt gctgcgggag gaggtatcat 6780
tcagagtagg actccacgag tacccggtgg ggtcgcaatt accttgcgag cccgaaccgg 6840
acgtagccgt gttgacgtcc atgctcactg atccctccca tataacagca gaggcggccg 6900
ggagaaggtt ggcgagaggg tcacccccctt ctatggccag ctcctcggct agccagctgt 6960
ccgctccatc tctcaaggca acttgcaccg ccaaccatga ctcccctgac gccgagctca 7020
tagaggctaa cctcctgtgg aggcaggaga tgggcggcaa catcaccagg gttgagtcag 7080
agaacaaagt ggtgattctg gactccttcg atccgcttgt ggcagaggag gatgagcggg 7140
aggtctccgt acctgcagaa attctgcgga agtctcggag attcgcccgg gccctgcccg 7200
tctgggcgcg gccggactac aacccccgc tagtagagac gtggaaaaag cctgactacg 7260
aaccacctgt ggtccatggc tgcccgctac cacctccacg gtcccctcct gtgcctccgc 7320
ctcggaaaaa gcgtacggtg gtcctcaccg aatcaaccct atctactgcc ttggccgagc 7380
ttgccaccaa aagttttggc agctcctcaa cttccggcat tacgggcgac aatacgacaa 7440
catcctctga gcccgcccct tctggctgcc cccccgactc cgacgttgag tcctattctt 7500
ccatgccccc cctggagggg gagcctgggg atccggatct cagcgacggg tcatggtcga 7560
cggtcagtag tggggccgac acggaagatg tcgtgtgctg ctcaatgtct tattcctgga 7620

-continued

```
caggcgcact cgtcaccccg tgcgctgcgg aagaacaaaa actgcccatc aacgcactga   7680
gcaactcgtt gctacgccat cacaatctgg tgtattccac cacttcacgc agtgcttgcc   7740
aaaggcagaa gaaagtcaca tttgacagac tgcaagttct ggacagccat taccaggacg   7800
tgctcaagga ggtcaaagca gcggcgtcaa aagtgaaggc taacttgcta tccgtagagg   7860
aagcttgcag cctgacgccc ccacattcag ccaaatccaa gtttggctat ggggcaaaag   7920
acgtccgttg ccatgccaga aaggccgtag cccacatcaa ctccgtgtgg aaagaccttc   7980
tggaagacag tgtaacacca atagacacta ccatcatggc caagaacgag gttttctgcg   8040
ttcagcctga gaagggggt cgtaagccag ctcgtctcat cgtgttcccc gacctgggcg   8100
tgcgcgtgtg cgagaagatg gccctgtacg acgtggttag caagctcccc ctggccgtga   8160
tgggaagctc ctacggattc caatactcac caggacagcg ggttgaattc ctcgtgcaag   8220
cgtggaagtc caagaagacc ccgatggggt tctcgtatga tacccgctgt tttgactcca   8280
cagtcactga gagcgacatc cgtacggagg aggcaattta ccaatgttgt gacctggacc   8340
cccaagcccg cgtggccatc aagtccctca ctgagaggct ttatgttggg ggccctctta   8400
ccaattcaag gggggaaaac tgcggctacc gcaggtgccg cgcgagcggc gtactgacaa   8460
ctagctgtgg taacaccctc acttgctaca tcaaggcccg ggcagcctgt cgagccgcag   8520
ggctccagga ctgcaccatg ctcgtgtgtg gcgacgactt agtcgttatc tgtgaaagtg   8580
cgggggtcca ggaggacgcg gcgagcctga gagccttcac ggaggctatg accaggtact   8640
ccgcccccc cggggacccc ccacaaccag aatacgactt ggagcttata acatcatgct   8700
cctccaacgt gtcagtcgcc cacgacggcg ctggaaagag ggtctactac cttacccgtg   8760
accctacaac ccccctcgcg agagccgcgt gggagacagc aagacacact ccagtcaatt   8820
cctggctagg caacataatc atgtttgccc ccacactgtg ggcgaggatg atactgatga   8880
cccatttctt tagcgtcctc atagccaggg atcagcttga acaggctctt aactgtgaga   8940
tctacggagc ctgctactcc atagaaccac tggatctacc tccaatcatt caaagactcc   9000
atggcctcag cgcattttca ctccacagtt actctccagg tgaaatcaat agggtggccg   9060
catgcctcag aaaacttggg gtcccgccct tgcgagcttg gagacaccgg gcccggagcg   9120
tccgcgctag gcttctgtcc agaggaggca gggctgccat atgtggcaag tacctcttca   9180
actgggcagt aagaacaaag ctcaaactca ctccaatagc ggccgctggc cggctggact   9240
tgtccggttg gttcacggct ggctacagcg gggagacat ttatcacagc gtgtctcatg   9300
cccggccccg ctggttctgg ttttgcctac tcctgctcgc tgcaggggta ggcatctacc   9360
tcctccccaa ccgatgaagg ttggggtaaa cactccggcc tcttaaggtt attttccacc   9420
atattgccgt cttttggcaa tgtgagggcc cggaaacctg gccctgtctt cttgacgagc   9480
attcctaggg gtctttcccc tctcgccaaa ggaatgcaag gtctgttgaa tgtcgtgaag   9540
gaagcagttc ctctggaagc ttcttgaaga caaacaacgt ctgtagcgac cctttgcagg   9600
cagcggaacc ccccacctgg cgacaggtgc ctctgcggcc aaaagccacg tgtataagat   9660
acacctgcaa aggcggcaca accccagtgc cacgttgtga gttggatagt tgtggaaaga   9720
gtcaaatggc tctcctcaag cgtattcaac aaggggctga aggatgccca gaaggtaccc   9780
cattgtatgg gatctgatct ggggcctcgg tgcacatgct ttacgtgtgt ttagtcgagg   9840
ttaaaaaacg tctaggcccc ccgaaccacg gggacgtggt tttcctttga aaaacacgat   9900
gataatatga ggcctatgga gccagtagat cctagactag agccctggaa gcatccagga   9960
```

-continued

```
agtcagccta aaactgcttg taccaattgc tattgtaaaa agtgttgctt tcattgccaa  10020

gtttgtttca taacaaaagc cttaggcatc tcctatggca ggaagaagcg gagacagcga  10080

cgaagacctc ctcaaggcag tcagactcat caagtttctc tatcaaagca acccacctcc  10140

caatcccgag gggacccgac aggcccgaag gaagaattcg accttcttaa gcttgcggga  10200

gacgtcgagt ccaaccctgg gcccggatcc atggccaagt tgaccagtgc cgttccggtg  10260

ctcaccgcgc gcgacgtcgc cggagcggtc gagttctgga ccgaccggct cgggttctcc  10320

cgggacttcg tggaggacga cttcgccggt gtggtccggg acgacgtgac cctgttcatc  10380

agcgcggtcc aggaccaggt ggtgccggac aacaccctgg cctgggtgtg ggtgcgcggc  10440

ctggacgagc tgtacgccga gtggtcggag gtcgtgtcca cgaacttccg ggacgcctcc  10500

gggccggcca tgaccgagat cggcgagcag ccgtgggggc gggagttcgc cctgcgcgac  10560

ccggccggca actgcgtgca cttcgtggcc gaggagcagg actgacttaa gccatttcct  10620

gttttttttt ttttttttt ttttttttc ttttttttt tctttccttt ccttcttttt  10680

ttcctttctt tttcccttct ttaatggtgg ctccatctta gccctagtca cggctagctg  10740

tgaaaggtcc gtgagccgca tgactgcaga gagtgctgat actggcctct ctgcagatca  10800

tgt                                                                10803
```

<210> SEQ ID NO 18
<211> LENGTH: 2239
<212> TYPE: DNA
<213> ORGANISM: artificial
<220> FEATURE:
<223> OTHER INFORMATION: Nucleotide sequence of HIVSEAP

<400> SEQUENCE: 18

```
acctggaaaa acatggagca atcacaagta gcaatacagc agctaccaat gctgcttgtg     60

cctggctaga agcacaagag gaggaggagg tgggttttcc agtcacacct caggtacctt    120

taagaccaat gacttacaag gcagctgtag atcttagcca ctttttaaaa gaaaaggggg    180

gactggaagg gctaattcac tcccaaagaa gacaagatat ccttgatctg tggatctacc    240

acacacaagg ctacttccct gattagcaga actacacacc agggccaggg gtcagatatc    300

cactgacctt tggatggtgc tacaagctag taccagttga gccagataag atagaagagg    360

ccaataaagg agagaacacc agcttgttac accctgtgag cctgcatggg atggatgacc    420

cggagagaga agtgttagag tggaggtttg acagccgcct agcatttcat cacgtggccc    480

gagagctgca tccggagtac ttcaagaact gctgacatcg agcttgctac aagggacttt    540

ccgctgggga ctttccaggg aggcgtggcc tgggcgggac tggggagtgg cgagccctca    600

gatcctgcat ataagcagct gctttttgcc tgtactgggt ctctctggtt agaccagatc    660

tgagcctggg agctctctgg ctaactaggg aacccactgc ttaagcctca ataaagcttc    720

tgcatgctgc tgctgctgct gctgctgggc ctgaggctac agctctccct gggcatcatc    780

ccagttgagg aggagaaccc ggacttctgg aaccgcgagg cagccgaggc cctgggtgcc    840

gccaagaagc tgcagcctgc acagacagcc gccaagaacc tcatcatctt cctgggcgat    900

gggatggggg tgtctacggt gacagctgcc aggatcctaa aagggcagaa gaaggacaaa    960

ctggggcctg agatacccct ggccatggac cgcttcccat atgtggctct gtccaagaca   1020

tacaatgtag acaaacatgt gccagacagt ggagccacag ccacggccta cctgtgcggg   1080

gtcaagggca acttccagac cattggcttg agtgcagccg cccgctttaa ccagtgcaac   1140

acgacacgcg gcaacgaggt catctccgtg atgaatcggg ccaagaaagc agggaagtca   1200
```

-continued

```
gtgggagtgg taaccaccac acgagtgcag cacgcctcgc cagccggcac ctacgcccac   1260

acggtgaacc gcaactggta ctcggacgcc gacgtgcctg cctcggcccg ccaggagggg   1320

tgccaggaca tcgctacgca gctcatctcc aacatggaca ttgacgtgat cctaggtgga   1380

ggccgaaagt acatgtttcc catgggaacc ccagaccctg agtacccaga tgactacagc   1440

caaggtggga ccaggctgga cgggaagaat ctggtgcagg aatggctggc gaagcgccag   1500

ggtgcccggt atgtgtggaa ccgcactgag ctcatgcagg cttccctgga cccgtctgtg   1560

acccatctca tgggtctctt tgagcctgga gacatgaaat acgagatcca ccgagactcc   1620

acactggacc cctccctgat ggagatgaca gaggctgccc tgcgcctgct gagcaggaac   1680

ccccgcggct tcttcctctt cgtggagggt ggtcgcatcg accatggtca tcatgaaagc   1740

agggcttacc gggcactgac tgagacgatc atgttcgacg acgccattga gagggcgggc   1800

cagctcacca gcgaggagga cacgctgagc ctcgtcactg ccgaccactc ccacgtcttc   1860

tccttcggag gctaccccct gcgagggagc tccatcttcg ggctggcccc tggcaaggcc   1920

cgggacagga aggcctacac ggtcctccta tacggaaacg gtccaggcta tgtgctcaag   1980

gacggcgccc ggccggatgt taccgagagc gagagcggga gccccgagta tcggcagcag   2040

tcagcagtgc ccctggacga agagacccac gcaggcgagg acgtggcggt gttcgcgcgc   2100

ggcccgcagg cgcacctggt tcacggcgtg caggagcaga ccttcatagc gcacgtcatg   2160

gccttcgccg cctgcctgga gccctacacc gcctgcgacc tggcgccccc cgccggcacc   2220

accgacgccg cgcacccgg                                                2239
```

<210> SEQ ID NO 19
<211> LENGTH: 86
<212> TYPE: PRT
<213> ORGANISM: HIV

<400> SEQUENCE: 19

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu
                85
```

<210> SEQ ID NO 20
<211> LENGTH: 3011
<212> TYPE: PRT
<213> ORGANISM: artificial
<220> FEATURE:
<223> OTHER INFORMATION: Polyprotein

<400> SEQUENCE: 20

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30
```

-continued

```
Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
```

-continued

```
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
    770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880
```

-continued

```
His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Gln
        995                 1000                1005

Glu Ile  Leu Leu Gly Pro Ala  Asp Gly Met Val Ser  Lys Gly Trp
    1010                 1015                 1020

Arg Leu  Leu Ala Pro Ile Thr  Ala Tyr Ala Gln Gln  Thr Arg Gly
    1025                 1030                 1035

Leu Leu  Gly Cys Ile Ile Thr  Ser Leu Thr Gly Arg  Asp Lys Asn
    1040                 1045                 1050

Gln Val  Glu Gly Glu Val Gln  Ile Val Ser Thr Ala  Thr Gln Thr
    1055                 1060                 1065

Phe Leu  Ala Thr Cys Ile Asn  Gly Val Cys Trp Thr  Val Tyr His
    1070                 1075                 1080

Gly Ala  Gly Thr Arg Thr Ile  Ala Ser Pro Lys Gly  Pro Val Ile
    1085                 1090                 1095

Gln Met  Tyr Thr Asn Val Asp  Gln Asp Leu Val Gly  Trp Pro Ala
    1100                 1105                 1110

Pro Gln  Gly Ser Arg Ser Leu  Thr Pro Cys Thr Cys  Gly Ser Ser
    1115                 1120                 1125

Asp Leu  Tyr Leu Val Thr Arg  His Ala Asp Val Ile  Pro Val Arg
    1130                 1135                 1140

Arg Arg  Gly Asp Ser Arg Gly  Ser Leu Leu Ser Pro  Arg Pro Ile
    1145                 1150                 1155

Ser Tyr  Leu Lys Gly Ser Ser  Gly Gly Pro Leu Leu  Cys Pro Ala
    1160                 1165                 1170

Gly His  Ala Val Gly Leu Phe  Arg Ala Ala Val Cys  Thr Arg Gly
    1175                 1180                 1185

Val Ala  Lys Ala Val Asp Phe  Ile Pro Val Glu Asn  Leu Gly Thr
    1190                 1195                 1200

Thr Met  Arg Ser Pro Val Phe  Thr Asp Asn Ser Ser  Pro Pro Ala
    1205                 1210                 1215

Val Pro  Gln Ser Phe Gln Val  Ala His Leu His Ala  Pro Thr Gly
    1220                 1225                 1230

Ser Gly  Lys Ser Thr Lys Val  Pro Ala Ala Tyr Ala  Ala Gln Gly
    1235                 1240                 1245

Tyr Lys  Val Leu Val Leu Asn  Pro Ser Val Ala Ala  Thr Leu Gly
    1250                 1255                 1260

Phe Gly  Ala Tyr Met Ser Lys  Ala His Gly Val Asp  Pro Asn Ile
    1265                 1270                 1275
```

-continued

```
Arg Thr  Gly Val Arg Thr Ile  Thr Thr Gly Ser Pro  Ile Thr Tyr
    1280                 1285                 1290

Ser Thr  Tyr Gly Lys Phe Leu  Ala Asp Gly Gly Cys  Ser Gly Gly
    1295                 1300                 1305

Ala Tyr  Asp Ile Ile Ile Cys  Asp Glu Cys His Ser  Thr Asp Ala
    1310                 1315                 1320

Thr Ser  Ile Leu Gly Ile Gly  Thr Val Leu Asp Gln  Ala Glu Thr
    1325                 1330                 1335

Ala Gly  Ala Arg Leu Val Val  Leu Ala Thr Ala Thr  Pro Pro Gly
    1340                 1345                 1350

Ser Val  Thr Val Ser His Pro  Asn Ile Glu Glu Val  Ala Leu Ser
    1355                 1360                 1365

Thr Thr  Gly Glu Ile Pro Phe  Tyr Gly Lys Ala Ile  Pro Leu Glu
    1370                 1375                 1380

Val Ile  Lys Gly Gly Arg His  Leu Ile Phe Cys His  Ser Lys Lys
    1385                 1390                 1395

Lys Cys  Asp Glu Leu Ala Ala  Lys Leu Val Ala Leu  Gly Ile Asn
    1400                 1405                 1410

Ala Val  Ala Tyr Tyr Arg Gly  Leu Asp Val Ser Val  Ile Pro Thr
    1415                 1420                 1425

Ser Gly  Asp Val Val Val Val  Ser Thr Asp Ala Leu  Met Thr Gly
    1430                 1435                 1440

Phe Thr  Gly Asp Phe Asp Ser  Val Ile Asp Cys Asn  Thr Cys Val
    1445                 1450                 1455

Thr Gln  Thr Val Asp Phe Ser  Leu Asp Pro Thr Phe  Thr Ile Glu
    1460                 1465                 1470

Thr Thr  Thr Leu Pro Gln Asp  Ala Val Ser Arg Thr  Gln Arg Arg
    1475                 1480                 1485

Gly Arg  Thr Gly Arg Gly Lys  Pro Gly Ile Tyr Arg  Phe Val Ala
    1490                 1495                 1500

Pro Gly  Glu Arg Pro Ser Gly  Met Phe Asp Ser Ser  Val Leu Cys
    1505                 1510                 1515

Glu Cys  Tyr Asp Ala Gly Cys  Ala Trp Tyr Glu Leu  Thr Pro Ala
    1520                 1525                 1530

Glu Thr  Thr Val Arg Leu Arg  Ala Tyr Met Asn Thr  Pro Gly Leu
    1535                 1540                 1545

Pro Val  Cys Gln Asp His Leu  Glu Phe Trp Glu Gly  Val Phe Thr
    1550                 1555                 1560

Gly Leu  Thr His Ile Asp Ala  His Phe Leu Ser Gln  Thr Lys Gln
    1565                 1570                 1575

Ser Gly  Glu Asn Phe Pro Tyr  Leu Val Ala Tyr Gln  Ala Thr Val
    1580                 1585                 1590

Cys Ala  Arg Ala Gln Ala Pro  Pro Pro Ser Trp Asp  Gln Met Trp
    1595                 1600                 1605

Lys Cys  Leu Ile Arg Leu Lys  Pro Thr Leu His Gly  Pro Thr Pro
    1610                 1615                 1620

Leu Leu  Tyr Arg Leu Gly Ala  Val Gln Asn Glu Val  Thr Leu Thr
    1625                 1630                 1635

His Pro  Ile Thr Lys Tyr Ile  Met Thr Cys Met Ser  Ala Asp Leu
    1640                 1645                 1650

Glu Val  Val Thr Ser Thr Trp  Val Leu Val Gly Gly  Val Leu Ala
    1655                 1660                 1665

Ala Leu  Ala Ala Tyr Cys Leu  Ser Thr Gly Cys Val  Val Ile Val
```

-continued

```
    1670                1675                1680

Gly Arg  Ile Val Leu Ser Gly  Lys Pro Ala Ile Ile  Pro Asp Arg
    1685                1690                1695

Glu Val  Leu Tyr Gln Glu Phe  Asp Glu Met Glu Glu  Cys Ser Gln
    1700                1705                1710

His Leu  Pro Tyr Ile Glu Gln  Gly Met Met Leu Ala  Glu Gln Phe
    1715                1720                1725

Lys Gln  Lys Ala Leu Gly Leu  Leu Gln Thr Ala Ser  Arg His Ala
    1730                1735                1740

Glu Val  Ile Thr Pro Ala Val  Gln Thr Asn Trp Gln  Lys Leu Glu
    1745                1750                1755

Val Phe  Trp Ala Lys His Met  Trp Asn Phe Ile Ser  Gly Ile Gln
    1760                1765                1770

Tyr Leu  Ala Gly Leu Ser Thr  Leu Pro Gly Asn Pro  Ala Ile Ala
    1775                1780                1785

Ser Leu  Met Ala Phe Thr Ala  Ala Val Thr Ser Pro  Leu Thr Thr
    1790                1795                1800

Gly Gln  Thr Leu Leu Phe Asn  Ile Leu Gly Gly Trp  Val Ala Ala
    1805                1810                1815

Gln Leu  Ala Ala Pro Gly Ala  Ala Thr Ala Phe Val  Gly Ala Gly
    1820                1825                1830

Leu Ala  Gly Ala Ala Ile Gly  Ser Val Gly Leu Gly  Lys Val Leu
    1835                1840                1845

Val Asp  Ile Leu Ala Gly Tyr  Gly Ala Gly Val Ala  Gly Ala Leu
    1850                1855                1860

Val Ala  Phe Lys Ile Met Ser  Gly Glu Val Pro Ser  Thr Glu Asp
    1865                1870                1875

Leu Val  Asn Leu Leu Pro Ala  Ile Leu Ser Pro Gly  Ala Leu Val
    1880                1885                1890

Val Gly  Val Val Cys Ala Ala  Ile Leu Arg Arg His  Val Gly Pro
    1895                1900                1905

Gly Glu  Gly Ala Val Gln Trp  Met Asn Arg Leu Ile  Ala Phe Ala
    1910                1915                1920

Ser Arg  Gly Asn His Val Ser  Pro Thr His Tyr Val  Pro Glu Ser
    1925                1930                1935

Asp Ala  Ala Ala Arg Val Thr  Ala Ile Leu Ser Ser  Leu Thr Val
    1940                1945                1950

Thr Gln  Leu Leu Arg Arg Leu  His Gln Trp Ile Ser  Ser Glu Cys
    1955                1960                1965

Thr Thr  Pro Cys Ser Gly Ser  Trp Leu Arg Asp Ile  Trp Asp Trp
    1970                1975                1980

Ile Cys  Glu Val Leu Ser Asp  Phe Lys Thr Trp Leu  Lys Ala Lys
    1985                1990                1995

Leu Met  Pro Gln Leu Pro Gly  Ile Pro Phe Val Ser  Cys Gln Arg
    2000                2005                2010

Gly Tyr  Arg Gly Val Trp Arg  Gly Asp Gly Ile Met  His Thr Arg
    2015                2020                2025

Cys His  Cys Gly Ala Glu Ile  Thr Gly His Val Lys  Asn Gly Thr
    2030                2035                2040

Met Arg  Ile Val Gly Pro Arg  Thr Cys Arg Asn Met  Trp Ser Gly
    2045                2050                2055

Thr Phe  Pro Ile Asn Ala Tyr  Thr Thr Gly Pro Cys  Thr Pro Leu
    2060                2065                2070
```

-continued

```
Pro Ala  Pro Asn Tyr Lys Phe  Ala Leu Trp Arg Val  Ser Ala Glu
    2075                 2080                 2085

Glu Tyr  Val Glu Ile Arg Arg  Val Gly Asp Phe His  Tyr Val Ser
    2090                 2095                 2100

Gly Met  Thr Thr Asp Asn Leu  Lys Cys Pro Cys Gln  Ile Pro Ser
    2105                 2110                 2115

Pro Glu  Phe Phe Thr Glu Leu  Asp Gly Val Arg Leu  His Arg Phe
    2120                 2125                 2130

Ala Pro  Pro Cys Lys Pro Leu  Leu Arg Glu Glu Val  Ser Phe Arg
    2135                 2140                 2145

Val Gly  Leu His Glu Tyr Pro  Val Gly Ser Gln Leu  Pro Cys Glu
    2150                 2155                 2160

Pro Glu  Pro Asp Val Ala Val  Leu Thr Ser Met Leu  Thr Asp Pro
    2165                 2170                 2175

Ser His  Ile Thr Ala Glu Ala  Ala Gly Arg Arg Leu  Ala Arg Gly
    2180                 2185                 2190

Ser Pro  Pro Ser Met Ala Ser  Ser Ser Ala Ser Gln  Leu Ser Ala
    2195                 2200                 2205

Pro Ser  Leu Lys Ala Thr Cys  Thr Ala Asn His Asp  Ser Pro Asp
    2210                 2215                 2220

Ala Glu  Leu Ile Glu Ala Asn  Leu Leu Trp Arg Gln  Glu Met Gly
    2225                 2230                 2235

Gly Asn  Ile Thr Arg Val Glu  Ser Glu Asn Lys Val  Val Ile Leu
    2240                 2245                 2250

Asp Ser  Phe Asp Pro Leu Val  Ala Glu Glu Asp Glu  Arg Glu Val
    2255                 2260                 2265

Ser Val  Pro Ala Glu Ile Leu  Arg Lys Ser Arg Arg  Phe Ala Arg
    2270                 2275                 2280

Ala Leu  Pro Val Trp Ala Arg  Pro Asp Tyr Asn Pro  Pro Leu Val
    2285                 2290                 2295

Glu Thr  Trp Lys Lys Pro Asp  Tyr Glu Pro Pro Val  Val His Gly
    2300                 2305                 2310

Cys Pro  Leu Pro Pro Pro Arg  Ser Pro Pro Val Pro  Pro Pro Arg
    2315                 2320                 2325

Lys Lys  Arg Thr Val Val Leu  Thr Glu Ser Thr Leu  Ser Thr Ala
    2330                 2335                 2340

Leu Ala  Glu Leu Ala Thr Lys  Ser Phe Gly Ser Ser  Ser Thr Ser
    2345                 2350                 2355

Gly Ile  Thr Gly Asp Asn Thr  Thr Thr Ser Ser Glu  Pro Ala Pro
    2360                 2365                 2370

Ser Gly  Cys Pro Pro Asp Ser  Asp Val Glu Ser Tyr  Ser Ser Met
    2375                 2380                 2385

Pro Pro  Leu Glu Gly Glu Pro  Gly Asp Pro Asp Leu  Ser Asp Gly
    2390                 2395                 2400

Ser Trp  Ser Thr Val Ser Ser  Gly Ala Asp Thr Glu  Asp Val Val
    2405                 2410                 2415

Cys Cys  Ser Met Ser Tyr Ser  Trp Thr Gly Ala Leu  Val Thr Pro
    2420                 2425                 2430

Cys Ala  Ala Glu Glu Gln Lys  Leu Pro Ile Asn Ala  Leu Ser Asn
    2435                 2440                 2445

Ser Leu  Leu Arg His His Asn  Leu Val Tyr Ser Thr  Thr Ser Arg
    2450                 2455                 2460
```

-continued

```
Ser Ala  Cys Gln Arg Gln Lys  Lys Val Thr Phe Asp  Arg Leu Gln
    2465                 2470                 2475

Val Leu  Asp Ser His Tyr Gln  Asp Val Leu Lys Glu  Val Lys Ala
    2480                 2485                 2490

Ala Ala  Ser Lys Val Lys Ala  Asn Leu Leu Ser Val  Glu Glu Ala
    2495                 2500                 2505

Cys Ser  Leu Thr Pro Pro His  Ser Ala Lys Ser Lys  Phe Gly Tyr
    2510                 2515                 2520

Gly Ala  Lys Asp Val Arg Cys  His Ala Arg Lys Ala  Val Ala His
    2525                 2530                 2535

Ile Asn  Ser Val Trp Lys Asp  Leu Leu Glu Asp Ser  Val Thr Pro
    2540                 2545                 2550

Ile Asp  Thr Thr Ile Met Ala  Lys Asn Glu Val Phe  Cys Val Gln
    2555                 2560                 2565

Pro Glu  Lys Gly Gly Arg Lys  Pro Ala Arg Leu Ile  Val Phe Pro
    2570                 2575                 2580

Asp Leu  Gly Val Arg Val Cys  Glu Lys Met Ala Leu  Tyr Asp Val
    2585                 2590                 2595

Val Ser  Lys Leu Pro Leu Ala  Val Met Gly Ser Ser  Tyr Gly Phe
    2600                 2605                 2610

Gln Tyr  Ser Pro Gly Gln Arg  Val Glu Phe Leu Val  Gln Ala Trp
    2615                 2620                 2625

Lys Ser  Lys Lys Thr Pro Met  Gly Phe Ser Tyr Asp  Thr Arg Cys
    2630                 2635                 2640

Phe Asp  Ser Thr Val Thr Glu  Ser Asp Ile Arg Thr  Glu Glu Ala
    2645                 2650                 2655

Ile Tyr  Gln Cys Cys Asp Leu  Asp Pro Gln Ala Arg  Val Ala Ile
    2660                 2665                 2670

Lys Ser  Leu Thr Glu Arg Leu  Tyr Val Gly Gly Pro  Leu Thr Asn
    2675                 2680                 2685

Ser Arg  Gly Glu Asn Cys Gly  Tyr Arg Arg Cys Arg  Ala Ser Gly
    2690                 2695                 2700

Val Leu  Thr Thr Ser Cys Gly  Asn Thr Leu Thr Cys  Tyr Ile Lys
    2705                 2710                 2715

Ala Arg  Ala Ala Cys Arg Ala  Ala Gly Leu Gln Asp  Cys Thr Met
    2720                 2725                 2730

Leu Val  Cys Gly Asp Asp Leu  Val Val Ile Cys Glu  Ser Ala Gly
    2735                 2740                 2745

Val Gln  Glu Asp Ala Ala Ser  Leu Arg Ala Phe Thr  Glu Ala Met
    2750                 2755                 2760

Thr Arg  Tyr Ser Ala Pro Pro  Gly Asp Pro Pro Gln  Pro Glu Tyr
    2765                 2770                 2775

Asp Leu  Glu Leu Ile Thr Ser  Cys Ser Ser Asn Val  Ser Val Ala
    2780                 2785                 2790

His Asp  Gly Ala Gly Lys Arg  Val Tyr Tyr Leu Thr  Arg Asp Pro
    2795                 2800                 2805

Thr Thr  Pro Leu Ala Arg Ala  Ala Trp Glu Thr Ala  Arg His Thr
    2810                 2815                 2820

Pro Val  Asn Ser Trp Leu Gly  Asn Ile Ile Met Phe  Ala Pro Thr
    2825                 2830                 2835

Leu Trp  Ala Arg Met Ile Leu  Met Thr His Phe Phe  Ser Val Leu
    2840                 2845                 2850

Ile Ala  Arg Asp Gln Leu Glu  Gln Ala Leu Asn Cys  Glu Ile Tyr
```

-continued

```
    2855                2860                2865

Gly Ala  Cys Tyr Ser Ile Glu  Pro Leu Asp Leu Pro  Pro Ile Ile
    2870                2875                2880

Gln Arg  Leu His Gly Leu Ser  Ala Phe Ser Leu His  Ser Tyr Ser
    2885                2890                2895

Pro Gly  Glu Ile Asn Arg Val  Ala Ala Cys Leu Arg  Lys Leu Gly
    2900                2905                2910

Val Pro  Pro Leu Arg Ala Trp  Arg His Arg Ala Arg  Ser Val Arg
    2915                2920                2925

Ala Arg  Leu Leu Ser Arg Gly  Gly Arg Ala Ala Ile  Cys Gly Lys
    2930                2935                2940

Tyr Leu  Phe Asn Trp Ala Val  Arg Thr Lys Leu Lys  Leu Thr Pro
    2945                2950                2955

Ile Ala  Ala Ala Gly Arg Leu  Asp Leu Ser Gly Trp  Phe Thr Ala
    2960                2965                2970

Gly Tyr  Ser Gly Gly Asp Ile  Tyr His Ser Val Ser  His Ala Arg
    2975                2980                2985

Pro Arg  Trp Phe Trp Phe Cys  Leu Leu Leu Leu Ala  Ala Gly Val
    2990                2995                3000

Gly Ile  Tyr Leu Leu Pro Asn  Arg
    3005                3010


<210> SEQ ID NO 21
<211> LENGTH: 232
<212> TYPE: PRT
<213> ORGANISM: artificial
<220> FEATURE:
<223> OTHER INFORMATION: Amino acid sequence encoded by the heterologous
      polynucleotide

<400> SEQUENCE: 21

Met Arg Pro Met Glu Pro Val Asp Pro Arg Leu Glu Pro Trp Lys His
1               5                   10                  15

Pro Gly Ser Gln Pro Lys Thr Ala Cys Thr Asn Cys Tyr Cys Lys Lys
            20                  25                  30

Cys Cys Phe His Cys Gln Val Cys Phe Ile Thr Lys Ala Leu Gly Ile
        35                  40                  45

Ser Tyr Gly Arg Lys Lys Arg Arg Gln Arg Arg Arg Pro Pro Gln Gly
    50                  55                  60

Ser Gln Thr His Gln Val Ser Leu Ser Lys Gln Pro Thr Ser Gln Ser
65                  70                  75                  80

Arg Gly Asp Pro Thr Gly Pro Lys Glu Glu Phe Asp Leu Leu Lys Leu
                85                  90                  95

Ala Gly Asp Val Glu Ser Asn Pro Gly Pro Gly Ser Met Ala Lys Leu
            100                 105                 110

Thr Ser Ala Val Pro Val Leu Thr Ala Arg Asp Val Ala Gly Ala Val
        115                 120                 125

Glu Phe Trp Thr Asp Arg Leu Gly Phe Ser Arg Asp Phe Val Glu Asp
    130                 135                 140

Asp Phe Ala Gly Val Val Arg Asp Asp Val Thr Leu Phe Ile Ser Ala
145                 150                 155                 160

Val Gln Asp Gln Val Val Pro Asp Asn Thr Leu Ala Trp Val Trp Val
                165                 170                 175

Arg Gly Leu Asp Glu Leu Tyr Ala Glu Trp Ser Glu Val Val Ser Thr
            180                 185                 190
```

-continued

```
Asn Phe Arg Asp Ala Ser Gly Pro Ala Met Thr Glu Ile Gly Glu Gln
        195                 200                 205

Pro Trp Gly Arg Glu Phe Ala Leu Arg Asp Pro Ala Gly Asn Cys Val
    210                 215                 220

His Phe Val Ala Glu Glu Gln Asp
225                 230


<210> SEQ ID NO 22
<211> LENGTH: 32
<212> TYPE: DNA
<213> ORGANISM: artificial
<220> FEATURE:
<223> OTHER INFORMATION: Primer

<400> SEQUENCE: 22

ggcctcttaa ggttattttc caccatattg cc                                   32


<210> SEQ ID NO 23
<211> LENGTH: 37
<212> TYPE: DNA
<213> ORGANISM: artificial
<220> FEATURE:
<223> OTHER INFORMATION: Primer

<400> SEQUENCE: 23

tccccgcgga aggcctcata ttatcatcgt gtttttc                              37


<210> SEQ ID NO 24
<211> LENGTH: 51
<212> TYPE: DNA
<213> ORGANISM: artificial
<220> FEATURE:
<223> OTHER INFORMATION: Primer

<400> SEQUENCE: 24

aattcgacct tcttaagctt gcgggagacg tcgagtccaa ccctgggccc g              51


<210> SEQ ID NO 25
<211> LENGTH: 51
<212> TYPE: DNA
<213> ORGANISM: artificial
<220> FEATURE:
<223> OTHER INFORMATION: Primer

<400> SEQUENCE: 25

gatccgggcc cagggttgga ctcgacgtct cccgcaagct taagaaggtc g              51


<210> SEQ ID NO 26
<211> LENGTH: 40
<212> TYPE: DNA
<213> ORGANISM: artificial
<220> FEATURE:
<223> OTHER INFORMATION: Primer

<400> SEQUENCE: 26

ccgctcgagg cctggatcca tggccaagtt gaccagtgcc                           40


<210> SEQ ID NO 27
<211> LENGTH: 33
<212> TYPE: DNA
<213> ORGANISM: artificial
<220> FEATURE:
<223> OTHER INFORMATION: Primer

<400> SEQUENCE: 27
```

-continued

```
ggcctcttaa gtcagtcctg ctcctcggcc acg                            33


<210> SEQ ID NO 28
<211> LENGTH: 29
<212> TYPE: DNA
<213> ORGANISM: artificial
<220> FEATURE:
<223> OTHER INFORMATION: Primer

<400> SEQUENCE: 28

gaaggcctat ggagccagta gatcctaga                                 29


<210> SEQ ID NO 29
<211> LENGTH: 30
<212> TYPE: DNA
<213> ORGANISM: artificial
<220> FEATURE:
<223> OTHER INFORMATION: Primer

<400> SEQUENCE: 29

cggaattctt ccttcgggcc tgtcgggtcc                                30


<210> SEQ ID NO 30
<211> LENGTH: 15
<212> TYPE: PRT
<213> ORGANISM: artificial
<220> FEATURE:
<223> OTHER INFORMATION: Fifteen amino acids of FMDV 2A

<400> SEQUENCE: 30

Phe Asp Leu Leu Lys Leu Ala Gly Asp Val Glu Ser Asn Pro Gly
1               5                   10                  15


<210> SEQ ID NO 31
<211> LENGTH: 14
<212> TYPE: PRT
<213> ORGANISM: artificial
<220> FEATURE:
<223> OTHER INFORMATION: NS3 recognition site

<400> SEQUENCE: 31

Gly Ala Asp Thr Glu Asp Val Val Cys Cys Ser Met Ser Tyr
1               5                   10


<210> SEQ ID NO 32
<211> LENGTH: 32
<212> TYPE: PRT
<213> ORGANISM: artificial
<220> FEATURE:
<223> OTHER INFORMATION: Amino acid sequence

<400> SEQUENCE: 32

Thr Leu Arg Pro Leu Lys Val Ile Phe His His Ile Ala Val Phe Trp
1               5                   10                  15

Gln Cys Glu Gly Pro Glu Thr Trp Pro Cys Leu Leu Asp Glu His Ser
            20                  25                  30


<210> SEQ ID NO 33
<211> LENGTH: 102
<212> TYPE: PRT
<213> ORGANISM: artificial
<220> FEATURE:
<223> OTHER INFORMATION: Amino acid sequence

<400> SEQUENCE: 33

Gly Ser Phe Pro Ser Arg Gln Arg Asn Ala Arg Ser Val Glu Cys Arg
```

-continued

```
1               5                   10                  15

Glu Gly Ser Ser Ser Ser Gly Ser Phe Leu Lys Thr Asn Asn Val Cys
            20                  25                  30

Ser Asp Pro Leu Gln Ala Ala Glu Pro Pro Thr Trp Arg Gln Val Pro
        35                  40                  45

Leu Arg Pro Lys Ala Thr Cys Ile Arg Tyr Thr Cys Lys Gly Gly Thr
    50                  55                  60

Thr Pro Val Pro Arg Cys Glu Leu Asp Ser Cys Gly Lys Ser Gln Met
65                  70                  75                  80

Ala Leu Leu Lys Arg Ile Gln Gln Gly Ala Glu Gly Cys Pro Glu Gly
                85                  90                  95

Thr Pro Leu Tyr Gly Ile
            100
```

<210> SEQ ID NO 34
<211> LENGTH: 30
<212> TYPE: PRT
<213> ORGANISM: artificial
<220> FEATURE:
<223> OTHER INFORMATION: Amino acid sequence

<400> SEQUENCE: 34

```
Ser Gly Ala Ser Val His Met Leu Tyr Val Cys Leu Val Glu Val Lys
1               5                   10                  15

Lys Arg Leu Gly Pro Pro Asn His Gly Asp Val Val Phe Leu
            20                  25                  30
```

<210> SEQ ID NO 35
<211> LENGTH: 341
<212> TYPE: DNA
<213> ORGANISM: ARTIFICIAL
<220> FEATURE:
<223> OTHER INFORMATION: nucleotide sequence of 5' NTR

<400> SEQUENCE: 35

```
gccagccccc tgatgggggc gacactccac catgaatcac tcccctgtga ggaactactg     60

tcttcacgca gaaagcgtct agccatggcg ttagtatgag tgtcgtgcag cctccaggac    120

ccccccctccc gggagagcca tagtggtctg cggaaccggt gagtacaccg gaattgccag    180

gacgaccggg tcctttcttg gataaacccg ctcaatgcct ggagatttgg gcgtgccccc    240

gcaagactgc tagccgagta gtgttgggtc gcgaaaggcc ttgtggtact gcctgatagg    300

gtgcttgcga gtgccccggg aggtctcgta gaccgtgcac c                        341
```

<210> SEQ ID NO 36
<211> LENGTH: 1158
<212> TYPE: DNA
<213> ORGANISM: ARTIFICIAL
<220> FEATURE:
<223> OTHER INFORMATION: nucleotide sequence of delta Ctat2ANeo

<400> SEQUENCE: 36

```
atgagcacga atcctaaacc tcaaagaaaa accaaagttc ctatggagcc agtagatcct     60

agactagagc cctggaagca tccaggaagt cagcctaaaa ctgcttgtac caattgctat    120

tgtaaaaagt gttgctttca ttgccaagtt tgtttcataa caaaagcctt aggcatctcc    180

tatggcagga agaagcggag acagcgacga agacctcctc aaggcagtca gactcatcaa    240

gtttctctat caaagcaacc cacctcccaa tcccgagggg acccgacagg cccgaaggaa    300

gaattcgacc ttcttaagct tgcgggagac gtcgagtcca accctgggcc cggatctgtt    360
```

-continued aacatgattg aacaagatgg attgcacgca ggttctccgg ccgcttgggt ggagaggcta 420
ttcggctatg actgggcaca acagacaatc ggctgctctg atgccgccgt gttccggctg 480
tcagcgcagg ggcgcccggt tctttttgtc aagaccgacc tgtccggtgc cctgaatgaa 540
ctgcaggacg aggcagcgcg gctatcgtgg ctggccacga cgggcgttcc ttgcgcagct 600
gtgctcgacg ttgtcactga agcgggaagg gactggctgc tattgggcga agtgccgggg 660
caggatctcc tgtcatctca ccttgctcct gccgagaaag tatccatcat ggctgatgca 720
atgcggcggc tgcatacgct tgatccggct acctgcccat tcgaccacca agcgaaacat 780
cgcatcgagc gagcacgtac tcggatggaa gccggtcttg tcgatcagga tgatctggac 840
gaagagcatc aggggctcgc gccagccgaa ctgttcgcca ggctcaaggc gcgcatgccc 900
gacggcgagg atctcgtcgt gacccatggc gatgcctgct tgccgaatat catggtggaa 960
aatggccgct tttctggatt catcgactgt ggccggctgg gtgtggcgga ccgctatcag 1020
gacatagcgt tggctacccg tgatattgct gaagagcttg gcggcgaatg ggctgaccgc 1080
ttcctcgtgc tttacggtat cgccgctccc gattcgcagc gcatcgcctt ctatcgcctt 1140
cttgacgagt tcttctga 1158

<210> SEQ ID NO 37
<211> LENGTH: 1116
<212> TYPE: DNA
<213> ORGANISM: ARTIFICIAL
<220> FEATURE:
<223> OTHER INFORMATION: nucleotide sequence of tat2ANeo

<400> SEQUENCE: 37
atggagccag tagatcctag actagagccc tggaagcatc caggaagtca gcctaaaact 60
gcttgtacca attgctattg taaaaagtgt tgctttcatt gccaagtttg tttcataaca 120
aaagccttag gcatctccta tggcaggaag aagcggagac agcgacgaag acctcctcaa 180
ggcagtcaga ctcatcaagt ttctctatca aagcaaccca cctcccaatc ccgaggggac 240
ccgacaggcc cgaaggaaga attcgacctt cttaagcttg cgggagacgt cgagtccaac 300
cctgggcccg gatctgttaa catgattgaa caagatggat tgcacgcagg ttctccggcc 360
gcttgggtgg agaggctatt cggctatgac tgggcacaac agacaatcgg ctgctctgat 420
gccgccgtgt tccggctgtc agcgcagggg cgcccggttc tttttgtcaa gaccgacctg 480
tccggtgccc tgaatgaact gcaggacgag gcagcgcggc tatcgtggct ggccacgacg 540
ggcgttcctt gcgcagctgt gctcgacgtt gtcactgaag cgggaaggga ctggctgcta 600
ttgggcgaag tgccggggca ggatctcctg tcatctcacc ttgctcctgc cgagaaagta 660
tccatcatgg ctgatgcaat gcggcggctg catacgcttg atccggctac ctgcccattc 720
gaccaccaag cgaaacatcg catcgagcga gcacgtactc ggatggaagc cggtcttgtc 780
gatcaggatg atctggacga agagcatcag gggctcgcgc cagccgaact gttcgccagg 840
ctcaaggcgc gcatgcccga cggcgaggat ctcgtcgtga cccatggcga tgcctgcttg 900
ccgaatatca tggtggaaaa tggccgcttt tctggattca tcgactgtgg ccggctgggt 960
gtggcggacc gctatcagga catagcgttg gctacccgtg atattgctga agagcttggc 1020
ggcgaatggg ctgaccgctt cctcgtgctt tacggtatcg ccgctcccga ttcgcagcgc 1080
atcgccttct atcgccttct tgacgagttc ttctga 1116

<210> SEQ ID NO 38

-continued

<211> LENGTH: 610
<212> TYPE: DNA
<213> ORGANISM: ARTIFICIAL
<220> FEATURE:
<223> OTHER INFORMATION: nucleotide sequence of EMCV IRES

<400> SEQUENCE: 38
agaccacaac ggtttccctc tagcgggatc aattccgccc ctctccctcc ccccccccta 60
acgttactgg ccgaagccgc ttggaataag gccggtgtgc gtttgtctat atgttatttt 120
ccaccatatt gccgtctttt ggcaatgtga gggcccggaaa cctggccctg tcttcttgac 180
gagcattcct aggggtcttt cccctctcgc caaaggaatg caaggtctgt tgaatgtcgt 240
gaaggaagca gttcctctgg aagcttcttg aagacaaaca acgtctgtag cgaccctttg 300
caggcagcgg aacccccccac ctggcgacag gtgcctctgc ggccaaaagc cacgtgtata 360
agatacacct gcaaaggcgg cacaacccca gtgccacgtt gtgagttgga tagttgtgga 420
aagagtcaaa tggctctcct caagcgtatt caacaagggg ctgaaggatg cccagaaggt 480
accccattgt atgggatctg atctggggcc tcggtgcaca tgctttacat gtgtttagtc 540
gaggttaaaa aacgtctagg ccccccgaac cacggggacg tggttttcct ttgaaaaaca 600
cgataatacc 610

<210> SEQ ID NO 39
<211> LENGTH: 9275
<212> TYPE: DNA
<213> ORGANISM: ARTIFICIAL
<220> FEATURE:
<223> OTHER INFORMATION: nucleotide sequence encoding hepatitis C virus polyprotein derived from HCV-N

<400> SEQUENCE: 39
atgagcacga atcctaaacc tcaaagaaaa accaaacgta acaccaaccg ccgcccacag 60
gacgtcaagt tcccgggcgg tggtcagatc gttggtggag tttacctgtt gccgcgcagg 120
ggccccaggt tgggtgtgcg cgcgatcagg aagacttccg agcggtcgca accccgtgga 180
aggcgacagc ctatccccaa ggctcgccgg cccgagggca gggcctgggc tcagcccggg 240
tatccttggc ccctctatgg caatgagggc atggggtggg caggatggct cctgtcaccc 300
cgcggctccc ggcctagttg gggccccacg gacccccggc gtaggtcgcg taatttgggt 360
aaggtcatcg ataccctcac atgcggcctc gccgacctca tggggtacat tccgctcgtc 420
ggcggccccc taggggggcgc tgccagggcc ttggcacatg gtgtccgggt tctggaggac 480
ggcgtgaact atgcaacagg gaacctgccc ggttgctctt tttctatctt cctcttggct 540
ctgctgtcct gtctgaccgt accagcttcc gctcatgaag tgcgtaacgc gtccggggta 600
taccatgtca cgaacgactg ctccaactca agcattgtgt ttgaggcggc ggacttgatc 660
atgcatactc ccgggtgcgt gccctgcgtt cgggagggta actcctcccg ctgctgggta 720
gcgctcactc ccacgctcgc ggccaggaat gctaccatcc ccactacgac aatacgacac 780
cacgtcgatt tgctcgttgg ggcggctgct ctctgctccg ctatgtacgt gggggacctc 840
tgcggatctg ttttcctcgt ctctcagctg ttcaccttct cgccccgccg gcatgcgaca 900
ttgcaggact gcaattgttc gatctacccc ggccacgcgt caggtcaccg catggcctgg 960
gacatgatga tgaactggtc acctacaaca gccctcgtag tgtcgcagtt actccggatc 1020
ccacaagccg tcatcgacat ggtggcgggg gcccactggg gagtcctggc gggccttgcc 1080
tactattcca tggcggggaa ctgggctaag gttttgattg tgatgctact tttgccggc 1140

-continued

```
gttgacgggc acaccctcac aacggggggg cacgctgccc gcctcaccag cgggttcgcg   1200
ggcctcttta cacctgggcc gtctcagaga atccagctta taaacaccaa tggcagttgg   1260
cacatcaaca ggactgccct gaactgcaat gactccctcc agactgggtt tcttgccgcg   1320
ctgttctacg cacataggtt caactcgtcc ggatgcccgg agcgcatggc cagctgccgc   1380
tccattgaca agttcgacca gggatggggt cctatcactt atgctgagcc tacaaaagac   1440
ccggaccaga ggccttattg ctggcactac ccacctcaac aatgtggtat cgtacctgcg   1500
tcgcaggtgt gtggtccagt gtattgcttc accccaagtc ctgttgtcgt ggggacaacc   1560
gatcgtctcg gcaaccctac gtacagctgg ggggagaacg atactgacgt gctgctcctt   1620
aacaacacgc ggccgccgca aggcaactgg ttcggctgta catggatgaa tagcactggg   1680
ttcaccaaga cgtgcggggc ccccccgtgt aacatcgggg gggtcggcaa taacaccttg   1740
acctgcccca cggactgctt ccggaagcac cccgaggcca cgtactcaaa atgtggctcg   1800
gggccttggt tgacacctag gtgcatggtt gactacccat acaggctctg gcactacccc   1860
tgcactgtca acttctccat ctttaaggtt aggatgtatg tgggggggcgt ggagcacagg   1920
cttaatgctg catgcaactg gacccgagga gagcgttgca acttggacga cagggacaga   1980
tcggagctca gcccgctgct gctctctaca acagagtggc aggttctgcc ctgctctttc   2040
accaccctac cggctctgtc cactggcttg atccacctcc atcagaacat cgtggacgtg   2100
caatacctgt acggtatagg gtcagcggtt gtctcctttg caatcaaatg ggagtatgtc   2160
gtgttgcttt tccttctcct ggcggacgcg cgcgtctgtg cctgcttgtg gatgatgctg   2220
ctgatagccc aggccgaggc cgccttagag aacctggtgg ccctcaatgc agcgtccgtt   2280
gccggagcgc acggcatcct ctccttcctc gtgttcttct gtgccgcttg gtacatcaag   2340
ggcaggctgg tccctggggc ggcatatgct ttctatggcg catggccgct gctcctgctc   2400
ctcttgacat taccaccacg agcttacgcc atggaccggg agatggctgc atcgtgcgga   2460
ggcgcggttt ttgtgggtct ggcattattg accttgtcgc catattacaa ggtgttcctc   2520
gctaggctcc tatggtggtt acaatatctt atcaccagag ctgaggcgca cttgcatgtg   2580
tgggttcccc ccctcaacgt ccggggaggc cgcgatgcca tcatcctcct cacgtgtgca   2640
gtccacccag agctaatctt tgatatcacc aaacttctga ttgccatact cggaccgctc   2700
atggtgctcc aagctggcat aactagggtg ccgtacttcg tacgcgctca agggctcatt   2760
cgtgcatgca tgttagtgcg gaaagtcgct gggggtcatt atgtccaaat ggccttcatg   2820
agactgggcg cgctgacggg cacgtacgtc tataatcacc tcaccccact gcgggattgg   2880
gcccacgccg gcctacggga ccttgcggta gcagtggagc ctgtcgtctt ctctgacatg   2940
gagaccaaga tcatcacctg gggggcggac accgcggcgt gtggggacat catcctgggc   3000
ctacctgtct ccgcccgaag ggaagggag atactcctgg ggccggccga tagtctagta   3060
gggcaggggt ggcgactcct tgcgcccatc acggcctact cccaacagac ccggggccta   3120
cttggttgca tcatcacgag tctcacaggc cgggacaaga accaggtcga gggggaggtt   3180
caagtggtct ccaccgcaac acaatctttc ctggcgacct gcgtcaacgg cgtatgttgg   3240
actgtctacc atggtgctgg ctcaaagact ctagccggcc caaaaggccc aatcgcccag   3300
atgtacacta atgtagacca ggatctcgtc ggctggccgg cgccccccgg ggcgcgttcc   3360
ctgacaccat gcacctgtgg cagctcggac ctttacttgg ttacgagaca tgcagatgtt   3420
attccggtgc gccggcgggg cgacaataga gggagcttgc tctcccccag gcctgtctcc   3480
tacttgaagg gctcttcggg tggcccactg ctctgccctt cggggcacgc tgtgggcgtc   3540
```

-continued

```
ttccgggccg ctgtatgcac ccggggggtt gcaaaggcgg tggattttgt ccccgttgag   3600
tccatggaaa ctactatgcg gtccccggtc ttcacagaca actcatctcc cccggccgta   3660
ccgcaaacat tccaagtggc ccatctacac gctcccactg gcagcggcaa gagcactaga   3720
gtgccggccg catatgcggc ccaagggtac aaggtgcttg tcctgaaccc gtctgttgcc   3780
gctaccttag gttttggggc gtatatgtct aaagcacatg gtaccgaccc taacatcagg   3840
actggggtaa ggaccattac cacgggcgcc cccattacgt actccaccta tggcaagttc   3900
cttgccgacg gtggttgctc cgggggcgct tacgacatca taatgtgcga tgagtgccac   3960
tcaactgact caactactat cttgggcatc ggcacagtcc tggaccaagc ggagacggct   4020
ggagcgcggc ttgtcgtgct cgccaccgct acgcctccag gatcggtcac cgtgccacac   4080
cccaatatcg aggaggtggc cctgtcgaac actggagaga tccccttcta cggcaaagcc   4140
atccccatcg aagccatcaa ggggggaagg cacctcattt tctgtcactc caagaagaag   4200
tgcgacgagc ttgccgcaaa gctgtcaggc ctcggaatca atgctgtagc gtattaccgg   4260
ggtcttgatg tgtccgtcat accgaccagc ggagacgtcg ttgtcgtggc aacagacgct   4320
ctaatgacgg gctataccgg tgactttgat tcagtgatcg actgtaatac gtgtgtcacc   4380
cagacagtcg acttcagctt ggaccccacc ttcaccattg agacgacgac cgtgccccaa   4440
gacgcagtgt cgcgctcgca gcggcggggt aggactggca ggggcagggg gggcatatac   4500
aggtttgtaa ctccggggga acggccctcg ggcatgttcg attcctcggt cctgtgcgag   4560
tgctatgacg cgggctgtgc ttggtacgag ctcacccccg ctgagacctc ggttaggttg   4620
cgggcttacc taaatacacc aggattgccc gtttgccagg accatctgga gttctgggag   4680
agcgtcttca caggcctcac ccatatagat gcccacttcc tgtcccagac caagcaggca   4740
ggagataact tcccctacct ggtggcatac caagccacag tgtgcgccag ggctcaggcc   4800
ccacctccat cgtgggatca aatgtggaag tgtctcatac ggctaaaacc cacgctgcac   4860
gggccaacgc ccctgctgta taggctaggg gccgtccaaa atgaggtcac cctcacacac   4920
cccataacca aatacatcat ggcatgcatg tcggccgacc tggaagtcgt caccagcacc   4980
tgggtgctgg taggcggagt cctcgcagct ctggccgcat attgcctgac aacaggcagt   5040
gtggttatcg tgggtaggat catcttgtcc gggaggccgg ctgtcgttcc cgatagggaa   5100
gtcctctacc gggagttcga tgaaatggaa gaatgcgcct cgcacctccc ttacatcgaa   5160
cagggaatgc aactcgccga gcaattcaag cagaaggcgc tcgggttgtt gcaaacagcc   5220
accaagcagg cggaggctgc cgctcccgtg gtggagtcca agtggcgagc tttggagacc   5280
ttctgggcaa agcacaagtg gaatttcatc agcgggatac agtacttagc gggcttatcc   5340
accctgcctg ggaaccccgc gatagcatca ctgatggcat tcacagcctc tatcaccagc   5400
ccgctcacca cccagaacac cctcctgttt aacatcttgg gggggtgggt agccgcccaa   5460
ctcgctcccc ccagcgctgc ttcggctttc gtgggcgctg gtatcgctgg tgcggctgtt   5520
ggcagcatag gtcttgggaa ggtgctagtg gacattctgg cgggctatgg ggcagggtg    5580
gctggcgcgc tcgtggcctt caaggtcatg agcggcgagg cgccctctgc cgaggacctg   5640
atcaatttgc tccctgccat cctctctcct ggtgccctgg tcgtcggagt cgtgtgtgca   5700
gcaatactgc gtcggcatgt gggcccggga gagggggccg tgcagtggat gaaccggctg   5760
atagcgttcg cttcgcgggg taaccatgtc tcccccacgc actatgtgcc tgagagcgac   5820
gccgcagcgc gtgtcactca ggtcctctcc agccttacca tcacccagct gctgaagagg   5880
```

-continued ctccaccagt ggattaatga ggactgttct acgccgtgtt ccggctcgtg gctgagggat 5940
gtttgggact gggtgtgcac ggtgttgagt gacttcaaga cctggctcca gtccaagctc 6000
ctgccgcggt taccgggtgt ccctttcctc tcatgccaac gtgggtacaa gggagtctgg 6060
cggggggacg gcatcatgca caccacctgc ccatgtggag cacagatcgc cggacatgtc 6120
aaaaacggtt ccatgaggat catcgggccg aaaacctgca gcaacacgtg gcatggaaca 6180
ttccccatca acgcgtacac cacgggcccc tgcacgcctt ccccggcgcc aaactattcc 6240
aaggcgctgt ggcgggtggc tgctgaggag tacgtggagg tcacgcgggt gggggatttc 6300
cactacgtga cgggcataac caccgacaac gtaaagtgcc catgtcaggt tccagctcct 6360
gagtttttca cggaggtgga tggggtgcgg ttgcacaggt acgccccggt gtgcaaacct 6420
ctcttacggg atgaggttgt attccaggtc gggctcaatc aatacctggt tgggtcacag 6480
ctcccatgcg agcccgaacc ggacgtagca gtgctcactt ccatgctcac cgacccctcc 6540
cacattacag cagaggcggc taagcgtagg ttggccaggg ggtctccccc ctccttggcc 6600
agctcttcag ctagccagct gtctgcgccc tccttgaggg cgacatgcac tacccattct 6660
tcctataatc ttgactctcc ggacgtcgac ctcattgcgg ccaacctcct gtggcggcag 6720
gagatgggcg gaaacatcac ccgcgtggag tcggagaaca aggtggtagt cctagactct 6780
ttcgagccgc ttcgagcgga gggggatgag aatgaaatat ccattgcggc ggagatcctg 6840
cggaagtcca agaagttccc cgcggcgata cccatatggg cacggccgga ttacaatcct 6900
ccattgttag agtcttggaa gaacccggac tacgtccctc cggtggtaca cgggtgccca 6960
ttgccacctg tcaaggcccc tccaatacca cctccacgga gaaaaaggac ggttgtcctg 7020
acggactcca ccgtgtcttc tgttttggcg gagctcgcta ccaaaacctt cggcagctcc 7080
gaattgtcgg ccgccgacag cggcacggcg accgcccctc ctgaccagac ctccgacaac 7140
ggcggcaaag actccgacgc tgagtcatgc tcctctatgc cccccttga gggggagccg 7200
ggggaccccg atctcagcga cggtcttggg tctaccgtga gcgaggaggc tggtgagagc 7260
gtcgtctgct gctcaatgtc ctacacatgg acaggtgccc tgatcacgcc atgcgccgcg 7320
gaagaaagca agctgcccat caacgcgttg agcaactctt tgctgcgcca tcacaacatg 7380
gtctacgcca cgacatcccg cagcgcgggc ctgcggcaga agaaggtcac ctttgacaga 7440
ctgcaggtcc tggatgacca ttaccgggac gtgcttaagg agatgaaggc aaaggcgtcc 7500
acagtcaagg ctaaacttct atccatagaa gaagcctgcc gcctgacgcc cccacattcg 7560
gccaaatcca agtttggcta tggggcaaag gacgtccgga acctatccag cagggccatc 7620
aaccacatcc gctccgtgtg ggaggacttg ctggaggaca ctgtgacacc aattgacacc 7680
accgtcatgg caaagaatga ggttttctgc gtccaaccag agaagggagg ccgcaagcca 7740
gcccgcctta tcgtattccc agatttggga gttcgtgtat gcgagaagat ggctctctac 7800
gatgtggtct ccacccttcc tcaagccgtg atgggctcct catacggatt ccagtactct 7860
cccgggcagc gggtcgagtt cctggtaaaa gcctggaaat caaagaaaaa ccctatgggc 7920
ttctcatatg acacccgctg ttttgactca acggtcactg agaatgacat ccgtgttgag 7980
gagtcaattt accaatgttg tgacttggcc cccgaagcca gacaggctat aaaatcgctc 8040
acagagcggc tttatatcgg gggtcccctg actaattcaa aagggcagag ctgtggttat 8100
cgccggtgcc gcgcgagcgg cgtgctgacg actagctgcg gtaataccct cacatgttac 8160
ttgaaagcct ctgccgcctg tcgagctgca aagctccagg actgcacgat gctcgtgaac 8220
ggggacgacc ttgtcgttat ctgcgaaagc gcgggaaccc aggaggatgc ggcgagccta 8280

-continued

```
cgagtcttca cggaggctat gactaggtac tccgcccccc ccggggactt gccccaacca   8340
gaatacgact tggagttgat aacatcatgt tcctccaatg tgtcggtcgc gcacgatgca   8400
tctggcaaaa gggtgtacta cctcactcgc gatcccacca cccccatcgc acgggctgcg   8460
tgggaaacag ctagacacac tccagttaac tcctggctag gcaacattat catgtatgcg   8520
cccaccttat gggcaaggat gattctgatg acccatttct tctccatcct tctagctcag   8580
gagcaacttg aaaaagccct ggattgccaa atctacgggg cctgttactc cattgagcca   8640
cttgacctac ctcagatcat tgaaggactc catggtctta gcgcattttc actccatagt   8700
tactctccag gtgagatcaa tagggtggct tcatgcctca ggaaacttgg ggtaccgccc   8760
ttgcgagtct ggagacatcg ggccagggac gtccgcgcta aactactgtc ccaggggggg   8820
agggccgcca cttgcggcaa atacctcttc aactgggcag taaagaccaa gctcaaactc   8880
actccaatcc cggctgcgtc ccagttggac ttatccggct ggttcgttgc tggctacagc   8940
gggggagaca tatatcacag cctgtctcgt gcccgacccc gctggttcat gctgtgccta   9000
ctcctacttt ctgtaggggt aggcatctac ttgctcccca atcgatgaac ggggagctaa   9060
acactccagg ccaataggcc atttcctgtt tttttttttt tttggttttt tttttttttt   9120
tttttttttt tttttttttt ttttcctttc cttctttttt ttttttttccc tctttatggt   9180
ggctccgtct tagccctagt cacggctagc tgtgaaaggt ccgtgagccg catgactgca   9240
gagagtgctg atactggcct ctctgcagat catgt                              9275
```

<210> SEQ ID NO 40
<211> LENGTH: 2985
<212> TYPE: PRT
<213> ORGANISM: ARTIFICIAL
<220> FEATURE:
<223> OTHER INFORMATION: amino acid sequence encoded by nucleotides
      2077-11121 of SEQ ID NO:39

<400> SEQUENCE: 40

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Ile Arg Lys Thr Ser Glu Arg Ser Gln Pro Arg Gly Arg Arg Gln Pro
    50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Leu Ala Asp Leu Met Gly Tyr Ile Pro Leu Val Gly Gly Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175
```

-continued

```
Phe Leu Leu Ala Leu Leu Ser Cys Leu Thr Val Pro Ala Ser Ala His
            180                 185                 190

Glu Val Arg Asn Ala Ser Gly Val Tyr His Val Thr Asn Asp Cys Ser
        195                 200                 205

Asn Ser Ser Ile Val Phe Glu Ala Ala Asp Leu Ile Met His Thr Pro
    210                 215                 220

Gly Cys Val Pro Cys Val Arg Glu Gly Asn Ser Ser Arg Cys Trp Val
225                 230                 235                 240

Ala Leu Thr Pro Thr Leu Ala Ala Arg Asn Ala Thr Ile Pro Thr Thr
                245                 250                 255

Thr Ile Arg His His Val Asp Leu Leu Val Gly Ala Ala Ala Leu Cys
            260                 265                 270

Ser Ala Met Tyr Val Gly Asp Leu Cys Gly Ser Val Phe Leu Val Ser
        275                 280                 285

Gln Leu Phe Thr Phe Ser Pro Arg Arg His Ala Thr Leu Gln Asp Cys
    290                 295                 300

Asn Cys Ser Ile Tyr Pro Gly His Ala Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Ile Asp Met Val Ala Gly Ala His
            340                 345                 350

Trp Gly Val Leu Ala Gly Leu Ala Tyr Tyr Ser Met Ala Gly Asn Trp
        355                 360                 365

Ala Lys Val Leu Ile Val Met Leu Leu Phe Ala Gly Val Asp Gly His
    370                 375                 380

Thr Leu Thr Thr Gly Gly His Ala Ala Arg Leu Thr Ser Gly Phe Ala
385                 390                 395                 400

Gly Leu Phe Thr Pro Gly Pro Ser Gln Arg Ile Gln Leu Ile Asn Thr
                405                 410                 415

Asn Gly Ser Trp His Ile Asn Arg Thr Ala Leu Asn Cys Asn Asp Ser
            420                 425                 430

Leu Gln Thr Gly Phe Leu Ala Ala Leu Phe Tyr Ala His Arg Phe Asn
        435                 440                 445

Ser Ser Gly Cys Pro Glu Arg Met Ala Ser Cys Arg Ser Ile Asp Lys
    450                 455                 460

Phe Asp Gln Gly Trp Gly Pro Ile Thr Tyr Ala Glu Pro Thr Lys Asp
465                 470                 475                 480

Pro Asp Gln Arg Pro Tyr Cys Trp His Tyr Pro Pro Gln Gln Cys Gly
                485                 490                 495

Ile Val Pro Ala Ser Gln Val Cys Gly Pro Val Tyr Cys Phe Thr Pro
            500                 505                 510

Ser Pro Val Val Val Gly Thr Thr Asp Arg Leu Gly Asn Pro Thr Tyr
        515                 520                 525

Ser Trp Gly Glu Asn Asp Thr Asp Val Leu Leu Leu Asn Asn Thr Arg
    530                 535                 540

Pro Pro Gln Gly Asn Trp Phe Gly Cys Thr Trp Met Asn Ser Thr Gly
545                 550                 555                 560

Phe Thr Lys Thr Cys Gly Ala Pro Pro Cys Asn Ile Gly Gly Val Gly
                565                 570                 575

Asn Asn Thr Leu Thr Cys Pro Thr Asp Cys Phe Arg Lys His Pro Glu
            580                 585                 590

Ala Thr Tyr Ser Lys Cys Gly Ser Gly Pro Trp Leu Thr Pro Arg Cys
```

-continued

```
        595                 600                 605

Met Val Asp Tyr Pro Tyr Arg Leu Trp His Tyr Pro Cys Thr Val Asn
    610                 615                 620

Phe Ser Ile Phe Lys Val Arg Met Tyr Val Gly Gly Val Glu His Arg
625                 630                 635                 640

Leu Asn Ala Ala Cys Asn Trp Thr Arg Gly Glu Arg Cys Asn Leu Asp
                645                 650                 655

Asp Arg Asp Arg Ser Glu Leu Ser Pro Leu Leu Leu Ser Thr Thr Glu
            660                 665                 670

Trp Gln Val Leu Pro Cys Ser Phe Thr Thr Leu Pro Ala Leu Ser Thr
        675                 680                 685

Gly Leu Ile His Leu His Gln Asn Ile Val Asp Val Gln Tyr Leu Tyr
    690                 695                 700

Gly Ile Gly Ser Ala Val Val Ser Phe Ala Ile Lys Trp Glu Tyr Val
705                 710                 715                 720

Val Leu Leu Phe Leu Leu Leu Ala Asp Ala Arg Val Cys Ala Cys Leu
                725                 730                 735

Trp Met Met Leu Leu Ile Ala Gln Ala Glu Ala Ala Leu Glu Asn Leu
            740                 745                 750

Val Ala Leu Asn Ala Ala Ser Val Ala Gly Ala His Gly Ile Leu Ser
        755                 760                 765

Phe Leu Val Phe Phe Cys Ala Ala Trp Tyr Ile Lys Gly Arg Leu Val
    770                 775                 780

Pro Gly Ala Ala Tyr Ala Phe Tyr Gly Ala Trp Pro Leu Leu Leu Leu
785                 790                 795                 800

Leu Leu Thr Leu Pro Pro Arg Ala Tyr Ala Met Asp Arg Glu Met Ala
                805                 810                 815

Ala Ser Cys Gly Gly Ala Val Phe Val Gly Leu Ala Leu Leu Thr Leu
            820                 825                 830

Ser Pro Tyr Tyr Lys Val Phe Leu Ala Arg Leu Leu Trp Trp Leu Gln
        835                 840                 845

Tyr Leu Ile Thr Arg Ala Glu Ala His Leu His Val Trp Val Pro Pro
    850                 855                 860

Leu Asn Val Arg Gly Gly Arg Asp Ala Ile Ile Leu Leu Thr Cys Ala
865                 870                 875                 880

Val His Pro Glu Leu Ile Phe Asp Ile Thr Lys Leu Leu Ile Ala Ile
                885                 890                 895

Leu Gly Pro Leu Met Val Leu Gln Ala Gly Ile Thr Arg Val Pro Tyr
            900                 905                 910

Phe Val Arg Ala Gln Gly Leu Ile Arg Ala Cys Met Leu Val Arg Lys
        915                 920                 925

Val Ala Gly Gly His Tyr Val Gln Met Ala Phe Met Arg Leu Gly Ala
    930                 935                 940

Leu Thr Gly Thr Tyr Val Tyr Asn His Leu Thr Pro Leu Arg Asp Trp
945                 950                 955                 960

Ala His Ala Gly Leu Arg Asp Leu Ala Val Ala Val Glu Pro Val Val
                965                 970                 975

Phe Ser Asp Met Glu Thr Lys Ile Ile Thr Trp Gly Ala Asp Thr Ala
            980                 985                 990

Ala Cys Gly Asp Ile Ile Leu Gly  Leu Pro Val Ser Ala  Arg Arg Gly
        995                 1000                 1005

Arg Glu  Ile Leu Leu Gly Pro  Ala Asp Ser Leu Val  Arg Asp Lys
    1010                 1015                 1020
```

-continued

```
Asn Gln  Val Glu Gly Glu Val  Gln Val Val Ser Thr  Ala Thr Gln
    1025                 1030                 1035

Ser Phe  Leu Ala Thr Cys Val  Asn Gly Val Cys Trp  Thr Val Tyr
    1040                 1045                 1050

His Gly  Ala Gly Ser Lys Thr  Leu Ala Gly Pro Lys  Gly Pro Ile
    1055                 1060                 1065

Ala Gln  Met Tyr Thr Asn Val  Asp Gln Asp Leu Val  Gly Trp Pro
    1070                 1075                 1080

Ala Pro  Pro Gly Ala Arg Ser  Leu Thr Pro Cys Thr  Cys Gly Ser
    1085                 1090                 1095

Ser Asp  Leu Tyr Leu Val Thr  Arg His Ala Asp Val  Ile Pro Val
    1100                 1105                 1110

Arg Arg  Arg Gly Asp Asn Arg  Gly Ser Leu Leu Ser  Pro Arg Pro
    1115                 1120                 1125

Val Ser  Tyr Leu Lys Gly Ser  Ser Gly Gly Pro Leu  Leu Cys Pro
    1130                 1135                 1140

Ser Gly  His Ala Val Gly Val  Phe Arg Ala Ala Val  Cys Thr Arg
    1145                 1150                 1155

Gly Val  Ala Lys Ala Val Asp  Phe Val Pro Val Glu  Ser Met Glu
    1160                 1165                 1170

Thr Thr  Met Arg Ser Pro Val  Phe Thr Asp Asn Ser  Ser Pro Pro
    1175                 1180                 1185

Ala Val  Pro Gln Thr Phe Gln  Val Ala His Leu His  Ala Pro Thr
    1190                 1195                 1200

Gly Ser  Gly Lys Ser Thr Arg  Val Pro Ala Ala Tyr  Ala Ala Gln
    1205                 1210                 1215

Gly Tyr  Lys Val Leu Val Leu  Asn Pro Ser Val Ala  Ala Thr Leu
    1220                 1225                 1230

Gly Phe  Gly Ala Tyr Met Ser  Lys Ala His Gly Thr  Asp Pro Asn
    1235                 1240                 1245

Ile Arg  Thr Gly Val Arg Thr  Ile Thr Thr Gly Ala  Pro Ile Thr
    1250                 1255                 1260

Tyr Ser  Thr Tyr Gly Lys Phe  Leu Ala Asp Gly Gly  Cys Ser Gly
    1265                 1270                 1275

Gly Ala  Tyr Asp Ile Ile Met  Cys Asp Glu Cys His  Ser Thr Asp
    1280                 1285                 1290

Ser Thr  Thr Ile Leu Gly Ile  Gly Thr Val Leu Asp  Gln Ala Glu
    1295                 1300                 1305

Thr Ala  Gly Ala Arg Leu Val  Val Leu Ala Thr Ala  Thr Pro Pro
    1310                 1315                 1320

Gly Ser  Val Thr Val Pro His  Pro Asn Ile Glu Glu  Val Ala Leu
    1325                 1330                 1335

Ser Asn  Thr Gly Glu Ile Pro  Phe Tyr Gly Lys Ala  Ile Pro Ile
    1340                 1345                 1350

Glu Ala  Ile Lys Gly Gly Arg  His Leu Ile Phe Cys  His Ser Lys
    1355                 1360                 1365

Lys Lys  Cys Asp Glu Leu Ala  Ala Lys Leu Ser Gly  Leu Gly Ile
    1370                 1375                 1380

Asn Ala  Val Ala Tyr Tyr Arg  Gly Leu Asp Val Ser  Val Ile Pro
    1385                 1390                 1395

Thr Ser  Gly Asp Val Val Val  Val Ala Thr Asp Ala  Leu Met Thr
    1400                 1405                 1410
```

-continued

```
Gly Tyr  Thr Gly Asp Phe Asp  Ser Val Ile Asp Cys  Asn Thr Cys
    1415                 1420                 1425

Val Thr  Gln Thr Val Asp Phe  Ser Leu Asp Pro Thr  Phe Thr Ile
    1430                 1435                 1440

Glu Thr  Thr Thr Val Pro Gln  Asp Ala Val Ser Arg  Ser Gln Arg
    1445                 1450                 1455

Arg Gly  Arg Thr Gly Arg Gly  Arg Gly Gly Ile Tyr  Arg Phe Val
    1460                 1465                 1470

Thr Pro  Gly Glu Arg Pro Ser  Gly Met Phe Asp Ser  Ser Val Leu
    1475                 1480                 1485

Cys Glu  Cys Tyr Asp Ala Gly  Cys Ala Trp Tyr Glu  Leu Thr Pro
    1490                 1495                 1500

Ala Glu  Thr Ser Val Arg Leu  Arg Ala Tyr Leu Asn  Thr Pro Gly
    1505                 1510                 1515

Leu Pro  Val Cys Gln Asp His  Leu Glu Phe Trp Glu  Ser Val Phe
    1520                 1525                 1530

Thr Gly  Leu Thr His Ile Asp  Ala His Phe Leu Ser  Gln Thr Lys
    1535                 1540                 1545

Gln Ala  Gly Asp Asn Phe Pro  Tyr Leu Val Ala Tyr  Gln Ala Thr
    1550                 1555                 1560

Val Cys  Ala Arg Ala Gln Ala  Pro Pro Pro Ser Trp  Asp Gln Met
    1565                 1570                 1575

Trp Lys  Cys Leu Ile Arg Leu  Lys Pro Thr Leu His  Gly Pro Thr
    1580                 1585                 1590

Pro Leu  Leu Tyr Arg Leu Gly  Ala Val Gln Asn Glu  Val Thr Leu
    1595                 1600                 1605

Thr His  Pro Ile Thr Lys Tyr  Ile Met Ala Cys Met  Ser Ala Asp
    1610                 1615                 1620

Leu Glu  Val Val Thr Ser Thr  Trp Val Leu Val Gly  Gly Val Leu
    1625                 1630                 1635

Ala Ala  Leu Ala Ala Tyr Cys  Leu Thr Thr Gly Ser  Val Val Ile
    1640                 1645                 1650

Val Gly  Arg Ile Ile Leu Ser  Gly Arg Pro Ala Val  Val Pro Asp
    1655                 1660                 1665

Arg Glu  Val Leu Tyr Arg Glu  Phe Asp Glu Met Glu  Glu Cys Ala
    1670                 1675                 1680

Ser His  Leu Pro Tyr Ile Glu  Gln Gly Met Gln Leu  Ala Glu Gln
    1685                 1690                 1695

Phe Lys  Gln Lys Ala Leu Gly  Leu Leu Gln Thr Ala  Thr Lys Gln
    1700                 1705                 1710

Ala Glu  Ala Ala Ala Pro Val  Val Glu Ser Lys Trp  Arg Ala Leu
    1715                 1720                 1725

Glu Thr  Phe Trp Ala Lys His  Lys Trp Asn Phe Ile  Ser Gly Ile
    1730                 1735                 1740

Gln Tyr  Leu Ala Gly Leu Ser  Thr Leu Pro Gly Asn  Pro Ala Ile
    1745                 1750                 1755

Ala Ser  Leu Met Ala Phe Thr  Ala Ser Ile Thr Ser  Pro Leu Thr
    1760                 1765                 1770

Thr Gln  Asn Thr Leu Leu Phe  Asn Ile Leu Gly Gly  Trp Val Ala
    1775                 1780                 1785

Ala Gln  Leu Ala Pro Pro Ser  Ala Ala Ser Ala Phe  Val Gly Ala
    1790                 1795                 1800

Gly Ile  Ala Gly Ala Ala Val  Gly Ser Ile Gly Leu  Gly Lys Val
```

-continued

```
        1805                1810                1815

Leu Val Asp Ile Leu Ala Gly Tyr Gly Ala Gly Val Ala Gly Ala
    1820                1825                1830

Leu Val Ala Phe Lys Val Met Ser Gly Glu Ala Pro Ser Ala Glu
    1835                1840                1845

Asp Leu Ile Asn Leu Leu Pro Ala Ile Leu Ser Pro Gly Ala Leu
    1850                1855                1860

Val Val Gly Val Val Cys Ala Ala Ile Leu Arg Arg His Val Gly
    1865                1870                1875

Pro Gly Glu Gly Ala Val Gln Trp Met Asn Arg Leu Ile Ala Phe
    1880                1885                1890

Ala Ser Arg Gly Asn His Val Ser Pro Thr His Tyr Val Pro Glu
    1895                1900                1905

Ser Asp Ala Ala Ala Arg Val Thr Gln Val Leu Ser Ser Leu Thr
    1910                1915                1920

Ile Thr Gln Leu Leu Lys Arg Leu His Gln Trp Ile Asn Glu Asp
    1925                1930                1935

Cys Ser Thr Pro Cys Ser Gly Ser Trp Leu Arg Asp Val Trp Asp
    1940                1945                1950

Trp Val Cys Thr Val Leu Ser Asp Phe Lys Thr Trp Leu Gln Ser
    1955                1960                1965

Lys Leu Leu Pro Arg Leu Pro Gly Val Pro Phe Leu Ser Cys Gln
    1970                1975                1980

Arg Gly Tyr Lys Gly Val Trp Arg Gly Asp Gly Ile Met His Thr
    1985                1990                1995

Thr Cys Pro Cys Gly Ala Gln Ile Ala Gly His Val Lys Asn Gly
    2000                2005                2010

Ser Met Arg Ile Ile Gly Pro Lys Thr Cys Ser Asn Thr Trp His
    2015                2020                2025

Gly Thr Phe Pro Ile Asn Ala Tyr Thr Thr Gly Pro Cys Thr Pro
    2030                2035                2040

Ser Pro Ala Pro Asn Tyr Ser Lys Ala Leu Trp Arg Val Ala Ala
    2045                2050                2055

Glu Glu Tyr Val Glu Val Thr Arg Val Gly Asp Phe His Tyr Val
    2060                2065                2070

Thr Gly Ile Thr Thr Asp Asn Val Lys Cys Pro Cys Gln Val Pro
    2075                2080                2085

Ala Pro Glu Phe Phe Thr Glu Val Asp Gly Val Arg Leu His Arg
    2090                2095                2100

Tyr Ala Pro Val Cys Lys Pro Leu Leu Arg Asp Glu Val Val Phe
    2105                2110                2115

Gln Val Gly Leu Asn Gln Tyr Leu Val Gly Ser Gln Leu His Arg
    2120                2125                2130

Tyr Ala Pro Val Cys Lys Pro Leu Leu Arg Asp Glu Val Val Phe
    2135                2140                2145

Gln Val Gly Leu Asn Gln Tyr Leu Val Gly Ser Gln Leu Ala Arg
    2150                2155                2160

Gly Ser Pro Pro Ser Leu Ala Ser Ser Ser Ala Ser Gln Leu Ser
    2165                2170                2175

Ala Pro Ser Leu Arg Ala Thr Cys Thr Thr His Ser Ser Tyr Asn
    2180                2185                2190

Leu Asp Ser Pro Asp Val Asp Leu Ile Ala Ala Asn Leu Leu Trp
    2195                2200                2205
```

-continued

Arg Gln Glu Met Gly Gly Asn Ile Thr Arg Val Glu Ser Glu Asn
2210 2215 2220

Lys Val Val Val Leu Asp Ser Phe Glu Pro Leu Arg Ala Glu Gly
2225 2230 2235

Asp Glu Asn Glu Ile Ser Ile Ala Ala Glu Ile Leu Arg Lys Ser
2240 2245 2250

Lys Lys Phe Pro Ala Ala Ile Pro Ile Trp Ala Arg Pro Asp Tyr
2255 2260 2265

Asn Pro Pro Leu Leu Glu Ser Trp Lys Asn Pro Asp Tyr Val Pro
2270 2275 2280

Pro Val Val His Gly Cys Pro Leu Pro Pro Val Lys Ala Pro Pro
2285 2290 2295

Ile Pro Pro Pro Arg Arg Lys Arg Thr Val Val Leu Thr Asp Ser
2300 2305 2310

Thr Val Ser Ser Val Leu Ala Glu Leu Ala Thr Lys Thr Phe Gly
2315 2320 2325

Ser Ser Glu Leu Ser Ala Ala Asp Ser Gly Thr Ala Thr Ala Pro
2330 2335 2340

Pro Asp Gln Thr Ser Asp Asn Gly Gly Lys Asp Ser Asp Ala Glu
2345 2350 2355

Ser Cys Ser Ser Met Pro Pro Leu Glu Gly Glu Pro Gly Asp Pro
2360 2365 2370

Asp Leu Ser Asp Gly Ser Trp Ser Thr Val Ser Glu Glu Ala Gly
2375 2380 2385

Glu Ser Val Val Cys Cys Ser Met Ser Tyr Thr Trp Thr Gly Ala
2390 2395 2400

Leu Ile Thr Pro Cys Ala Ala Glu Glu Ser Lys Leu Pro Ile Asn
2405 2410 2415

Ala Leu Ser Asn Ser Leu Leu Arg His His Asn Met Val Tyr Ala
2420 2425 2430

Thr Thr Ser Arg Ser Ala Gly Leu Arg Gln Lys Lys Val Thr Phe
2435 2440 2445

Asp Arg Leu Gln Val Leu Asp Asp His Tyr Arg Asp Val Leu Lys
2450 2455 2460

Glu Met Lys Ala Lys Ala Ser Thr Val Lys Ala Lys Leu Leu Ser
2465 2470 2475

Ile Glu Glu Ala Cys Arg Leu Thr Pro Pro His Ser Ala Lys Ser
2480 2485 2490

Lys Phe Gly Tyr Gly Ala Lys Asp Val Arg Asn Leu Ser Ser Arg
2495 2500 2505

Ala Ile Asn His Ile Arg Ser Val Trp Glu Asp Leu Leu Glu Asp
2510 2515 2520

Thr Val Thr Pro Ile Asp Thr Thr Val Met Ala Lys Asn Glu Val
2525 2530 2535

Phe Cys Val Gln Pro Glu Lys Gly Gly Arg Lys Pro Ala Arg Leu
2540 2545 2550

Ile Val Phe Pro Asp Leu Gly Val Arg Val Cys Glu Lys Met Ala
2555 2560 2565

Leu Tyr Asp Val Val Ser Thr Leu Pro Gln Ala Val Met Gly Ser
2570 2575 2580

Ser Tyr Gly Phe Gln Tyr Ser Pro Gly Gln Arg Val Glu Phe Leu
2585 2590 2595

-continued

```
Val Lys  Ala Trp Lys Ser Lys  Lys Asn Pro Met Gly  Phe Ser Tyr
    2600                 2605                 2610

Asp Thr  Arg Cys Phe Asp Ser  Thr Val Thr Glu Asn  Asp Ile Arg
    2615                 2620                 2625

Val Glu  Glu Ser Ile Tyr Gln  Cys Cys Asp Leu Ala  Pro Glu Ala
    2630                 2635                 2640

Arg Gln  Ala Ile Lys Ser Leu  Thr Glu Arg Leu Tyr  Ile Gly Gly
    2645                 2650                 2655

Pro Leu  Thr Asn Ser Lys Gly  Gln Ser Cys Gly Tyr  Arg Arg Cys
    2660                 2665                 2670

Arg Ala  Ser Gly Val Leu Thr  Thr Ser Cys Gly Asn  Thr Leu Thr
    2675                 2680                 2685

Cys Tyr  Leu Lys Ala Ser Ala  Ala Cys Arg Ala Ala  Lys Leu Gln
    2690                 2695                 2700

Asp Cys  Thr Met Leu Val Asn  Gly Asp Asp Leu Val  Val Ile Cys
    2705                 2710                 2715

Glu Ser  Ala Gly Thr Gln Glu  Asp Ala Ala Ser Leu  Arg Val Phe
    2720                 2725                 2730

Thr Glu  Ala Met Thr Arg Tyr  Ser Ala Pro Pro Gly  Asp Leu Pro
    2735                 2740                 2745

Gln Pro  Glu Tyr Asp Leu Glu  Leu Ile Thr Ser Cys  Ser Ser Asn
    2750                 2755                 2760

Val Ser  Val Ala His Asp Ala  Ser Gly Lys Arg Val  Tyr Tyr Leu
    2765                 2770                 2775

Thr Arg  Asp Pro Thr Thr Pro  Ile Ala Arg Ala Ala  Trp Glu Thr
    2780                 2785                 2790

Ala Arg  His Thr Pro Val Asn  Ser Trp Leu Gly Asn  Ile Ile Met
    2795                 2800                 2805

Tyr Ala  Pro Thr Leu Trp Ala  Arg Met Ile Leu Met  Thr His Phe
    2810                 2815                 2820

Phe Ser  Ile Leu Leu Ala Gln  Glu Gln Leu Glu Lys  Ala Leu Asp
    2825                 2830                 2835

Cys Gln  Ile Tyr Gly Ala Cys  Tyr Ser Ile Glu Pro  Leu Asp Leu
    2840                 2845                 2850

Pro Gln  Ile Ile Glu Gly Leu  His Gly Leu Ser Ala  Phe Ser Leu
    2855                 2860                 2865

His Ser  Tyr Ser Pro Gly Glu  Ile Asn Arg Val Ala  Ser Cys Leu
    2870                 2875                 2880

Arg Lys  Leu Gly Val Pro Pro  Leu Arg Val Trp Arg  His Arg Ala
    2885                 2890                 2895

Arg Asp  Val Arg Ala Lys Leu  Leu Ser Gln Gly Gly  Arg Ala Ala
    2900                 2905                 2910

Thr Cys  Gly Lys Tyr Leu Phe  Asn Trp Ala Val Lys  Thr Lys Leu
    2915                 2920                 2925

Lys Leu  Thr Pro Ile Pro Ala  Ala Ser Gln Leu Asp  Leu Ser Gly
    2930                 2935                 2940

Trp Phe  Val Ala Gly Tyr Ser  Gly Gly Asp Ile Tyr  His Ser Leu
    2945                 2950                 2955

Ser Arg  Ala Arg Pro Arg Trp  Phe Met Leu Cys Leu  Leu Leu Leu
    2960                 2965                 2970

Ser Val  Gly Val Gly Ile Tyr  Leu Leu Pro Asn Arg
    2975                 2980                 2985
```

-continued

<210> SEQ ID NO 41
<211> LENGTH: 6189
<212> TYPE: DNA
<213> ORGANISM: ARTIFICIAL
<220> FEATURE:
<223> OTHER INFORMATION: nucleotide sequence encoding hepatitis
C virus polyprotein derived from Con1

<400> SEQUENCE: 41
atggcgccta ttacggccta ctcccaacag acgcgaggcc tacttggctg catcatcact 60
agcctcacag gccgggacag gaaccaggtc gagggggagg tccaagtggt ctccaccgca 120
acacaatctt tcctggcgac ctgcgtcaat ggcgtgtgtt ggactgtcta tcatggtgcc 180
ggctcaaaga cccttgccgg cccaaagggc ccaatcaccc aaatgtacac caatgtggac 240
caggacctcg tcggctggca agcgcccccc ggggcgcgtt ccttgacacc atgcacctgc 300
ggcagctcgg acctttactt ggtcacgagg catgccgatg tcattccggt gcgccggcgg 360
ggcgacagca gggggagcct actctccccc aggcccgtct cctacttgaa gggctcttcg 420
ggcggtccac tgctctgccc ctcggggcac gctgtgggca tctttcgggc tgccgtgtgc 480
acccgagggg ttgcgaaggc ggtggacttt gtacccgtcg agtctatgga aaccactatg 540
cggtccccgg tcttcacgga caactcgtcc cctccggccg taccgcagac attccaggtg 600
gcccatctac acgcccctac tggtagcggc aagagcacta aggtgccggc tgcgtatgca 660
gcccaagggt ataaggtgct tgtcctgaac ccgtccgtcg ccgccaccct aggtttcggg 720
gcgtatatgt ctaaggcaca tggtatcgac cctaacatca gaaccggggt aaggaccatc 780
accacgggtg cccccatcac gtactccacc tatggcaagt ttcttgccga cggtggttgc 840
tctgggggcg cctatgacat cataatatgt gatgagtgcc actcaactga ctcgaccact 900
atcctgggca tcggcacagt cctggaccaa gcggagacgg ctggagcgcg actcgtcgtg 960
ctcgccaccg ctacgcctcc gggatcggtc accgtgccac atccaaacat cgaggaggtg 1020
gctctgtcca gcactggaga aatccccttt tatggcaaag ccatccccat cgagaccatc 1080
aaggggggga ggcacctcat tttctgccat tccaagaaga aatgtgatga gctcgccgcg 1140
aagctgtccg gcctcggact caatgctgta gcatattacc ggggccttga tgtatccgtc 1200
ataccaacta gcggagacgt cattgtcgta gcaacggacg ctctaatgac gggctttacc 1260
ggcgatttcg actcagtgat cgactgcaat acatgtgtca cccagacagt cgacttcagc 1320
ctggacccga ccttcaccat tgagacgacg accgtgccac aagacgcggt gtcacgctcg 1380
cagcggcgag gcaggactgg taggggcagg atgggcattt acaggtttgt gactccagga 1440
gaacggccct cgggcatgtt cgattcctcg gttctgtgcg agtgctatga cgcgggctgt 1500
gcttggtacg agctcacgcc cgccgagacc tcagttaggt tgcgggctta cctaaacaca 1560
ccagggttgc ccgtctgcca ggaccatctg gagttctggg agagcgtctt tacaggcctc 1620
acccacatag acgcccattt cttgtcccag actaagcagg caggagacaa cttcccctac 1680
ctggtagcat accaggctac ggtgtgcgcc agggctcagg ctccacctcc atcgtgggac 1740
caaatgtgga agtgtctcat acggctaaag cctacgctgc acgggccaac gcccctgctg 1800
tataggctgg gagccgttca aaacgaggtt actaccacac accccataac caaatacatc 1860
atggcatgca tgtcggctga cctggaggtc gtcacgagca cctgggtgct ggtaggcgga 1920
gtcctagcag ctctggccgc gtattgcctg acaacaggca gcgtggtcat tgtgggcagg 1980
atcatcttgt ccggaaagcc ggccatcatt cccgacaggg aagtccttta ccgggagttc 2040
gatgagatgg aagagtgcgc ctcacacctc ccttacatcg aacagggaat gcagctcgcc 2100

-continued

```
gaacaattca aacagaaggc aatcgggttg ctgcaaacag ccaccaagca agcggaggct   2160
gctgctcccg tggtggaatc caagtggcgg accctcgaag ccttctgggc gaagcatatg   2220
tggaatttca tcagcgggat acaatattta gcaggcttgt ccactctgcc tggcaacccc   2280
gcgatagcat cactgatggc attcacagcc tctatcacca gcccgctcac cacccaacat   2340
accctcctgt ttaacatcct gggggggatgg gtggccgccc aacttgctcc tcccagcgct   2400
gcttctgctt tcgtaggcgc cggcatcgct ggagcggctg ttggcagcat aggccttggg   2460
aaggtgcttg tggatatttt ggcaggttat ggagcagggg tggcaggcgc gctcgtggcc   2520
tttaaggtca tgagcggcga gatgccctcc accgaggacc tggttaacct actccctgct   2580
atcctctccc ctggcgccct agtcgtcggg gtcgtgtgcg cagcgatact gcgtcggcac   2640
gtgggcccag gggagggggc tgtgcagtgg atgaaccggc tgatagcgtt cgcttcgcgg   2700
ggtaaccacg tctcccccac gcactatgtg cctgagagcg acgctgcagc acgtgtcact   2760
cagatcctct ctagtcttac catcactcag ctgctgaaga ggcttcacca gtggatcaac   2820
gaggactgct ccacgccatg ctccggctcg tggctaagag atgtttggga ttggatatgc   2880
acggtgttga ctgatttcaa gacctggctc cagtccaagc tcctgccgcg attgccggga   2940
gtccccttct tctcatgtca acgtgggtac aagggagtct ggcggggcga cggcatcatg   3000
caaaccacct gcccatgtgg agcacagatc accggacatg tgaaaaacgg ttccatgagg   3060
atcgtggggc ctaggacctg tagtaacacg tggcatggaa cattccccat taacgcgtac   3120
accacgggcc cctgcacgcc ctccccggcg ccaaattatt ctagggcgct gtggcgggtg   3180
gctgctgagg agtacgtgga ggttacgcgg gtgggggatt tccactacgt gacgggcatg   3240
accactgaca acgtaaagtg cccgtgtcag gttccggccc ccgaattctt cacagaagtg   3300
gatggggtgc ggttgcacag gtacgctcca gcgtgcaaac ccctcctacg ggaggaggtc   3360
acattcctgg tcgggctcaa tcaatacctg gttgggtcac agctcccatg cgagcccgaa   3420
ccggacgtag cagtgctcac ttccatgctc accgacccct cccacattac ggcggagacg   3480
gctaagcgta ggctggccag gggatctccc ccctccttgg ccagctcatc agctatccag   3540
ctgtctgcgc cttccttgaa ggcaacatgc actacccgtc atgactcccc ggacgctgac   3600
ctcatcgagg ccaacctcct gtggcggcag gagatgggcg ggaacatcac ccgcgtggag   3660
tcagaaaata aggtagtaat tttggactct ttcgagccgc tccaagcgga ggaggatgag   3720
agggaagtat ccgttccggc ggagatcctg cggaggtcca ggaaattccc tcgagcgatg   3780
cccatatggg cacgcccgga ttacaaccct ccactgttag agtcctggaa ggacccggac   3840
tacgtccctc cagtggtaca cgggtgtcca ttgccgcctg ccaaggcccc tccgatacca   3900
cctccacgga ggaagaggac ggttgtcctg tcagaatcta ccgtgtcttc tgccttggcg   3960
gagctcgcca caaagacctt cggcagctcc gaatcgtcgg ccgtcgacag cggcacggca   4020
acggcctctc ctgaccagcc ctccgacgac ggcgacgcgg gatccgacgt tgagtcgtac   4080
tcctccatgc cccccctga gggggagccg ggggatcccg atctcagcga cgggtcttgg   4140
tctaccgtaa gcgaggaggc tagtgaggac gtcgtctgct gctcgatgtc ctacacatgg   4200
acaggcgccc tgatcacgcc atgcgctgcg gaggaaacca agctgcccat caatgcactg   4260
agcaactctt tgctccgtca ccacaacttg gtctatgcta caacatctcg cagcgcaagc   4320
ctgcggcaga agaaggtcac ctttgacaga ctgcaggtcc tggacgacca ctaccgggac   4380
gtgctcaagg agatgaaggc gaaggcgtcc acagttaagg ctaaacttct atccgtggag   4440
```

-continued

```
gaagcctgta agctgacgcc cccacattcg gccagatcta aatttggcta tggggcaaag   4500

gacgtccgga acctatccag caaggccgtt aaccacatcc gctccgtgtg gaaggacttg   4560

ctggaagaca ctgagacacc aattgacacc accatcatgg caaaaaatga ggttttctgc   4620

gtccaaccag agaagggggg ccgcaagcca gctcgcctta tcgtattccc agatttgggg   4680

gttcgtgtgt gcgagaaaat ggccctttac gatgtggtct ccaccctccc tcaggccgtg   4740

atgggctctt catacggatt ccaatactct cctggacagc gggtcgagtt cctggtgaat   4800

gcctggaaag cgaagaaatg ccctatgggc ttcgcatatg acacccgctg ttttgactca   4860

acggtcactg agaatgacat ccgtgttgag gagtcaatct accaatgttg tgacttggcc   4920

cccgaagcca gacaggccat aaggtcgctc acagagcggc tttacatcgg gggccccctg   4980

actaattcta aagggcagaa ctgcggctat cgccggtgcc gcgcgagcgg tgtactgacg   5040

accagctgcg gtaataccct cacatgttac ttgaaggccg ctgcggcctg tcgagctgcg   5100

aagctccagg actgcacgat gctcgtatgc ggagacgacc ttgtcgttat ctgtgaaagc   5160

gcggggaccc aagaggacga ggcgagccta cgggccttca cggaggctat gactagatac   5220

tctgcccccc ctggggaccc gcccaaacca gaatacgact tggagttgat aacatcatgc   5280

tcctccaatg tgtcagtcgc gcacgatgca tctggcaaaa gggtgtacta tctcacccgt   5340

gaccccacca ccccccttgc gcgggctgcg tgggagacag ctagacacac tccagtcaat   5400

tcctggctag gcaacatcat catgtatgcg cccaccttgt gggcaaggat gatcctgatg   5460

actcatttct tctccatcct tctagctcag gaacaacttg aaaaagccct agattgtcag   5520

atctacgggg cctgttactc cattgagcca cttgacctac ctcagatcat tcaacgactc   5580

catggcctta gcgcattttc actccatagt tactctccag gtgagatcaa tagggtggct   5640

tcatgcctca ggaaacttgg ggtaccgccc ttgcgagtct ggagacatcg ggccagaagt   5700

gtccgcgcta ggctactgtc ccaggggggg agggctgcca cttgtggcaa gtacctcttc   5760

aactgggcag taaggaccaa gctcaaactc actccaatcc cggctgcgtc ccagttggat   5820

ttatccagct ggttcgttgc tggttacagc gggggagaca tatatcacag cctgtctcgt   5880

gcccgacccc gctggttcat gtggtgccta ctcctacttt ctgtaggggt aggcatctat   5940

ctactcccca accgatgaac ggggagctaa acactccagg ccaataggcc atcctgtttt   6000

tttccctttt tttttttctt tttttttttt tttttttttt tttttttttt ttctcctttt   6060

tttttcctct ttttttcctt ttctttcctt tggtggctcc atcttagccc tagtcacggc   6120

tagctgtgaa aggtccgtga gccgcttgac tgcagagagt gctgatactg gcctctctgc   6180

agatcaagt                                                           6189
```

<210> SEQ ID NO 42
<211> LENGTH: 1985
<212> TYPE: PRT
<213> ORGANISM: ARTIFICIAL
<220> FEATURE:
<223> OTHER INFORMATION: amino acid sequence encoded by the nucleotides 2119-8073 of SEQ ID NO:41

<400> SEQUENCE: 42

```
Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Arg Asn Gln Val Glu Gly
            20                  25                  30

Glu Val Gln Val Val Ser Thr Ala Thr Gln Ser Phe Leu Ala Thr Cys
        35                  40                  45
```

-continued

```
Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Thr Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Ile Thr Tyr Ser Thr Tyr Gly
            260                 265                 270

Lys Phe Leu Ala Asp Gly Gly Cys Ser Gly Gly Ala Tyr Asp Ile Ile
        275                 280                 285

Ile Cys Asp Glu Cys His Ser Thr Asp Ser Thr Thr Ile Leu Gly Ile
    290                 295                 300

Gly Thr Val Leu Asp Gln Ala Glu Thr Ala Gly Ala Arg Leu Val Val
305                 310                 315                 320

Leu Ala Thr Ala Thr Pro Pro Gly Ser Val Thr Val Pro His Pro Asn
                325                 330                 335

Ile Glu Glu Val Ala Leu Ser Ser Thr Gly Glu Ile Pro Phe Tyr Gly
            340                 345                 350

Lys Ala Ile Pro Ile Glu Thr Ile Lys Gly Gly Arg His Leu Ile Phe
        355                 360                 365

Cys His Ser Lys Lys Lys Cys Asp Glu Leu Ala Ala Lys Leu Ser Gly
    370                 375                 380

Leu Gly Leu Asn Ala Val Ala Tyr Tyr Arg Gly Leu Asp Val Ser Val
385                 390                 395                 400

Ile Pro Thr Ser Gly Asp Val Ile Val Val Ala Thr Asp Ala Leu Met
                405                 410                 415

Thr Gly Phe Thr Gly Asp Phe Asp Ser Val Ile Asp Cys Asn Thr Cys
            420                 425                 430

Val Thr Gln Thr Val Asp Phe Ser Leu Asp Pro Thr Phe Thr Ile Glu
        435                 440                 445

Thr Thr Thr Val Pro Gln Asp Ala Val Ser Arg Ser Gln Arg Arg Gly
    450                 455                 460
```

-continued

```
Arg Thr Gly Arg Gly Arg Met Gly Ile Tyr Arg Phe Val Thr Pro Gly
465                 470                 475                 480

Glu Arg Pro Ser Gly Met Phe Asp Ser Ser Val Leu Cys Glu Cys Tyr
                485                 490                 495

Asp Ala Gly Cys Ala Trp Tyr Glu Leu Thr Pro Ala Glu Thr Ser Val
            500                 505                 510

Arg Leu Arg Ala Tyr Leu Asn Thr Pro Gly Leu Pro Val Cys Gln Asp
        515                 520                 525

His Leu Glu Phe Trp Glu Ser Val Phe Thr Gly Leu Thr His Ile Asp
    530                 535                 540

Ala His Phe Leu Ser Gln Thr Lys Gln Ala Gly Asp Asn Phe Pro Tyr
545                 550                 555                 560

Leu Val Ala Tyr Gln Ala Thr Val Cys Ala Arg Ala Gln Ala Pro Pro
                565                 570                 575

Pro Ser Trp Asp Gln Met Trp Lys Cys Leu Ile Arg Leu Lys Pro Thr
            580                 585                 590

Leu His Gly Pro Thr Pro Leu Leu Tyr Arg Leu Gly Ala Val Gln Asn
        595                 600                 605

Glu Val Thr Thr Thr His Pro Ile Thr Lys Tyr Ile Met Ala Cys Met
    610                 615                 620

Ser Ala Asp Leu Glu Val Val Thr Ser Thr Trp Val Leu Val Gly Gly
625                 630                 635                 640

Val Leu Ala Ala Leu Ala Ala Tyr Cys Leu Thr Thr Gly Ser Val Val
                645                 650                 655

Ile Val Gly Arg Ile Ile Leu Ser Gly Lys Pro Ala Ile Ile Pro Asp
            660                 665                 670

Arg Glu Val Leu Tyr Arg Glu Phe Asp Glu Met Glu Glu Cys Ala Ser
        675                 680                 685

His Leu Pro Tyr Ile Glu Gln Gly Met Gln Leu Ala Glu Gln Phe Lys
    690                 695                 700

Gln Lys Ala Ile Gly Leu Leu Gln Thr Ala Thr Lys Gln Ala Glu Ala
705                 710                 715                 720

Ala Ala Pro Val Val Glu Ser Lys Trp Arg Thr Leu Glu Ala Phe Trp
                725                 730                 735

Ala Lys His Met Trp Asn Phe Ile Ser Gly Ile Gln Tyr Leu Ala Gly
            740                 745                 750

Leu Ser Thr Leu Pro Gly Asn Pro Ala Ile Ala Ser Leu Met Ala Phe
        755                 760                 765

Thr Ala Ser Ile Thr Ser Pro Leu Thr Thr Gln His Thr Leu Leu Phe
    770                 775                 780

Asn Ile Leu Gly Gly Trp Val Ala Ala Gln Leu Ala Pro Pro Ser Ala
785                 790                 795                 800

Ala Ser Ala Phe Val Gly Ala Gly Ile Ala Gly Ala Ala Val Gly Ser
                805                 810                 815

Ile Gly Leu Gly Lys Val Leu Val Asp Ile Leu Ala Gly Tyr Gly Ala
            820                 825                 830

Gly Val Ala Gly Ala Leu Val Ala Phe Lys Val Met Ser Gly Glu Met
        835                 840                 845

Pro Ser Thr Glu Asp Leu Val Asn Leu Leu Pro Ala Ile Leu Ser Pro
    850                 855                 860

Gly Ala Leu Val Val Gly Val Val Cys Ala Ala Ile Leu Arg Arg His
865                 870                 875                 880

Val Gly Pro Gly Glu Gly Ala Val Gln Trp Met Asn Arg Leu Ile Ala
```

-continued

```
                885                 890                 895

Phe Ala Ser Arg Gly Asn His Val Ser Pro Thr His Tyr Val Pro Glu
            900                 905                 910

Ser Asp Ala Ala Ala Arg Val Thr Gln Ile Leu Ser Ser Leu Thr Ile
        915                 920                 925

Thr Gln Leu Leu Lys Arg Leu His Gln Trp Ile Asn Glu Asp Cys Ser
    930                 935                 940

Thr Pro Cys Ser Gly Ser Trp Leu Arg Asp Val Trp Asp Trp Ile Cys
945                 950                 955                 960

Thr Val Leu Thr Asp Phe Lys Thr Trp Leu Gln Ser Lys Leu Leu Pro
                965                 970                 975

Arg Leu Pro Gly Val Pro Phe Phe Ser Cys Gln Arg Gly Tyr Lys Gly
            980                 985                 990

Val Trp Arg Gly Asp Gly Ile Met  Gln Thr Thr Cys Pro  Cys Gly Ala
        995                 1000                1005

Gln Ile  Thr Gly His Val Lys  Asn Gly Ser Met Arg  Ile Val Gly
    1010                 1015                 1020

Pro Arg  Thr Cys Ser Asn Thr  Trp His Gly Thr Phe  Pro Ile Asn
    1025                 1030                 1035

Ala Tyr  Thr Thr Gly Pro Cys  Thr Pro Ser Pro Ala  Pro Asn Tyr
    1040                 1045                 1050

Ser Arg  Ala Leu Trp Arg Val  Ala Ala Glu Glu Tyr  Val Glu Val
    1055                 1060                 1065

Thr Arg  Val Gly Asp Phe His  Tyr Val Thr Gly Met  Thr Thr Asp
    1070                 1075                 1080

Asn Val  Lys Cys Pro Cys Gln  Val Pro Ala Pro Glu  Phe Phe Thr
    1085                 1090                 1095

Glu Val  Asp Gly Val Arg Leu  His Arg Tyr Ala Pro  Ala Cys Lys
    1100                 1105                 1110

Pro Leu  Leu Arg Glu Glu Val  Thr Phe Leu Val Gly  Leu Asn Gln
    1115                 1120                 1125

Tyr Leu  Val Gly Ser Gln Leu  Pro Cys Glu Pro Glu  Pro Asp Val
    1130                 1135                 1140

Ala Val  Leu Thr Ser Met Leu  Thr Asp Pro Ser His  Ile Thr Ala
    1145                 1150                 1155

Glu Thr  Ala Lys Arg Arg Leu  Ala Arg Gly Ser Pro  Pro Ser Leu
    1160                 1165                 1170

Ala Ser  Ser Ser Ala Ile Gln  Leu Ser Ala Pro Ser  Leu Lys Ala
    1175                 1180                 1185

Thr Cys  Thr Thr Arg His Asp  Ser Pro Asp Ala Asp  Leu Ile Glu
    1190                 1195                 1200

Ala Asn  Leu Leu Trp Arg Gln  Glu Met Gly Gly Asn  Ile Thr Arg
    1205                 1210                 1215

Val Glu  Ser Glu Asn Lys Val  Val Ile Leu Asp Ser  Phe Glu Pro
    1220                 1225                 1230

Leu Gln  Ala Glu Glu Asp Glu  Arg Glu Val Ser Val  Pro Ala Glu
    1235                 1240                 1245

Ile Leu  Arg Arg Ser Arg Lys  Phe Pro Arg Ala Met  Pro Ile Trp
    1250                 1255                 1260

Ala Arg  Pro Asp Tyr Asn Pro  Pro Leu Leu Glu Ser  Trp Lys Asp
    1265                 1270                 1275

Pro Asp  Tyr Val Pro Pro Val  Val His Gly Cys Pro  Leu Pro Pro
    1280                 1285                 1290
```

-continued

```
Ala Lys Ala Pro Pro Ile Pro Pro Pro Arg Arg Lys Arg Thr Val
    1295                1300                1305

Val Leu Ser Glu Ser Thr Val Ser Ser Ala Leu Ala Glu Leu Ala
    1310                1315                1320

Thr Lys Thr Phe Gly Ser Ser Glu Ser Ser Ala Val Asp Ser Gly
    1325                1330                1335

Thr Ala Thr Ala Ser Pro Asp Gln Pro Ser Asp Asp Gly Asp Ala
    1340                1345                1350

Gly Ser Asp Val Glu Ser Tyr Ser Ser Met Pro Pro Leu Glu Gly
    1355                1360                1365

Glu Pro Gly Asp Pro Asp Leu Ser Asp Gly Ser Trp Ser Thr Val
    1370                1375                1380

Ser Glu Glu Ala Ser Glu Asp Val Val Cys Cys Ser Met Ser Tyr
    1385                1390                1395

Thr Trp Thr Gly Ala Leu Ile Thr Pro Cys Ala Ala Glu Glu Thr
    1400                1405                1410

Lys Leu Pro Ile Asn Ala Leu Ser Asn Ser Leu Leu Arg His His
    1415                1420                1425

Asn Leu Val Tyr Ala Thr Thr Ser Arg Ser Ala Ser Leu Arg Gln
    1430                1435                1440

Lys Lys Val Thr Phe Asp Arg Leu Gln Val Leu Asp Asp His Tyr
    1445                1450                1455

Arg Asp Val Leu Lys Glu Met Lys Ala Lys Ala Ser Thr Val Lys
    1460                1465                1470

Ala Lys Leu Leu Ser Val Glu Glu Ala Cys Lys Leu Thr Pro Pro
    1475                1480                1485

His Ser Ala Arg Ser Lys Phe Gly Tyr Gly Ala Lys Asp Val Arg
    1490                1495                1500

Asn Leu Ser Ser Lys Ala Val Asn His Ile Arg Ser Val Trp Lys
    1505                1510                1515

Asp Leu Leu Glu Asp Thr Glu Thr Pro Ile Asp Thr Thr Ile Met
    1520                1525                1530

Ala Lys Asn Glu Val Phe Cys Val Gln Pro Glu Lys Gly Gly Arg
    1535                1540                1545

Lys Pro Ala Arg Leu Ile Val Phe Pro Asp Leu Gly Val Arg Val
    1550                1555                1560

Cys Glu Lys Met Ala Leu Tyr Asp Val Val Ser Thr Leu Pro Gln
    1565                1570                1575

Ala Val Met Gly Ser Ser Tyr Gly Phe Gln Tyr Ser Pro Gly Gln
    1580                1585                1590

Arg Val Glu Phe Leu Val Asn Ala Trp Lys Ala Lys Lys Cys Pro
    1595                1600                1605

Met Gly Phe Ala Tyr Asp Thr Arg Cys Phe Asp Ser Thr Val Thr
    1610                1615                1620

Glu Asn Asp Ile Arg Val Glu Glu Ser Ile Tyr Gln Cys Cys Asp
    1625                1630                1635

Leu Ala Pro Glu Ala Arg Gln Ala Ile Arg Ser Leu Thr Glu Arg
    1640                1645                1650

Leu Tyr Ile Gly Gly Pro Leu Thr Asn Ser Lys Gly Gln Asn Cys
    1655                1660                1665

Gly Tyr Arg Arg Cys Arg Ala Ser Gly Val Leu Thr Thr Ser Cys
    1670                1675                1680
```

-continued

Gly Asn Thr Leu Thr Cys Tyr Leu Lys Ala Ala Ala Ala Cys Arg
1685 1690 1695

Ala Ala Lys Leu Gln Asp Cys Thr Met Leu Val Cys Gly Asp Asp
1700 1705 1710

Leu Val Val Ile Cys Glu Ser Ala Gly Thr Gln Glu Asp Glu Ala
1715 1720 1725

Ser Leu Arg Ala Phe Thr Glu Ala Met Thr Arg Tyr Ser Ala Pro
1730 1735 1740

Pro Gly Asp Pro Pro Lys Pro Glu Tyr Asp Leu Glu Leu Ile Thr
1745 1750 1755

Ser Cys Ser Ser Asn Val Ser Val Ala His Asp Ala Ser Gly Lys
1760 1765 1770

Arg Val Tyr Tyr Leu Thr Arg Asp Pro Thr Thr Pro Leu Ala Arg
1775 1780 1785

Ala Ala Trp Glu Thr Ala Arg His Thr Pro Val Asn Ser Trp Leu
1790 1795 1800

Gly Asn Ile Ile Met Tyr Ala Pro Thr Leu Trp Ala Arg Met Ile
1805 1810 1815

Leu Met Thr His Phe Phe Ser Ile Leu Leu Ala Gln Glu Gln Leu
1820 1825 1830

Glu Lys Ala Leu Asp Cys Gln Ile Tyr Gly Ala Cys Tyr Ser Ile
1835 1840 1845

Glu Pro Leu Asp Leu Pro Gln Ile Ile Gln Arg Leu His Gly Leu
1850 1855 1860

Ser Ala Phe Ser Leu His Ser Tyr Ser Pro Gly Glu Ile Asn Arg
1865 1870 1875

Val Ala Ser Cys Leu Arg Lys Leu Gly Val Pro Pro Leu Arg Val
1880 1885 1890

Trp Arg His Arg Ala Arg Ser Val Arg Ala Arg Leu Leu Ser Gln
1895 1900 1905

Gly Gly Arg Ala Ala Thr Cys Gly Lys Tyr Leu Phe Asn Trp Ala
1910 1915 1920

Val Arg Thr Lys Leu Lys Leu Thr Pro Ile Pro Ala Ala Ser Gln
1925 1930 1935

Leu Asp Leu Ser Ser Trp Phe Val Ala Gly Tyr Ser Gly Gly Asp
1940 1945 1950

Ile Tyr His Ser Leu Ser Arg Ala Arg Pro Arg Trp Phe Met Trp
1955 1960 1965

Cys Leu Leu Leu Leu Ser Val Gly Val Gly Ile Tyr Leu Leu Pro
1970 1975 1980

Asn Arg
1985

<210> SEQ ID NO 43
<211> LENGTH: 32
<212> TYPE: DNA
<213> ORGANISM: ARTIFICIAL
<220> FEATURE:
<223> OTHER INFORMATION: primer

<400> SEQUENCE: 43
tccctctaga cggaccgcta tcaggacata gc 32

<210> SEQ ID NO 44
<211> LENGTH: 35
<212> TYPE: DNA

-continued

<213> ORGANISM: ARTIFICIAL
<220> FEATURE:
<223> OTHER INFORMATION: primer

<400> SEQUENCE: 44
attcgtgctc atggtattat cgtgtttttc aaagg 35

<210> SEQ ID NO 45
<211> LENGTH: 34
<212> TYPE: DNA
<213> ORGANISM: ARTIFICIAL
<220> FEATURE:
<223> OTHER INFORMATION: primer

<400> SEQUENCE: 45
cacgataata ccatgagcac gaatcctaaa cctc 34

<210> SEQ ID NO 46
<211> LENGTH: 34
<212> TYPE: DNA
<213> ORGANISM: ARTIFICIAL
<220> FEATURE:
<223> OTHER INFORMATION: primer

<400> SEQUENCE: 46
ccgctcgagg cagtcgttcg tgacatggta tacc 34

<210> SEQ ID NO 47
<211> LENGTH: 32
<212> TYPE: DNA
<213> ORGANISM: ARTIFICIAL
<220> FEATURE:
<223> OTHER INFORMATION: primer

<400> SEQUENCE: 47
tccctctaga cggaccgcta tcaggacata gc 32

<210> SEQ ID NO 48
<211> LENGTH: 38
<212> TYPE: DNA
<213> ORGANISM: ARTIFICIAL
<220> FEATURE:
<223> OTHER INFORMATION: primer

<400> SEQUENCE: 48
agagcaaccg ggcatggtat tatcgtgttt ttcaaagg 38

<210> SEQ ID NO 49
<211> LENGTH: 40
<212> TYPE: DNA
<213> ORGANISM: ARTIFICIAL
<220> FEATURE:
<223> OTHER INFORMATION: primer

<400> SEQUENCE: 49
cacgataata ccatgcccgg ttgctctttt tctatcttcc 40

<210> SEQ ID NO 50
<211> LENGTH: 22
<212> TYPE: DNA
<213> ORGANISM: ARTIFICIAL
<220> FEATURE:
<223> OTHER INFORMATION: primer

<400> SEQUENCE: 50
atgtacagcc gaaccagttg cc 22

-continued

<210> SEQ ID NO 51
<211> LENGTH: 32
<212> TYPE: DNA
<213> ORGANISM: ARTIFICIAL
<220> FEATURE:
<223> OTHER INFORMATION: primer

<400> SEQUENCE: 51
tccctctaga cggaccgcta tcaggacata gc 32

<210> SEQ ID NO 52
<211> LENGTH: 35
<212> TYPE: DNA
<213> ORGANISM: ARTIFICIAL
<220> FEATURE:
<223> OTHER INFORMATION: primer

<400> SEQUENCE: 52
ctcccggtcc atggtattat cgtgtttttc aaagg 35

<210> SEQ ID NO 53
<211> LENGTH: 32
<212> TYPE: DNA
<213> ORGANISM: ARTIFICIAL
<220> FEATURE:
<223> OTHER INFORMATION: primer

<400> SEQUENCE: 53
cacgataata ccatggaccg ggagatggct gc 32

<210> SEQ ID NO 54
<211> LENGTH: 24
<212> TYPE: DNA
<213> ORGANISM: ARTIFICIAL
<220> FEATURE:
<223> OTHER INFORMATION: primer

<400> SEQUENCE: 54
gagcggtccg agtatggcaa tcag 24

<210> SEQ ID NO 55
<211> LENGTH: 17
<212> TYPE: DNA
<213> ORGANISM: ARTIFICIAL
<220> FEATURE:
<223> OTHER INFORMATION: primer

<400> SEQUENCE: 55
agcctcttca gcagctg 17

<210> SEQ ID NO 56
<211> LENGTH: 18
<212> TYPE: DNA
<213> ORGANISM: ARTIFICIAL
<220> FEATURE:
<223> OTHER INFORMATION: primer

<400> SEQUENCE: 56
aggaaatggc ctattggc 18

<210> SEQ ID NO 57
<211> LENGTH: 19
<212> TYPE: DNA
<213> ORGANISM: ARTIFICIAL
<220> FEATURE:

-continued

<223> OTHER INFORMATION: primer

<400> SEQUENCE: 57
tttccaccat attgccgtc 19

<210> SEQ ID NO 58
<211> LENGTH: 18
<212> TYPE: DNA
<213> ORGANISM: ARTIFICIAL
<220> FEATURE:
<223> OTHER INFORMATION: primer

<400> SEQUENCE: 58
ttgacgcagg tcgccagg 18

<210> SEQ ID NO 59
<211> LENGTH: 20
<212> TYPE: DNA
<213> ORGANISM: ARTIFICIAL
<220> FEATURE:
<223> OTHER INFORMATION: primer

<400> SEQUENCE: 59
gaaccaggtc gagggggagg 20

<210> SEQ ID NO 60
<211> LENGTH: 20
<212> TYPE: DNA
<213> ORGANISM: ARTIFICIAL
<220> FEATURE:
<223> OTHER INFORMATION: primer

<400> SEQUENCE: 60
tcgatgggga tggctttgcc 20

<210> SEQ ID NO 61
<211> LENGTH: 20
<212> TYPE: DNA
<213> ORGANISM: ARTIFICIAL
<220> FEATURE:
<223> OTHER INFORMATION: primer

<400> SEQUENCE: 61
ctcgccaccg ctacgcctcc 20

<210> SEQ ID NO 62
<211> LENGTH: 19
<212> TYPE: DNA
<213> ORGANISM: ARTIFICIAL
<220> FEATURE:
<223> OTHER INFORMATION: primer

<400> SEQUENCE: 62
actccgccta ccagcaccc 19

<210> SEQ ID NO 63
<211> LENGTH: 20
<212> TYPE: DNA
<213> ORGANISM: ARTIFICIAL
<220> FEATURE:
<223> OTHER INFORMATION: primer

<400> SEQUENCE: 63
accccataac caaatacatc 20

-continued

<210> SEQ ID NO 64
<211> LENGTH: 17
<212> TYPE: DNA
<213> ORGANISM: ARTIFICIAL
<220> FEATURE:
<223> OTHER INFORMATION: primer

<400> SEQUENCE: 64
agcctcttca gcagctg 17

<210> SEQ ID NO 65
<211> LENGTH: 20
<212> TYPE: DNA
<213> ORGANISM: ARTIFICIAL
<220> FEATURE:
<223> OTHER INFORMATION: primer

<400> SEQUENCE: 65
tatgtgcctg agagcgacgc 20

<210> SEQ ID NO 66
<211> LENGTH: 20
<212> TYPE: DNA
<213> ORGANISM: ARTIFICIAL
<220> FEATURE:
<223> OTHER INFORMATION: primer

<400> SEQUENCE: 66
tatgtgcctg agagcgacgc 20

<210> SEQ ID NO 67
<211> LENGTH: 19
<212> TYPE: DNA
<213> ORGANISM: ARTIFICIAL
<220> FEATURE:
<223> OTHER INFORMATION: primer

<400> SEQUENCE: 67
aaccttctgt ggcggcagg 19

<210> SEQ ID NO 68
<211> LENGTH: 20
<212> TYPE: DNA
<213> ORGANISM: ARTIFICIAL
<220> FEATURE:
<223> OTHER INFORMATION: primer

<400> SEQUENCE: 68
ctggttggac gcagaaaacc 20

<210> SEQ ID NO 69
<211> LENGTH: 50
<212> TYPE: DNA
<213> ORGANISM: ARTIFICIAL
<220> FEATURE:
<223> OTHER INFORMATION: primer

<400> SEQUENCE: 69
gatccgggcc cagggttgga ctcgacgtct cccgcaagct taagaaggcg 50

<210> SEQ ID NO 70
<211> LENGTH: 20
<212> TYPE: DNA
<213> ORGANISM: ARTIFICIAL
<220> FEATURE:
<223> OTHER INFORMATION: primer -continued

```
<400> SEQUENCE: 70

aaccacatcc gctccgtgtg                                                    20


<210> SEQ ID NO 71
<211> LENGTH: 20
<212> TYPE: DNA
<213> ORGANISM: ARTIFICIAL
<220> FEATURE:
<223> OTHER INFORMATION: primer

<400> SEQUENCE: 71

tggctcaatg gagtaacagg                                                    20


<210> SEQ ID NO 72
<211> LENGTH: 18
<212> TYPE: DNA
<213> ORGANISM: ARTIFICIAL
<220> FEATURE:
<223> OTHER INFORMATION: primer

<400> SEQUENCE: 72

ttctccatcc ttctagct                                                      18


<210> SEQ ID NO 73
<211> LENGTH: 19
<212> TYPE: DNA
<213> ORGANISM: ARTIFICIAL
<220> FEATURE:
<223> OTHER INFORMATION: primer

<400> SEQUENCE: 73

aacaggaaat ggcctattg                                                     19
```